(12) United States Patent
Hoffman

(10) Patent No.: US 10,429,381 B2
(45) Date of Patent: Oct. 1, 2019

(54) CHEMICALLY-SENSITIVE FIELD EFFECT TRANSISTORS, SYSTEMS, AND METHODS FOR MANUFACTURING AND USING THE SAME

(71) Applicant: Agilome, Inc., San Diego, CA (US)

(72) Inventor: Paul Hoffman, San Diego, CA (US)

( * ) Notice: Subject to any disclaimer, the term of this patent is extended or adjusted under 35 U.S.C. 154(b) by 0 days.

(21) Appl. No.: 16/014,838

(22) Filed: Jun. 21, 2018

(65) Prior Publication Data

US 2019/0120830 A1    Apr. 25, 2019

Related U.S. Application Data

(63) Continuation of application No. 15/256,493, filed on Sep. 2, 2016, now Pat. No. 10,006,910, which is a
(Continued)

(51) Int. Cl.
*H01L 29/66*    (2006.01)
*G01N 33/543*    (2006.01)
*G01N 27/414*    (2006.01)

(52) U.S. Cl.
CPC ..... *G01N 33/5438* (2013.01); *G01N 27/4146* (2013.01)

(58) Field of Classification Search
CPC . A01H 3/00; A01H 5/00; A23K 10/30; A23V 2002/00; C07K 14/415;
(Continued)

(56) References Cited

U.S. PATENT DOCUMENTS

| 3,377,893 A | 4/1968 | Shorb |
| 3,466,874 A | 9/1969 | Holl |

(Continued)

FOREIGN PATENT DOCUMENTS

| CN | 102703594 A | 10/2012 |
| CN | 202854094 U | 4/2013 |

(Continued)

OTHER PUBLICATIONS

Basu et al. Recent Advances in Carbon Nanotubes Based Biosensors, Sensors, 8:1-x manuscripts, downloaded from: http://www.mdpi.org/sensorstaccepted/sensors-util-24-21-malhorta-in-PRE-PUBLISHED-VERSION-0422.pdf (Jan. 31, 2008). 34 pages.

(Continued)

*Primary Examiner* — Robert G Bachner
(74) *Attorney, Agent, or Firm* — Mintz Levin Cohn Ferris Glovsky and Popeo, P.C.

(57) ABSTRACT

This invention concerns Chemically-sensitive Field Effect Transistors (ChemFETs) that are preferably fabricated using semiconductor fabrication methods on a semiconductor wafer, and in preferred embodiments, on top of an integrated circuit structure made using semiconductor fabrication methods. The instant ChemFETs typically comprise a conductive source, a conductive drain, and a channel composed of a one-dimensional (1D) or two-dimensional (2D) transistor nanomaterial, which channel extends from the source to the drain and is fabricated using semiconductor fabrication techniques on top of a wafer. The ChemFET also includes a gate, often the gate voltage is provided through a fluid or solution proximate the ChemFET. Such ChemFETs, preferably configured in independently addressable arrays, may be employed to detect a presence and/or concentration changes of various analyte types in chemical and/or biological samples, including nucleic acid hybridization and/or sequencing reactions.

20 Claims, 120 Drawing Sheets

Related U.S. Application Data continuation of application No. 15/239,800, filed on Aug. 17, 2016, now Pat. No. 9,857,328, which is a continuation-in-part of application No. 15/182,533, filed on Jun. 14, 2016, now Pat. No. 9,859,394, said application No. 15/239,800 is a continuation-in-part of application No. 15/065,744, filed on Mar. 9, 2016, now Pat. No. 9,618,474, which is a continuation-in-part of application No. 14/963,253, filed on Dec. 9, 2015, said application No. 15/239,800 is a continuation-in-part of application No. 14/963,253, said application No. 15/256,493 is a continuation of application No. 15/225,764, filed on Aug. 1, 2016, now Pat. No. 10,020,300, which is a continuation-in-part of application No. 15/182,533, and a continuation-in-part of application No. 15/065,744, and a continuation-in-part of application No. 14/963,253, said application No. 15/256,493 is a continuation-in-part of application No. 15/182,533, and a continuation-in-part of application No. 15/065,744, and a continuation-in-part of application No. 14/963,253.

(60) Provisional application No. 62/175,351, filed on Jun. 14, 2015, provisional application No. 62/130,621, filed on Mar. 10, 2015, provisional application No. 62/206,228, filed on Aug. 17, 2015, provisional application No. 62/199,987, filed on Aug. 1, 2015, provisional application No. 62/130,594, filed on Mar. 9, 2015, provisional application No. 62/094,016, filed on Dec. 18, 2014, provisional application No. 62/130,598, filed on Mar. 9, 2015, provisional application No. 62/130,601, filed on Mar. 9, 2015, provisional application No. 62/206,372, filed on Aug. 18, 2015, provisional application No. 62/206,814, filed on Aug. 18, 2015, provisional application No. 62/206,224, filed on Aug. 17, 2015, provisional application No. 62/205,803, filed on Aug. 17, 2015, provisional application No. 62/205,808, filed on Aug. 17, 2015, provisional application No. 62/206,166, filed on Aug. 17, 2015, provisional application No. 62/199,956, filed on Jul. 31, 2015, provisional application No. 62/215,018, filed on Sep. 6, 2015, provisional application No. 62/214,910, filed on Sep. 4, 2015, provisional application No. 62/214,850, filed on Sep. 4, 2015, provisional application No. 62/214,892, filed on Sep. 4, 2015, provisional application No. 62/214,901, filed on Sep. 4, 2015, provisional application No. 62/214,912, filed on Sep. 5, 2015, provisional application No. 62/213,112, filed on Sep. 2, 2015, provisional application No. 62/213,151, filed on Sep. 2, 2015.

(58) Field of Classification Search
CPC ............ C12N 15/8245; C12N 15/8246; C12N 15/8247; C12N 15/8251; A23L 19/00; A23L 7/198; A23L 1/1041; A23L 1/212
See application file for complete search history.

(56) References Cited

U.S. PATENT DOCUMENTS

| | | |
|---|---|---|
| 3,564,151 A | 2/1971 | Shlesinger, Jr. |
| 3,605,428 A | 9/1971 | Smith et al. |
| 3,691,109 A | 9/1972 | Larsen |
| 3,772,069 A | 11/1973 | Daniel |
| 3,828,094 A | 8/1974 | Widdig et al. |
| 3,892,139 A | 7/1975 | Harris |
| 3,931,401 A | 1/1976 | Prasad et al. |
| 5,397,863 A | 3/1995 | Afzali-Ardakani et al. |
| 5,556,899 A | 9/1996 | Afzali-Ardakani et al. |
| 5,571,852 A | 11/1996 | Afzali-Ardakani et al. |
| 5,591,285 A | 1/1997 | Afzali-Ardakani et al. |
| 5,639,660 A | 6/1997 | Kinet et al. |
| 5,701,256 A | 12/1997 | Marr et al. |
| 5,958,784 A | 9/1999 | Benner |
| 6,001,611 A | 12/1999 | Will |
| 6,377,893 B1 | 4/2002 | Benner |
| 6,466,874 B1 | 10/2002 | Eisenberg et al. |
| 6,564,151 B1 | 5/2003 | Pellegrini et al. |
| 6,605,428 B2 | 8/2003 | Kilger et al. |
| 6,691,109 B2 | 2/2004 | Bjornson et al. |
| 6,772,069 B1 | 8/2004 | Eisenberg et al. |
| 6,828,094 B2 | 12/2004 | Kilger et al. |
| 6,892,139 B2 | 5/2005 | Eisenberg et al. |
| 6,931,401 B2 | 8/2005 | Gibson et al. |
| 7,008,764 B1 | 3/2006 | Honold et al. |
| 7,247,877 B2 | 7/2007 | Hakey et al. |
| 7,253,431 B2 | 8/2007 | Afzali-Ardakani et al. |
| 7,333,980 B2 | 2/2008 | Bjornson et al. |
| 7,462,468 B1 | 12/2008 | Williams et al. |
| 7,484,423 B2 | 2/2009 | Hakey et al. |
| 7,492,015 B2 | 2/2009 | Chen et al. |
| 7,504,132 B2 | 3/2009 | Afzali-Ardakani et al. |
| 7,514,063 B1 | 4/2009 | Tulevski et al. |
| 7,544,546 B2 | 6/2009 | Afzali-Ardakani et al. |
| 7,612,270 B1 | 11/2009 | Zhu |
| 7,670,810 B2 | 3/2010 | Gunderson et al. |
| 7,727,505 B2 | 6/2010 | Afazali-Ardakani et al. |
| 7,732,119 B2 | 6/2010 | Afzali-Ardakani et al. |
| 7,745,118 B2 | 6/2010 | Green et al. |
| 7,750,908 B2 | 7/2010 | Kincaid et al. |
| 7,761,462 B2 | 7/2010 | Bjornson et al. |
| 7,771,695 B2 | 8/2010 | Afzali-Ardakani et al. |
| 7,855,133 B2 | 12/2010 | Afzali-Ardakani et al. |
| 7,867,469 B2 | 1/2011 | Afzali-Ardakani et al. |
| 7,879,307 B2 | 2/2011 | Afzali-Ardakani et al. |
| 7,883,685 B1 | 2/2011 | Afzali-Ardakani et al. |
| 7,888,528 B2 | 2/2011 | Afzali-Ardakani et al. |
| 7,917,299 B2 | 3/2011 | Buhler et al. |
| 7,932,029 B1 | 4/2011 | Lok |
| 7,948,015 B2 | 5/2011 | Rothberg et al. |
| 7,951,424 B2 | 5/2011 | Afzali-Ardakani et al. |
| 7,955,585 B2 | 6/2011 | Afzali-Ardakani et al. |
| 7,955,931 B2 | 6/2011 | Appenzeller et al. |
| 7,982,274 B2 | 7/2011 | Afzali-Ardakani et al. |
| 7,993,842 B2 | 8/2011 | McKernan et al. |
| 8,017,934 B2 | 9/2011 | Appenzeller et al. |
| 8,032,305 B2 | 10/2011 | Shibuya |
| 8,039,334 B2 | 10/2011 | Furukawa et al. |
| 8,039,909 B2 | 10/2011 | Afzali-Ardakani et al. |
| 8,057,984 B2 | 11/2011 | Afzali-Ardakani et al. |
| 8,084,012 B2 | 12/2011 | Afzali-Ardakani et al. |
| 8,095,508 B2 | 1/2012 | Chamberlain et al. |
| 8,124,463 B2 | 2/2012 | Chen et al. |
| 8,138,102 B2 | 3/2012 | Afzali-Ardakani et al. |
| 8,138,491 B2 | 3/2012 | Appenzeller et al. |
| 8,138,492 B2 | 3/2012 | Afzali-Ardakani et al. |
| 8,143,030 B2 | 3/2012 | Maxham et al. |
| 8,153,375 B2 | 4/2012 | Travers et al. |
| 8,182,989 B2 | 5/2012 | Bignell et al. |
| 8,182,993 B2 | 5/2012 | Tomaney et al. |
| 8,209,130 B1 | 6/2012 | Kennedy et al. |
| 8,211,735 B2 | 7/2012 | Graham et al. |
| 8,211,741 B2 | 7/2012 | Appenzeller et al. |
| 8,217,433 B1 | 7/2012 | Fife |
| 8,227,171 B2 | 7/2012 | Afzali-Ardakani et al. |
| 8,244,479 B2 | 8/2012 | Kain et al. |
| 8,283,453 B2 | 10/2012 | Afzali-Ardakani et al. |
| 8,283,703 B2 | 10/2012 | Solomon |
| 8,293,607 B2 | 10/2012 | Afzali-Ardakani et al. |
| 8,296,075 B2 | 10/2012 | Den Hartog |
| 8,306,757 B2 | 11/2012 | Rothberg et al. |
| 8,309,330 B2 | 11/2012 | Travers et al. |
| 8,329,400 B2 | 12/2012 | Lok |
| 8,383,345 B2 | 2/2013 | Shendure et al. |
| 8,383,369 B2 | 2/2013 | Maxham et al. |

(56) References Cited

U.S. PATENT DOCUMENTS

| | | |
|---|---|---|
| 8,394,727 B1 | 3/2013 | Afzali-Ardakani et al. |
| 8,395,774 B2 | 3/2013 | Afzali et al. |
| 8,445,945 B2 | 5/2013 | Rothberg et al. |
| 8,455,193 B2 | 6/2013 | Travers et al. |
| 8,455,297 B1 | 6/2013 | Avouris et al. |
| 8,455,311 B2 | 6/2013 | Solomon |
| 8,463,555 B2 | 6/2013 | Zhang |
| 8,465,647 B2 | 6/2013 | Bol et al. |
| 8,471,249 B2 | 6/2013 | Chiu et al. |
| 8,481,413 B2 | 7/2013 | Afzali-Ardakani et al. |
| 8,486,630 B2 | 7/2013 | Pan et al. |
| 8,491,769 B2 | 7/2013 | Afzali-Ardakani et al. |
| 8,492,293 B1 | 7/2013 | Afzali-Ardakani et al. |
| 8,492,748 B2 | 7/2013 | Chang et al. |
| 8,512,458 B2 | 8/2013 | Holmes et al. |
| 8,515,682 B2 | 8/2013 | Buhler et al. |
| 8,518,829 B2 | 8/2013 | Dang et al. |
| 8,524,487 B2 | 9/2013 | Fife |
| 8,535,882 B2 | 9/2013 | Christians et al. |
| 8,546,246 B2 | 10/2013 | Lin et al. |
| 8,554,492 B2 | 10/2013 | Ahn et al. |
| 8,557,097 B2 | 10/2013 | Afzali-Ardakani et al. |
| 8,558,288 B2 | 10/2013 | Rothberg et al. |
| 8,574,892 B2 | 11/2013 | Su |
| 8,587,065 B2 | 11/2013 | Chen et al. |
| 8,594,951 B2 | 11/2013 | Homer |
| 8,598,569 B2 | 12/2013 | Afzali-Ardakani et al. |
| 8,603,792 B2 | 12/2013 | Nikiforov et al. |
| 8,604,559 B2 | 12/2013 | Afzali-Ardakani et al. |
| 8,609,481 B1 | 12/2013 | Franklin et al. |
| 8,610,989 B2 | 12/2013 | Avouris et al. |
| 8,614,436 B2 | 12/2013 | Solomon |
| 8,617,941 B2 | 12/2013 | Farmer et al. |
| 8,620,881 B2 | 12/2013 | Chamberlain et al. |
| 8,628,940 B2 | 1/2014 | Sorenson et al. |
| 8,637,374 B2 | 1/2014 | Appenzeller et al. |
| 8,642,432 B2 | 2/2014 | Afzali-Ardakani et al. |
| 8,674,412 B2 | 3/2014 | Franklin et al. |
| 8,688,388 B2 | 4/2014 | Dzakula et al. |
| 8,698,226 B2 | 4/2014 | Jain et al. |
| 8,700,341 B2 | 4/2014 | Rava et al. |
| 8,716,029 B1 | 5/2014 | Kim et al. |
| 8,716,597 B2 | 5/2014 | Mann et al. |
| 8,725,422 B2 | 5/2014 | Halpern et al. |
| 8,738,300 B2 | 5/2014 | Porreca et al. |
| 8,741,678 B2 | 6/2014 | Chen et al. |
| 8,741,751 B2 | 6/2014 | Cao et al. |
| 8,741,756 B2 | 6/2014 | Franklin et al. |
| 8,751,166 B2 | 6/2014 | Friedlander et al. |
| 8,751,452 B2 | 6/2014 | Chamberlain et al. |
| 8,753,816 B2 | 6/2014 | Rigatti et al. |
| 8,753,912 B2 | 6/2014 | Graham et al. |
| 8,754,393 B2 | 6/2014 | Cao et al. |
| 8,765,547 B2 | 7/2014 | Farmer et al. |
| 8,766,345 B2 | 7/2014 | Farmer et al. |
| 8,772,141 B2 | 7/2014 | Afzali-Ardakani et al. |
| 8,772,910 B2 | 7/2014 | Afzali-Ardakani et al. |
| 8,779,414 B2 | 7/2014 | Chang et al. |
| 8,785,262 B2 | 7/2014 | Farmer et al. |
| 8,785,911 B2 | 7/2014 | Chen et al. |
| 8,786,018 B2 | 7/2014 | Farmer et al. |
| 8,795,961 B2 | 8/2014 | Rank et al. |
| 8,796,642 B2 | 8/2014 | Boday et al. |
| 8,796,668 B2 | 8/2014 | Lin et al. |
| 8,797,059 B2 | 8/2014 | Boday et al. |
| 8,803,129 B2 | 8/2014 | Chang et al. |
| 8,803,131 B2 | 8/2014 | Lin et al. |
| 8,803,132 B2 | 8/2014 | Farmer et al. |
| 8,805,148 B2 | 8/2014 | Avouris et al. |
| 8,809,153 B2 | 8/2014 | Afzali-Ardakani et al. |
| 8,809,837 B2 | 8/2014 | Farmer et al. |
| 8,816,328 B2 | 8/2014 | Chang et al. |
| 8,816,787 B2 | 8/2014 | Jenkins et al. |
| 8,828,762 B2 | 9/2014 | Chu et al. |
| 8,834,967 B2 | 9/2014 | Afzali-Ardakani et al. |
| 8,835,686 B2 | 9/2014 | Afzali-Ardakani et al. |
| 8,852,342 B2 | 10/2014 | Dimitrakopoulos et al. |
| 8,852,985 B2 | 10/2014 | Cai et al. |
| 8,853,034 B2 | 10/2014 | Afzali-Ardakani et al. |
| 8,859,048 B2 | 10/2014 | Afzali-Ardakani et al. |
| 8,859,439 B1 | 10/2014 | Avouris et al. |
| 8,877,340 B2 | 11/2014 | Chu et al. |
| 8,878,193 B2 | 11/2014 | Avouris et al. |
| 8,890,116 B2 | 11/2014 | Chen et al. |
| 8,890,121 B1 | 11/2014 | Han et al. |
| 8,895,372 B2 | 11/2014 | Guo et al. |
| 8,895,417 B2 | 11/2014 | Afzali-Ardakani et al. |
| 8,900,538 B2 | 12/2014 | Abou-Kandil et al. |
| 8,900,918 B2 | 12/2014 | Avouris et al. |
| 8,901,680 B2 | 12/2014 | Cai et al. |
| 8,901,689 B1 | 12/2014 | Avouris et al. |
| 8,911,972 B2 | 12/2014 | Chaisson et al. |
| 8,912,525 B2 | 12/2014 | Afzali-Ardakani et al. |
| 8,916,451 B2 | 12/2014 | Bayram et al. |
| 8,927,057 B2 | 1/2015 | Bol et al. |
| 8,932,919 B2 | 1/2015 | Farmer et al. |
| 8,936,763 B2 | 1/2015 | Rothberg et al. |
| 8,951,727 B2 | 2/2015 | Jaramillo-Botero et al. |
| 8,952,258 B2 | 2/2015 | Plucinski et al. |
| 8,957,405 B2 | 2/2015 | Adkisson et al. |
| 8,957,463 B2 | 2/2015 | Afzali-Ardakani et al. |
| 8,963,215 B2 | 2/2015 | Afzali-Ardakani et al. |
| 8,968,582 B2 | 3/2015 | Franklin et al. |
| 8,969,090 B2 | 3/2015 | Sun et al. |
| 8,969,115 B2 | 3/2015 | Chen et al. |
| 8,969,118 B2 | 3/2015 | Afzali-Ardakani et al. |
| 8,975,095 B2 | 3/2015 | Han et al. |
| 8,987,740 B2 | 3/2015 | Avouris et al. |
| 9,000,499 B2 | 4/2015 | Franklin et al. |
| 9,000,594 B2 | 4/2015 | Ott et al. |
| 9,014,989 B2 | 4/2015 | McMillen et al. |
| 9,017,813 B2 | 4/2015 | El-Ashry et al. |
| 9,029,841 B2 | 5/2015 | Farmer et al. |
| 9,040,364 B2 | 5/2015 | Farmer et al. |
| 9,045,796 B2 | 6/2015 | Gunderson et al. |
| 9,045,842 B2 | 6/2015 | Han et al. |
| 9,051,611 B2 | 6/2015 | Christians et al. |
| 9,059,188 B1 | 6/2015 | Dimitrakopoulos et al. |
| 9,062,389 B2 | 6/2015 | Han et al. |
| 9,064,698 B1 | 6/2015 | Khakifirooz et al. |
| 9,064,776 B2 | 6/2015 | Lin et al. |
| 9,064,842 B2 | 6/2015 | Bol et al. |
| 9,068,221 B2 | 6/2015 | Merriman et al. |
| 9,068,936 B2 | 6/2015 | Guo et al. |
| 9,076,873 B2 | 7/2015 | Chen et al. |
| 9,082,856 B2 | 7/2015 | Chen et al. |
| 9,085,802 B2 | 7/2015 | Liu et al. |
| 9,087,691 B2 | 7/2015 | Zhu et al. |
| 9,091,648 B2 | 7/2015 | Afzali-Ardakani et al. |
| 9,093,507 B2 | 7/2015 | Cohen et al. |
| 9,093,631 B2 | 7/2015 | Davis |
| 9,097,658 B2 | 8/2015 | Afzali-Ardakani et al. |
| 9,099,542 B2 | 8/2015 | Franklin et al. |
| 9,102,118 B2 | 8/2015 | Afzali-Ardakani et al. |
| 9,102,540 B2 | 8/2015 | Afzali-Ardakani et al. |
| 9,103,776 B2 | 8/2015 | Afzali-Ardakani et al. |
| 9,105,702 B2 | 8/2015 | Franklin et al. |
| 9,105,853 B2 | 8/2015 | Afzali-Ardakani et al. |
| 9,123,454 B2 | 9/2015 | Franklin et al. |
| 9,142,471 B2 | 9/2015 | Abou-Kandil et al. |
| 9,145,295 B2 | 9/2015 | Peng |
| 9,146,209 B2 | 9/2015 | Johnson et al. |
| 9,150,918 B2 | 10/2015 | Turner et al. |
| 9,157,887 B2 | 10/2015 | Guo et al. |
| 9,162,883 B2 | 10/2015 | El-Ashry et al. |
| 9,174,413 B2 | 11/2015 | Avouris et al. |
| 9,174,414 B2 | 11/2015 | Avouris et al. |
| 9,177,688 B2 | 11/2015 | Bol et al. |
| 9,179,579 B2 | 11/2015 | Hada et al. |
| 9,281,305 B1 | 3/2016 | Yang et al. |
| 9,618,474 B2 | 4/2017 | van Rooyen et al. |
| 2002/0164588 A1 | 11/2002 | Eisenberg et al. |
| 2002/0194173 A1 | 12/2002 | Bjornson et al. |
| 2003/0033279 A1 | 2/2003 | Gibson et al. |

(56) References Cited

U.S. PATENT DOCUMENTS

| | | |
|---|---|---|
| 2003/0200033 A1 | 10/2003 | Segal et al. |
| 2003/0224384 A1 | 12/2003 | Sayood et al. |
| 2003/0228618 A1 | 12/2003 | Levanon et al. |
| 2004/0072204 A1 | 4/2004 | Shibuya |
| 2004/0110227 A1 | 6/2004 | Levanon et al. |
| 2004/0142347 A1 | 7/2004 | Stockwell et al. |
| 2004/0143571 A1 | 7/2004 | Bjornson et al. |
| 2004/0152108 A1 | 8/2004 | Keith et al. |
| 2004/0241730 A1 | 12/2004 | Yakhini et al. |
| 2004/0248189 A1 | 12/2004 | Bulaj et al. |
| 2005/0009771 A1 | 1/2005 | Levanon et al. |
| 2005/0038609 A1 | 2/2005 | Benner |
| 2005/0039123 A1 | 2/2005 | Kuchinsky et al. |
| 2005/0107961 A1 | 5/2005 | Uemura et al. |
| 2005/0131649 A1 | 6/2005 | Larsen et al. |
| 2005/0188294 A1 | 8/2005 | Kuchinsky et al. |
| 2005/0197783 A1 | 9/2005 | Kuchinsky et al. |
| 2005/0240352 A1 | 10/2005 | Liang |
| 2006/0016699 A1 | 1/2006 | Kamahori et al. |
| 2006/0028471 A1 | 2/2006 | Kincaid et al. |
| 2006/0064247 A1 | 3/2006 | Yuan et al. |
| 2006/0100788 A1 | 5/2006 | Carrino et al. |
| 2006/0106545 A1 | 5/2006 | Balaji et al. |
| 2006/0141529 A1 | 6/2006 | Koleske et al. |
| 2006/0275794 A1 | 12/2006 | Carrino et al. |
| 2006/0294059 A1 | 12/2006 | Chamberlain et al. |
| 2007/0063304 A1 | 3/2007 | Matsumoto et al. |
| 2007/0067108 A1 | 3/2007 | Buhler et al. |
| 2007/0088510 A1 | 4/2007 | Li et al. |
| 2007/0134692 A1 | 6/2007 | Valmeekam et al. |
| 2007/0138463 A1 | 6/2007 | Herlogsson et al. |
| 2007/0152335 A1 | 7/2007 | Chun |
| 2007/0196816 A1 | 8/2007 | Schwartz et al. |
| 2007/0232060 A1 | 10/2007 | Niu |
| 2007/0259337 A1 | 11/2007 | Hully et al. |
| 2007/0277036 A1 | 11/2007 | Chamberlain et al. |
| 2008/0035494 A1 | 2/2008 | Gomez et al. |
| 2008/0063566 A1 | 3/2008 | Matsumoto et al. |
| 2008/0086274 A1 | 4/2008 | Chamberlain et al. |
| 2008/0104041 A1 | 5/2008 | Bjornson et al. |
| 2008/0154567 A1 | 6/2008 | Qiu et al. |
| 2008/0250016 A1 | 10/2008 | Farrar |
| 2008/0274912 A1 | 11/2008 | Johnson et al. |
| 2008/0283875 A1 | 11/2008 | Mukasa et al. |
| 2009/0008629 A1 | 1/2009 | Matsumoto et al. |
| 2009/0014757 A1 | 1/2009 | Takulapalli et al. |
| 2009/0119313 A1 | 5/2009 | Pearce |
| 2009/0125248 A1 | 5/2009 | Shams et al. |
| 2009/0153130 A1 | 6/2009 | Shim et al. |
| 2009/0156431 A1 | 6/2009 | Lok |
| 2009/0171647 A1 | 7/2009 | Mannava et al. |
| 2009/0278556 A1 | 11/2009 | Man et al. |
| 2009/0292665 A1 | 11/2009 | Den Hartog |
| 2009/0325239 A1 | 12/2009 | Lok |
| 2010/0025660 A1 | 2/2010 | Jain et al. |
| 2010/0035254 A1 | 2/2010 | Williams |
| 2010/0069263 A1 | 3/2010 | Shendure et al. |
| 2010/0075309 A1 | 3/2010 | Maxham et al. |
| 2010/0075327 A1 | 3/2010 | Maxham et al. |
| 2010/0077267 A1 | 3/2010 | Perego et al. |
| 2010/0082805 A1 | 4/2010 | Orton et al. |
| 2010/0088040 A1 | 4/2010 | Johnson, Jr. |
| 2010/0105202 A1 | 4/2010 | Daamen |
| 2010/0121582 A1 | 5/2010 | Pan et al. |
| 2010/0227384 A1 | 9/2010 | Vann |
| 2010/0228496 A1 | 9/2010 | Leong et al. |
| 2010/0293167 A1 | 11/2010 | Biasci et al. |
| 2010/0304989 A1 | 12/2010 | Von Hoff et al. |
| 2010/0327847 A1 | 12/2010 | Leiber et al. |
| 2011/0003301 A1 | 1/2011 | Raymond et al. |
| 2011/0004413 A1 | 1/2011 | Carnevali et al. |
| 2011/0042673 A1 | 2/2011 | Yamabayashi et al. |
| 2011/0098193 A1 | 4/2011 | Kingsmore et al. |
| 2011/0121273 A1 | 5/2011 | Jo et al. |
| 2011/0177517 A1 | 7/2011 | Rava et al. |
| 2011/0195406 A1 | 8/2011 | Sorenson et al. |
| 2011/0201507 A1 | 8/2011 | Rava et al. |
| 2011/0210314 A1 | 9/2011 | Chung et al. |
| 2011/0212464 A1 | 9/2011 | Hagmann et al. |
| 2011/0224087 A1 | 9/2011 | Quake et al. |
| 2011/0227043 A1 | 9/2011 | Guo et al. |
| 2011/0230358 A1 | 9/2011 | Rava |
| 2011/0231446 A1 | 9/2011 | Buhler et al. |
| 2011/0237444 A1 | 9/2011 | Clancy et al. |
| 2011/0245085 A1 | 10/2011 | Rava et al. |
| 2011/0252008 A1 | 10/2011 | Chamberlain et al. |
| 2011/0257889 A1 | 10/2011 | Klammer et al. |
| 2011/0270533 A1 | 11/2011 | Zhang et al. |
| 2011/0281740 A1 | 11/2011 | Beechem et al. |
| 2011/0281768 A1 | 11/2011 | Travers et al. |
| 2011/0295514 A1 | 12/2011 | Breu et al. |
| 2011/0295858 A1 | 12/2011 | Ahn et al. |
| 2011/0295977 A1 | 12/2011 | Shibuya |
| 2011/0296543 A1 | 12/2011 | Chang et al. |
| 2012/0001615 A1 | 1/2012 | Levine |
| 2012/0010085 A1 | 1/2012 | Rava et al. |
| 2012/0011086 A1 | 1/2012 | Zhang et al. |
| 2012/0021918 A1 | 1/2012 | Bashir et al. |
| 2012/0046175 A1 | 2/2012 | Rodesch et al. |
| 2012/0046877 A1 | 2/2012 | Hyland et al. |
| 2012/0053845 A1 | 3/2012 | Bruestle et al. |
| 2012/0089339 A1 | 4/2012 | Ganeshalingam et al. |
| 2012/0094849 A1 | 4/2012 | Rava et al. |
| 2012/0095697 A1 | 4/2012 | Halpern et al. |
| 2012/0100548 A1 | 4/2012 | Rava et al. |
| 2012/0102041 A1 | 4/2012 | Park et al. |
| 2012/0109849 A1 | 5/2012 | Chamberlain et al. |
| 2012/0110316 A1 | 5/2012 | Chamberlain et al. |
| 2012/0116688 A1 | 5/2012 | Mishra et al. |
| 2012/0149582 A1 | 6/2012 | Rava et al. |
| 2012/0156677 A1 | 6/2012 | Bitinaite et al. |
| 2012/0165203 A1 | 6/2012 | Quake et al. |
| 2012/0197623 A1 | 8/2012 | Homer |
| 2012/0203792 A1 | 8/2012 | Zhang et al. |
| 2012/0208706 A1 | 8/2012 | Downing et al. |
| 2012/0214172 A1 | 8/2012 | Chen et al. |
| 2012/0214678 A1 | 8/2012 | Rava et al. |
| 2012/0220053 A1 | 8/2012 | Lee et al. |
| 2012/0221249 A1 | 8/2012 | Lizardi et al. |
| 2012/0221432 A1 | 8/2012 | Yuan et al. |
| 2012/0237928 A1 | 9/2012 | Rava et al. |
| 2012/0264121 A1 | 10/2012 | Rava et al. |
| 2012/0270739 A1 | 10/2012 | Rava et al. |
| 2012/0271558 A1 | 10/2012 | Hur et al. |
| 2012/0286244 A1 | 11/2012 | Chiu et al. |
| 2012/0289408 A1 | 11/2012 | Travers et al. |
| 2012/0289412 A1 | 11/2012 | Seitz et al. |
| 2012/0295260 A1 | 11/2012 | Pan et al. |
| 2012/0330559 A1 | 12/2012 | Jiang et al. |
| 2012/0330566 A1 | 12/2012 | Chaisson |
| 2013/0018599 A1 | 1/2013 | Peng |
| 2013/0029852 A1 | 1/2013 | Rava et al. |
| 2013/0034546 A1 | 2/2013 | Rava et al. |
| 2013/0054151 A1 | 2/2013 | Kermani et al. |
| 2013/0054508 A1 | 2/2013 | Kermani et al. |
| 2013/0059740 A1 | 3/2013 | Drmanac et al. |
| 2013/0085681 A1 | 4/2013 | Deciu et al. |
| 2013/0091121 A1 | 4/2013 | Galinsky |
| 2013/0091126 A1 | 4/2013 | Krishnaswami et al. |
| 2013/0091176 A1 | 4/2013 | Harris et al. |
| 2013/0096011 A1 | 4/2013 | Rava et al. |
| 2013/0096841 A1 | 4/2013 | Kermani et al. |
| 2013/0103320 A1 | 4/2013 | Dzakula et al. |
| 2013/0124100 A1 | 5/2013 | Drmanac et al. |
| 2013/0137588 A1 | 5/2013 | Shendure et al. |
| 2013/0137605 A1 | 5/2013 | Shendure et al. |
| 2013/0138355 A1 | 5/2013 | Inglis et al. |
| 2013/0138358 A1 | 5/2013 | Tang et al. |
| 2013/0140518 A1 | 6/2013 | Jain et al. |
| 2013/0150253 A1 | 6/2013 | Deciu et al. |
| 2013/0157870 A1 | 6/2013 | Pushkarev et al. |
| 2013/0164859 A1 | 6/2013 | Johnson et al. |
| 2013/0166221 A1 | 6/2013 | Inglis et al. |
| 2013/0184161 A1 | 7/2013 | Kingsmore et al. |

(56) References Cited

U.S. PATENT DOCUMENTS

| | | |
|---|---|---|
| 2013/0190211 A1 | 7/2013 | Bustillo et al. |
| 2013/0194882 A1 | 8/2013 | Ishii et al. |
| 2013/0204851 A1 | 8/2013 | Bhola et al. |
| 2013/0211729 A1 | 8/2013 | Sastry-Dent et al. |
| 2013/0230909 A1 | 9/2013 | Pan et al. |
| 2013/0237432 A1 | 9/2013 | Li et al. |
| 2013/0240378 A1 | 9/2013 | Lee et al. |
| 2013/0245958 A1 | 9/2013 | Forster et al. |
| 2013/0251726 A1 | 9/2013 | Mascola et al. |
| 2013/0261983 A1 | 10/2013 | Dzakula et al. |
| 2013/0273543 A1 | 10/2013 | Gudmundsson et al. |
| 2013/0288244 A1 | 10/2013 | Deciu et al. |
| 2013/0288901 A1 | 10/2013 | Kennedy et al. |
| 2013/0296175 A1 | 11/2013 | Rafnar et al. |
| 2013/0297221 A1 | 11/2013 | Johnson et al. |
| 2013/0304392 A1 | 11/2013 | Deciu et al. |
| 2013/0307029 A1 | 11/2013 | Xu et al. |
| 2013/0309666 A1 | 11/2013 | Deciu et al. |
| 2013/0309678 A1 | 11/2013 | Travers et al. |
| 2013/0310260 A1 | 11/2013 | Kim et al. |
| 2013/0311106 A1 | 11/2013 | White et al. |
| 2013/0316331 A1 | 11/2013 | Isakov et al. |
| 2013/0316915 A1 | 11/2013 | Halpern et al. |
| 2013/0316916 A1 | 11/2013 | Flusberg et al. |
| 2013/0324417 A1 | 12/2013 | Kennedy et al. |
| 2013/0324419 A1 | 12/2013 | Seshagiri |
| 2013/0325360 A1 | 12/2013 | Deciu et al. |
| 2013/0325666 A1 | 12/2013 | Carrino et al. |
| 2013/0332081 A1 | 12/2013 | Reese et al. |
| 2013/0338012 A1 | 12/2013 | Sulem et al. |
| 2013/0338933 A1 | 12/2013 | Deciu et al. |
| 2013/0338934 A1 | 12/2013 | Asadi et al. |
| 2013/0345066 A1 | 12/2013 | Brinza et al. |
| 2014/0024536 A1 | 1/2014 | Richards et al. |
| 2014/0024541 A1 | 1/2014 | Richards et al. |
| 2014/0024542 A1 | 1/2014 | Richards et al. |
| 2014/0025312 A1 | 1/2014 | Chin et al. |
| 2014/0031240 A1 | 1/2014 | Behlke et al. |
| 2014/0033125 A1 | 1/2014 | Merel |
| 2014/0034880 A1 | 2/2014 | Blouin et al. |
| 2014/0038830 A1 | 2/2014 | Srinivasan et al. |
| 2014/0045705 A1 | 2/2014 | Bustamante et al. |
| 2014/0051154 A1 | 2/2014 | Hyland et al. |
| 2014/0051588 A9 | 2/2014 | Drmanac et al. |
| 2014/0053294 A1 | 2/2014 | Gresshoff |
| 2014/0066317 A1 | 3/2014 | Talasaz |
| 2014/0067830 A1 | 3/2014 | Buhler et al. |
| 2014/0087961 A1 | 3/2014 | Sulem et al. |
| 2014/0100792 A1 | 4/2014 | Deciu et al. |
| 2014/0114582 A1 | 4/2014 | Mittelman et al. |
| 2014/0121116 A1 | 5/2014 | Richards et al. |
| 2014/0122509 A1 | 5/2014 | Pantaleoni et al. |
| 2014/0129201 A1 | 5/2014 | Kennedy et al. |
| 2014/0134629 A1 | 5/2014 | Turner et al. |
| 2014/0148346 A1 | 5/2014 | Spormann et al. |
| 2014/0149049 A1 | 5/2014 | Chen et al. |
| 2014/0152291 A1 | 6/2014 | Afzali-Ardakani et al. |
| 2014/0155298 A1 | 6/2014 | Von Hoff et al. |
| 2014/0156199 A1 | 6/2014 | Von Hoff et al. |
| 2014/0162278 A1 | 6/2014 | Richards et al. |
| 2014/0163900 A1 | 6/2014 | Erlich et al. |
| 2014/0166487 A1 | 6/2014 | Lieber et al. |
| 2014/0172319 A1 | 6/2014 | Von Hoff et al. |
| 2014/0173606 A1 | 6/2014 | Pantaleoni |
| 2014/0193938 A1 | 7/2014 | Fife |
| 2014/0200166 A1 | 7/2014 | Van Rooyen et al. |
| 2014/0209982 A1 | 7/2014 | Putnam et al. |
| 2014/0236490 A1 | 8/2014 | Van Rooyen et al. |
| 2014/0248692 A1 | 9/2014 | Lagace et al. |
| 2014/0249052 A1 | 9/2014 | Mehmet et al. |
| 2014/0260547 A1 | 9/2014 | Balandin |
| 2014/0264467 A1 | 9/2014 | Cheng et al. |
| 2014/0264469 A1 | 9/2014 | Fife et al. |
| 2014/0274774 A1 | 9/2014 | Li et al. |
| 2014/0297196 A1 | 10/2014 | Olson |
| 2014/0309944 A1 | 10/2014 | van Rooyen et al. |
| 2014/0315199 A1 | 10/2014 | Rhodes et al. |
| 2014/0363808 A1 | 12/2014 | Gu et al. |
| 2014/0371109 A1 | 12/2014 | McMillen et al. |
| 2014/0371110 A1 | 12/2014 | Van Rooyen et al. |
| 2015/0065353 A1 | 3/2015 | Turner et al. |
| 2015/0069329 A1 | 3/2015 | Jeon et al. |
| 2015/0087534 A1 | 3/2015 | Gormley et al. |
| 2015/0101931 A1 | 4/2015 | Garaj et al. |
| 2015/0111759 A1 | 4/2015 | Ju et al. |
| 2015/0123080 A1 | 5/2015 | Yamaguchi |
| 2015/0137078 A1 | 5/2015 | Guo et al. |
| 2015/0159196 A1 | 6/2015 | Travers et al. |
| 2015/0159212 A1 | 6/2015 | Pantoja et al. |
| 2015/0160159 A1 | 6/2015 | Afzali-Ardakani et al. |
| 2015/0176071 A1 | 6/2015 | Fisher et al. |
| 2015/0211054 A1 | 7/2015 | Kostem et al. |
| 2015/0218630 A1 | 8/2015 | Sun et al. |
| 2015/0225785 A1 | 8/2015 | Zhao et al. |
| 2015/0232929 A1 | 8/2015 | Stephens et al. |
| 2015/0233864 A1 | 8/2015 | Shen et al. |
| 2015/0239947 A1 | 8/2015 | Brinkmann et al. |
| 2015/0243917 A1 | 8/2015 | Kim et al. |
| 2015/0259743 A1 | 9/2015 | Burgess et al. |
| 2015/0302143 A1 | 10/2015 | Ma et al. |
| 2015/0302144 A1 | 10/2015 | Chin et al. |
| 2015/0307936 A1 | 10/2015 | Goldsmith |
| 2015/0307947 A1 | 10/2015 | Basu et al. |
| 2015/0339437 A1 | 11/2015 | McMillen et al. |
| 2015/0368638 A1 | 12/2015 | Steemers et al. |
| 2016/0004298 A1 | 1/2016 | Mazed et al. |
| 2016/0122792 A1 | 5/2016 | Peterson et al. |
| 2016/0171153 A1 | 6/2016 | Van Rooyen et al. |
| 2016/0178569 A1 | 6/2016 | Hoffman et al. |
| 2016/0180019 A1 | 6/2016 | Van Rooyen et al. |
| 2016/0231251 A1 | 8/2016 | Ou et al. |
| 2016/0265047 A1 | 9/2016 | van Rooyen et al. |
| 2017/0018626 A1 | 1/2017 | Hoffman et al. |
| 2017/0053908 A1 | 2/2017 | Hoffman |
| 2017/0059514 A1 | 3/2017 | Hoffman |
| 2017/0102358 A1 | 4/2017 | Hoffman |

FOREIGN PATENT DOCUMENTS

| | | |
|---|---|---|
| CN | 103293209 A | 9/2013 |
| CN | 104237352 A | 12/2014 |
| DE | 19813317 A1 | 9/1999 |
| EP | 2163646 A1 | 3/2010 |
| EP | 2334802 A1 | 6/2011 |
| EP | 2535429 A1 | 12/2012 |
| EP | 3 235 010 A1 | 10/2017 |
| JP | 2004085392 A | 3/2004 |
| JP | 2010172290 A | 8/2010 |
| WO | WO-1999049403 A1 | 9/1999 |
| WO | WO-2000045322 A1 | 8/2000 |
| WO | WO-200113432 A1 | 2/2001 |
| WO | WO-2002090978 A1 | 11/2002 |
| WO | WO-2003046220 A1 | 6/2003 |
| WO | WO-2004029298 A2 | 4/2004 |
| WO | WO-2004090100 A2 | 10/2004 |
| WO | WO-2004104161 A2 | 12/2004 |
| WO | WO-2005026925 A2 | 3/2005 |
| WO | WO-2005029059 A1 | 3/2005 |
| WO | WO-2005048134 A2 | 5/2005 |
| WO | WO-2005090961 A1 | 9/2005 |
| WO | WO-2005113812 A2 | 12/2005 |
| WO | WO-2006015084 A2 | 2/2006 |
| WO | WO-2006019892 A2 | 2/2006 |
| WO | WO-2006096324 A2 | 9/2006 |
| WO | WO-2007064758 A2 | 6/2007 |
| WO | WO-2007076726 A1 | 7/2007 |
| WO | WO-2008022036 A2 | 2/2008 |
| WO | WO-2008098014 A2 | 8/2008 |
| WO | WO-2008127213 A2 | 10/2008 |
| WO | WO-2008143679 A2 | 11/2008 |
| WO | WO-2008156773 A1 | 12/2008 |
| WO | WO-2009035647 A1 | 3/2009 |
| WO | WO-2009120372 A2 | 10/2009 |
| WO | WO-2009143212 A1 | 11/2009 |

(56) References Cited

FOREIGN PATENT DOCUMENTS

| | | |
|---|---|---|
| WO | WO-2010003316 A1 | 1/2010 |
| WO | WO-2010027497 A2 | 3/2010 |
| WO | WO-2010036287 A1 | 4/2010 |
| WO | WO-2010036311 A2 | 4/2010 |
| WO | WO-2010051773 A1 | 5/2010 |
| WO | WO-2010072382 A1 | 7/2010 |
| WO | WO-2010093465 A1 | 8/2010 |
| WO | WO-2010127045 A2 | 11/2010 |
| WO | WO-2010129019 A2 | 11/2010 |
| WO | WO-2010129301 A2 | 11/2010 |
| WO | WO-2010132814 A1 | 11/2010 |
| WO | WO-2011025819 A1 | 3/2011 |
| WO | WO-2011050341 A1 | 4/2011 |
| WO | WO-2011056688 A2 | 5/2011 |
| WO | WO-2011063210 A2 | 5/2011 |
| WO | WO-2011071923 A2 | 6/2011 |
| WO | WO-2011082178 A1 | 7/2011 |
| WO | WO-2011090556 A1 | 7/2011 |
| WO | WO-2011090557 A1 | 7/2011 |
| WO | WO-2011090558 A1 | 7/2011 |
| WO | WO-2011090559 A1 | 7/2011 |
| WO | WO-2011091046 A1 | 7/2011 |
| WO | WO-2011091063 A1 | 7/2011 |
| WO | WO-2011095501 A1 | 8/2011 |
| WO | WO-2011137368 A2 | 11/2011 |
| WO | WO-2011139797 A2 | 11/2011 |
| WO | WO-2011143525 A2 | 11/2011 |
| WO | WO-2011145954 A1 | 11/2011 |
| WO | WO-2011145955 A1 | 11/2011 |
| WO | WO-2012006291 A2 | 1/2012 |
| WO | WO-2012029080 A1 | 3/2012 |
| WO | WO-2012051346 A1 | 4/2012 |
| WO | WO-2012058459 A2 | 5/2012 |
| WO | WO-2012065228 A1 | 5/2012 |
| WO | WO-2012066582 A1 | 5/2012 |
| WO | WO-2012085948 A1 | 6/2012 |
| WO | WO-2012092336 A2 | 7/2012 |
| WO | WO-2012092426 A1 | 7/2012 |
| WO | WO-2012095872 A1 | 7/2012 |
| WO | WO-2012101643 A1 | 8/2012 |
| WO | WO-2012123972 A1 | 9/2012 |
| WO | WO-2012142334 A2 | 10/2012 |
| WO | WO-2012142531 A2 | 10/2012 |
| WO | WO-2012168803 A2 | 12/2012 |
| WO | WO-2012168815 A2 | 12/2012 |
| WO | WO-2012170715 A1 | 12/2012 |
| WO | WO-2012172575 A1 | 12/2012 |
| WO | WO-2012177774 A2 | 12/2012 |
| WO | WO-2012177792 A2 | 12/2012 |
| WO | WO-2013043909 A1 | 3/2013 |
| WO | WO-2013052907 A2 | 4/2013 |
| WO | WO-2013052913 A2 | 4/2013 |
| WO | WO-2013055817 A1 | 4/2013 |
| WO | WO-2013058907 A1 | 4/2013 |
| WO | WO-2013062856 A1 | 5/2013 |
| WO | WO-2013065072 A1 | 5/2013 |
| WO | WO-2013067167 A2 | 5/2013 |
| WO | WO-2013080227 A1 | 6/2013 |
| WO | WO-2013088457 A1 | 6/2013 |
| WO | WO-2013109935 A1 | 7/2013 |
| WO | WO-2013109981 A1 | 7/2013 |
| WO | WO-2013119770 A1 | 8/2013 |
| WO | WO-2013123330 A1 | 8/2013 |
| WO | WO-2013/128371 A1 | 9/2013 |
| WO | WO-2013148400 A1 | 10/2013 |
| WO | WO-2013166517 A1 | 11/2013 |
| WO | WO-2013177086 A1 | 11/2013 |
| WO | WO-2013177581 A2 | 11/2013 |
| WO | WO-2013184643 A1 | 12/2013 |
| WO | WO-2013192562 A1 | 12/2013 |
| WO | WO-2014008447 A1 | 1/2014 |
| WO | WO-2014012051 A1 | 1/2014 |
| WO | WO-2014014497 A1 | 1/2014 |
| WO | WO-2014014498 A1 | 1/2014 |
| WO | WO-2014014950 A1 | 1/2014 |
| WO | WO-2014015084 A2 | 1/2014 |
| WO | WO-2014015319 A1 | 1/2014 |
| WO | WO-2014018093 A1 | 1/2014 |
| WO | WO-2014024041 A1 | 2/2014 |
| WO | WO-2014026168 A1 | 2/2014 |
| WO | WO-2014036488 A1 | 3/2014 |
| WO | WO-2014039556 A1 | 3/2014 |
| WO | WO-2014041380 A1 | 3/2014 |
| WO | WO-2014/060305 A1 | 4/2014 |
| WO | WO-2014052909 A2 | 4/2014 |
| WO | WO-2014055774 A1 | 4/2014 |
| WO | WO-2014/074246 A1 | 5/2014 |
| WO | WO-2014071070 A1 | 5/2014 |
| WO | WO-2014071279 A2 | 5/2014 |
| WO | WO-2014078739 A1 | 5/2014 |
| WO | WO-2014089241 A2 | 6/2014 |
| WO | WO-2014/112199 A1 | 7/2014 |
| WO | WO-2014142850 A1 | 9/2014 |
| WO | WO-2014153188 A2 | 9/2014 |
| WO | WO-2014/176524 A2 | 10/2014 |
| WO | WO-2014166535 A1 | 10/2014 |
| WO | WO-2014171969 A1 | 10/2014 |
| WO | WO-2014172046 A2 | 10/2014 |
| WO | WO-2015033229 A2 | 3/2015 |
| WO | WO-2015123444 A2 | 8/2015 |
| WO | WO-2016/205253 A1 | 12/2016 |

OTHER PUBLICATIONS

Cheng, Zengguang et al. "Sensitivity Limits and Scaling of Bioelectronic Graphene Transducers.", *Nano Letters*, (2013), pp. 2902-2907, 13(6), ACS Publications.

Cheng, Zengguang et al. "Supporting Information for: Sensitivity Limits and Scaling of Bioelectronic Graphene Transducers.", (2013), 26 pages, pubs.acs.org. [retreived from the Internet on Nov. 7, 2017].

Cheng, Zengguang et al. "Suspended Graphene Sensors with Improved Signal and Reduced Noise." *Nano Letters*, (2010), pp. 1864-1868, 10(5), pubs.acs.org.

Cooper et al., Experimental Review of Graphene, ISRN Condensed Matter Physics 2012: Art. ID 501686, 56 pages (2012).

Definition of "Well", http://www.merriam-webster.com (2016). 1 page.

DeVolder et al., Carbon Nanotubes: Present and Future Commercial Applications, Science, 339: 535-539 (Feb. 1, 2013).

Fakih et al., Large area graphene ion sensitive field effect transistors with tantalum pentoxide sensing layers for pH measurement at the Nernstian limit, Applied Physics Letters 105: 083101 (Aug. 25, 2014). 6 pages.

Gao et al., the new age of carbon nanotubes: An updated review of functionalized carbon nanotubes in electrochemical sensors, Nanoscale 4:1948-1963. (2012).

Green et al., Interactions of DNA with graphene and sensing applications of graphene field-effect transistor devices: A review, Analytica Chimica Acta 853:127-142 (2015).

Kim, Kihyun et al. "Electrical and pH Sensing Characteristics of Si Nanowire-Based Suspended Fet Biosensors." *Proceedings of the 14th IEEE, International Conference on Nanotechnology*, IEEE, (Aug. 18-21, 2014), pp. 768-771.

Kim, Kihyun et al. "Suspended honeycomb nanowire ISFETs for improved stiction-free performance." *Nanotechnology*,(2014), pp. 345-501 (7 pages), 25(34), IOP Publishing, Bristol, GB.

Kim. Lecture Notes, 2.76/2.760 Multiscale Systems Design & Manufacturing, downloaded from: http://ocw.mitedu/ murses/ mechanical-engineering/2-76-multi-scale-system-design-fall-2004/ lecture-notes/lecture_15.pdf (Fall 2004). 49 pages.

Liu, Song and Xuefeng Guo, "Carbon nanomaterials field-effect-transistor-based biosensors." NPG Asia Materials (2012), pp. 1-10, 4, e23; doi: 10.1038/sm.2012.42:published online Aug. 17, 2012.

Park et al., High-density integration of carbon nanotubes via chemical self-assembly, Nature Nanotechnology 7:787- 791 (2012).

Schwierz, Frank; Graphene Transistors, Nature Nanotechnology 5:487-496 (May 30, 2010).

(56) References Cited

OTHER PUBLICATIONS

Tulevski et al., Toward High-Performance Digital Logic Technology with Carbon Nanotubes, ACS Nano 8(9):8730-8745. (Aug. 21, 2014).
Wang, Bei et al. "Oxide-on-graphene field effect bio-ready sensors." *Nano Research*, (2014), 7(9):pp. 1263-1270. Tsinghua University Press, CN.
Xu et al. "Electrophoretic and field-effect graphene for all-electrical DNA array technology." Nature Communications, (2014) 5:4866. 9 pages.
Zhan et al., Graphene Field-Effect Transistor and Its Application for Electronic Sensing, Small 10(20):4042-4065 (Aug. 29, 2014).

Section X-X

Section X-X

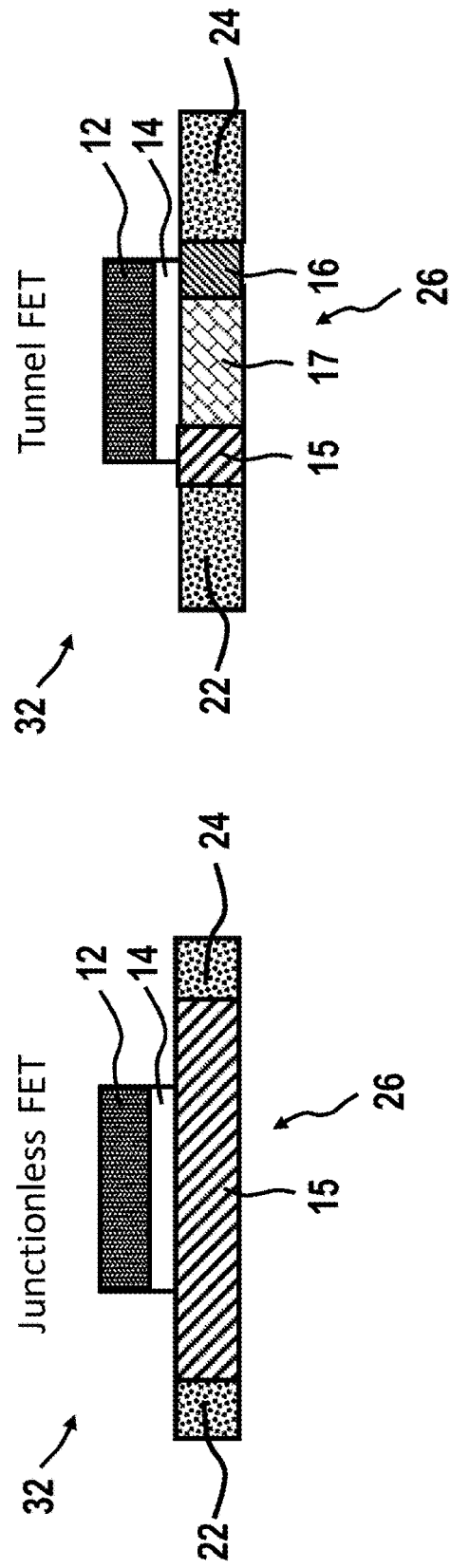

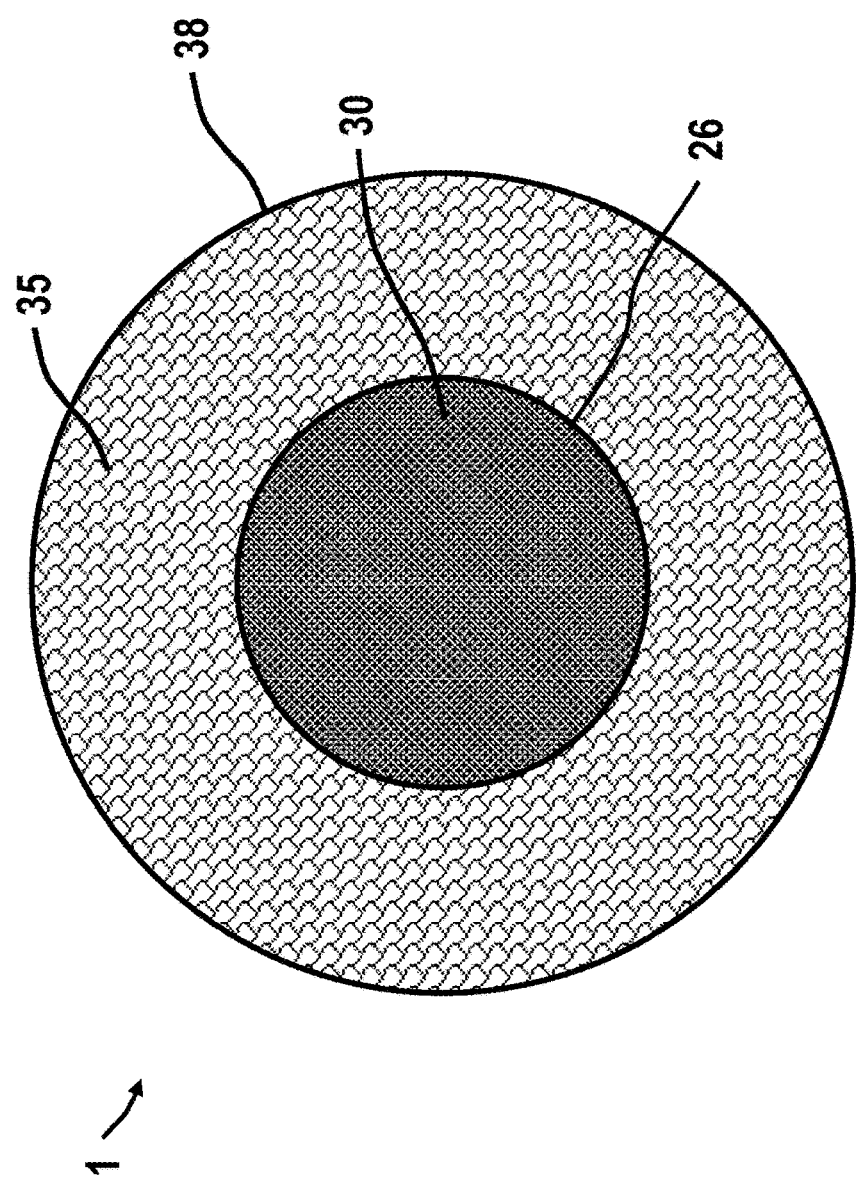

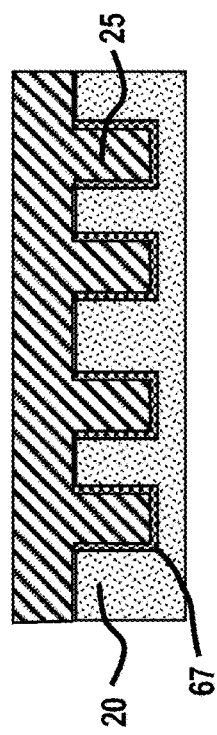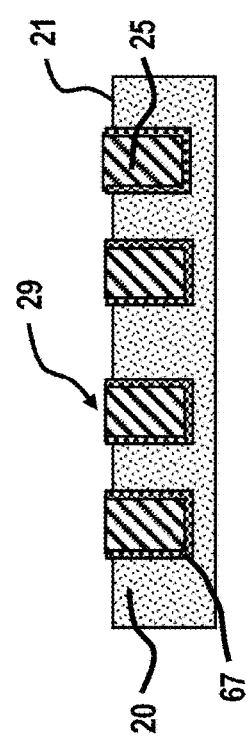
FIG. 5A
FIG. 5B

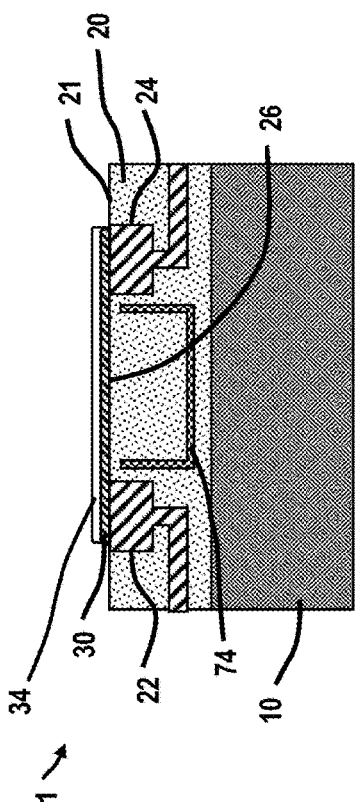
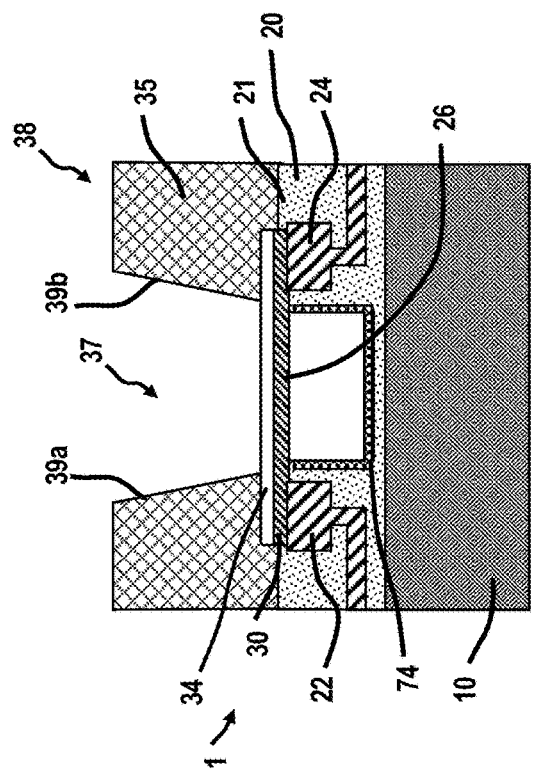
FIG. 9A
FIG. 9B

Gate all around

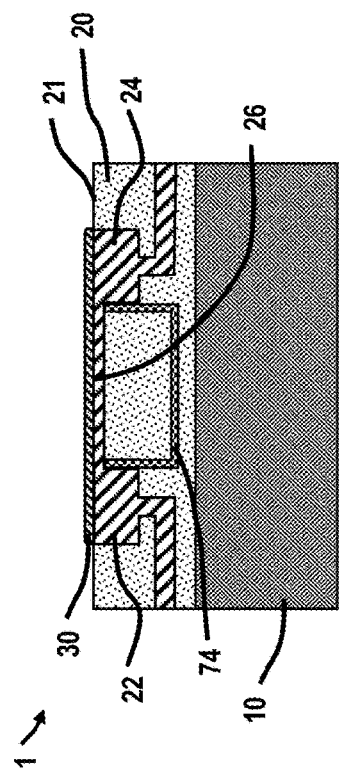
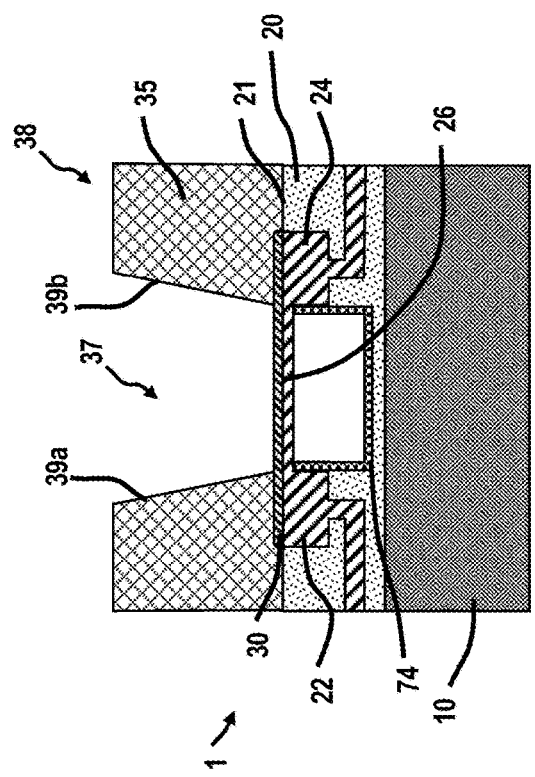
FIG. 10A
FIG. 10B

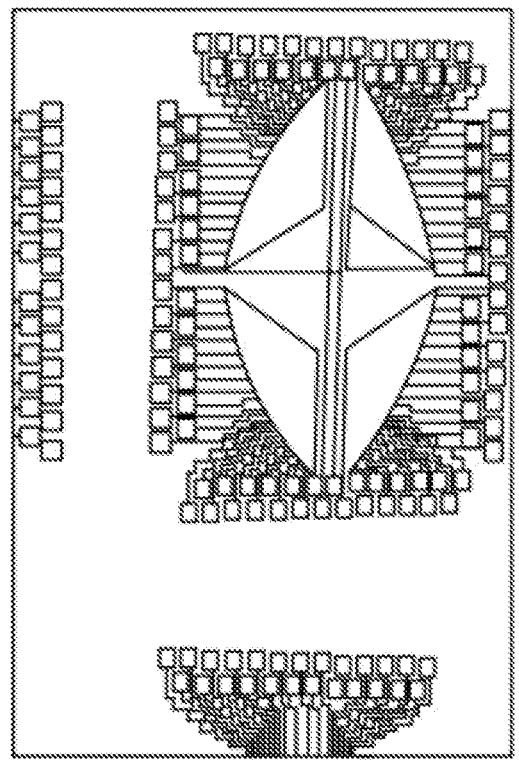
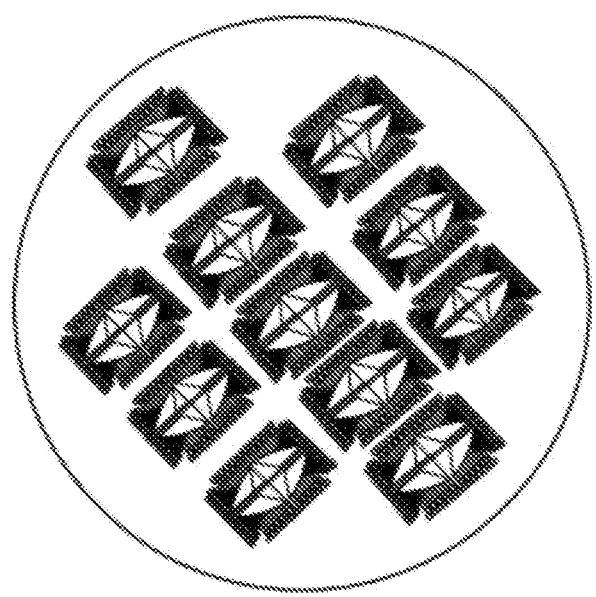
FIG. 14A

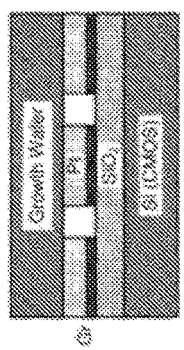
FIG. 26A
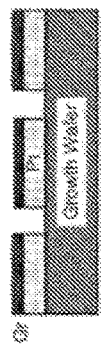
FIG. 26B
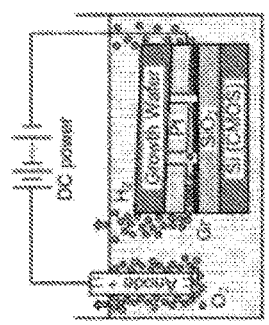
FIG. 26C
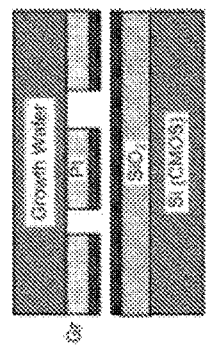
FIG. 26D
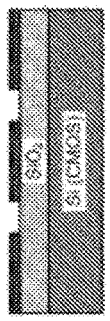
FIG. 26E
FIG. 26F Process flow with contact to top of channel material

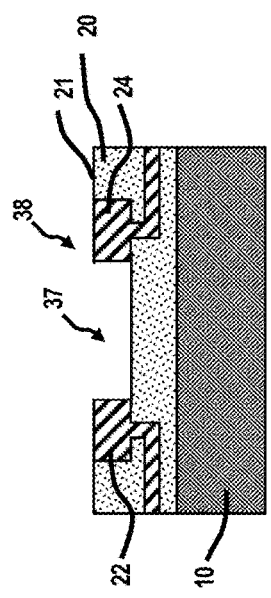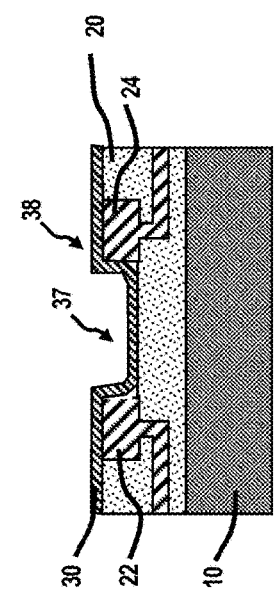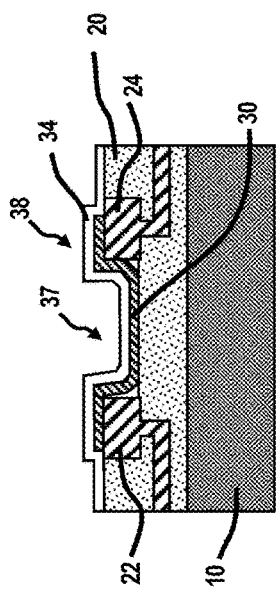

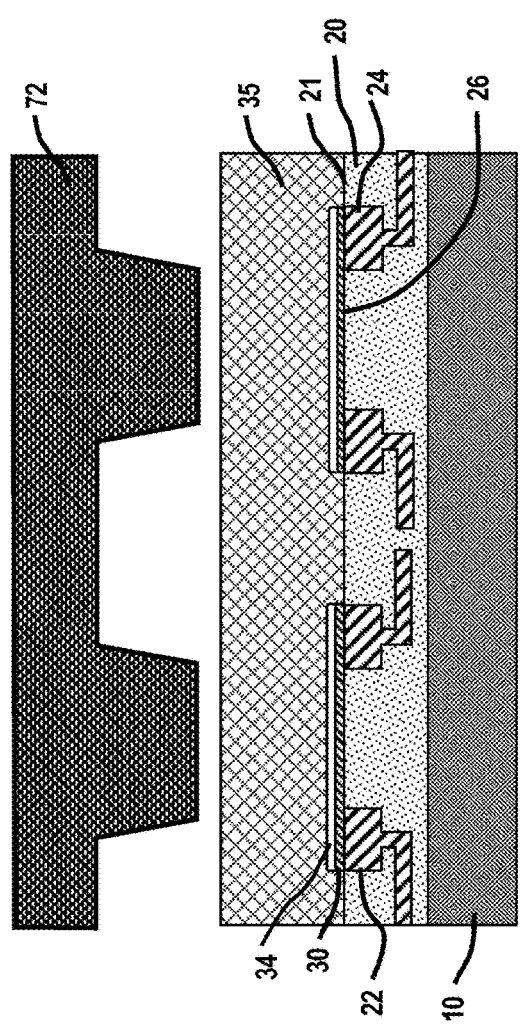
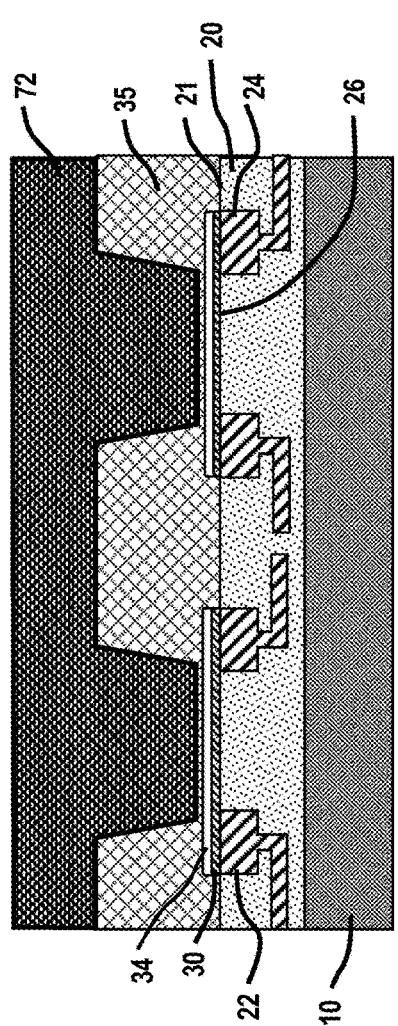
FIG. 36A
FIG. 36B

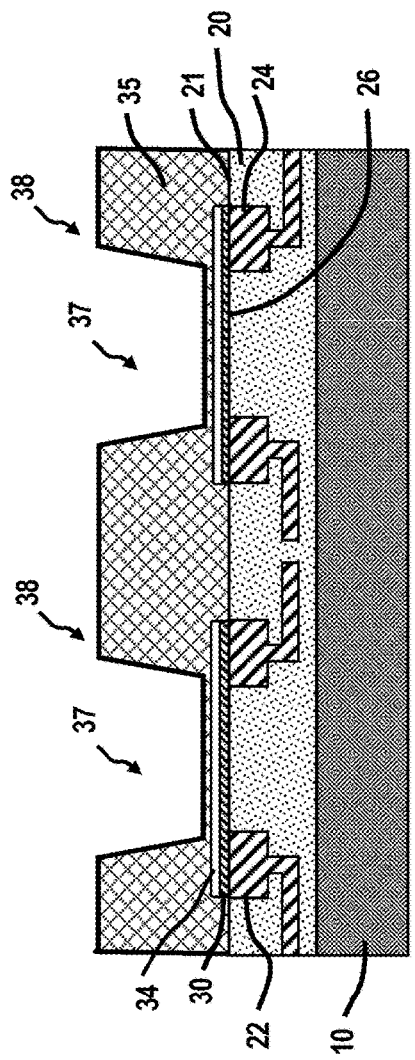
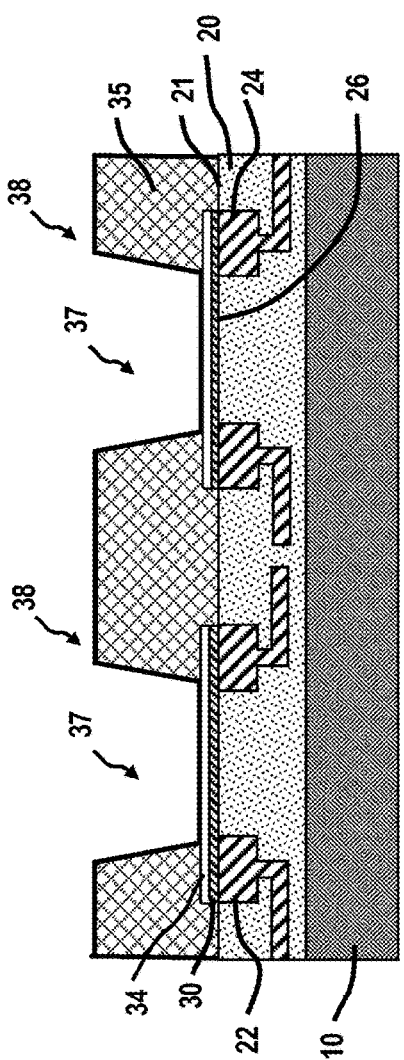
FIG. 36C
FIG. 36D

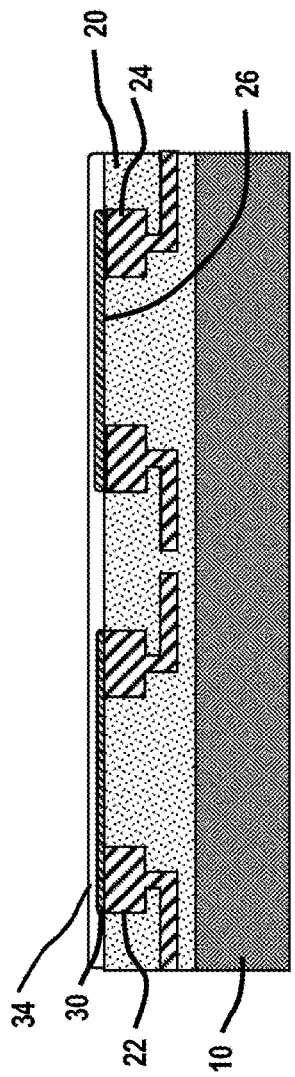
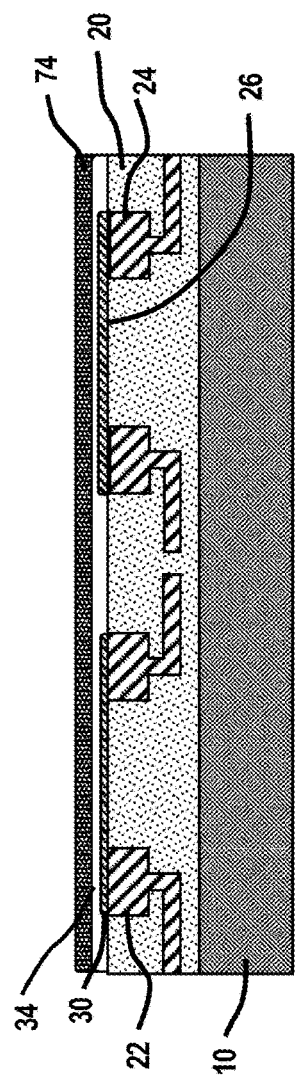
FIG. 37A
FIG. 37B

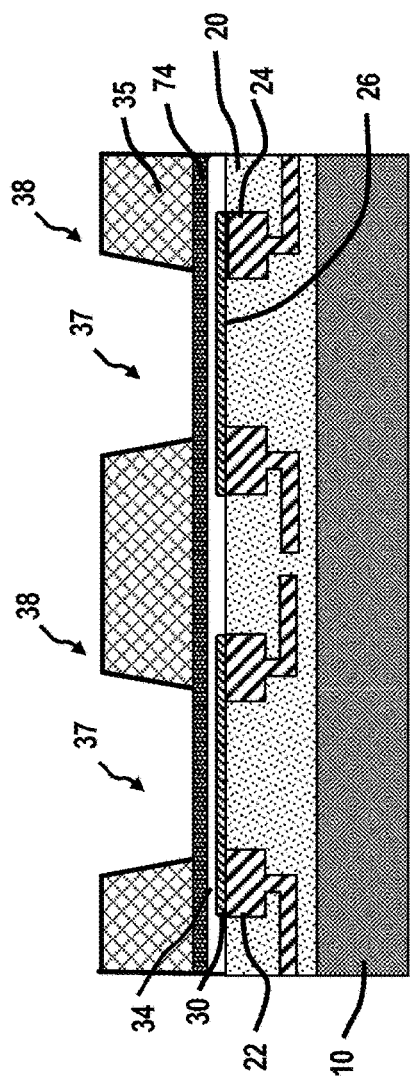
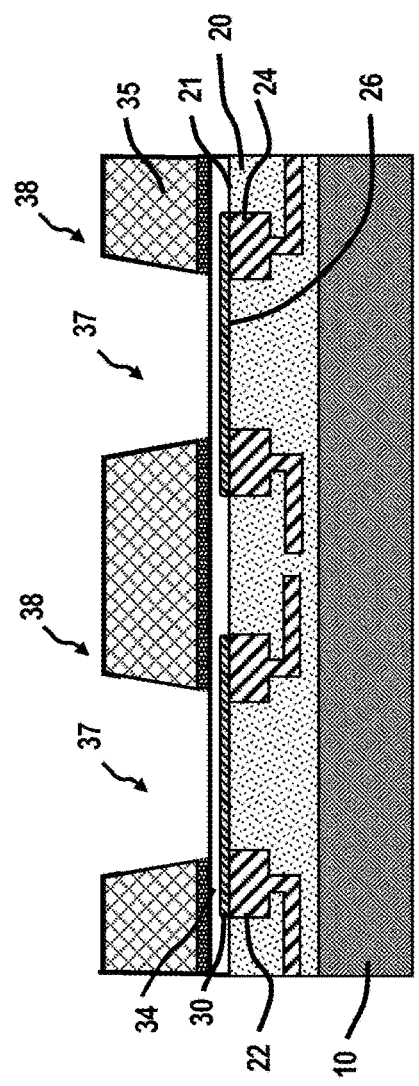
FIG. 37C
FIG. 37D

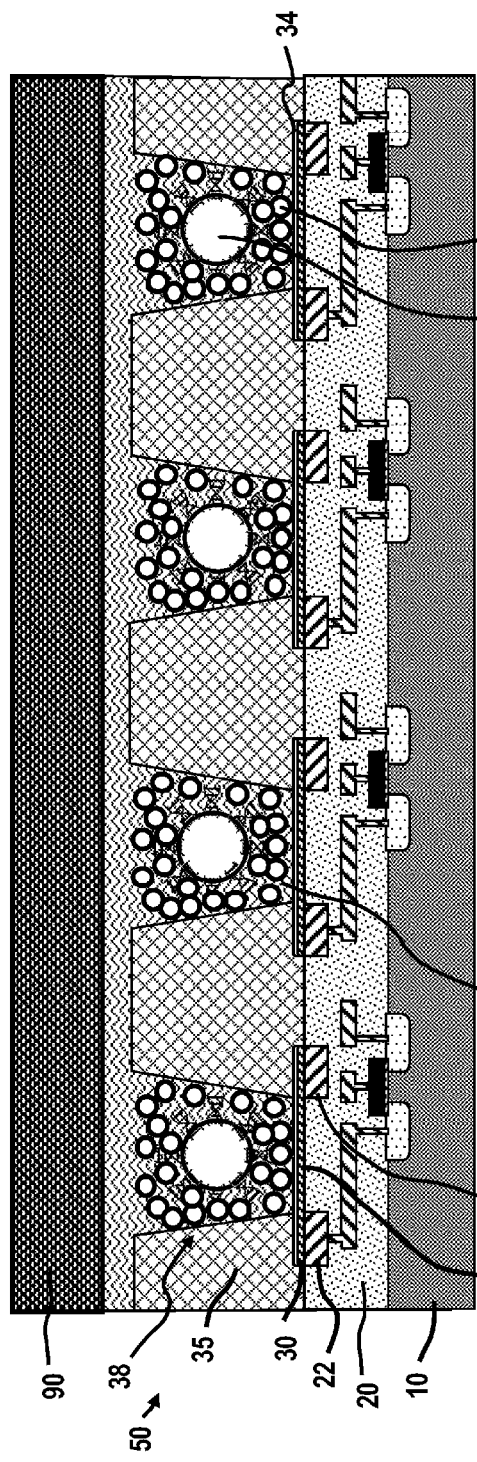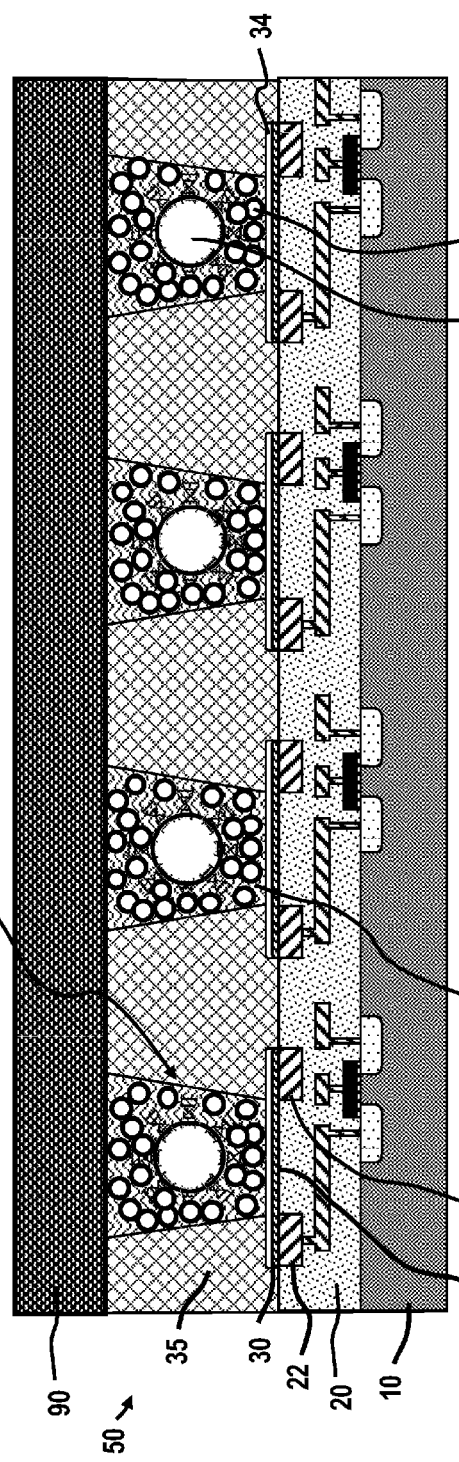

CHEMICALLY-SENSITIVE FIELD EFFECT TRANSISTORS, SYSTEMS, AND METHODS FOR MANUFACTURING AND USING THE SAME

CROSS REFERENCE TO RELATED APPLICATIONS

This application claims the benefit of and priority to U.S. Continuation-in-Part application Ser. No. 15/256,493, filed Sep. 2, 2016, which claims the benefit of and priority to commonly-owned, U.S. provisional patent application Ser. No. 62/214,910, filed Sep. 4, 2015; U.S. provisional patent application Ser. No. 62/213,112, filed Sep. 2, 2015; U.S. provisional patent application Ser. No. 62/213,117, filed Sep. 2, 2015; U.S. provisional patent application Ser. No. 62/213,151, filed Sep. 2, 2015; U.S. provisional patent application Ser. No. 62/214,850, filed Sep. 4, 2015; U.S. provisional patent application Ser. No. 62/214,892, filed Sep. 4, 2015; U.S. provisional patent application Ser. No. 62/214,901, filed Sep. 4, 2015; U.S. provisional patent application Ser. No. 62/214,912, filed Sep. 4, 2015; U.S. provisional patent application Ser. No. 62/215,018, filed Sep. 6, 2015. This application is a continuation in part U.S. application Ser. No. 15/239,800, filed on Aug. 17, 2016, which in turn claims benefit of priority to U.S. Provisional Application Ser. No. 62/206,228, filed on Aug. 17, 2015; U.S. Provisional Application Ser. No. 62/206,224, filed on Aug. 17, 2015; U.S. Provisional Application Ser. No. 62/205,803, filed on Aug. 17, 2015; U.S. Provisional Application Ser. No. 62/205,808, filed on Aug. 17, 2015; U.S. Provisional Application Ser. No. 62/206,166, filed on Aug. 17, 2015; U.S. Provisional Application Ser. No. 62/206,372, filed on Aug. 18, 2015; U.S. Provisional Application Ser. No. 62/206,814, filed on Aug. 18, 2015. This application is a continuation in part of U.S. application Ser. No. 15/225,764, filed on Aug. 1, 2016, which in turn claims benefit of U.S. Provisional Application Ser. No. 62/199,956, filed on Jul. 31, 2015 and U.S. Provisional Application Ser. No. 62/199,987, filed on Aug. 1, 2015. This application is a continuation in part of U.S. application Ser. No. 15/065,744, filed on Mar. 9, 2016, which in turn claims benefit of U.S. Provisional Application Ser. No. 62/130,598, filed on Mar. 9, 2015; U.S. Provisional Application Ser. No. 62/130,594, filed on Mar. 9, 2015; U.S. Provisional Application Ser. No. 62/130,601, filed on Mar. 9, 2015; U.S. Provisional Application Ser. No. 62/130,621, filed on Mar. 10, 2015; U.S. application Ser. No. 15/065,744 is a continuation in part of U.S. application Ser. No. 14/963,253, filed on Dec. 9, 2015, which in turn claims benefit of U.S. Provisional Application Ser. No. 62/094,016, filed on Dec. 18, 2014; U.S. Provisional Application Ser. No. 62/130,594, filed on Mar. 9, 2015; U.S. Provisional Application Ser. No. 62/199,987, filed on Aug. 1, 2015; and U.S. Provisional Application Ser. No. 62/206,228, filed on Aug. 17, 2015. This application is a continuation in part of U.S. application Ser. No. 15/182,533, filed on Jun. 14, 2016, which in turn claims benefit of U.S. Provisional Application Ser. No. 62/175,351, filed on Jun. 14, 2015. This application is a continuation in part of U.S. application Ser. No. 14/963,253, filed on Dec. 9, 2015, which in turn claims benefit of U.S. Provisional Application Ser. No. 62/094,016, filed on Dec. 18, 2014; U.S. Provisional Application Ser. No. 62/130,594, filed on Mar. 9, 2015; U.S. Provisional Application Ser. No. 62/199,987, filed on Aug. 1, 2015; and U.S. Provisional Application Ser. No. 62/206,228, filed on Aug. 17, 2015, the disclosures of which are incorporated herein in their entirety.

STATEMENT REGARDING FEDERALLY SPONSORED RESEARCH OR DEVELOPMENT

Not Applicable

BACKGROUND OF THE DISCLOSURE

Field of the Disclosure

The present disclosure generally relates to field effect transistors and methods of making and using the same for sequencing, diagnostics, the analysis of biological or chemical materials or reactions and bioinformatics processing. More specifically, the present disclosure relates to one-dimensional and two-dimensional nanomaterial-based field effect transistors useful for chemical and biological analysis.

Description of the Related Art

The detection and sequencing of nucleic acids, such as deoxyribonucleic acid (DNA) or ribonucleic acid (RNA), is a fundamental part of biological discovery. Detection and/or sequencing are useful for a variety of purposes, and are often used in scientific research, drug discovery, medical diagnostics, and in the prevention, monitoring, and treatment of disease. For instance, the genomics and bioinformatics fields, which rely on nucleic acid detection and sequencing techniques, are concerned with the application of information technology and computer science to the field of molecular biology. In particular, bioinformatics techniques can be applied to process and analyze various genomic data, such as from an individual so as to determine qualitative and quantitative information about that data that can then be used by various practitioners in the development of diagnostic, prophylactic, and/or therapeutic methods and products for detecting, preventing, treating, or at least ameliorating disease states, thus improving the safety, quality, and effectiveness of health care. The need for such diagnostic, therapeutic, and prophylactic advancements has led to a high demand for low-cost nucleic acid detection and sequencing methods, devices, and reagents, which in turn have driven, for example, the development of high-throughput sequencing, termed as Next Generation Sequencing (NGS).

Generally, the approach to DNA and/or RNA analysis, such as for genetic diagnostics and/or sequencing, involves nucleic acid hybridization and detection. For example, various conventional hybridization and detection approaches include the following steps. For genetic analysis, an RNA or DNA sample obtained from a subject to be analyzed is isolated and immobilized on a substrate. A detectable probe of a known genetic sequence, e.g., having a nucleotide sequence that corresponds to a disease marker (e.g., a marker evidencing a bacterial, fungal, or viral infection, a single nucleotide polymorphism (SNP) associated with a particular disease such as cancer, an autoimmune disease, etc.) is then added to the substrate, typically in a reaction mixture containing the requisite reagents to allow the probe to interact with its target, if present in the sample. If the disease marker is present, a binding event, e.g., hybridization, will occur and because the probe is detectable (e.g., via the inclusion in the probe of a detectable label such as a fluorescent dye if the detection scheme is optically-based), the hybridization event can either be or not be detected, thereby indicating the presence or absence of the disease marker in the subject's sample.

For DNA/RNA sequencing and/or detection, first, an unknown nucleic acid sequence to be identified, e.g., a single-stranded sequence of DNA/RNA from a subject, is isolated, amplified, and immobilized on a substrate. Next, in the presence of a primer complementary to a portion of the isolated nucleic acid sequence to be sequenced and/or identified, (preferably labeled) nucleotides, and a suitable DNA polymerase, a nucleic acid sequencing and/or detection reaction may take place. In such an instance, where the primer recognizes a corresponding sequence of the isolated and/or bound nucleic acid sequence, the polymerase can begin to add one or more labeled nucleotides to extend the primer in the presence of the unknown nucleic acid sequence, using the unknown nucleic acid sequence as the template. When the primer is extended, the most recently added labeled nucleotide, which hybridizes via hydrogen-bonding to its complementary base in the unknown sequence immobilized on the surface of the substrate, the most recent nucleotide's addition can then be detected, e.g., optically or electrically. These steps are then repeated until the entire DNA/RNA molecule has been completely sequenced. Typically, these steps are performed on a Next Gen Sequencer wherein thousands to millions of DNA fragments can be sequenced concurrently in the NGS process.

As will be appreciated, a central challenge in DNA sequencing based on the sequencing of numerous short DNA fragments is assembling full-length genomic sequences, e.g., chromosomal sequences, from a sample of genetic material, as the sequencing methods used in NGS processes do not produce full-length gene or chromosomal sequences from the sample DNA that can then be used for a desired genetic analysis, assessment of genetic variation or identity between the subject's sample and a reference gene, genome, etc. Rather, sequence fragments, typically from 100-1,000 nucleotides in length, are produced without any indication as to where in the genome they reside. Therefore, in order to generate full-length gene or chromosomal genomic constructs, or determine variants with respect to a reference genomic sequence, such DNA sequence fragments need to be mapped, aligned, merged, and/or compared to a reference genomic sequence. This is true also for SNP genotyping, even though in that case a full-length gene or chromosomal sequence need not be constructed, but at least a length of base pairs that encompasses the loci of the SNP must be constructed, e.g. lengths of 250 base pairs, 150 base pairs, or even 50 base pairs may be sufficient for SNP identification. Through such processes the variants of the sample genomic sequences from the reference genomic sequences may be determined by suitable bioinformatics approaches, such as by implementing a suitable variant calling application.

Even so, as the human genome comprises approximately 3.1 billion base pairs, and as each sequence fragment in an NGS process is typically only from 100 to 500 to 1,000 nucleotides in length, the time and effort that goes into building full-length genomic sequences and determining the genetic variants therein is quite extensive, often requiring the use of several different computer resources applying several different algorithms over prolonged periods of time. This is because in a given NGS analysis, thousands, millions, or even billions of DNA sequences are generated, which sequences must then be aligned and merged in order to construct a genomic sequence that approximates a chromosome or genome in size. A step in this process often includes comparing the DNA fragment sequences to a reference sequence to determine where in the genome the fragments reside.

In order to perform an NGS analysis, genetic material from a subject must be pre-processed. This preprocessing may be done manually or via an automated preparation system. Typically, preprocessing involves obtaining a biological sample from a subject, such as through venipuncture (blood, plasma, serum), buccal swab, urine, saliva, etc., and treating the sample to isolate the DNA therefrom. Once isolated, the DNA is then fragmented and denatured. The DNA (or portions thereof) may then be amplified, e.g., via polymerase chain reaction (PCR), so as to build a library of replicated strands that are now ready to be sequenced, such as by an automated sequencer. The sequencing machine is configured to sequence the amplified DNA strands, e.g., by synthesis of new, complementary strands that include labeled nucleotides, from which the nucleotide sequences that make up the DNA in the sample can be determined.

Further, in various instances, such as in building the library of amplified strands, it may be useful to provide for over-coverage or over-representation when preprocessing a given portion of the DNA. To provide this over-representation, increased sample preparation may be required, thus making the process more expensive, although such steps often yield an enhanced probability of the end result being more accurate.

Once a library of amplified DNA strands has been generated, the strands may be injected into an automated sequencer that can then determine the nucleotide sequences of the strands, such as by synthesis. For instance, amplified single-stranded DNA can be attached to a nano- or micro-bead and inserted into a test vessel, e.g., an array. All the necessary components for synthesis of its complementary strand, including labeled nucleotides (for adenine (A), cytosine (C), guanine (G), and thymine (T)), are also added to the vessel but in a sequential fashion. In some instances, one or more the nucleotides, e.g., "A", "C", "G", and "T's" that are added may be configured so as to be reversible terminators, e.g., such that once incorporated into a growing strand being synthesized cause the synthesis reaction for that particular strand to be terminated at that point of incorporation, thereby producing several strands of terminated sequences that collectively represent the entire template nucleic acid sequence. Hence, in performing a nucleic acid synthesis or detection reaction all of the necessary nucleotide reactants are added, either one at a time or all together, to see which of the nucleotides is used to extend a primer molecule.

Particularly for an optically-based NGS system, after each addition, unincorporated nucleotides are washed away and a light, e.g., a laser, is then shone on the array. If the label fluoresces, that fluorescence can be detected, thereby indicating which nucleotide has been added and, due to the nature of the genetic code, which complementary nucleotide was present in the template DNA fragment in the subject location. In processes where labeled nucleotides are added one at a time, if extension occurs, then it's indicative fluorescence will be observed. If extension does not occur, the test vessel may be washed and the procedure repeated until the appropriate one of the four nucleotides binds to its complement and is incorporated by the polymerase into the growing DNA strand at the subject location such that its indicative fluorescence of its label can be detected.

Where all four reversible terminator nucleotides are added at the same time, each may be labeled with a different fluorescent indicator; when the complementary labeled nucleotide binds to its complement in the template DNA strand such that it is then added by the polymerase during the elongation step, the identity of the added, labeled nucleotide at the subject position can then be determined, such as by the color of its label's fluorescence. As will be appreciated, the use of all four labeled nucleotides in a given reaction greatly accelerates the synthesis process.

After each elongation reaction, the complex is then washed and the synthesis steps are repeated for the next position. This process of elongation and detection is then repeated for all nucleotides for as many positions as are present in the input DNA fragments or for so long as the sequencing machine directs (e.g., 100, 500, 1,000, or more cycles), thereby generating "sequence reads" of the oversampled nucleic acid segments. The resulting sequence data is collected.

Usually a typical length of a sequence replicated in this manner is from about 100 to about 500 or about 1000 base pairs, such as between 150 to about 400 base pairs, including from about 200 to about 350 base pairs, such as about 250 base pairs to about 300 base pairs dependent on the sequencing protocol being employed. Further, the length of these segments may be predetermined, e.g., engineered, to accord with any particular sequencing machinery and/or protocol by which it is run. In any event, the end result is a readout, or "read", that is comprised of an extended DNA fragment synthesized from an input DNA fragment.

Extended DNA fragments typically range from about 100 to about 1,000 nucleotides in length, and each nucleotide is labeled in such a manner that every nucleotide in the sequence can be identified because of its label. Hence, since the human genome is comprised of about 3.1 billion base pairs, and various known sequencing protocols usually result in labeled replicated sequences, e.g., reads, from about 100 or 101 bases to about 250 or about 300 or about 400 bases, the total number of segments that need to be sequenced, and consequently the total number of reads generated for single read coverage can be anywhere from about 10,000,000 to about 40,000,000, such as about 15,000,000 to about 30,000,000, dependent on how long the label replicated sequences are.

Therefore, the sequencer may typically generate about 30,000,000 reads, such as where the read length is 100 nucleotides in length, so as to cover the genome once. However, to ensure the accuracy of a particular base call (e.g., A, C, G, or T) at a particular nucleotide position, it is desirable that copies of each fragment in a sample be sequenced 5, 10, 20, 30, or more times, in some cases up to 500 or more times. Such over-sampling thus results in even more reads, thereby requiring more analysis. Fragment amplification in the pre-processing phase helps to facilitate such redundancy.

However, in part, due to the need for the use of optically detectable, e.g., fluorescent, labels in the sequencing reactions being performed, the required instrumentation for performing such high throughput sequencing is bulky, costly, relatively slow and not portable. For this reason, a number of new approaches for direct, label-free DNA sequencing have been proposed. For instance, among the new approaches are detection methods that are based on the use of various electronic analytic devices. Such direct electronic detection methods have several advantages over the conventional NGS platform. For example, the detector may be incorporated in or on the substrate of a semiconductor Integrated Circuit (IC) chip itself, such as employing a biosystem-on-a-chip device, such as a Complementary Metal Oxide Semiconductor ("CMOS") IC device.

More particularly, in using a semiconductor IC device in genetic detection, the output signal representative of a nucleotide's addition in a DNA sequencing reaction can be directly acquired and processed on an IC chip. In such an instance, automatic recognition is achievable in real time and at a lower cost than is currently achievable using conventional NGS processes and equipment. Moreover, due to the maturity and high integration available with semiconductor IC devices, such as CMOS devices, they may be employed for such electronic detection, making the process simple, fast, inexpensive, and portable.

Particularly, in order for NGS methods to become widely used for diagnostic and therapeutic applications in the healthcare industry, sequencing instrumentation will need to be mass produced with a high degree of quality and economy. One way to achieve this is to recast DNA sequencing in a format that fully leverages the manufacturing base created for IC chips, such as CMOS chip fabrication, which is the current pinnacle of high technology large scale, high quality, low-cost manufacturing. To achieve this, ideally, the entire sensory apparatus of the sequencing device should be embodied in a semiconductor IC chip, manufactured in the same fabrication ("Fab") facilities used for logic and memory chips. Recently, such a sequencing IC chip, and the associated sequencing platform, has been developed and commercialized by Ion Torrent, a division of Thermo-Fisher, Inc. The promise of this idea has not been realized commercially, however, due to the fundamental limits of applying a Metal Oxide Semiconductor Field Effect Transistor, or MOSFET, comprised of a typical semiconductor, such as silicon, as a biosensor. In particular, when a MOSFET is coupled to an ion-sensitive sensing plate used in solution as a biosensor, it is referred to as an ISFET (Ion Sensitive Field Effect Transistor). Particular limitations of ISFET devices include a lack of sensor sensitivity and poor signal-to-noise characteristics as the semiconductor node scales down to lower geometries of the transistor (channel and gate length).

FIG. 1A illustrates an ISFET with a traditional semiconductor FET as the sensing transistor (FET). The ISFET (200) has a semiconductor base (10), e.g. a silicon wafer, within and upon which are formed semiconductor FETs. The semiconductor FETs are comprised of a source (202), drain (204), gate (208) and gate dielectric (210). The source (202) and drain (204) of a traditional semiconductor FET are formed by regions of implanted and diffused species (e.g. boron, arsenic or phosphorous ions) that alter the number of carriers (holes or electrons) within those regions, so for example n-type source and drain regions may be created by implanting and diffusion of arsenic ions in a p-type semiconductor substrate. Contacts, e.g. silicide, are formed to the source and drain diffusions, such as a source contact (212) and a drain contact (214), and metal interconnects (25) couple with the contacts and are used to connect to and between the plurality of transistors. The metal interconnects (25) are embedded in a dielectric layer (20). When an appropriate gate voltage is applied to the gate (208), such voltage being referenced to another component of the transistor, such as the source (202), the FET "turns on" and carriers will flow between the source (202) and the drain (204). The voltage required to turn on the FET is call the threshold voltage. When the traditional semiconductor FET is turned on the flow of carriers defines a channel region (206). Note that this channel region (206) is not a physical entity, but is a location of charge carriers within the semiconductor. There is no channel when the traditional semiconductor FET is turned off. An electrical characteristic of a FET, such as current flowing between the source (202) and the drain (204), may be modified by changes in the gate voltage—and this forms the basis for using a FET as a sensor, i.e. if the target, analyte or reaction to be detected creates a change in electric field or charge density which in turn changes the gate voltage—then this may be detected by a change in monitored electrical characteristic of the FET such as drain current. In the case of an ISFET (200) fabricated from traditional semiconductor FETs there must be a way to communicate the sensed electric field or charge density of the target reaction or analyte to the FET transistor. As depicted in FIG. 1, an ISFET (200) may comprise a sensing plate (216), typically a metal plate, that is connected by interconnects (25) to the sensor transistor gate (208). This sensing plate is in communication with or is proximate to region, such as a chamber (37) where the analyte or reaction to be detected will be present. The chamber (37) is part of a well structure (38) formed from insulating passivation material (35). The chamber (37) has sidewalls (39).

An ISFET relies on a fluid (64) that covers the sensing area and fills the chamber (37) to provide a minimum gate voltage to turn on the sensor transistor. The gate voltage is applied by a reference electrode (66) coupled to the fluid or solution—creating a solution gated FET. In some instances an analyte or reaction-sensitive layer (218) is formed over the sensing plate (216). The ISFET (200) is typically replicated many times on a semiconductor IC chip to form an array of ISFET sensor cells that comprise an sensor IC chip. In order to read a signal from just one of the ISFETs at one time from the array of ISFETs on the IC chip an access transistor, one for each ISFET, is used to control access to the selected ISFET to be read.

Thus for an ISFET based on traditional semiconductor FETs there are two transistors (the sensor transistor and the access transistor).required for each sensing location. The need for two semiconductor transistors per sensor has implication on the size of those transistors (i.e. the transistors for a cell defined by two transistors will necessarily have smaller transistors that a cell defined by one semiconductor transistor). Smaller transistors create more noise than larger transistors.

Another consideration is that more semiconductor transistors (e.g. 2 per cell versus 1 per cell) require more interconnect connections and will lead to the need for more levels of interconnect wiring to accomplish connecting to all the transistors. Increases in the number of levels of interconnect wiring and increases in the interconnect length have deleterious effects on the noise of the ISFET sensor. As this discussion has highlighted, the noise of an ISFET made from a traditional semiconductor FET may be higher than other FETs used for sensing. Noise in a sensor is important since the detection signal must be discriminated separately from the noise in the sensor. The higher the signal to noise ratio then the better the sensitivity of the sensor will be.

As is known, a Field Effect Transistor (FET) manufactured by typical semiconductor IC fabrication processes includes a gate over a channel region, a channel region formed by charge carriers in the semiconductor material connecting source and drain regions when an appropriate gate voltage is applied, and an insulating barrier separating the gate from the channel. The operation of a conventional FET relies on the control of the channel's conductivity, and thus the drain current, by a voltage, designated VGS, applied between the gate and source. For high-speed applications, and for the purposes of increasing sensor sensitivity, FETs should respond quickly to variations in VGS. However, this requires short channel lengths and fast carriers in the semiconductor channel.

Furthermore, for a sensor chip to be used for DNA sequencing, requiring on the order of 30,000,000 reads as previously described, the size of the individual sensors in the sensor array must be made small enough to fit millions of sensors on the chip. In this case there are physical limitations to the chip size due to the photolithography systems available for wafer and chip manufacturing (e.g. a maximum chip size on the order of 25 mm square) which in turn limit the size of the sensors on the chip given the large number of sensors needed in the array.

Another consideration is that an ISFET used for DNA sequencing is arranged as an array of sensors—each of which must be individually addressable to read the signal of any DNA hybridization that is occurring local to that sensor. To achieve both this individual sensor cell addressability as well as sensing function the sensor cell requires at least two CMOS (or other semiconductor) transistors—one to control the access to the cell for reading and the other as the sensor transistor to transduce the DNA binding or hybridization event into an electrical signal. Because of this need for a minimum of two CMOS transistors per sensor cell the transistors must be even smaller, e.g., at least 2 times smaller, than what would be required due to the aforementioned geometrical constraints derived from the maximum chip size and number of sensors in the array. This further constraint on the size of the CMOS transistor used for sensing directly relates to the channel length of that transistor.

Unfortunately, FETs with short channel lengths frequently suffer from degraded electrostatics and other problems (collectively known as short channel effects), such as threshold-voltage roll-off, drain-induced barrier lowering, and impaired drain-current saturation, which result in a decrease in sensor sensitivity. Nevertheless, scaling theory predicts that a FET with a thin barrier and a thin gate-controlled region (measured in the vertical direction) should be robust against short-channel effects down to very short channel lengths (measured in the horizontal direction).

Accordingly, the possibility of having channels that have high surface area to volume ratio (e.g. are very thin in the vertical dimension like a 2D nanomaterial or have a small cross-section area like a 1D nanomaterial) yet still allow for high-speed transmission of carriers would allow for increased sensor sensitivity and accuracy. What is needed, therefore, is a FET device that is configured in such a manner and comprises such materials that in combination of structure and materials it offers a FET sensitivity that is higher than is currently achievable in present FET applications. A solution that includes such a FET device designed for use in biological applications, such as for nucleic acid detection, sequencing, and/or other diagnostic applications, would be especially beneficial.

Glossary and Abbreviations

Unless otherwise noted, or as may be evident from the context of their usage, any terms, abbreviations, acronyms or scientific symbols and notations used herein are to be given their ordinary meaning in the technical discipline to which the disclosure most nearly pertains. The following terms, abbreviations and acronyms may be used throughout the descriptions presented herein and should generally be given the following meaning unless contradicted or elaborated upon by other descriptions set forth herein.

ChemFET: a chemically-sensitive Field Effect Transistor (FET),

CMOS: Complementary Metal Oxide Semiconductor,

CNT: Carbon Nanotube, a type of 1D nanomaterial formed of carbon atoms arranged in a tube-like structure that has a small cross-section area in comparison to its length, Damascene: a fabrication process whereby a trench is formed first in a dielectric material and then the trench is filled with a conductive material in a second process step, DNA: deoxyribonucleic acid, ESL: Etch Stop Layer, a layer upon which an etching process may stop or be significantly attenuated, FET: a Field Effect Transistor, GAA: Gate All-Around, a transistor gate structure wherein the gate surrounds a portion of the channel, GFET: a FET with a graphene nanomaterial channel, I: current. If there is a subscript, such as Id, the subscript indicates the location at which the current is flowing (e.g. Id is the current flow at the transistor drain)

IC: an Integrated Circuit,

ISFET: and Ion Sensitive FET,

MOSFET: a Metal Oxide Semiconductor Field Effect Transistor,

Nanomaterial: a material in which at least one principle dimension (e.g. length, thickness, width) is in the range of 1 to 100 nanometers, NGS: Next Generation Sequencing, NW: Nanowire, a 1D nanomaterial that has a small cross-section area in comparison to its length, Passivation: the topmost or final insulating protective layer on an IC chip, RNA: ribonucleic acid, ROIC: Read-Out Integrated Circuit is circuitry that assists with reading out signals from a sensor or sensor array and may comprise such circuits as analog to digital converters, amplifiers, filters, row or column decoders, sample and hold circuits and the like, SNP: Single Nucleotide Polymorphism, V: voltage. If there is a subscript, such as $V_{gs}$, the subscript indicates between which points or locations the voltage potential is defined (e.g. $V_{gs}$ is the voltage between the gate and source of a transistor),

SUMMARY OF THE INVENTION

The present disclosure addresses the aforementioned mentioned shortcomings of conventional NGS systems and current ISFET-based sequencing approaches. This disclosure is directed to a patentable class of Chemically-sensitive Field-Effect Transistors (ChemFETs) that resolve many of the current issues associated with chemical and biological analyses, for example, nucleic acid hybridization, NGS sequencing, hybridization detection, genetic diagnostics, genome identification, species identification, nucleic acid capture, genotyping, analyte detection and identification, etc., systems incorporating such ChemFETs, and methods of making and using such ChemFETs.

One aspect of the present disclosure is a ChemFET. These ChemFETs are preferably fabricated using semiconductor IC fabrication methods on a semiconductor wafer used for semiconductor manufacturing, and in preferred embodiments, on top of or over an integrated circuit structure made using semiconductor IC fabrication methods. The instant ChemFETs typically comprise a conductive source, a conductive drain, and a channel composed of a one-dimensional nanomaterial (1D nanomaterials are very long in comparison to their cross-sectional area and may be thought of as wires or tubes, with silicon NanoWires (Si NWs) or Carbon NanoTubes (CNTs) being examples) or a 2D nanomaterial (2D nanomaterials are very thin and spread in two directions to form sheets, with graphene or MoS2 being examples) and/or a three-dimensional (3D) transistor material, which channel extends from the source to the drain and may be fabricated using semiconductor IC fabrication techniques on top of or over a wafer or other substrate. In some embodiments there may be multiple channels between the source and the drain. For instance, a substrate, such as a silicon substrate may be provided, upon which a non-conductive dielectric layer, e.g., an oxide layer, may be positioned, within which or over which the source and drain electrodes may be deposited, and a nanomaterial channel member formed there between, which channel member may additionally be at least partially covered or coated with another non-conductive insulation layer, such as an oxide or organic analyte or reaction sensing layer. Specifically, in various embodiments, a non-conductive, e.g., oxide, layer may be disposed on the channel member and/or across the channel region.

In some embodiments, the ChemFET may also include a gate or gate region, e.g., a solution gate, and/or a reference or gate electrode. In other embodiments the ChemFET may include more than one gate, such as a dual gate comprising, for example, a solution gate and a backgate. In such embodiments the backgate may be configured as a global backgate affecting multiple ChemFETs or may be a series of local backgates, one for each ChemFET. In another embodiment the gate may partially or even fully surround a portion of the channel (a so-called Gate All-Around or GAA structure). Associated circuitry, such as Read-Out Integrated Circuits (ROIC) or a processor, may also be included or otherwise be functionally associated with a ChemFET of the disclosure (or array thereof) in order to process and analyze signals generated thereby.

In use, desired chemical reactions or biologic activity that occurs in proximity to the ChemFET results in a change in electric charge or electric field strength that can be sensed. Particularly, changes in electric charge or electric field affect the gate voltage which in turn changes conductance through the 1D, 2D, and/or 3D channel member connecting the source and the drain electrodes—thus chemical reactions or biologic activity may be transduced and detected by the ChemFET. For instance, in some embodiments, sensing of a desired reaction or biologic activity produces an alteration, e.g., a shift, in an I–V curve, for example, an $I_d$–$V_g$ curve, where Id is the drain current and $V_g$ is the gate to source voltage, or a parameter of an I–$V_g$ curve, e.g., the curve's slope or position relative to the horizontal axis, corresponding to the ChemFET. A processor functionally associated with the ChemFET may be used to compare a reference I–V curve (or parameter thereof) for a well (or other capture region or structure) and an I–V curve (or the corresponding parameter thereof) generated in connection with a chemical reaction or biologic activity occurring in the well (or other capture region or structure associated with the ChemFET). If the processor detects a difference between the reference and reaction-associated curves that exceeds a predetermined threshold, a positive result can be indicated. Likewise, a negative result may be detected in the absence of such an effect.

Another aspect of the present disclosure concerns biosensors based on a ChemFET according to the devices, systems, and methods provided herein. Such biosensors may include a structure comprising a substrate and a non-conductive, e.g., oxide, dielectric layer comprising a conductive source and a conductive drain, a 1D, e.g. Si NW or CNT, or 2D, e.g., graphene, or 3D channel extending from the source to the drain, and further including a well, chamber, passivation opening or other structure suitable for analyte capture and analysis associated with an exterior surface of the analyte or reaction sensing insulation layer and/or the channel nanomaterial member. An additional non-conductive, e.g., oxide, passivation layer may be disposed on and/or around the channel nanomaterial and/or channel region, which passivation layer may be configured so as to form the well and/or chamber.

The analyte or reaction sensing insulation layer may be comprised of an oxide, for example, an aluminum oxide, hafnium oxide or a tantalum oxide. In some embodiments, the analyte or reaction sensing oxide layer may be a thin layer, such as a layer having a thickness of about 30 nanometers (nm), 20 nm, 15 nm, 10 nm, 7 nm, 4 nm, or less. The well structure (or other opening in the passivation) defines an opening allowing for direct contact with the channel nanomaterial, e.g., the graphene channel or direct contact with the analyte or reaction sensing insulation layer, if one is present. In some embodiments, sensing the occurrence of a desired chemical reaction, e.g., sensing the presence of a target biological compound or reactant thereof, is detectable such as by detecting a change in the conductance through the channel nanomaterial and/or the production of a shift in an I–V curve or an I–$V_g$ curve corresponding to that change in conductance as determined by the ChemFET.

Yet another aspect of the present disclosure is a chemically-sensitive Graphene Field Effect Transistor (GFET). A GFET according to the disclosure may include a CMOS structure comprising a damascene copper source, a damascene copper drain, and a graphene channel extending from the source to the drain. An analyte or reaction sensing insulation layer, e.g. an oxide layer, may also be included and disposed on or around the channel. The analyte or reaction sensing oxide layer may be composed of an aluminum oxide, a hafnium oxide or a tantalum oxide. In some embodiments, the oxide layer may be a thin layer, such as a layer having a thickness of about 30 nanometers (nm), or 20 nm, or 15 nm, or 10 nm, or 7 nm, or 4 nm, or less. In particular embodiments, sensing of a desired chemical reaction, e.g., detection of a target biological compound, produces a shift in an I–V curve or an $I_d$–$V_{gs}$ curve corresponding to the GFET.

Using Etch Stop Layers when Forming Wells or Passivation Openings

Another aspect of the disclosure relates to methods of making ChemFETs, particularly chemically-sensitive GFETs, of the disclosure. In some embodiments, these methods involve well formation on or over a 2D nanomaterial FET. In various instances, such methods include depositing a protective layer, e.g. an etch stop layer (ESL) or hard mask layer, on or over a channel of a 2D nanomaterial ChemFET device structure. These methods may include etching through a passivation layer and a portion of the ESL with a first etching method to create at least a well or opening in the passivation formed over a channel region that may include a channel nanomaterial configured to form a channel.

These methods may also include a second etching of the remaining protective ESL or hard mask layer over the channel to expose the channel nanomaterial or an analyte or reaction sensing layer over the channel nanomaterial within the formed well or opening in the passivation. In various embodiments, the protective passivation layer may be comprised of an inorganic material, for example, an oxide, a nitride, a carbide, an oxy-nitride, a carbon-doped oxide, or a fluorine-doped oxide material. In others embodiments, the protective passivation layer may be composed of an organic material, such as a polymer comprising polyimide or PBO. In yet other embodiments, the protective passivation layer is composed of both inorganic and organic materials.

Passivation Well or Opening Manufacturing Method

Other aspects of the disclosure concern methods for manufacturing a passivation well formation or opening for a 1D, 2D, and/or 3D nanomaterial ChemFET with an organic protective passivation layer. Such methods may include depositing an organic protective passivation layer over and/or or on a channel of a 1D, 2D, and/or 3D nanomaterial FET of a semiconductor device structure. The methods may also include lithographic patterning of the organic protective passivation layer to create one or more well formation or passivation opening locations over the channel. The method may further include removing the protective layer over the channel to expose the channel within the well formation or passivation opening.

Method to Form a Gate All-Around Structure

In a related manufacturing aspect, the methods of the disclosure include depositing a 1D or a 2D nanomaterial, for example, graphene, or 3D nanomaterial, to form a channel on an exposed conductive, e.g., metal, layer of an integrated circuit structure. The integrated circuit structure may include a semiconductor substrate, a dielectric layer and/or non-conductive layer, and the conductive, e.g., metal or electrode, layer. These methods may include utilizing a patterned material to expose a portion of a channel area and one or more adjacent areas.

These methods may also include etching the dielectric material, e.g., starting with the adjacent areas, thereby exposing a trench under the channel and exposing the metal in the channel area. Such methods may further include etching the metal from underneath and/or around the channel, e.g., graphene, material to create a ChemFET with a GAA structure.

Methods to Prepare a Growth Substrate

Another aspect of the disclosure relates to methods for preparing a growth substrate that are useful to produce the ChemFET channel nanomaterials, particularly graphene chemically-sensitive GFET channel nanomaterials, of the disclosure. These methods may include depositing a metal catalyst layer, e.g., Ni, Ru, Cu or Pt, on a substrate and/or a non-conductive layer thereof, and annealing the metal catalyst, wherein the annealing may occur in an environment that includes hydrogen, such that the resulting metal catalyst layer is a predominantly single crystalline metal catalyst layer with a crystal orientation. Such methods may include activating the metal catalyst layer, such as by a plasma method, which may include a hydrogen gas and/or a nitrogen-containing gas.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE DRAWINGS

In this description, like numbers refer to like elements in the figures.

FIG. 1N is a side sectional illustration, along section X-X of FIG. 1K, of a semiconductor nanowire transistor configured as a Junctionless FET.

FIG. 1O is a side sectional illustration, along section X-X of FIG. 1K, of a semiconductor nanowire transistor configured as a Tunnel FET.

FIG. 2C is a top plan view of a ChemFET with a well structure.

FIG. 5A shows electrodes overplated in trenches in an oxide layer.

FIG. 5B shows a side sectional view of electrodes in a dielectric layer after chemical-mechanical planarization (CMP) process. The CMP process partially etches part of the dielectric layer to allow the electrodes to project above the surface of the dielectric layer.

FIG. 9A is an illustration of a CMOS wafer with a graphene layer deposited on exposed metal electrodes and dielectric surface.

FIG. 9B is an illustration of etching the dielectric under the graphene channel.

FIG. 10A is an illustration of a CMOS wafer with a graphene layer deposited on exposed metal electrodes.

FIG. 10B is an illustration of etching the dielectric under the graphene channel and under the metal electrode.

14A is an illustration of an exemplary graphene field-effect transistor chip.

Figure 14B:
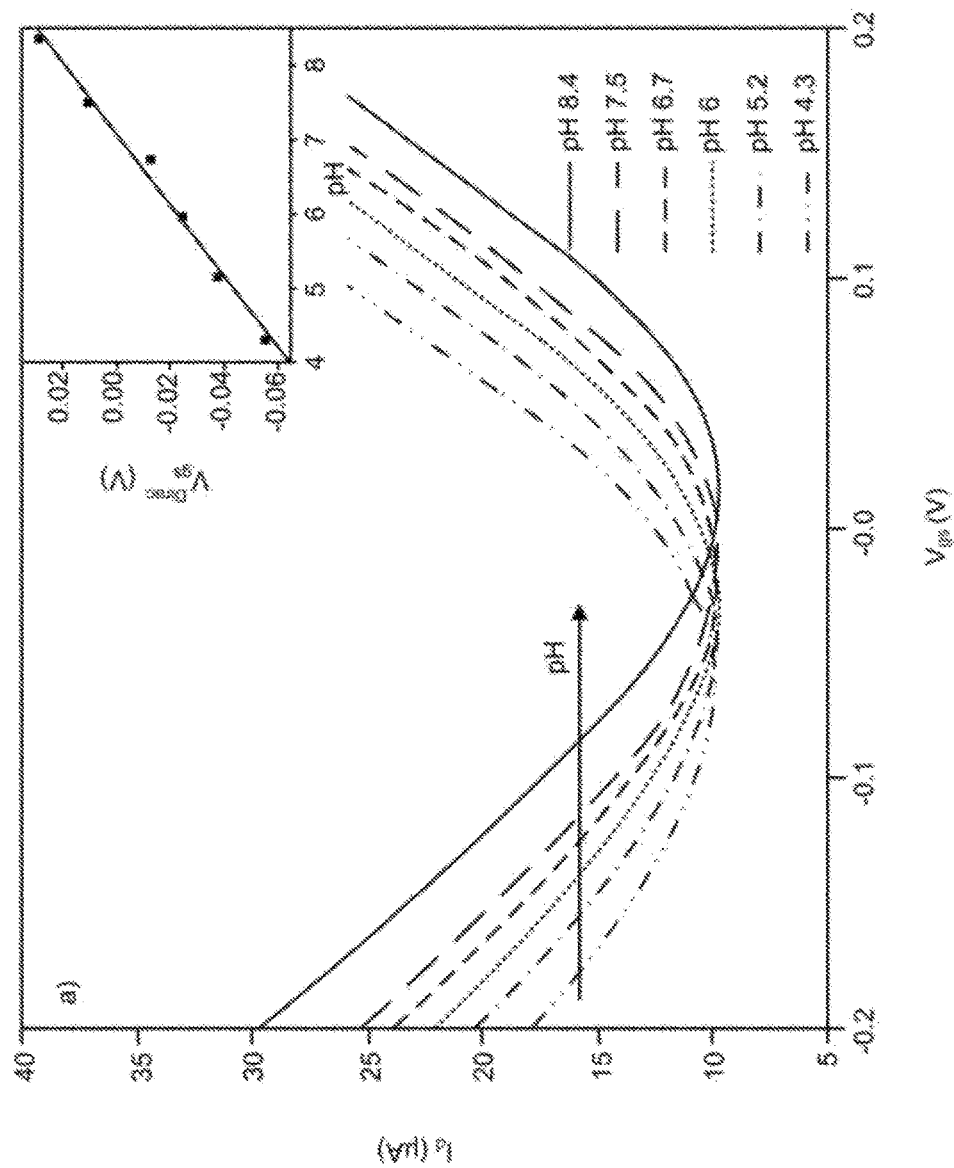

FIG. 14B is a graph of an $I_d$-$V_{gs}$ curve for various pH values.

Figure 14C:
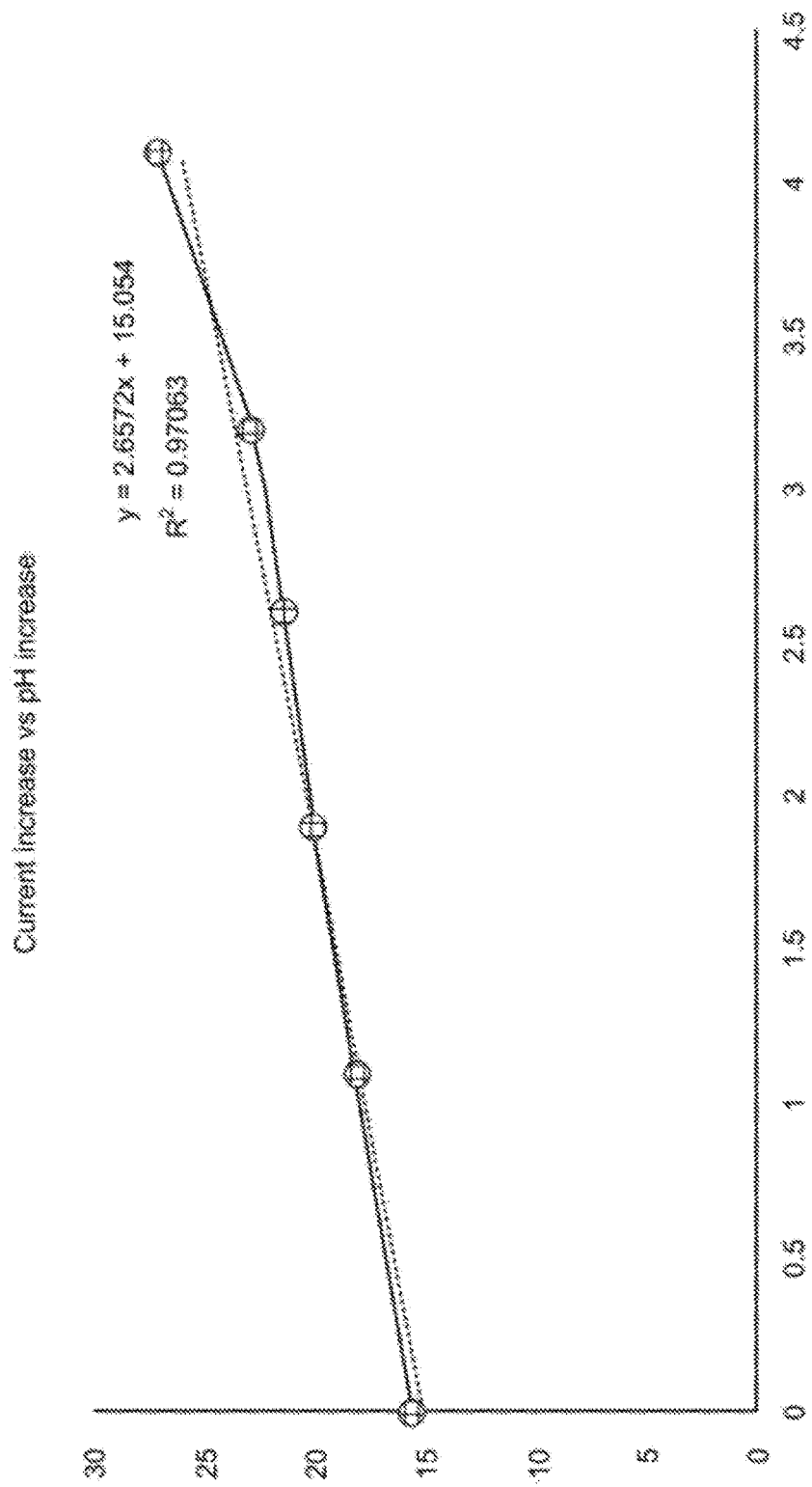

FIG. 14C is a graph of current increase vs. pH increase.

Figure 14D:
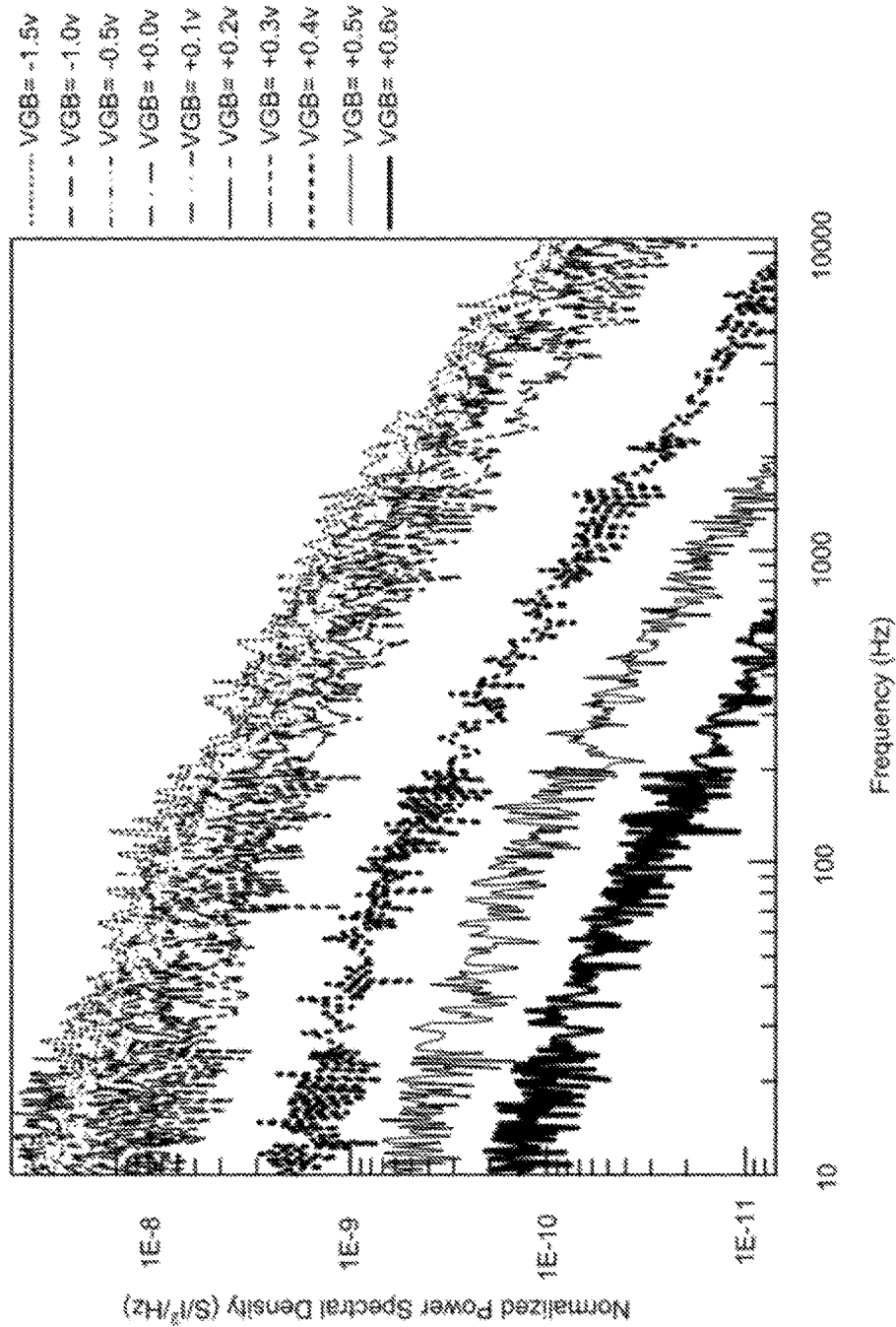

FIG. 14D is a graph of frequency vs. normalized power spectral density for silicon ISFET.

Figure 14E:
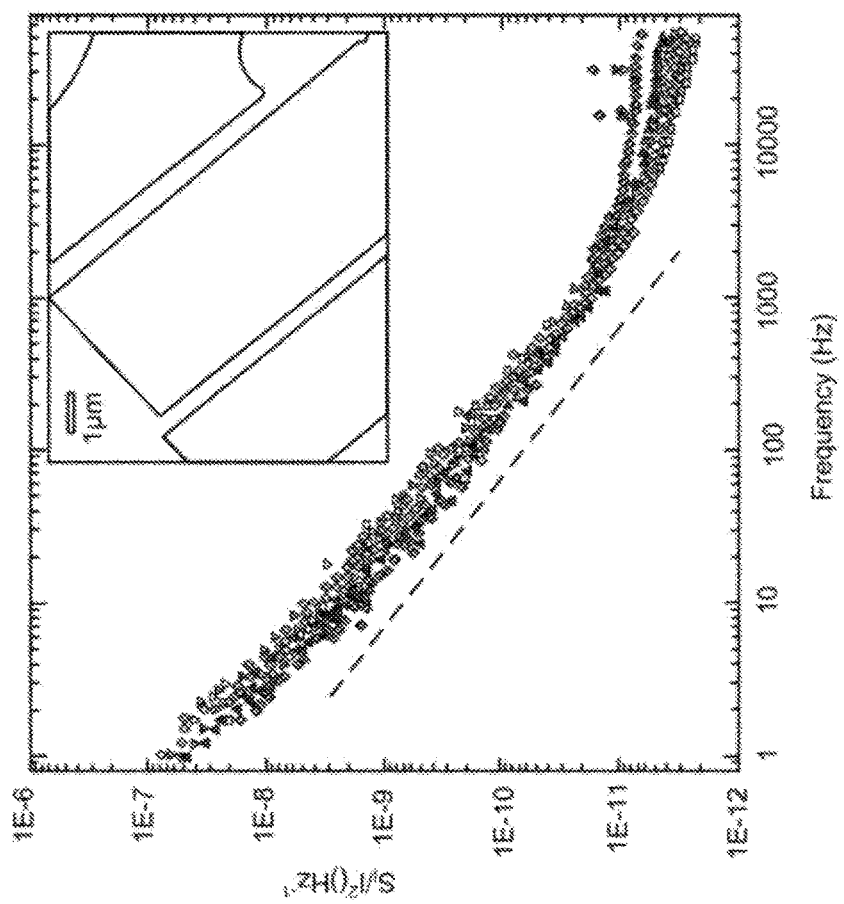

FIG. 14E is a graph of frequency vs. normalized power spectral density for a typical graphene FET.

Figure 14F:
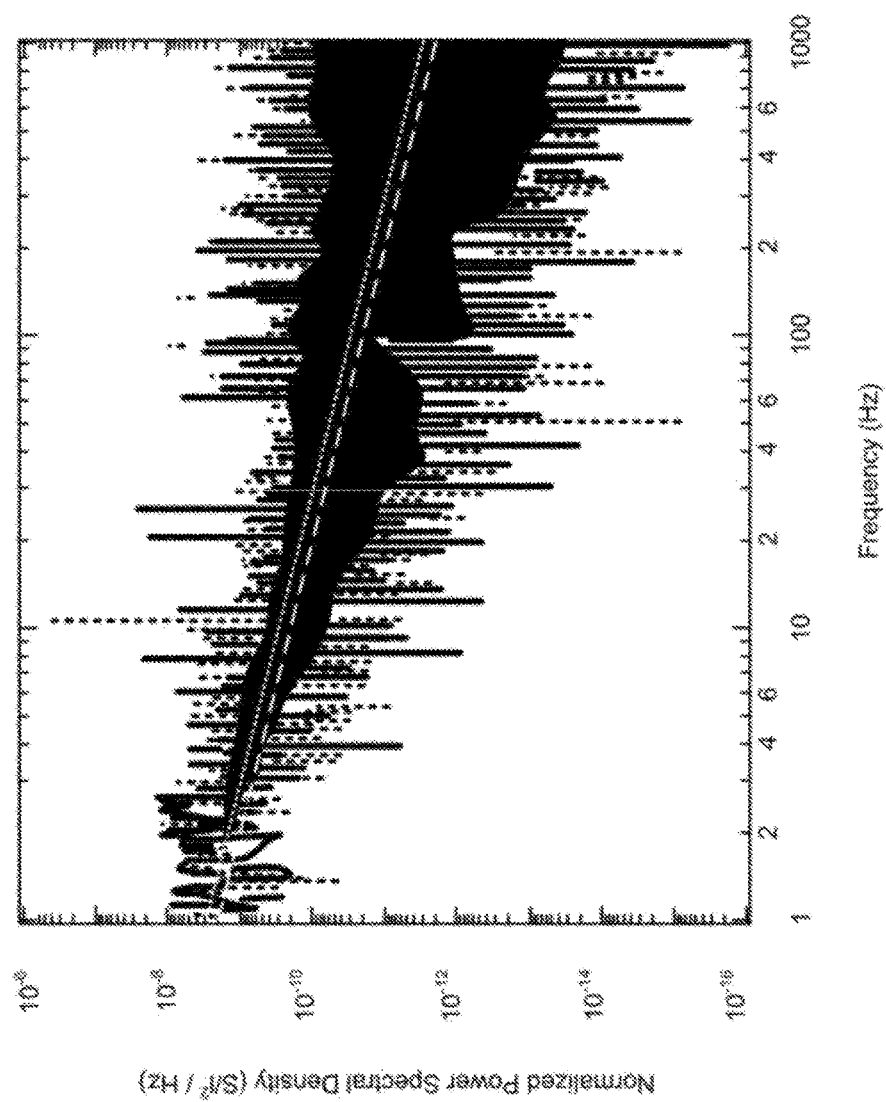

FIG. 14F is a graph of frequency vs. normalized power spectral density for a graphene FET of the present invention.

Figure 14G:
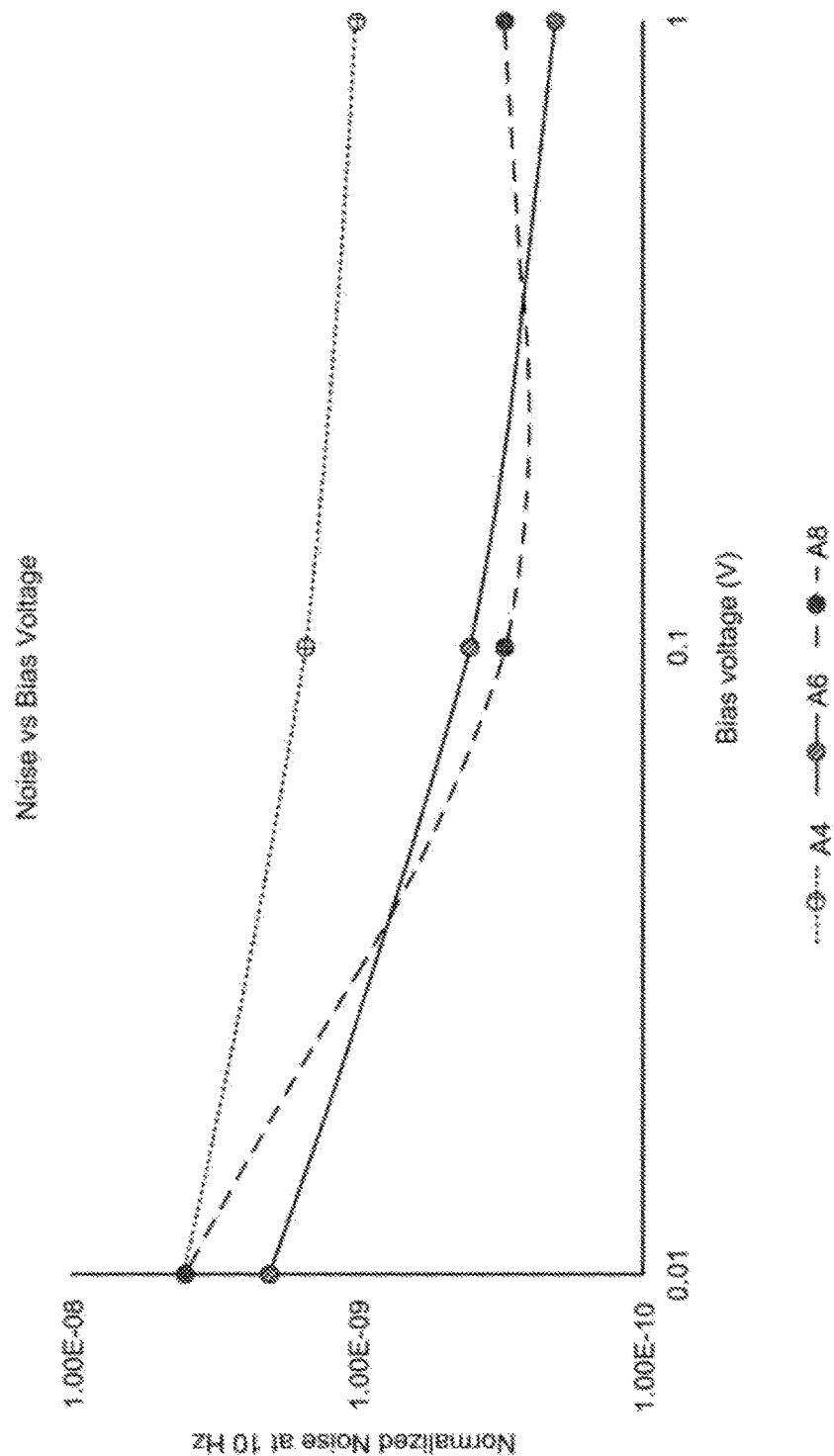

FIG. 14G is a graph of noise vs. bias voltage.

Figure 14H:
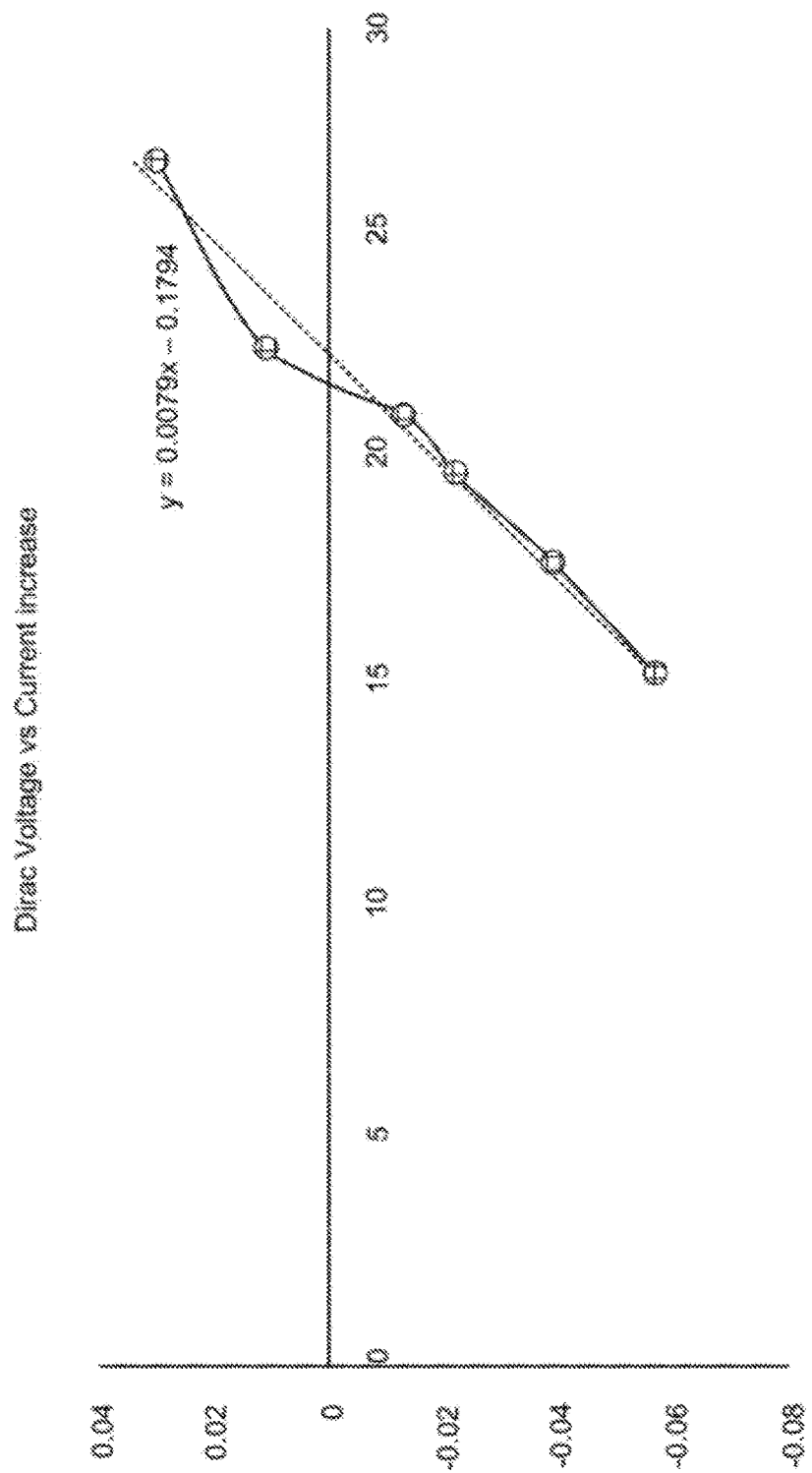

FIG. 14H is a graph of Dirac voltage vs. current increase.

Figure 15A:
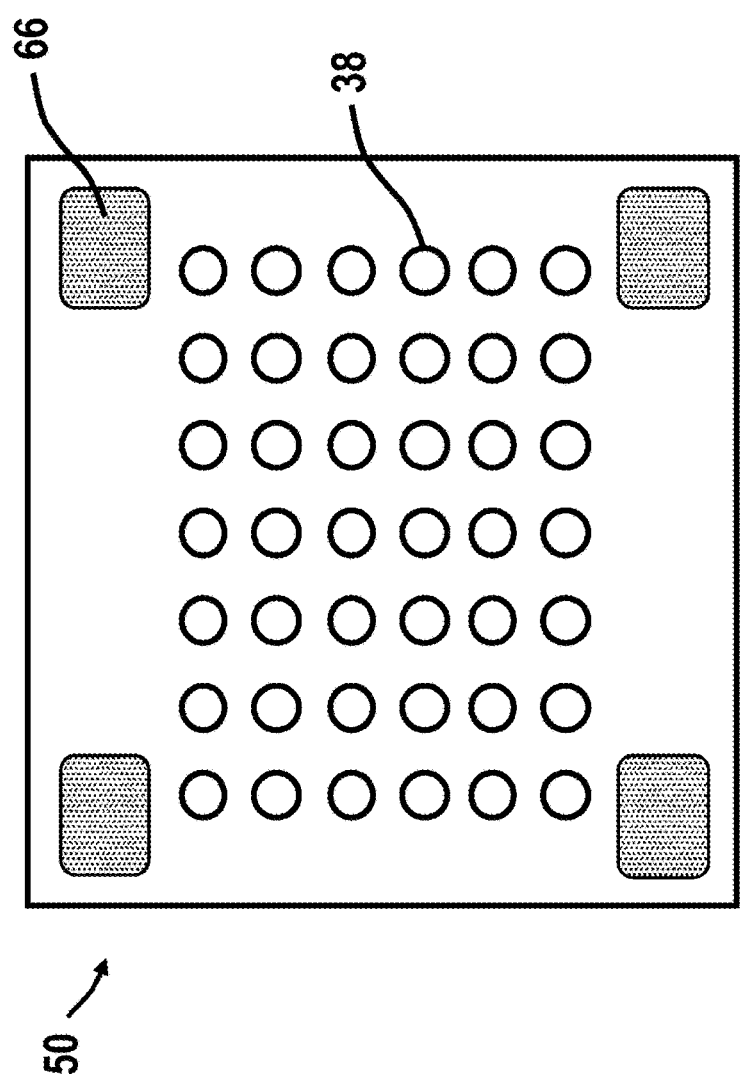

FIG. 15A is a top plan view of a sensor array IC for a system for analysis of biological or chemical materials, where the sensor array includes multiple chemically-sensitive field-effect transistors.

Figure 15B:
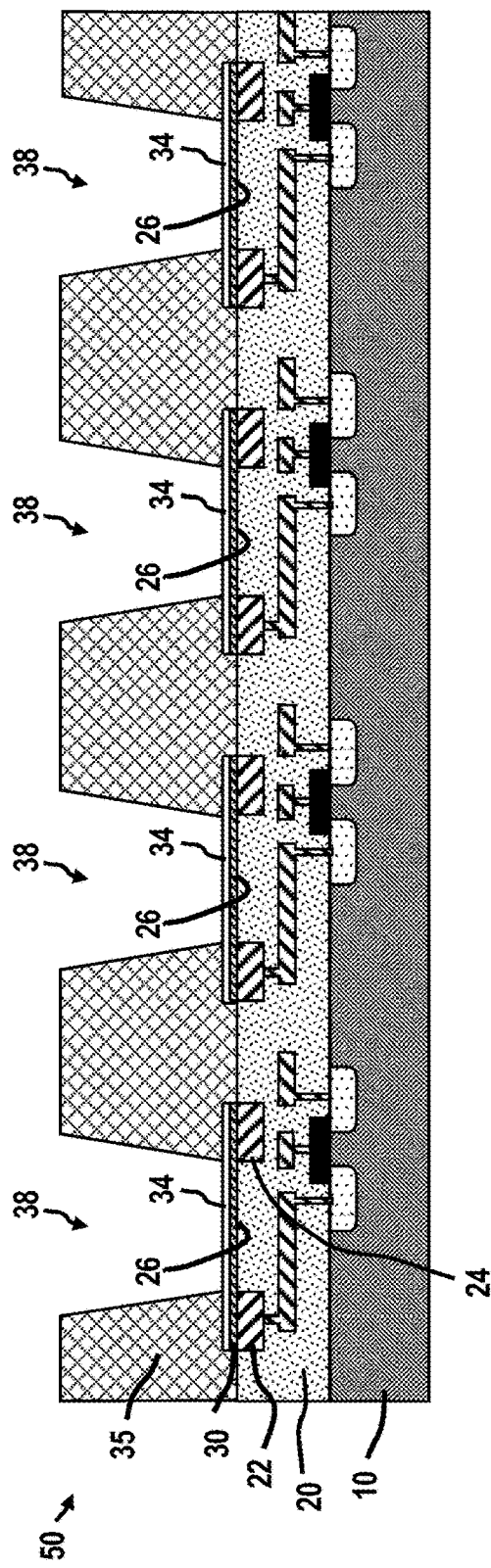

FIG. 15B depicts a ChemFET sensor IC chip.

Figure 15C:
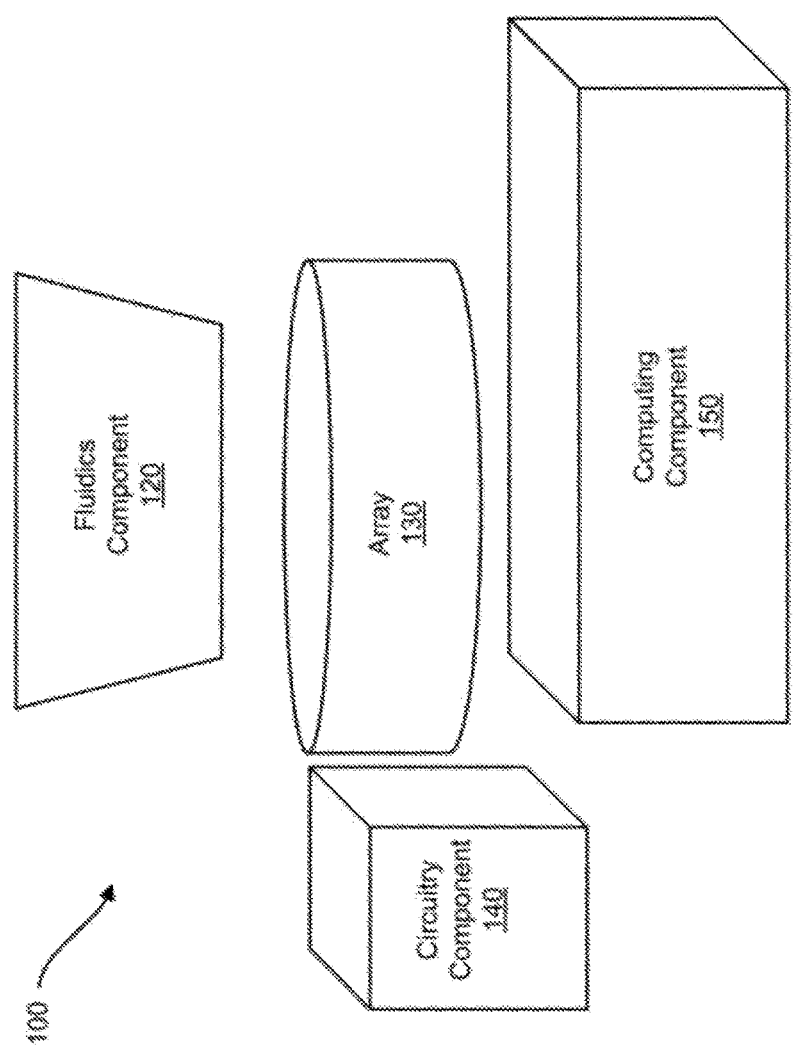

FIG. 15C is a block diagram of a system for analysis of biological or chemical materials.

Figure 15D:
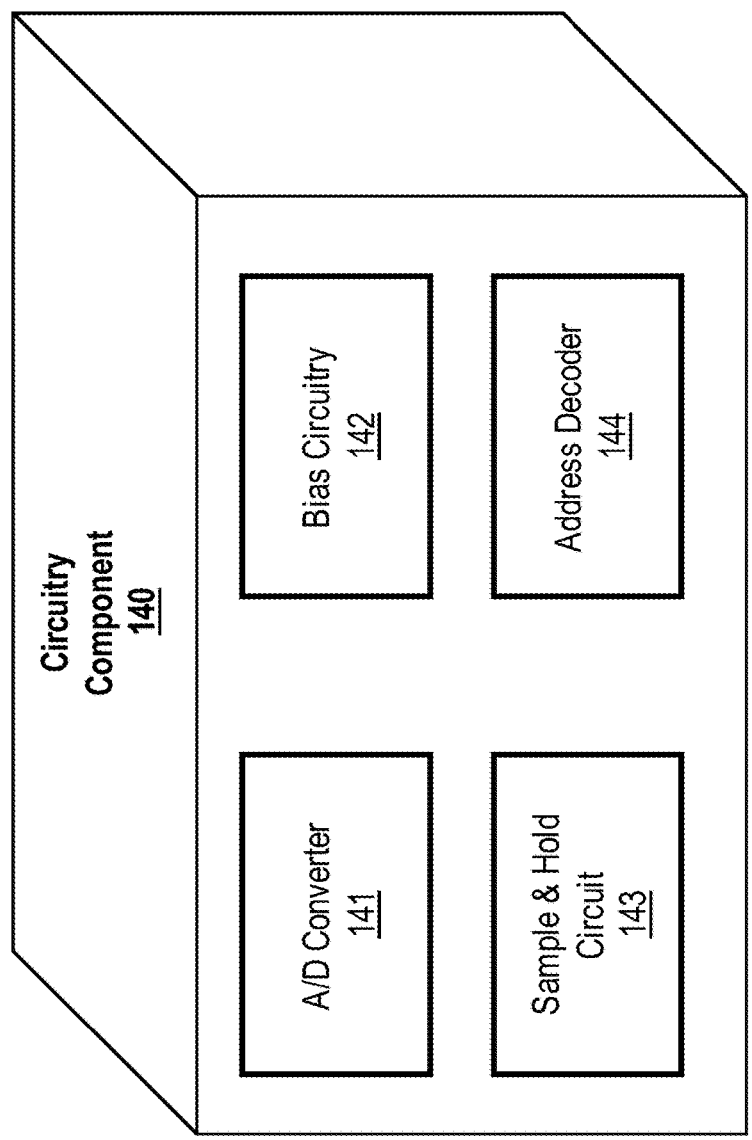

FIG. 15D is a block diagram of a circuitry component for a system for analysis of biological or chemical materials.

Figure 15E:
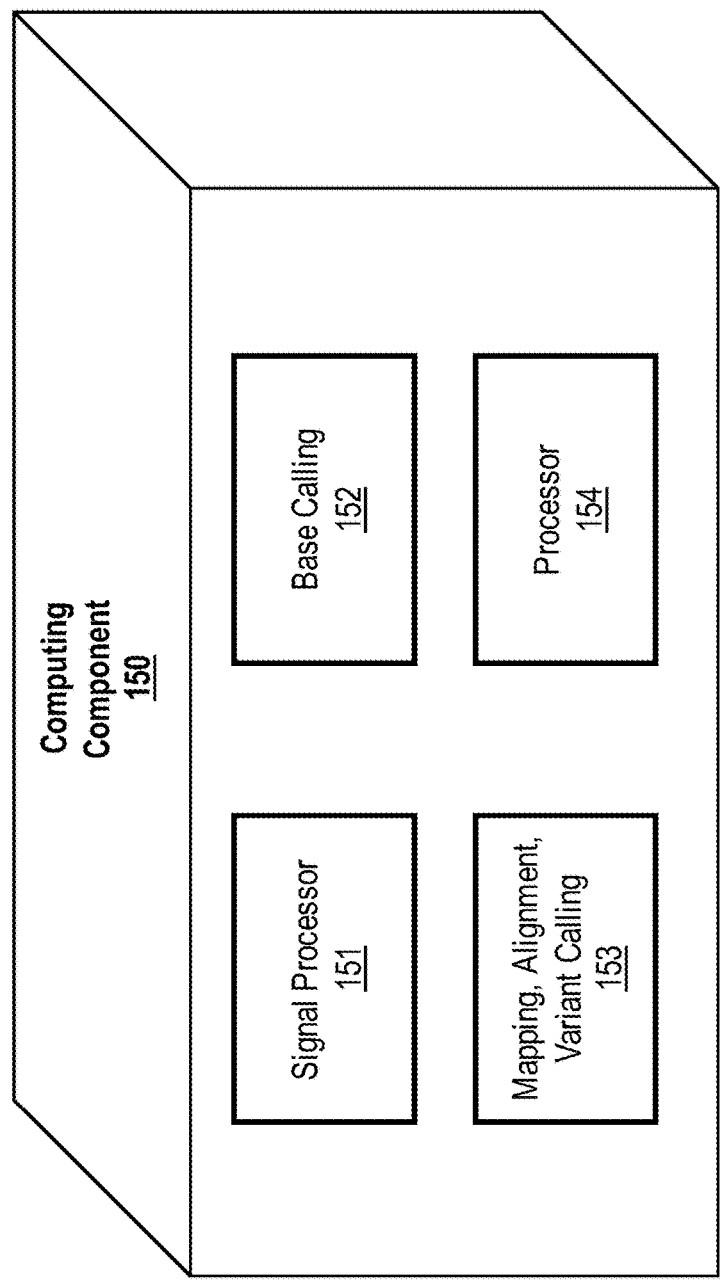

FIG. 15E is a block diagram of a computing component for a system for analysis of biological or chemical materials.

Figure 15F:
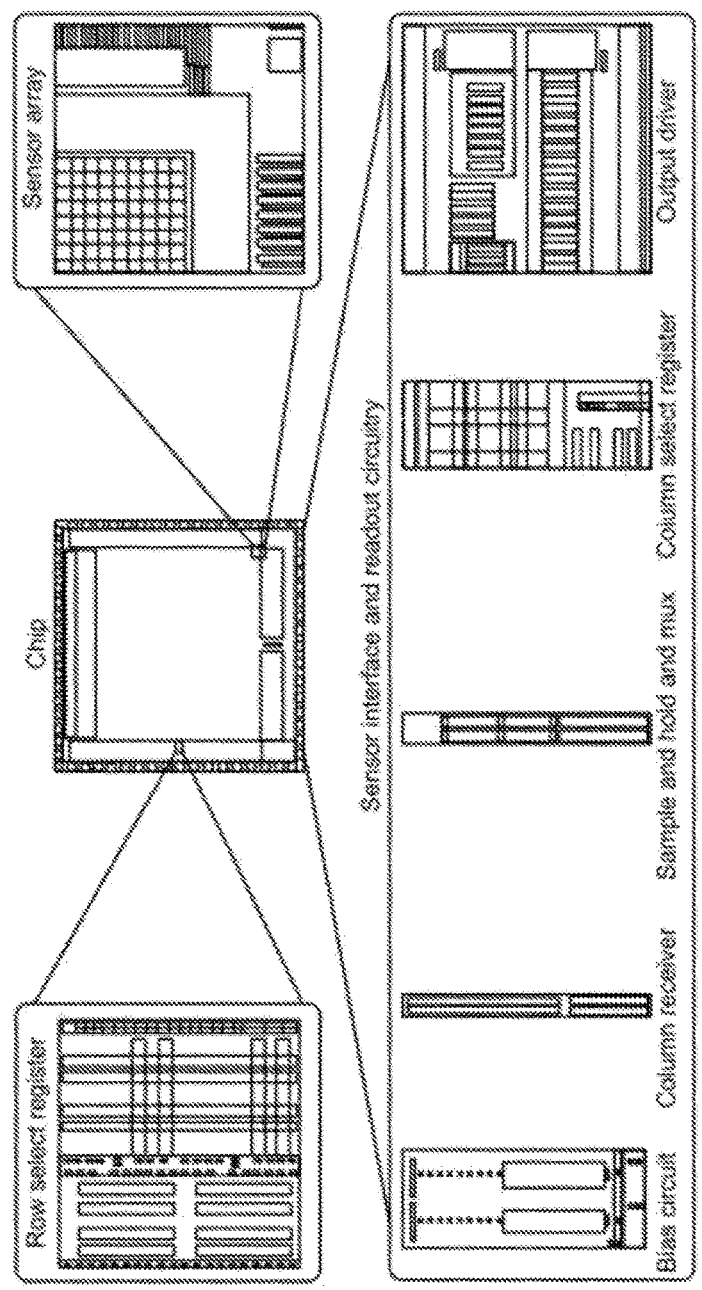

FIG. 15F is a block diagram of components for a system for analysis of biological or chemical materials.

Figure 16:
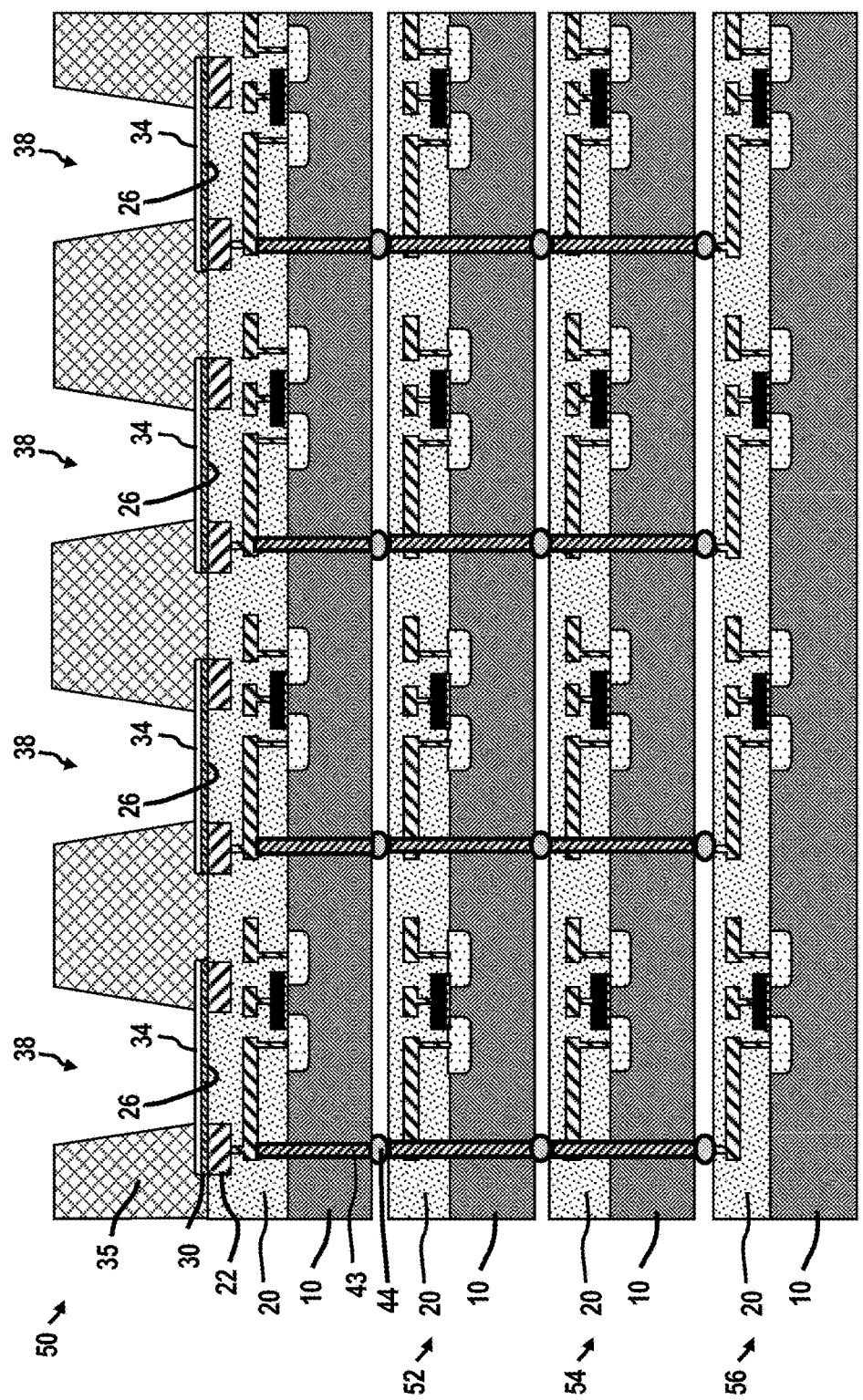

FIG. 16 depicts a stack of electrically connected IC chips, including a ChemFET sensor IC chip and one or more other IC chips such as a processor or memory IC chip.

Figure 17A:
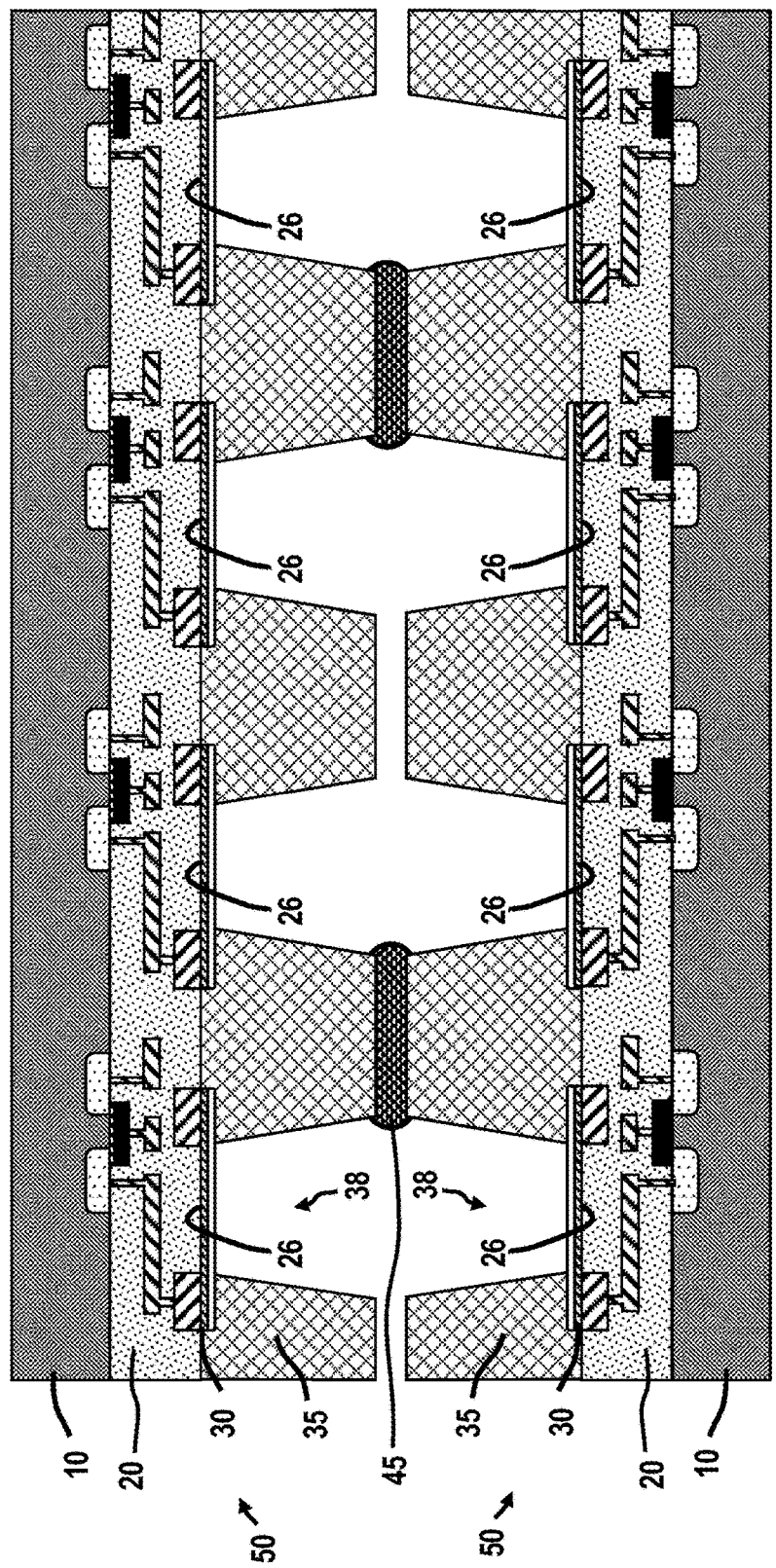

FIG. 17A depicts face to face stacked ChemFET sensor IC chips defining flow channels.

Figure 17B:
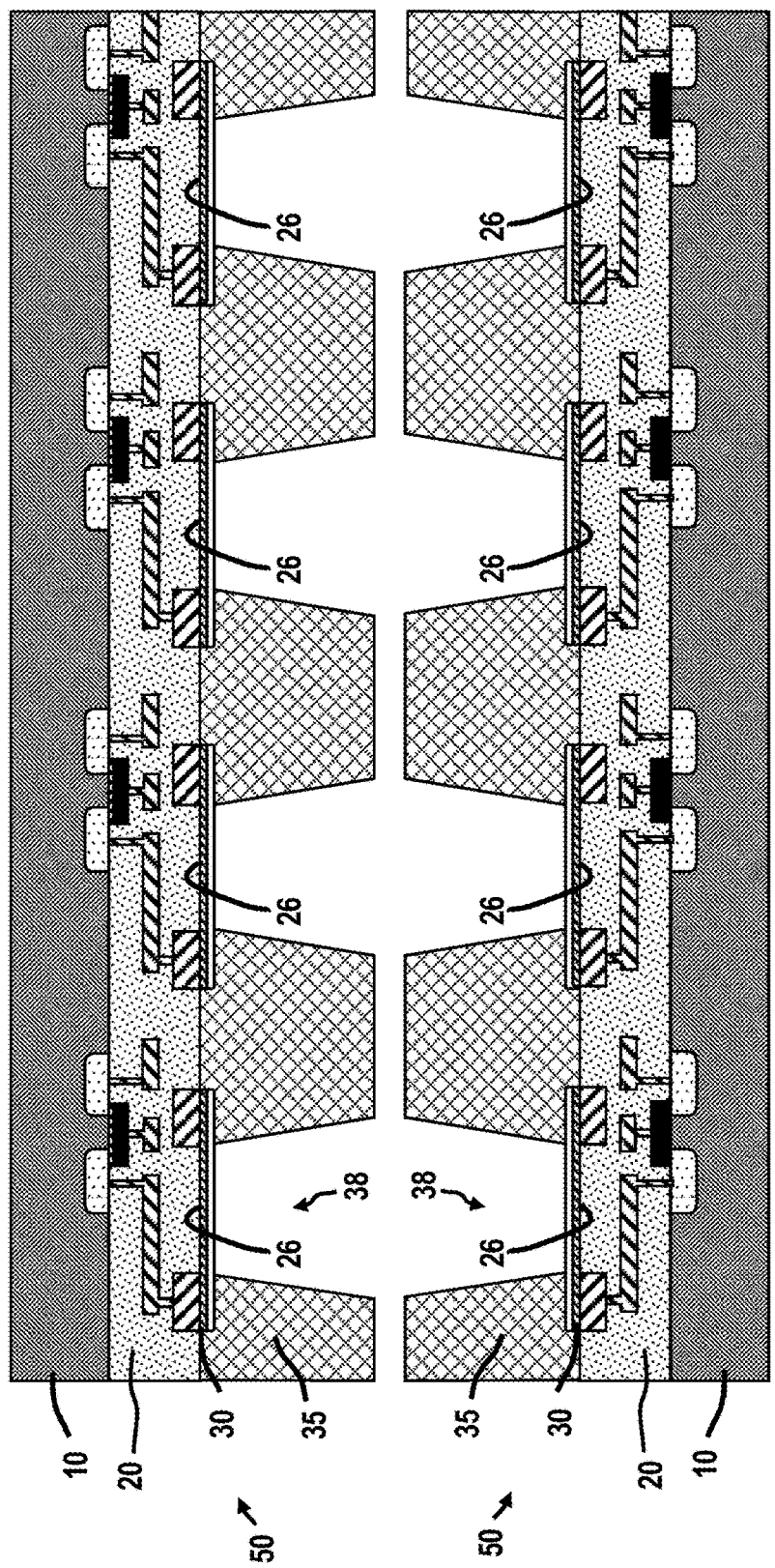

FIG. 17B depicts face to face stacked ChemFET sensor IC chips with their orientation provided by external members.

Figure 17C:
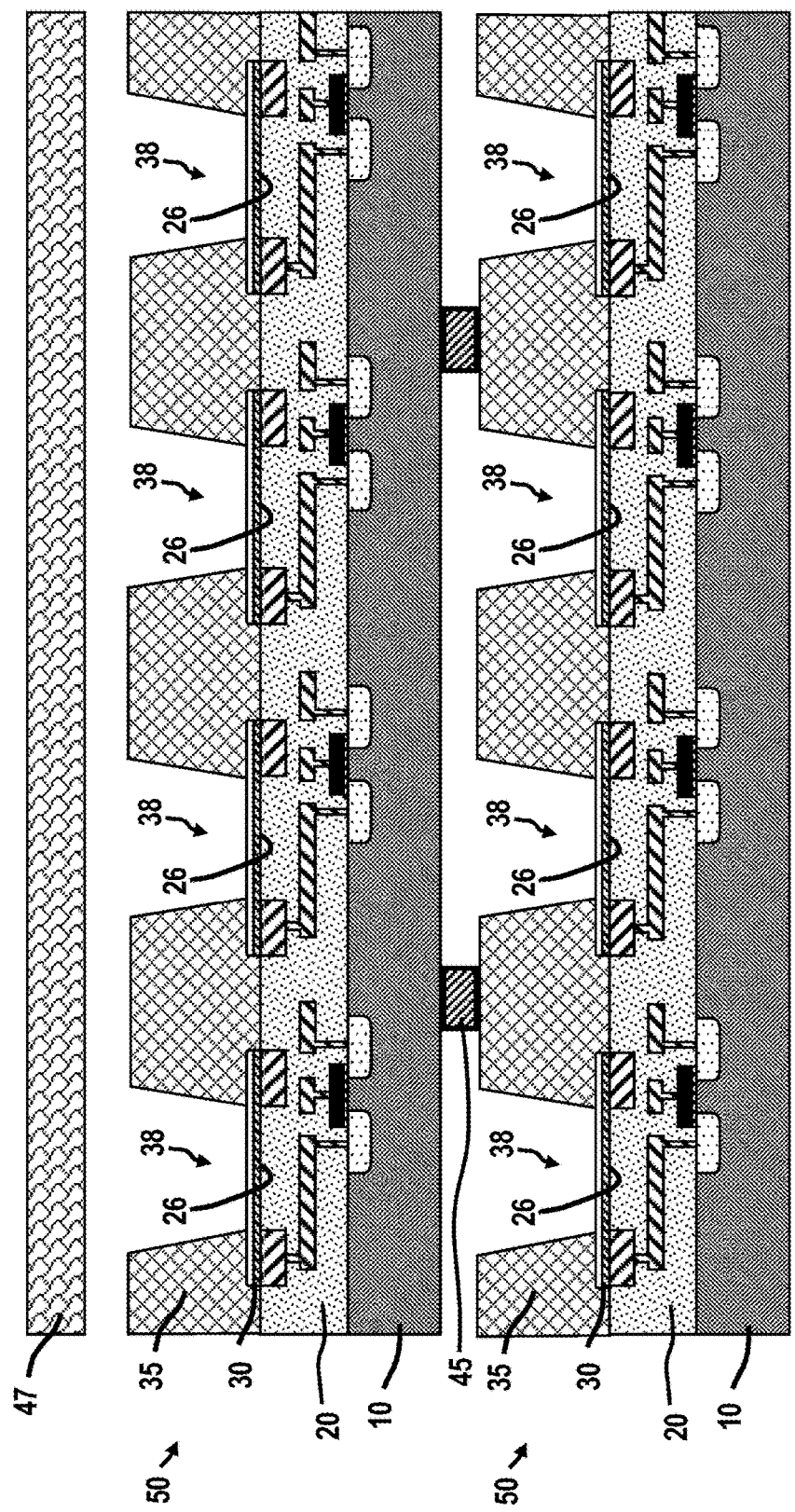

FIG. 17C depicts face up stacked ChemFET sensor IC chips and a package lid that together define fluid flow channels.

Figure 18A:
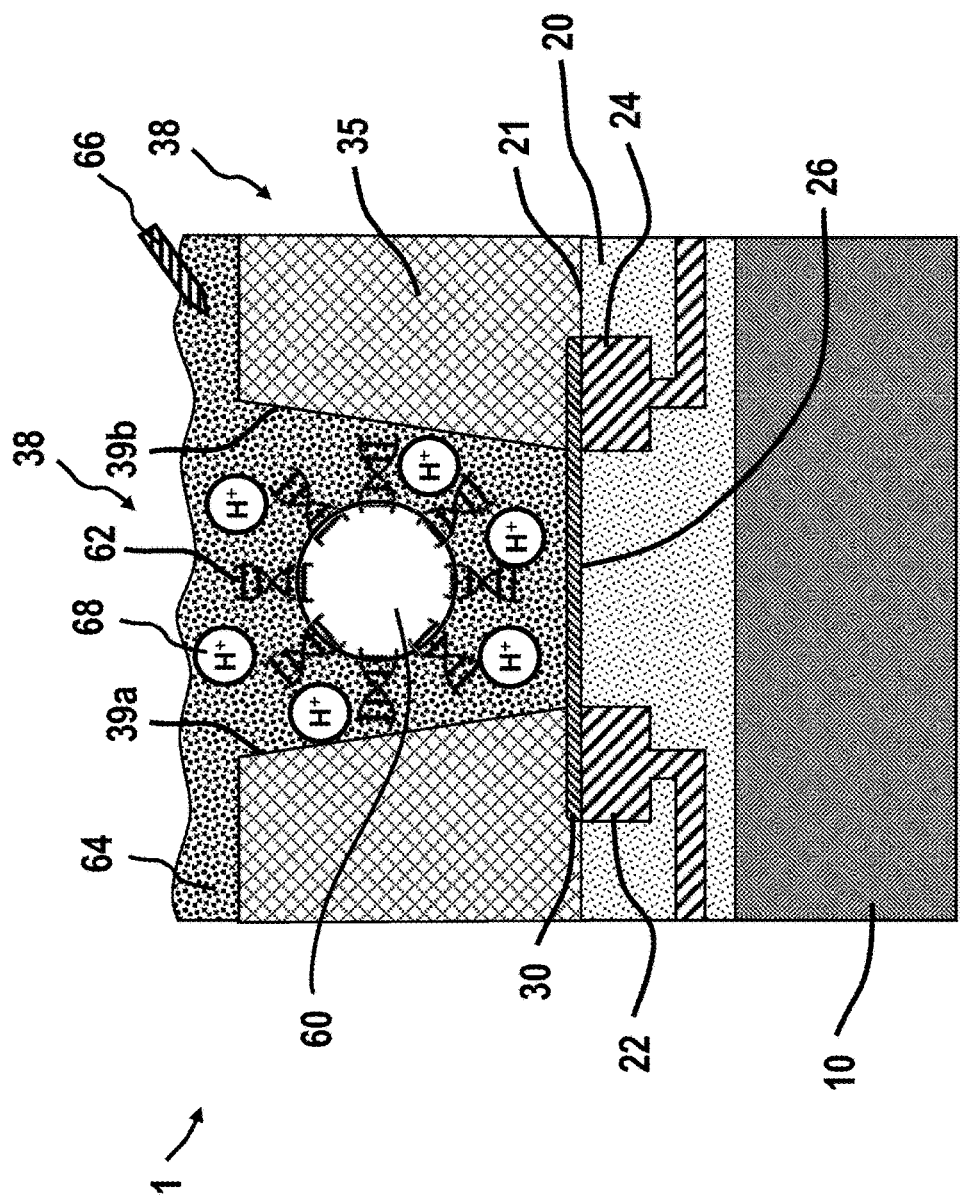

FIG. 18A is an illustration of a ChemFET having a graphene layered well structure that includes a microbead therein.

Figure 18B:
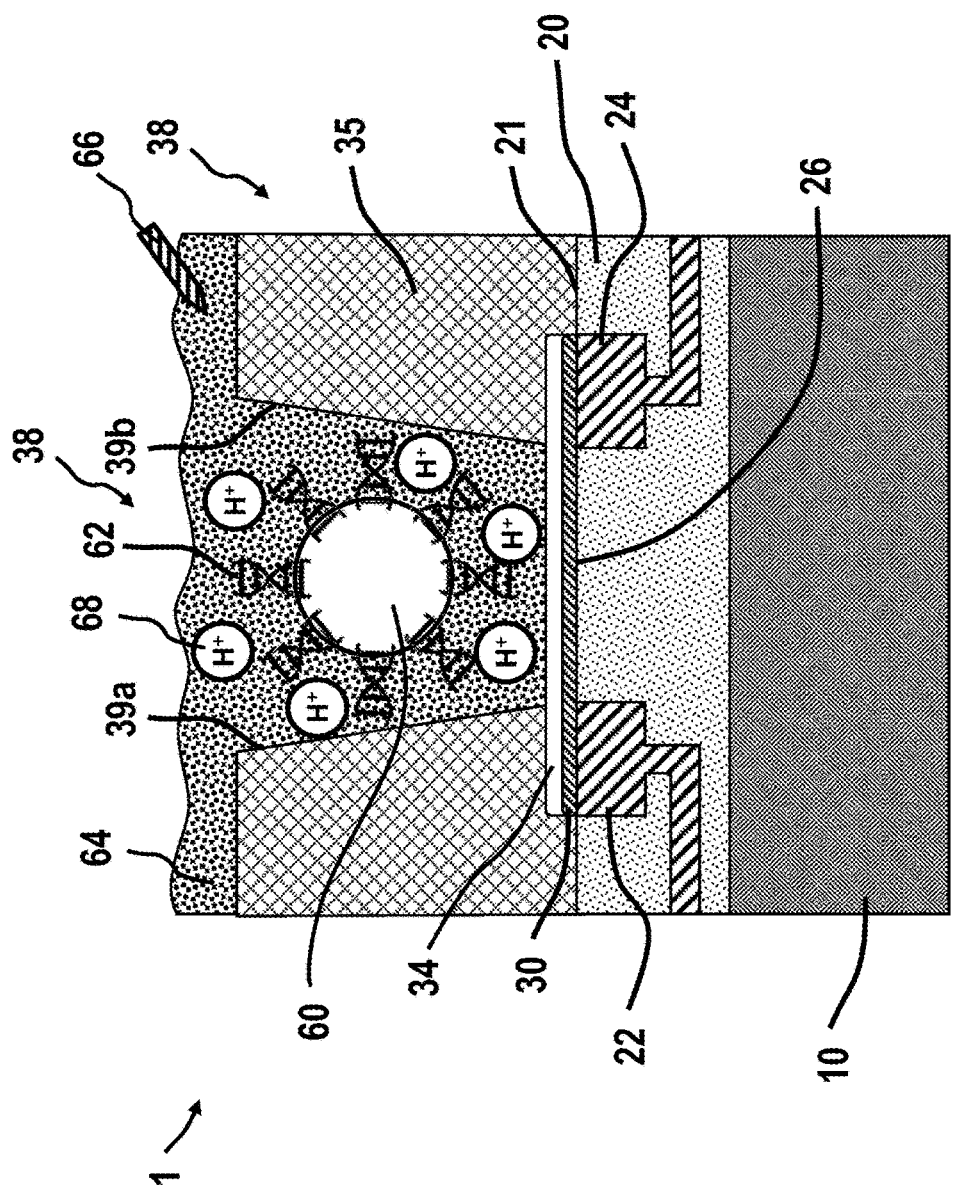

FIG. 18B is an illustration of a ChemFET, having a graphene layered well structure and an ion sensitive layer over the graphene, that includes a microbead therein.

Figure 18C:
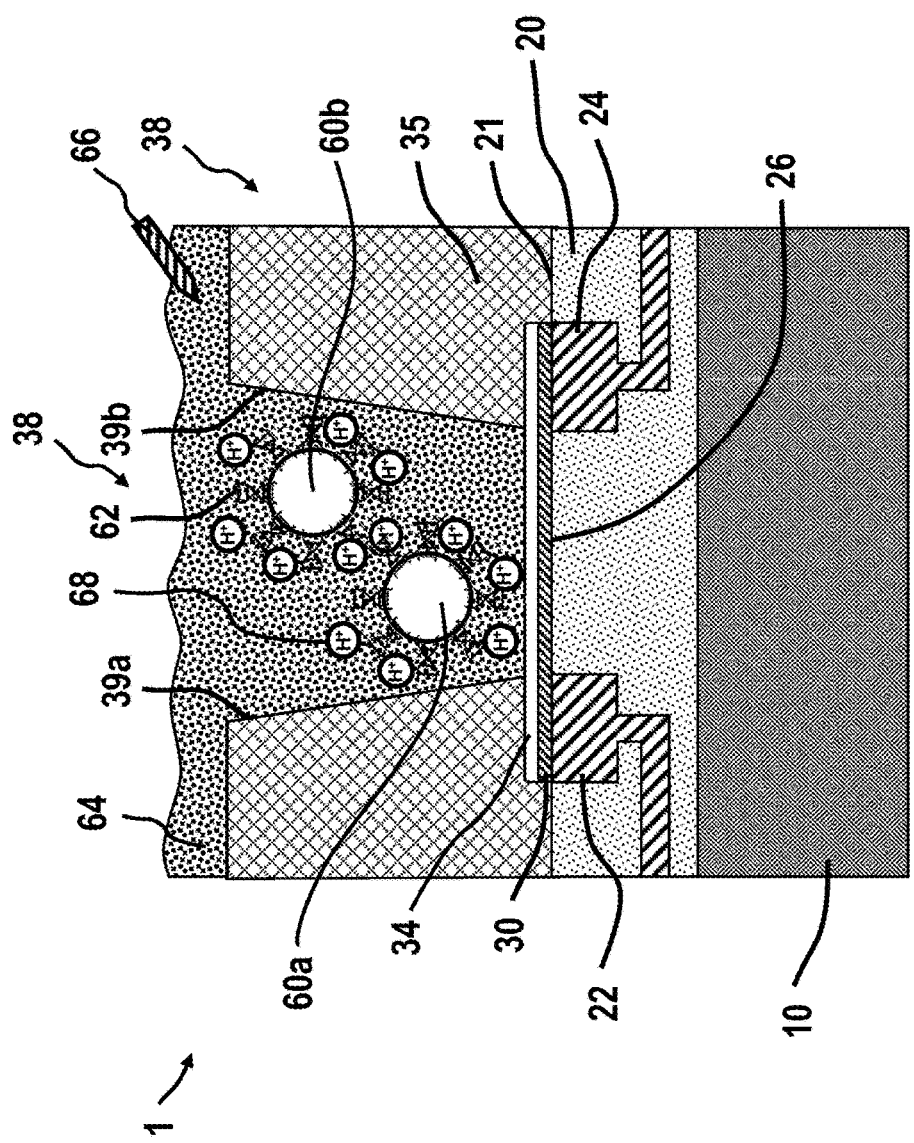

FIG. 18C is an illustration of a ChemFET having a graphene layered well structure that includes a plurality of microbeads therein.

Figure 2A:
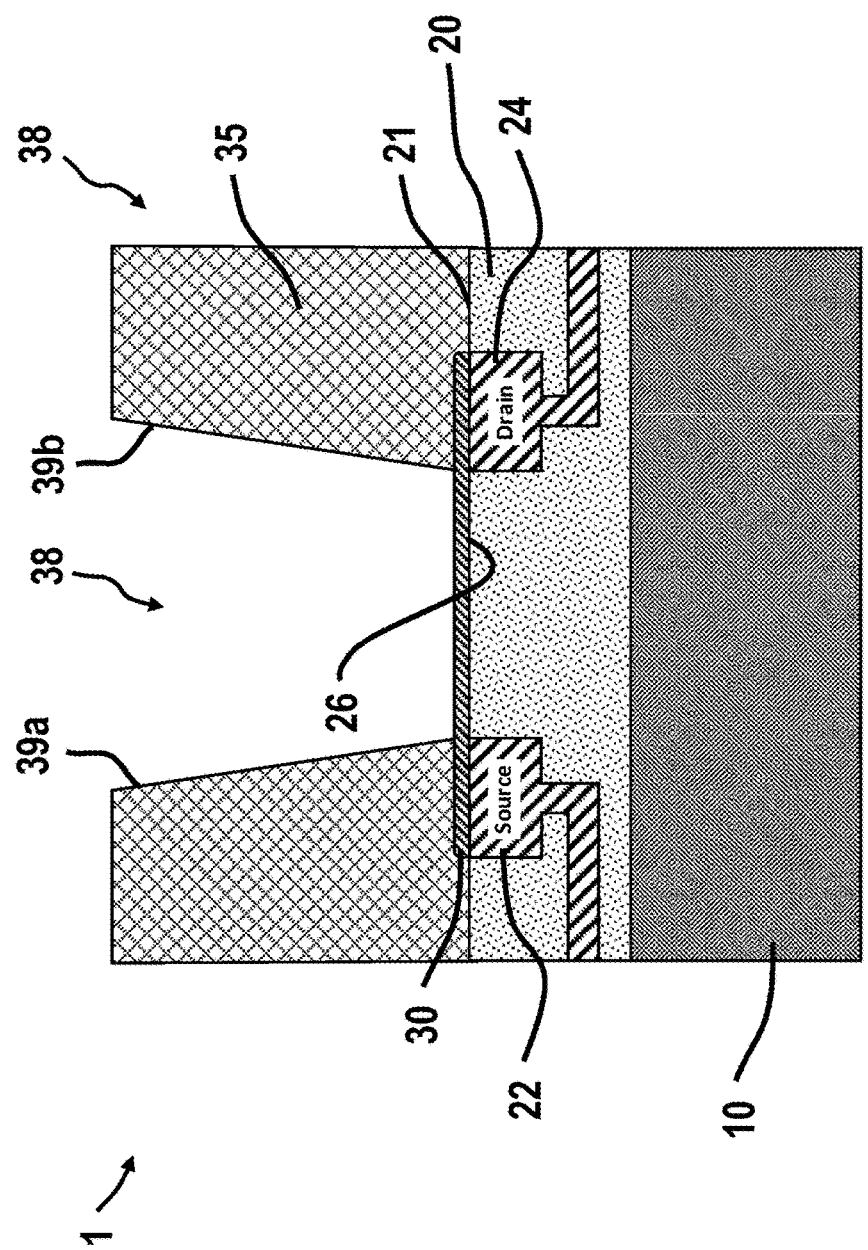
FIG. 2A is an illustration of a ChemFET having a graphene layered well structure, such as for a system for analysis of biological and/or chemical materials.
Figure 2B:
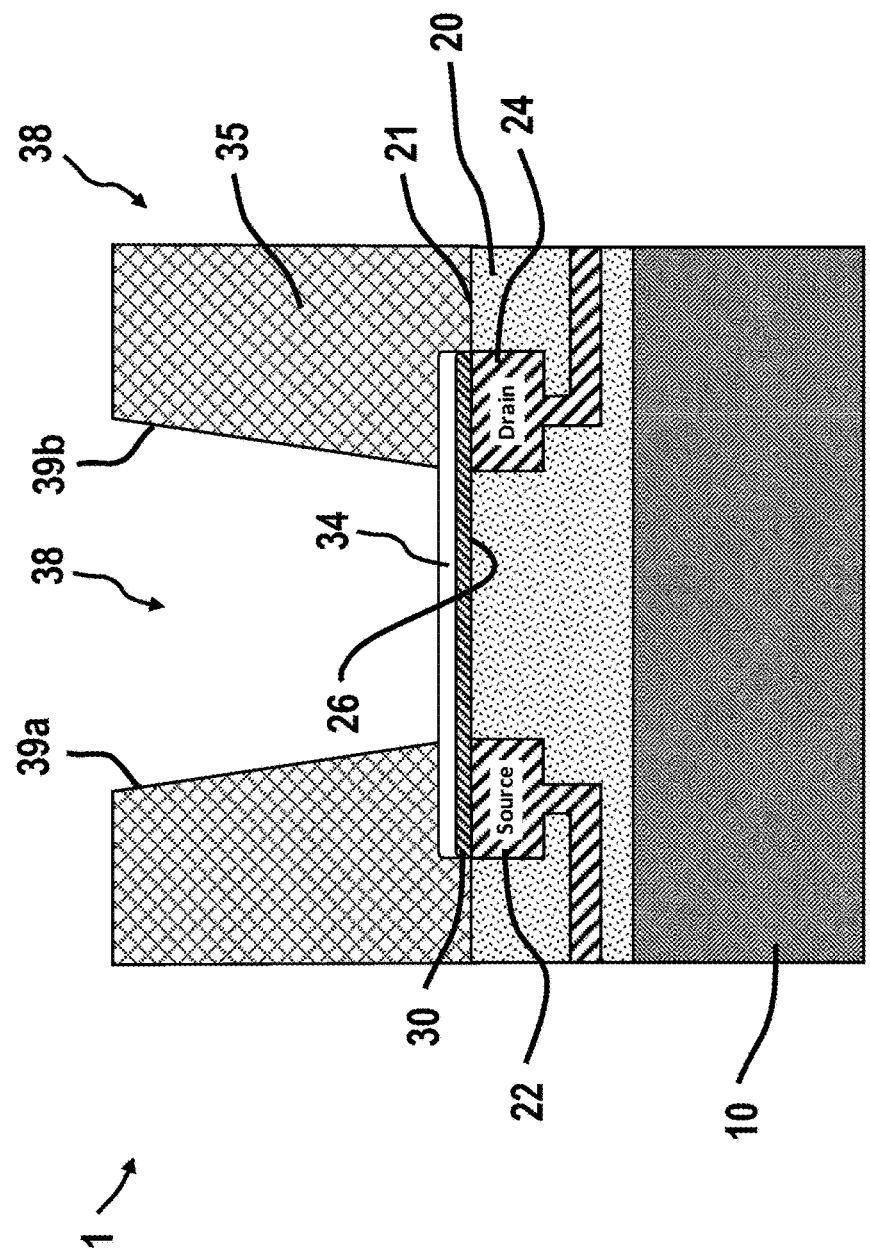
FIG. 2B is an illustration of a ChemFET of FIG. 2A, having a graphene layered well structure that further includes a sensing layer associated with the graphene layer, such as for a system for analysis of biological and/or chemical materials.
Figure 19A:
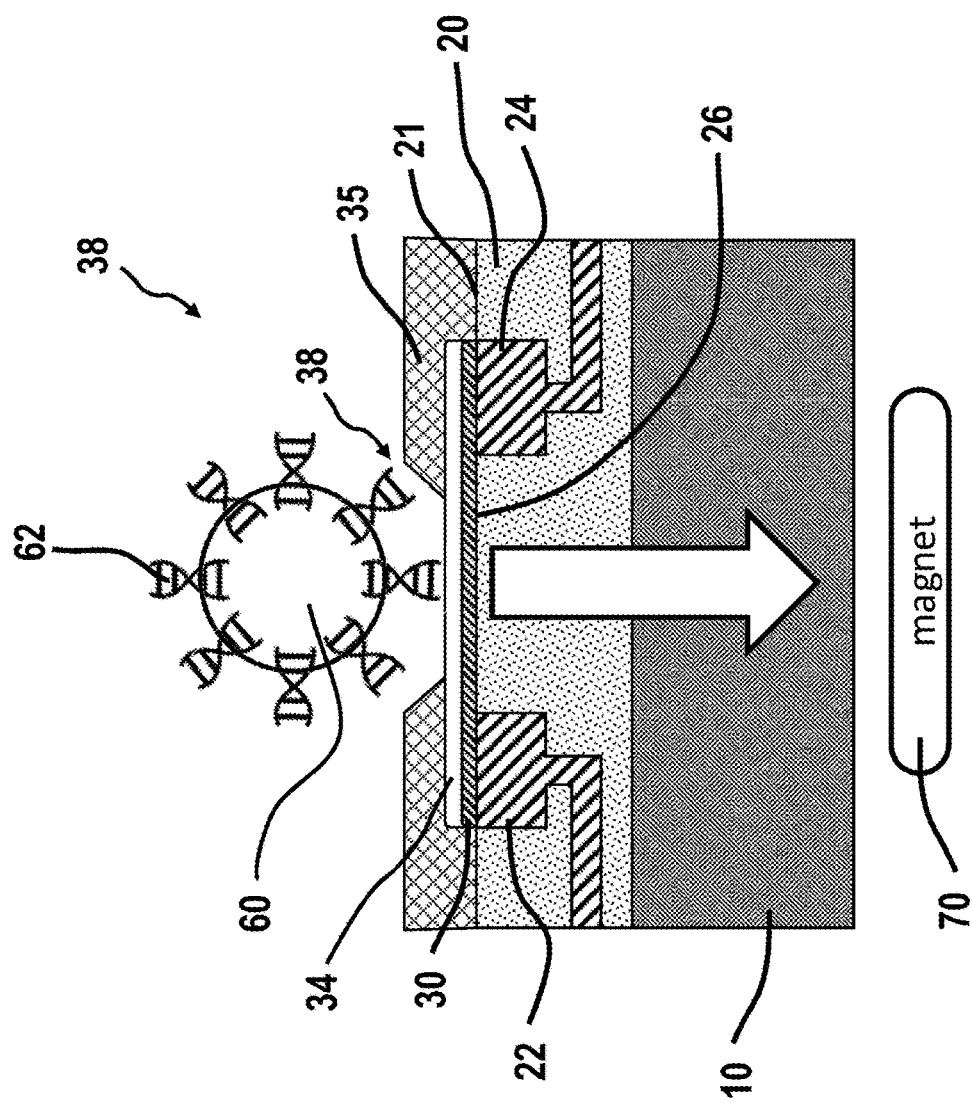

FIG. 19A is an illustration of the substrate of FIG. 2B, having a silicon dioxide layer positioned above a graphene layered sensing zone, and utilizing a magnetic field for the positioning of a nano- or microbead to be associated therewith.

Figure 19B:
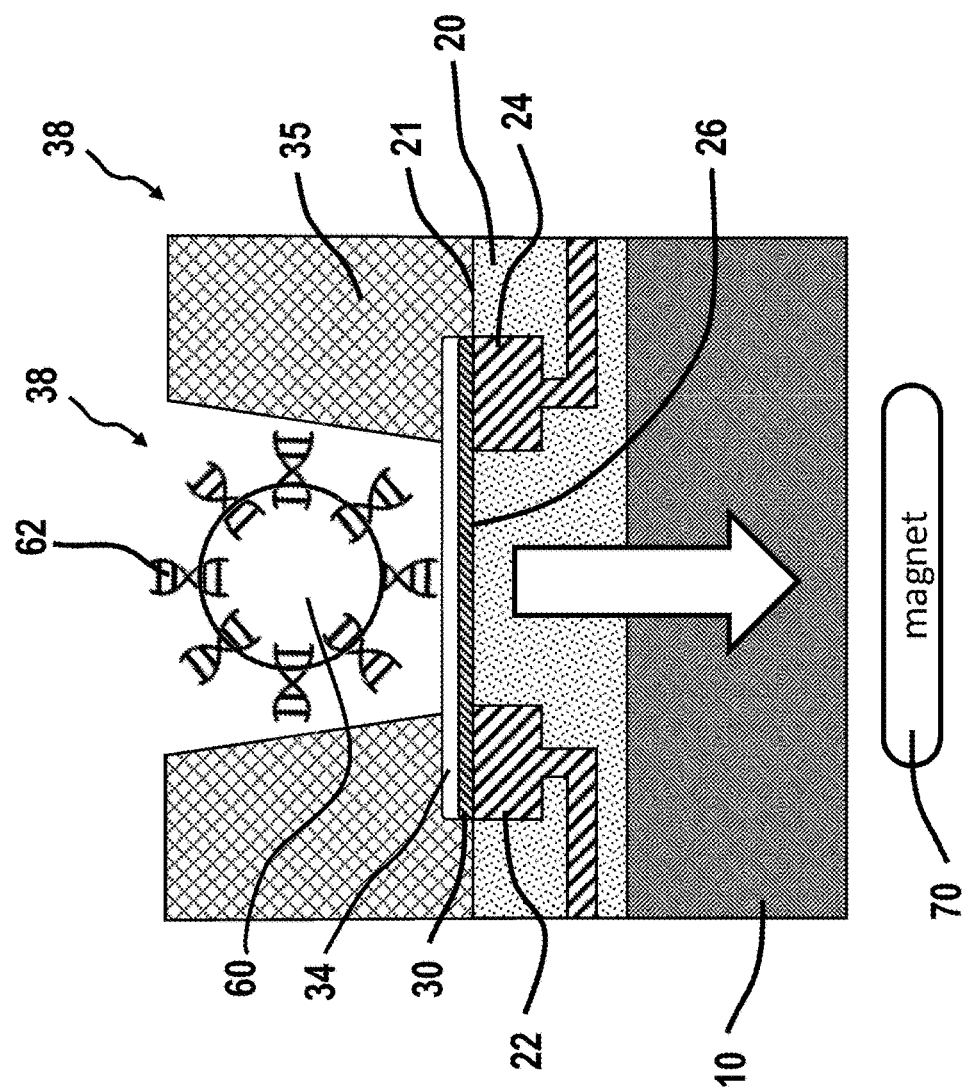

FIG. 19B is an illustration of the substrate of FIG. 2B, having a silicon dioxide layer positioned above a graphene layered sensing zone, and utilizing a magnetic field for the positioning of a nano- or microbead to be associated therewith.

Figure 19C:
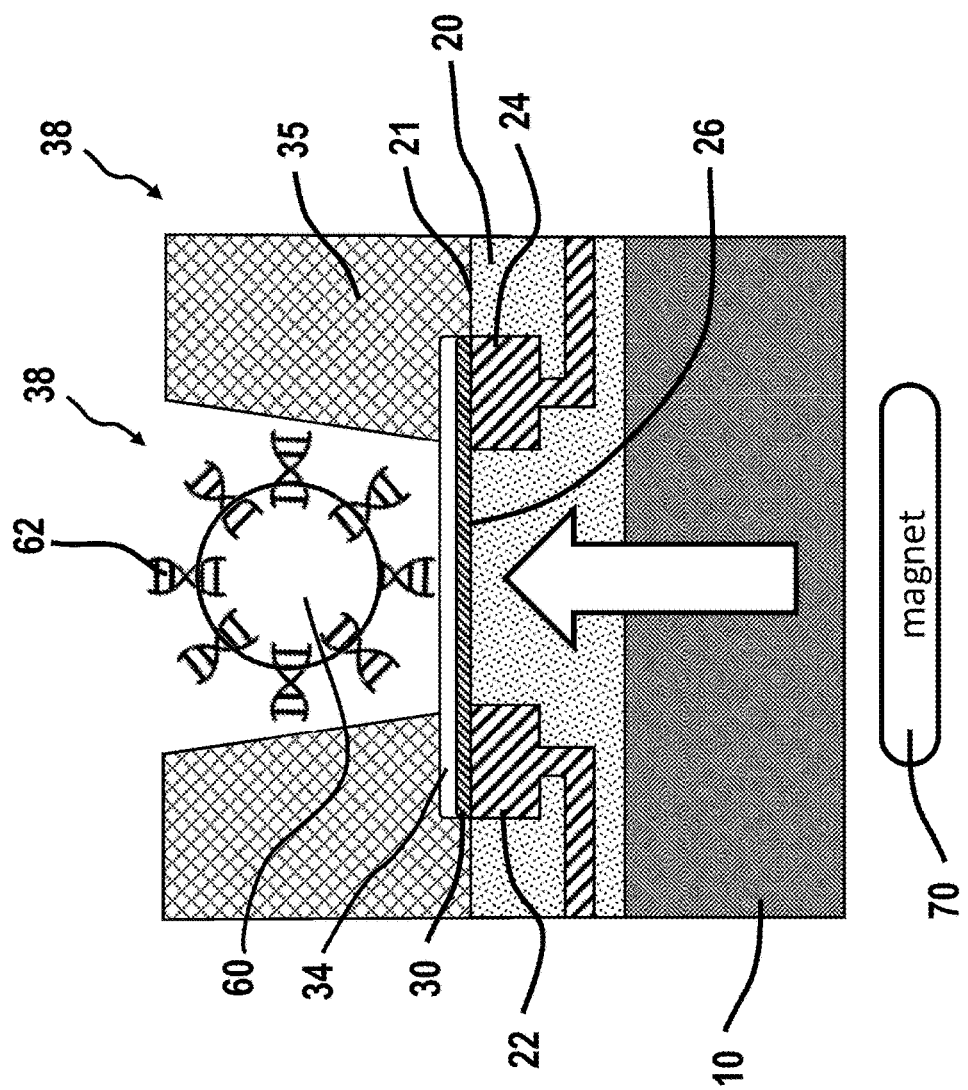

FIG. 19C is an illustration of the substrate of FIG. 19B, in an alternate configuration, such as utilizing a magnetic field reversal of a magnet to release a nano- or microbead.

Figure 19D:
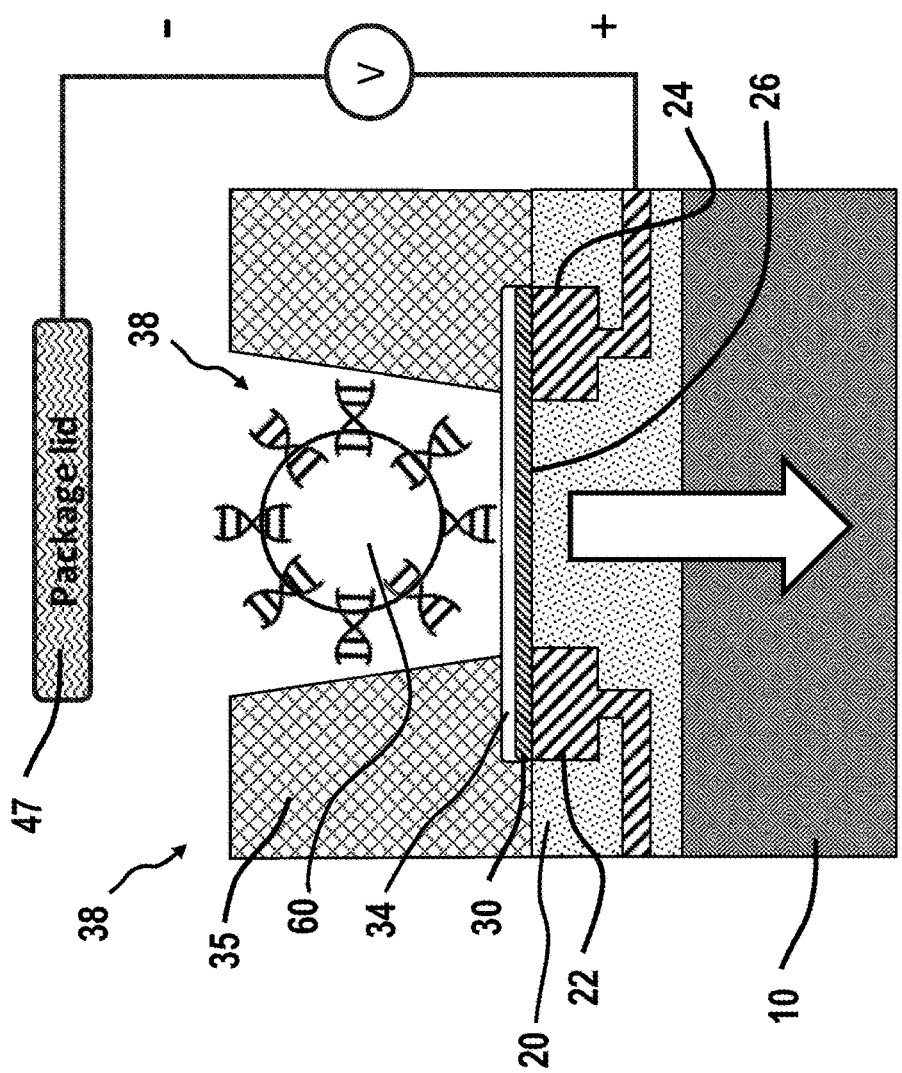

FIG. 19D is an illustration of the ChemFET of FIG. 2B, such as for a system for analysis of biological or chemical materials, utilizing an electric field for positioning of a nano- or microbead.

Figure 19E:
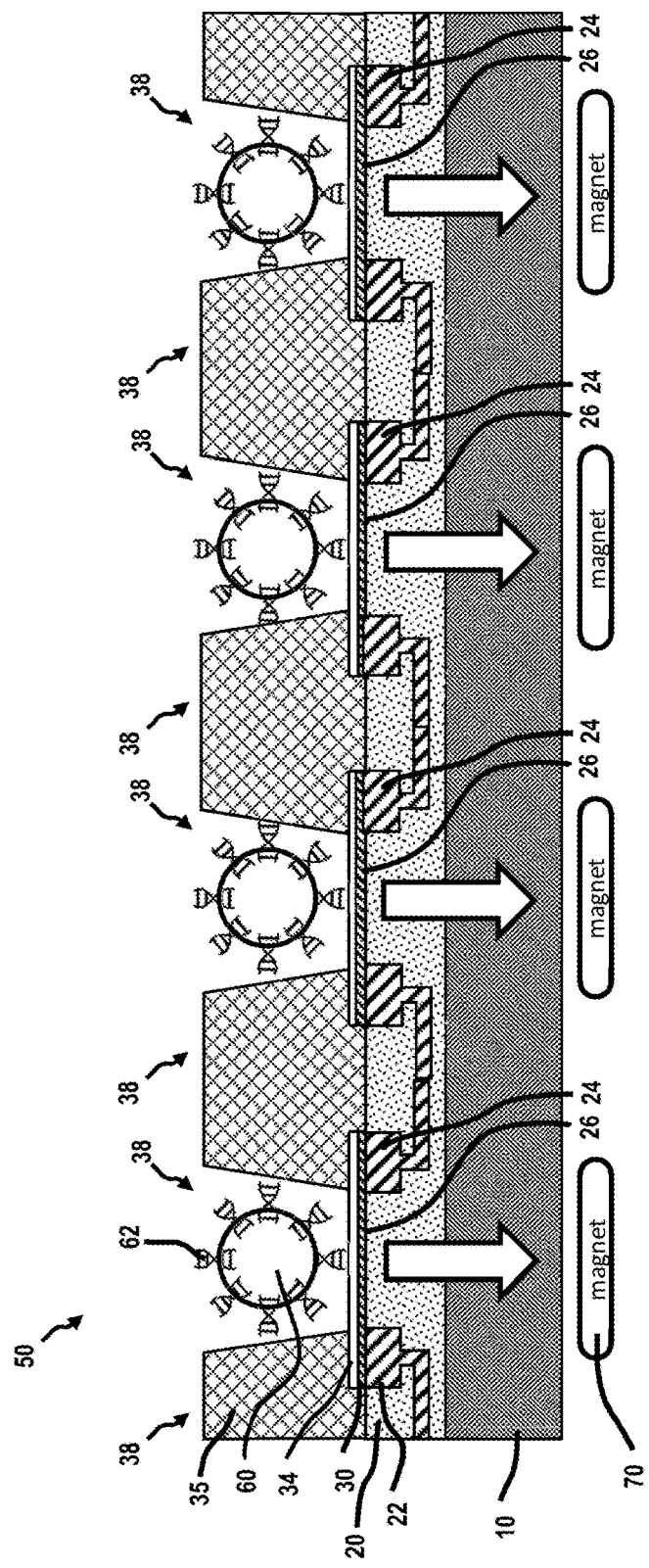

FIG. 19E is an illustration of an array of ChemFETs for a system for analysis of biological or chemical materials utilizing multiple magnets for generating a plurality of magnetic fields for positioning of nano- or microbeads within the wells.

Figure 20A:
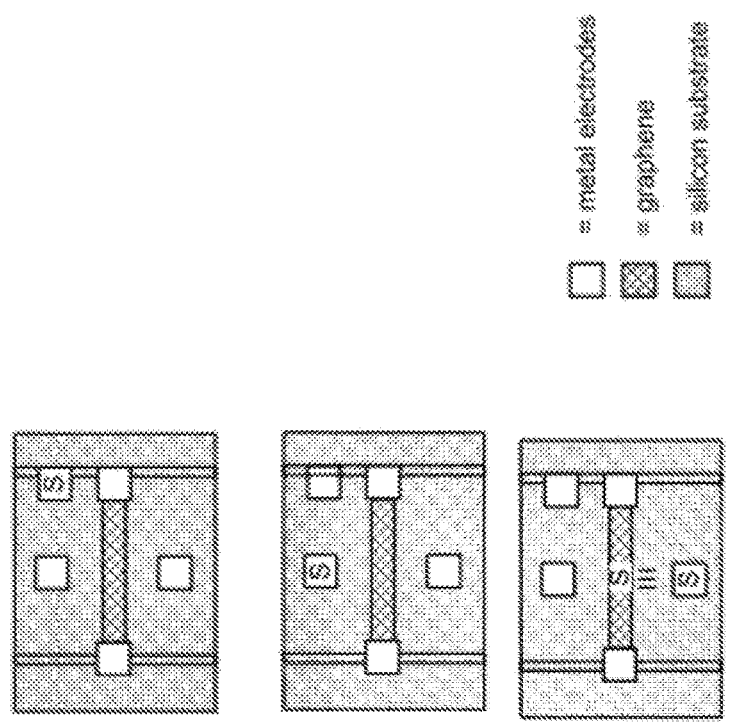

FIG. 20A is an illustration of electrowetting for biomolecule attachment.

Figure 20B:
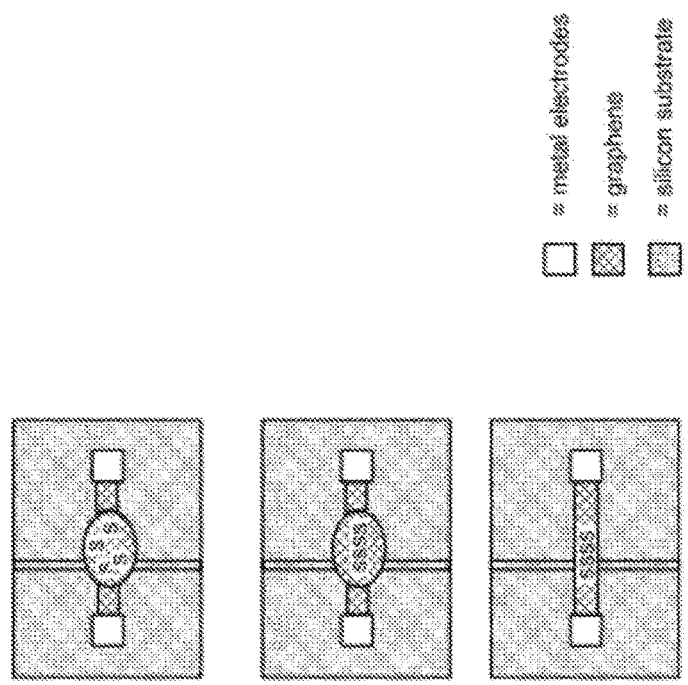

FIG. 20B is an illustration of electrophoresis for biomolecule attachment.

Figure 20C:
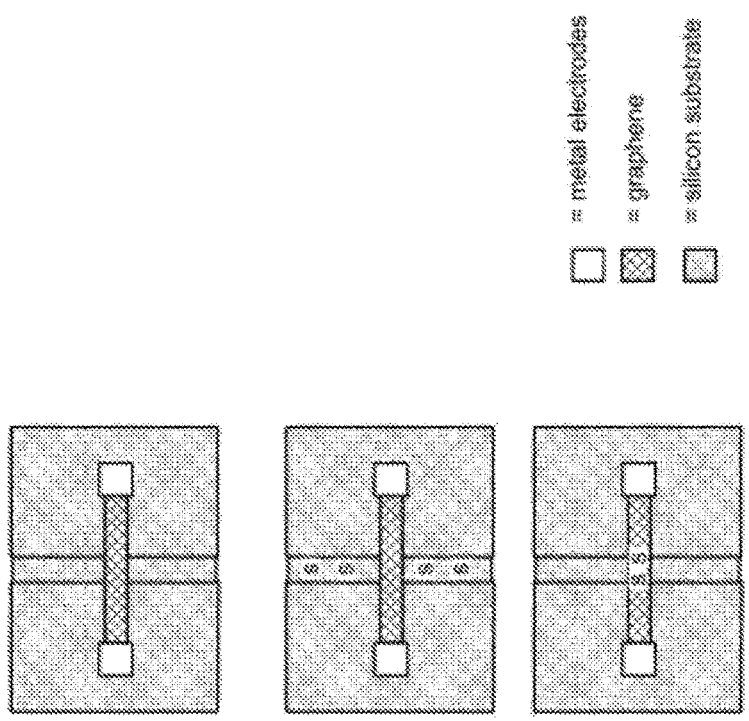

FIG. 20C is an illustration of microfluidics for biomolecule attachment.

Figure 20D:
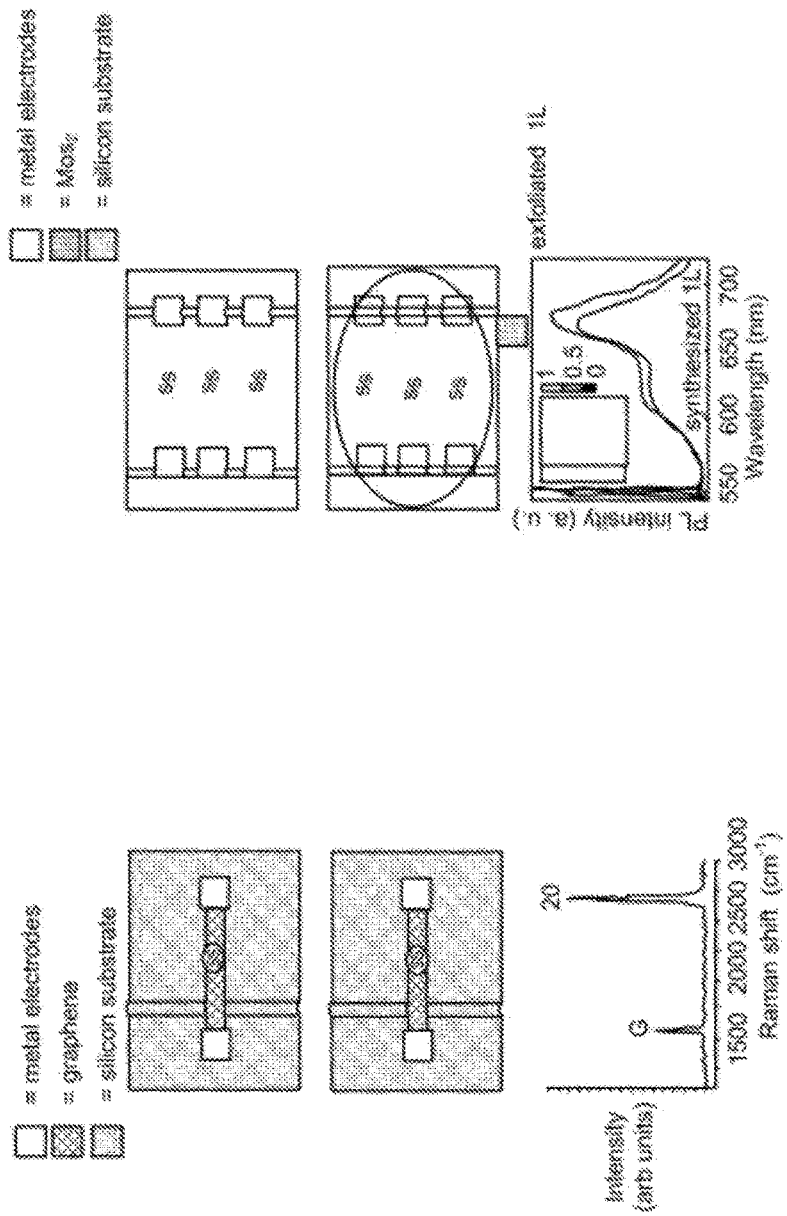

FIG. 20D is an illustration of an optical readout of DNA sequencing using nanomaterials.

Figure 21:
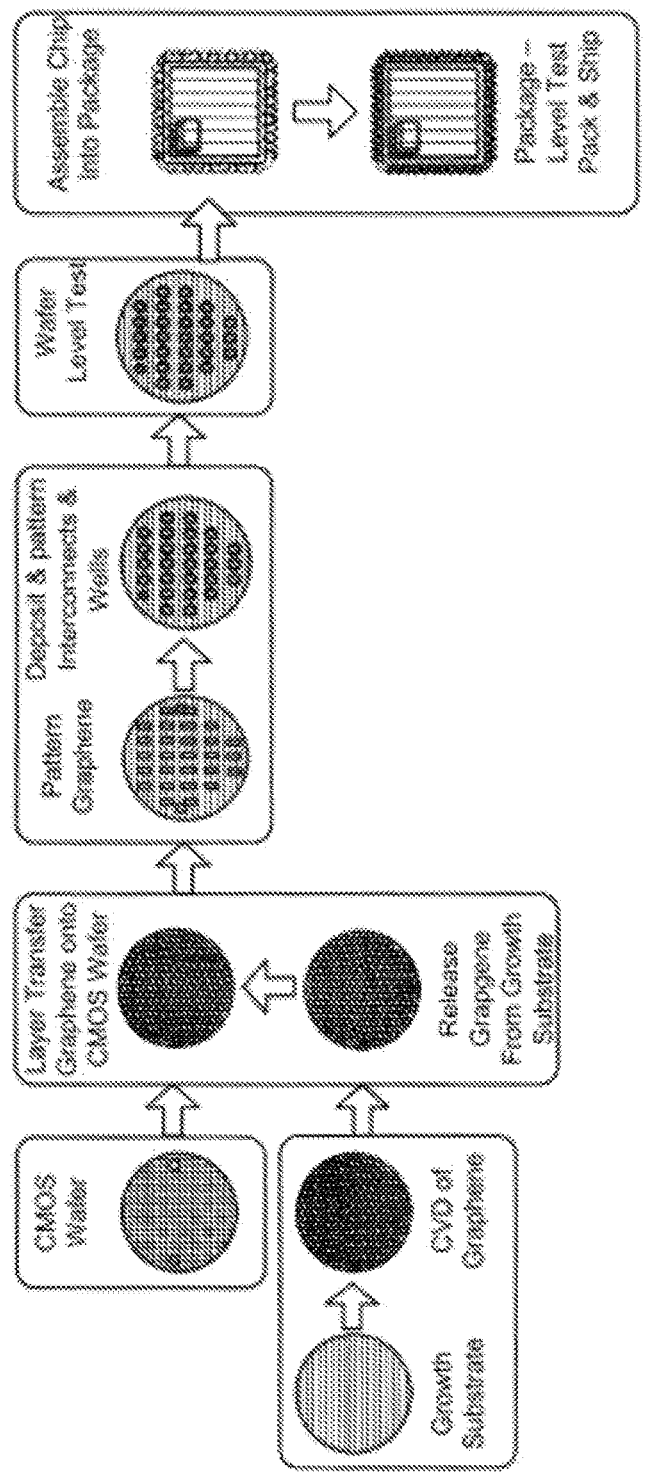

FIG. 21 is an illustration of an exemplary fabrication method as herein described.

Figure 22A:
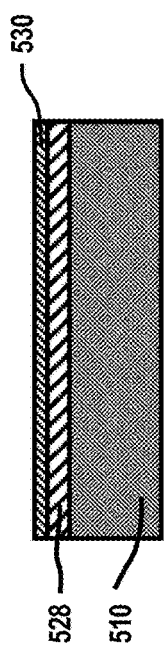

FIG. 22A illustrates a graphene growth step of direct bond transfer via Van der Waals forces, in accordance with the method steps set forth in FIG. 21.

Figure 22B:
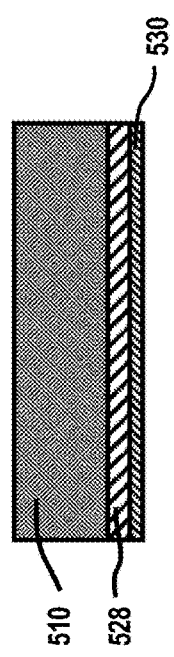

FIG. 22B illustrates a wafer-flipping step of direct bond transfer via Van der Waals forces.

Figure 22C:
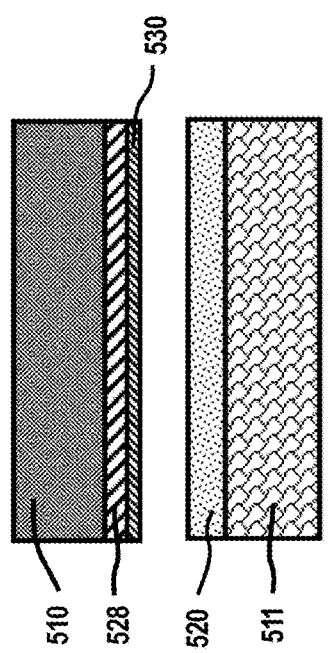

FIG. 22C illustrates a ROIC alignment step of direct bond transfer via Van der Waals forces.

Figure 22D:
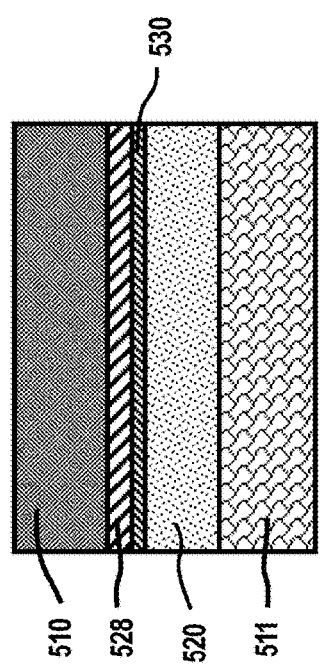

FIG. 22D illustrates a bonding graphene to an oxide on the ROIC wafer step of direct bond transfer via Van der Waals forces.

Figure 22E:
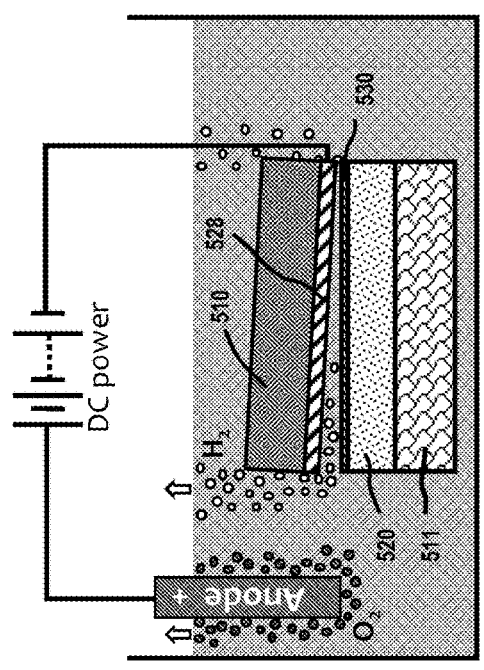

FIG. 22E illustrates a use of water electrolysis to create hydrogen bubbles to separate the graphene from the growth platform.

Figure 22F:
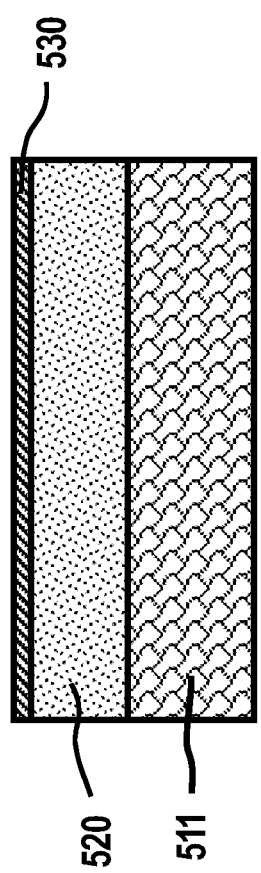

FIG. 22F illustrates a growth substrate removal step of direct bond transfer via Van der Waals forces.

Figure 23A:
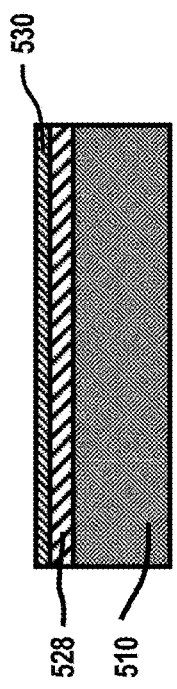

FIG. 23A illustrates a graphene growth step of direct bond transfer via fusion bonding.

Figure 23B:
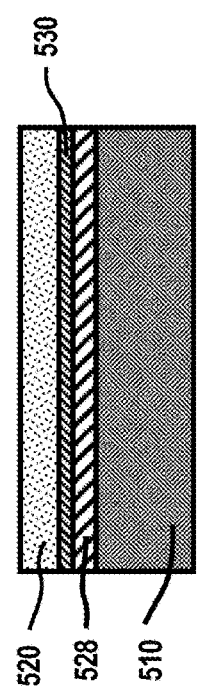

FIG. 23B illustrates a deposit cover material and CMP or polish surface step of direct bond transfer via fusion bonding.

Figure 23C:
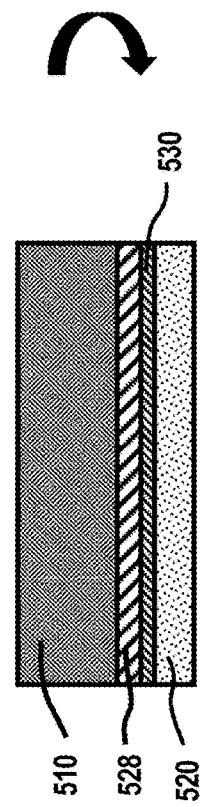

FIG. 23C illustrates a wafer-flipping step of direct bond transfer via fusion bonding.

Figure 23D:
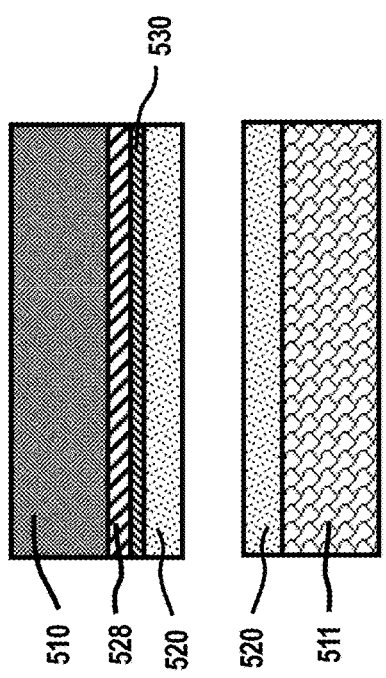

FIG. 23D illustrates a ROIC preparation and ROIC alignment step of direct bond transfer via fusion bonding.

Figure 23E:
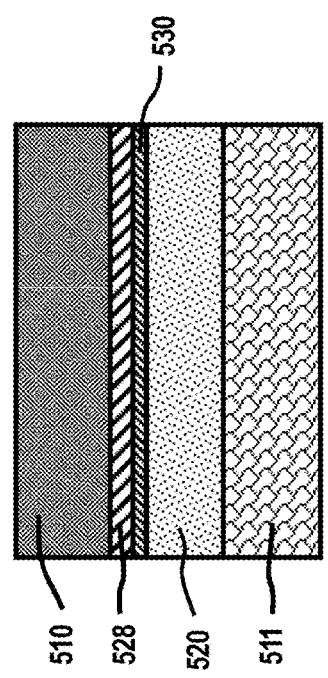

FIG. 23E illustrates a bonding a cover material to a ROIC wafer top insulator step of direct bond transfer via fusion bonding.

Figure 23F:
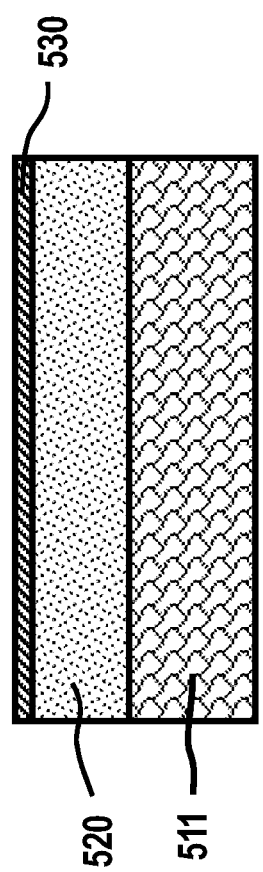

FIG. 23F illustrates a growth substrate removal from the ROIC wafer, leaving the graphene on the ROIC step of direct bond transfer via fusion bonding.

Figure 24A:
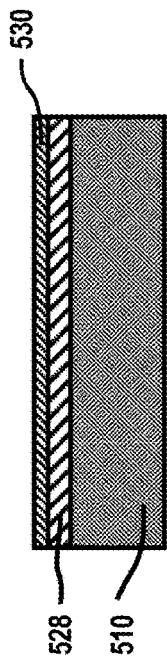

FIG. 24A illustrates a graphene growth step of direct bond transfer via fusion bonding.

Figure 24B:
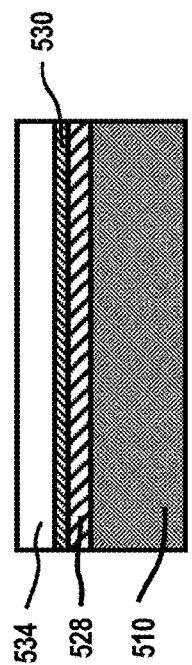

FIG. 24B illustrates an ion sensitive oxide formed on the graphene layer on a growth wafer.

Figure 24C:
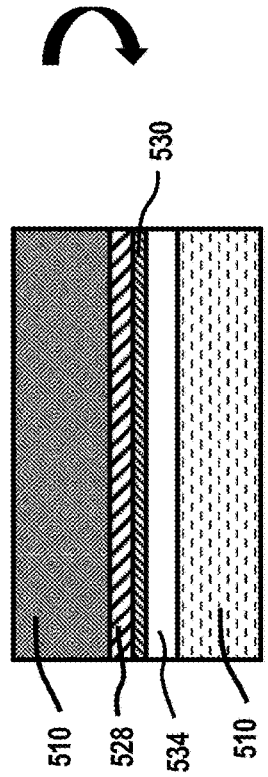

FIG. 24C illustrates a temporary bonding of the ion sensitive oxide to a handle wafer.

Figure 24D:
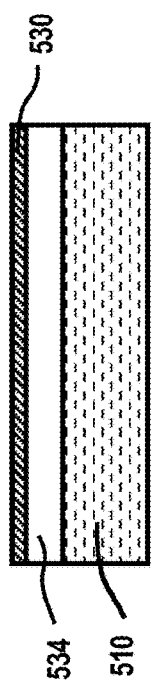

FIG. 24D illustrates a release of the graphene layer from the growth wafer.

Figure 24E:
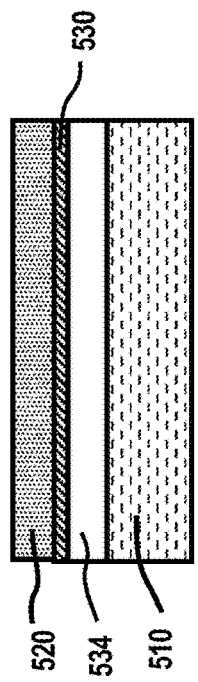

FIG. 24E illustrates a deposit of a cover material and CMP or polish surface step prior to direct bond transfer via fusion bonding.

Figure 24F:
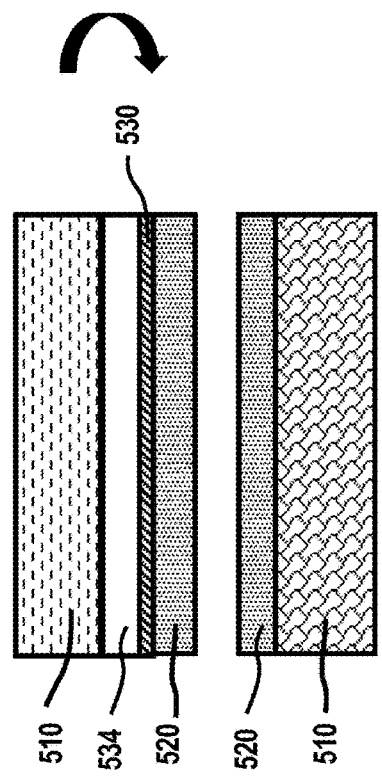

FIG. 24F illustrates a wafer-flipping and ROIC aligning step of direct bond transfer via fusion bonding.

Figure 24G:
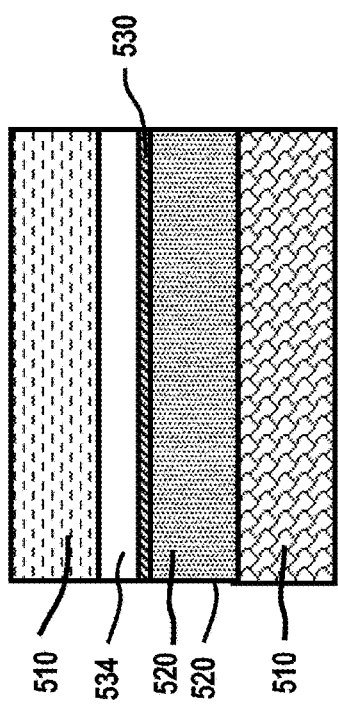

FIG. 24G illustrates a bonding a cover material to a ROIC wafer top insulator step of direct bond transfer via fusion bonding.

Figure 24H:
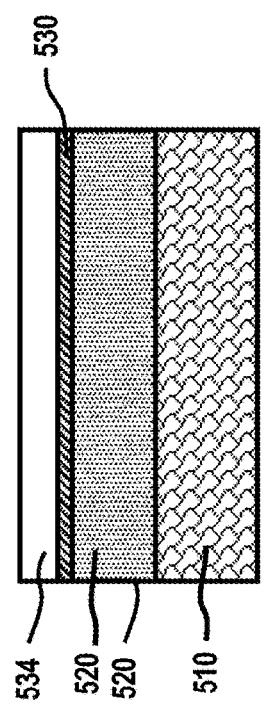

FIG. 24H illustrates a handle substrate removal from the ROIC wafer, leaving the graphene, covered by an ion sensitive layer, on the ROIC step of direct bond transfer via fusion bonding.

Figure 25:
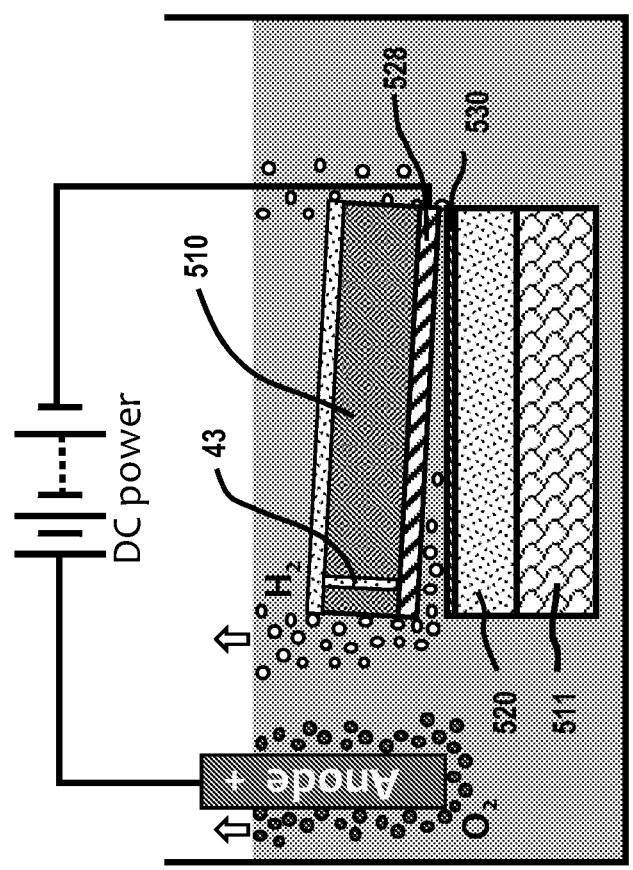

FIG. 25 illustrates a bubble release process for a graphene layer from its growth substrate aided by a through silicon via.

FIG. 26A illustrates a graphene with channels or divots for water access and more efficient bubble transfer growth step of direct bond transfer via Van der Waals forces, in accordance with the method steps set forth in FIG. 21.

FIG. 26B illustrates a wafer-flipping step of direct bond transfer via Van der Waals forces.

FIG. 26C illustrates a ROIC alignment step of direct bond transfer via Van der Waals forces.

FIG. 26D illustrates a bonding graphene to an oxide on the ROIC wafer step of direct bond transfer via Van der Waals forces.

FIG. 26E illustrates a use of water electrolysis to create hydrogen bubbles to separate the graphene from the growth platform step of direct bond transfer via Van der Waals forces.

FIG. 26F illustrates a growth substrate removal step of direct bond transfer via Van der Waals forces.

Figure 27:
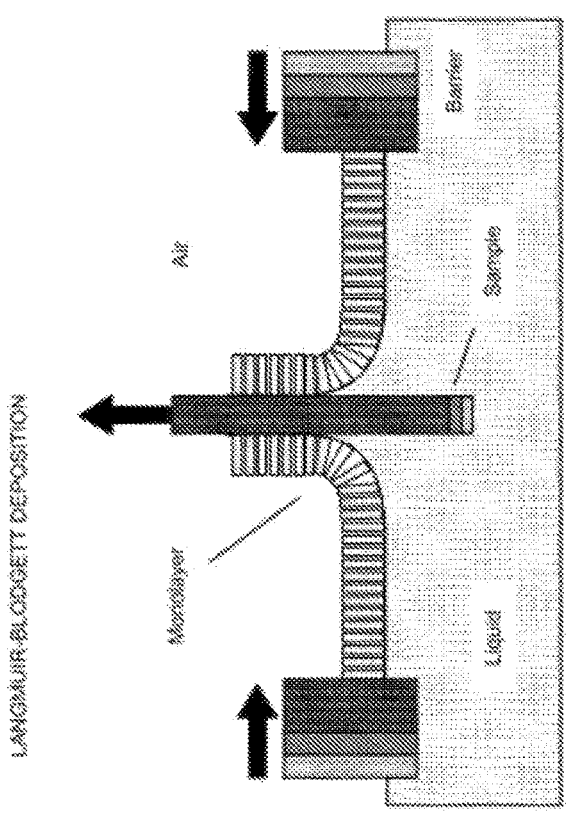

FIG. 27 illustrates a Langmuir Blodgett deposition process as an alternative option for the bubble release steps of FIG. 21.

Figure 28A:
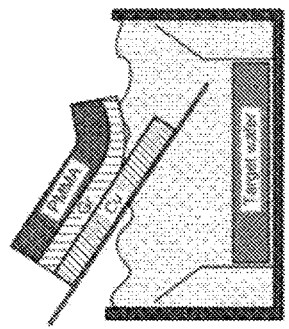

FIG. 28A illustrates a controlled immersion and bubble release step of the alternative option for the bubble release step of FIG. 21.

Figure 28B:
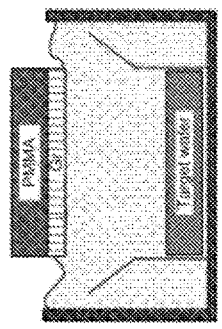

FIG. 28B illustrates a graphene and PMMA fully released step of the alternative option for the bubble release step of FIG. 21.

Figure 28C:
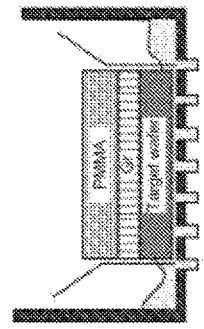

FIG. 28C illustrates a drain solution (while the graphene is aligned to the wafer) to transfer a layer onto a target step of the alternative option for the bubble release step of FIG. 21.

Figure 29E:
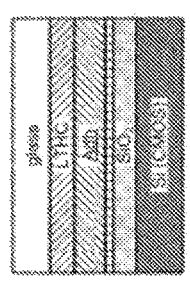
Figure 29F:
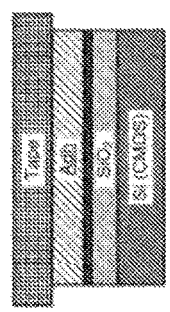
Figure 29G:
Figure 29A:

FIG. 29A illustrates a glass carrier preparation step of an adhesive temporary bond material process.

Figure 29B:
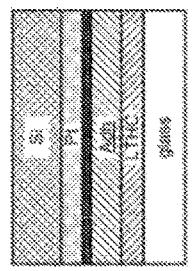

FIG. 29B illustrates room temperature ultraviolet energy bonding step of an adhesive temporary bond material process.

Figure 29C:
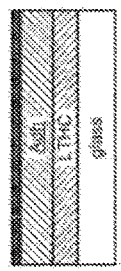

FIG. 29C illustrates an optional thin silicon wafer growth step of an adhesive temporary bond material process.

Figure 29D:
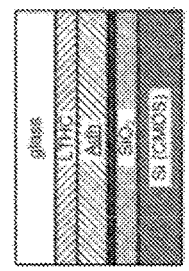

FIG. 29D illustrates a bonding the graphene layer to the target step of an adhesive temporary bond material process.

FIG. 29E illustrates a laser glass release step of an adhesive temporary bond material process.

FIG. 29F illustrates an apply tape step of an adhesive temporary bond material process.

FIG. 29G illustrates a peel off the adhesive material step of an adhesive temporary bond material process.

Figure 30:
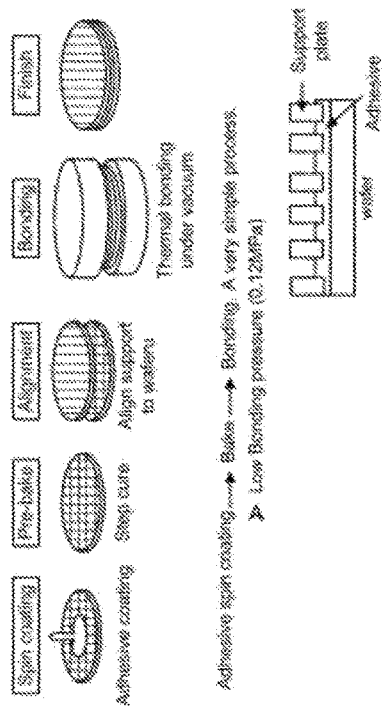

FIG. 30 illustrates an adhesive temporary bond material process.

Figure 31:
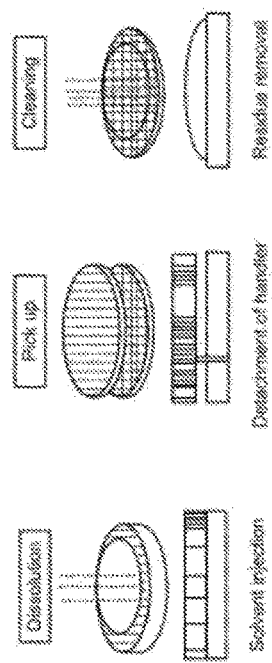

FIG. 31 illustrates an adhesive temporary bond material process.

Figure 32A:
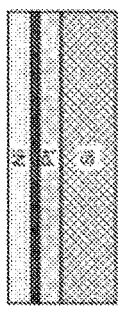

FIG. 32A illustrates a nickel deposition on a graphene layer step of an adhesive temporary bond process with a nickel deposition layer.

Figure 32B:
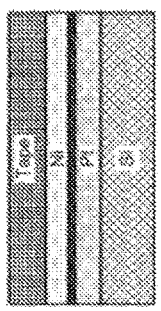

FIG. 32B illustrates a tape lamination step of an adhesive temporary bond process with a nickel deposition layer.

Figure 32C:
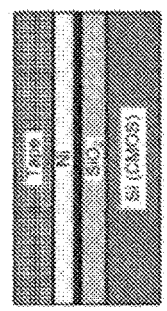

FIG. 32C illustrates a tape peel and graphene transfer step of an adhesive temporary bond material process with a nickel deposition layer.

Figure 32D:
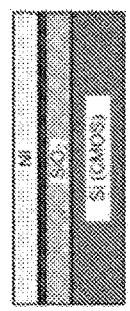

FIG. 32D illustrates a peel tape from the nickel layer step of an adhesive temporary bond material process with a nickel deposition layer.

Figure 32E:

FIG. 32E illustrates a wet etch to remove the nickel layer step of an adhesive temporary bond material process with a nickel deposition layer.

Figure 33A:
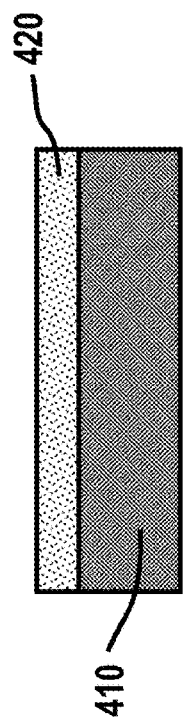

FIG. 33A shows a side sectional view of a semiconductor substrate coated with an insulated dielectric layer during fabrication of a ChemFET of the invention.

Figure 33B:
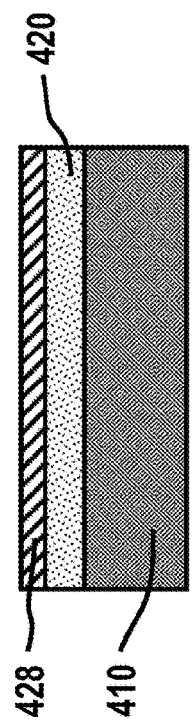

FIG. 33B illustrates a side sectional view of a conductive material layer on an insulated dielectric layer during fabrication of a ChemFET of the invention.

Figure 33C:
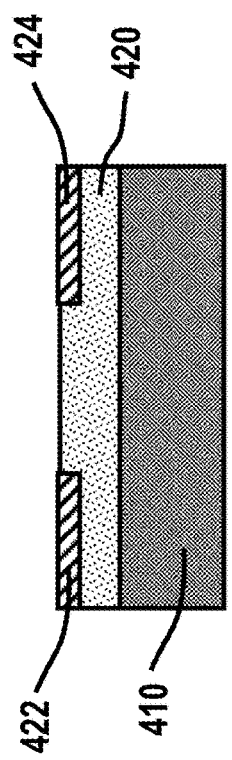

FIG. 33C shows a side sectional view of a patterned conductive material layer during fabrication of a ChemFET of the invention.

Figure 33D:
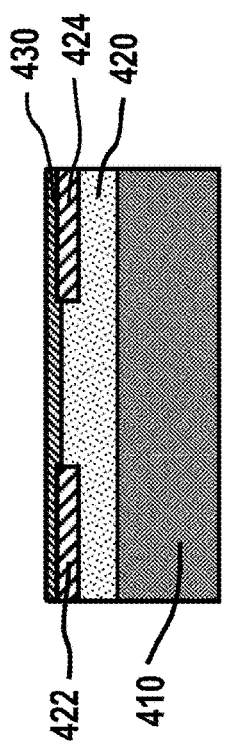

FIG. 33D illustrates a side sectional view of a 1D or 2D nanomaterial layer applied over electrodes during fabrication of a ChemFET of the invention.

Figure 33E:
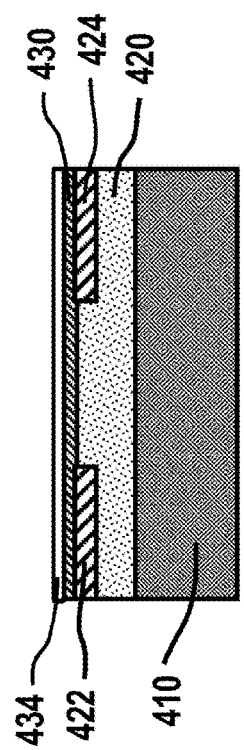

FIG. 33E shows a side sectional view of an analyte or reaction sensitive layer applied over a 1D or 2D nanomaterial layer during fabrication of a ChemFET of the invention.

Figure 33F:
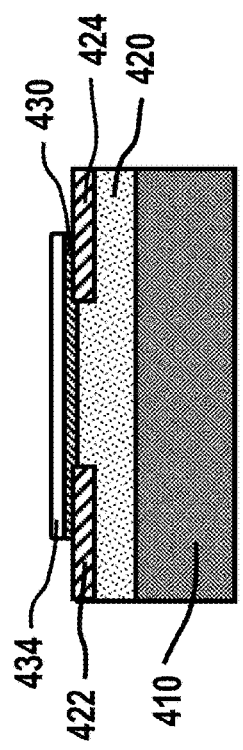

FIG. 33F illustrates a side sectional view of analyte or reaction sensitive and 1D or 2D nanomaterial layers that have been patterned during fabrication of a ChemFET of the invention.

Figure 33G:
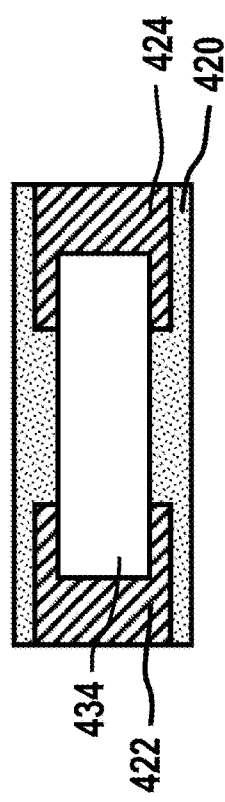

FIG. 33G shows a top down view of an analyte or reaction sensitive layer, a conductive material layer and an insulated dielectric layer during fabrication of a ChemFET of the invention.

Figure 33H:
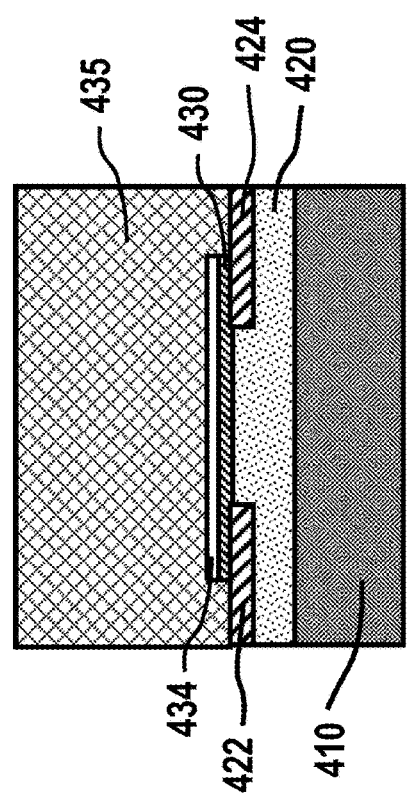

FIG. 33H shows a side sectional view of an integrated circuit with a insulating passivation layer during the process of forming a well proximate the integrated circuit.

Figure 33I:
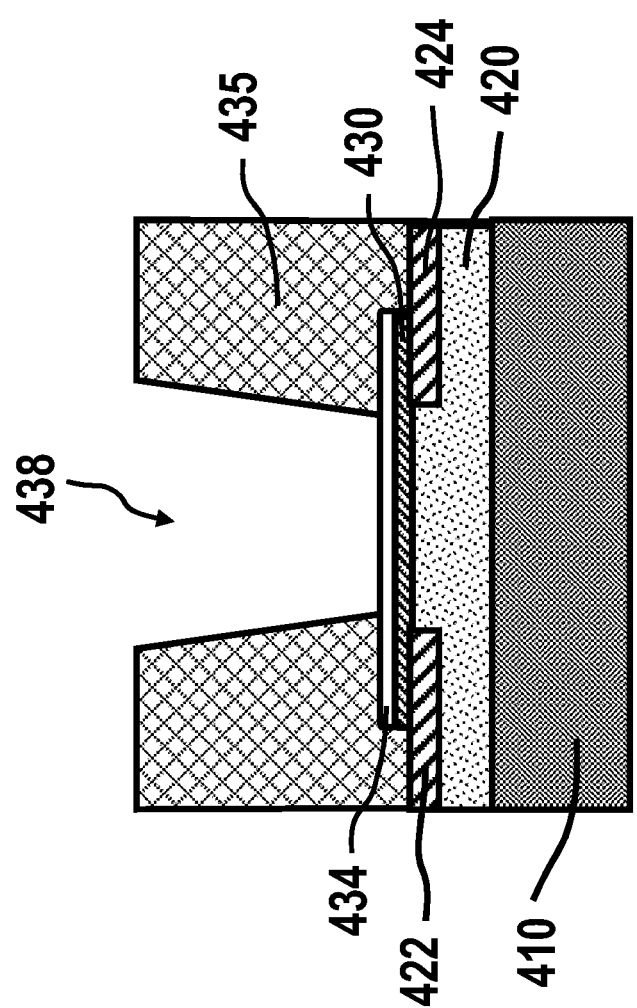

FIG. 33I illustrates a side sectional view of an integrated circuit with a patterned insulating passivation layer during the process of forming a well proximate the integrated circuit.

Figure 34A:
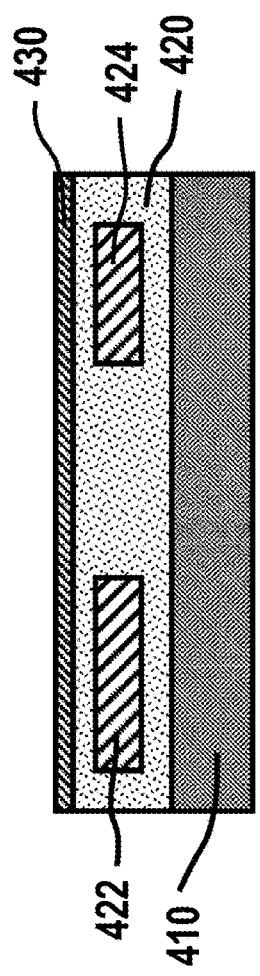

FIG. 34A illustrates a graphene on a ROIC wafer step of a CMOS integration method.

Figure 34B:
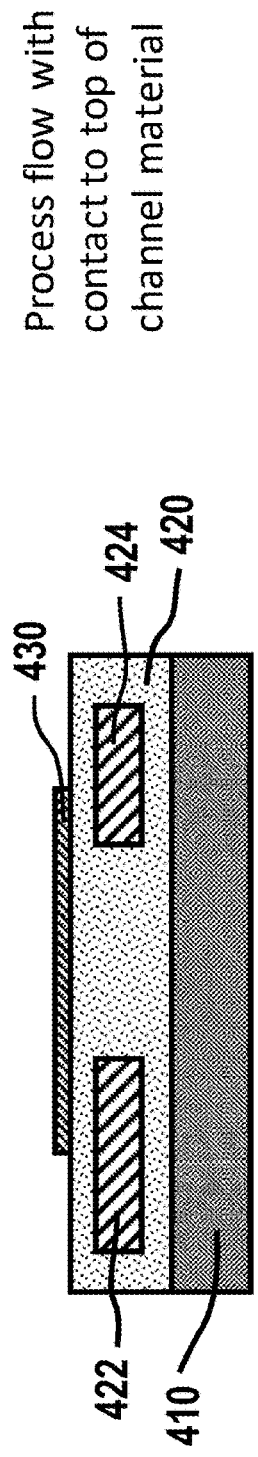

FIG. 34B illustrates a patterning a graphene layer to form channels step of a CMOS integration method.

Figure 34C:
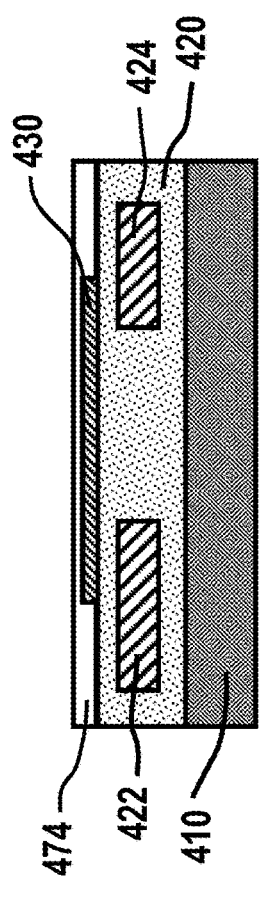

FIG. 34C illustrates a depositing an etch stop layer over a graphene layer to step of a CMOS integration method.

Figure 34D:
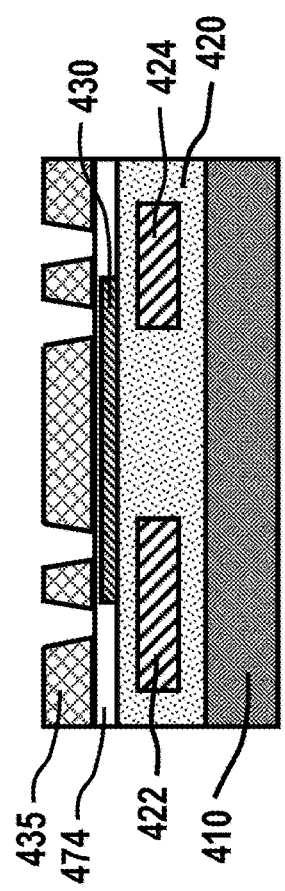

FIG. 34D illustrates a deposit, pattern and etch a thick insulator layer step of a CMOS integration method.

Figure 34E:
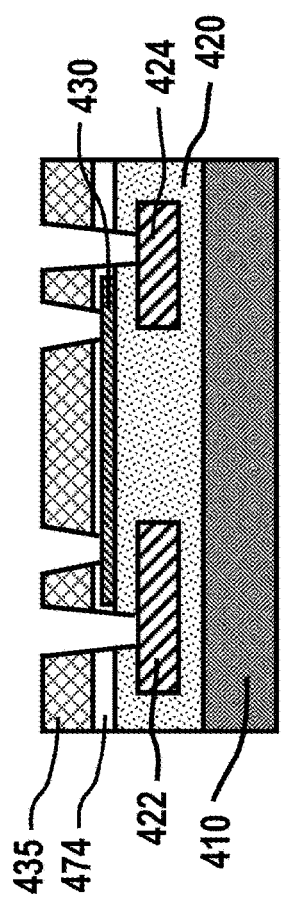

FIG. 34E illustrates a wet etch ESL, pattern and DRIE oxide over interconnects step of a CMOS integration method.

Figure 34F:
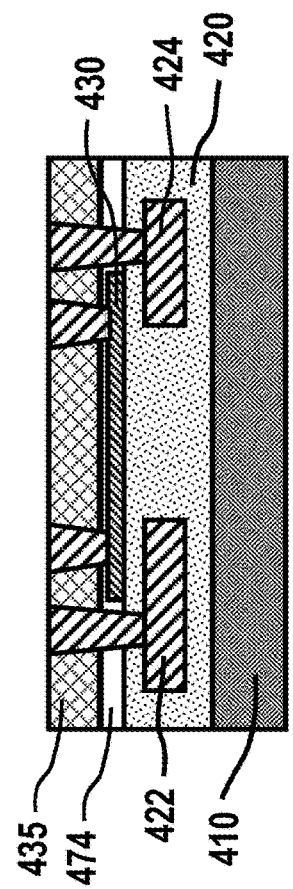

FIG. 34F illustrates a deposit a barrier, liner, copper plate, CMP step of a CMOS integration method.

Figure 34G:
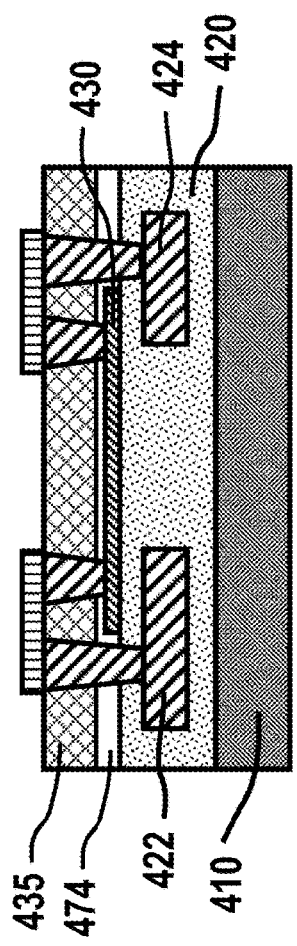

FIG. 34G illustrates a deposit a barrier/adhesion layer, deposit aluminum, pattern, etch aluminum interconnect and pad layer step of a CMOS integration method.

Figure 34H:
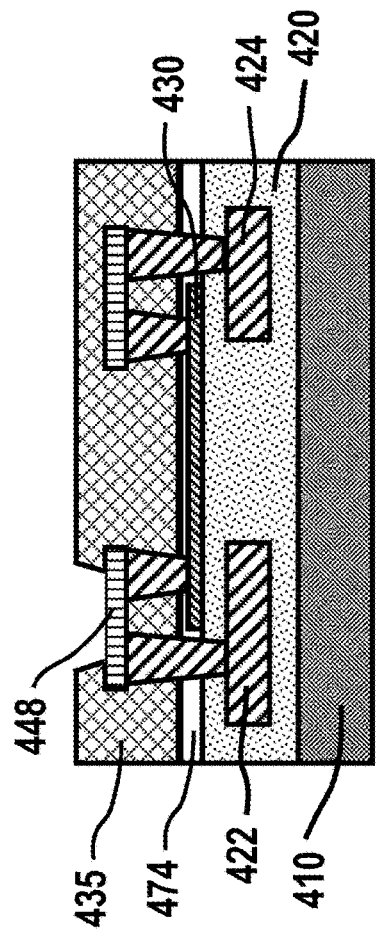

FIG. 34H illustrates a deposit SiO2 (e.g. CVD), CMP, pad open etch step of a CMOS integration method.

Figure 34I:
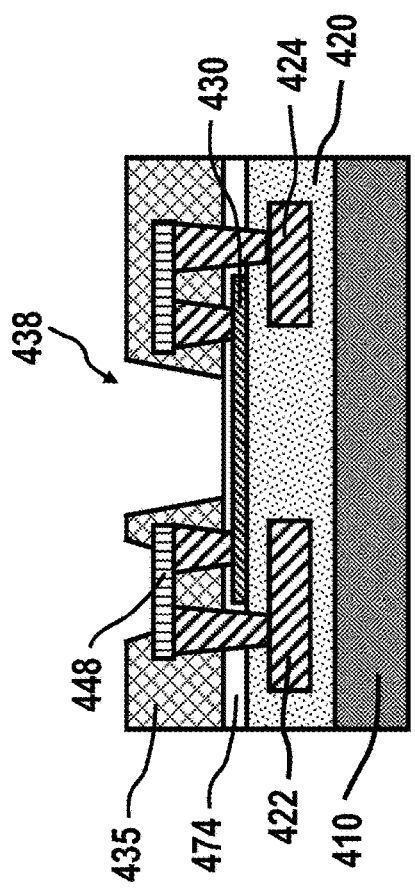

FIG. 34I illustrates a DRIE well insulator down to an etch stop layer step of a CMOS integration method.

Figure 34J:
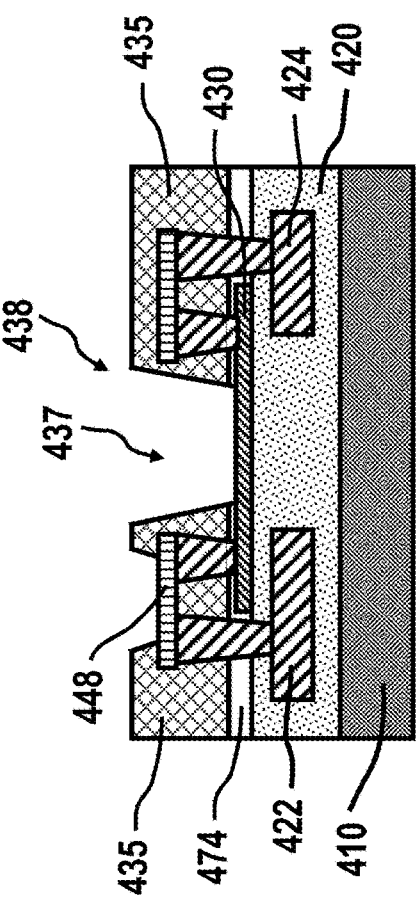

FIG. 34J illustrates a wet etch a thin etch stop layer step of a CMOS integration method.

FIG. 35A is an illustration of an oxide etching step for well formation on a GFET according to the invention.

FIG. 35B is an illustration of a graphene placement step for well formation on a GFET according to the invention.

FIG. 35C is an illustration of a graphene patterning step for well formation on a GFET according to the invention.

FIG. 36A is an illustration of nanoimprinting of a polymer material for well formation on a GFET according to the invention.

FIG. 36B is an illustration of nanoimprinting of a polymer material for well formation on a GFET according to the invention.

FIG. 36C is an illustration of nanoimprinting of a polymer material for well formation on a GFET according to the invention.

FIG. 36D is an illustration of nanoimprinting of a polymer material for well formation on a GFET according to the invention.

FIG. 37A is an illustration of an analyte sensitive layer or other functional layer placement on a graphene layer step for well formation on a GFET according to the invention.

FIG. 37B is an illustration of placement of a thin inorganic layer (etch stop layer) on the functional layer step for well formation on a GFET according to the invention.

FIG. 37C is an illustration of a dry etch the thick inorganic layer step for well formation on a GFET according to the invention.

FIG. 37D is an illustration of a wet or gaseous etch the thin inorganic layer step for well formation on a GFET according to the invention.

Figure 38A:
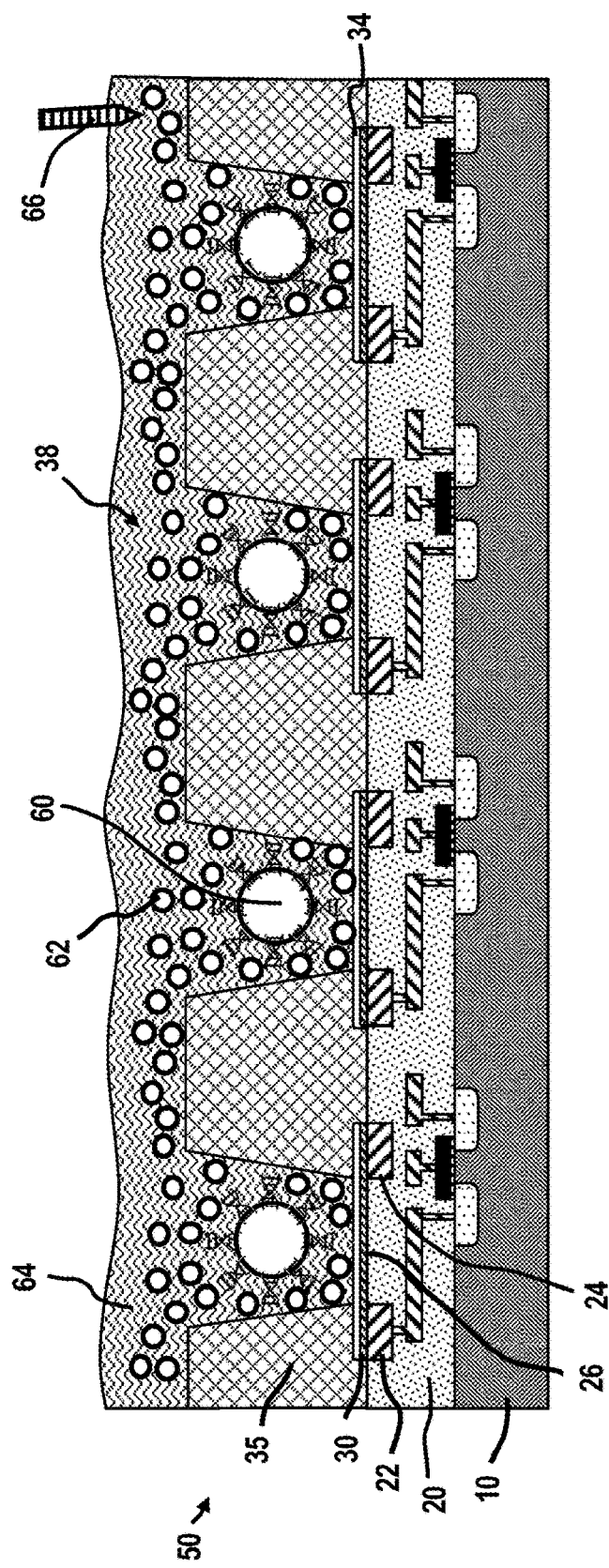

FIG. 38A is a ChemFET sensor IC chip with ions flowing between chambers.

FIG. 38B is a ChemFET sensor IC chip with a movable fluid seal in an upper position.

FIG. 38C is a ChemFET sensor IC chip with a movable fluid seal in a sealed position.

Figure 38D:
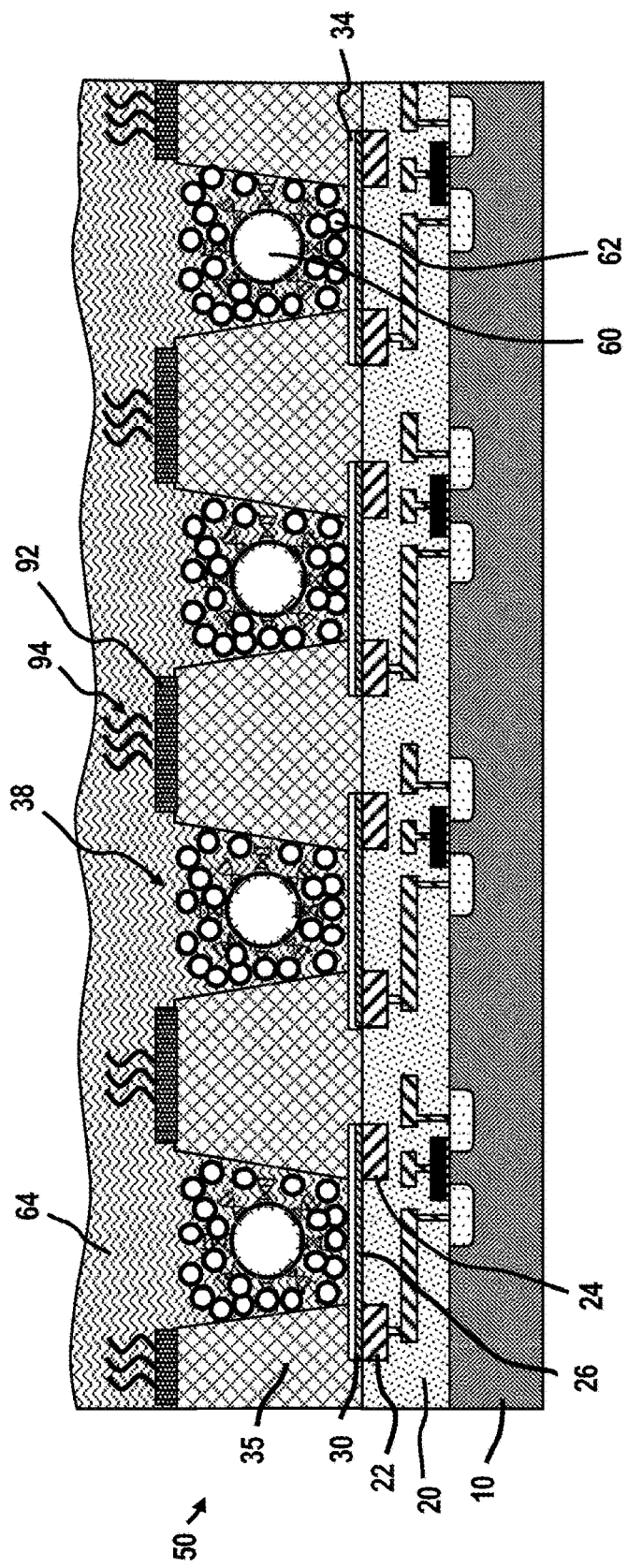

FIG. 38D is a ChemFET sensor IC chip with a barrier generator and electromagnet barrier fields.

Figure 38E:
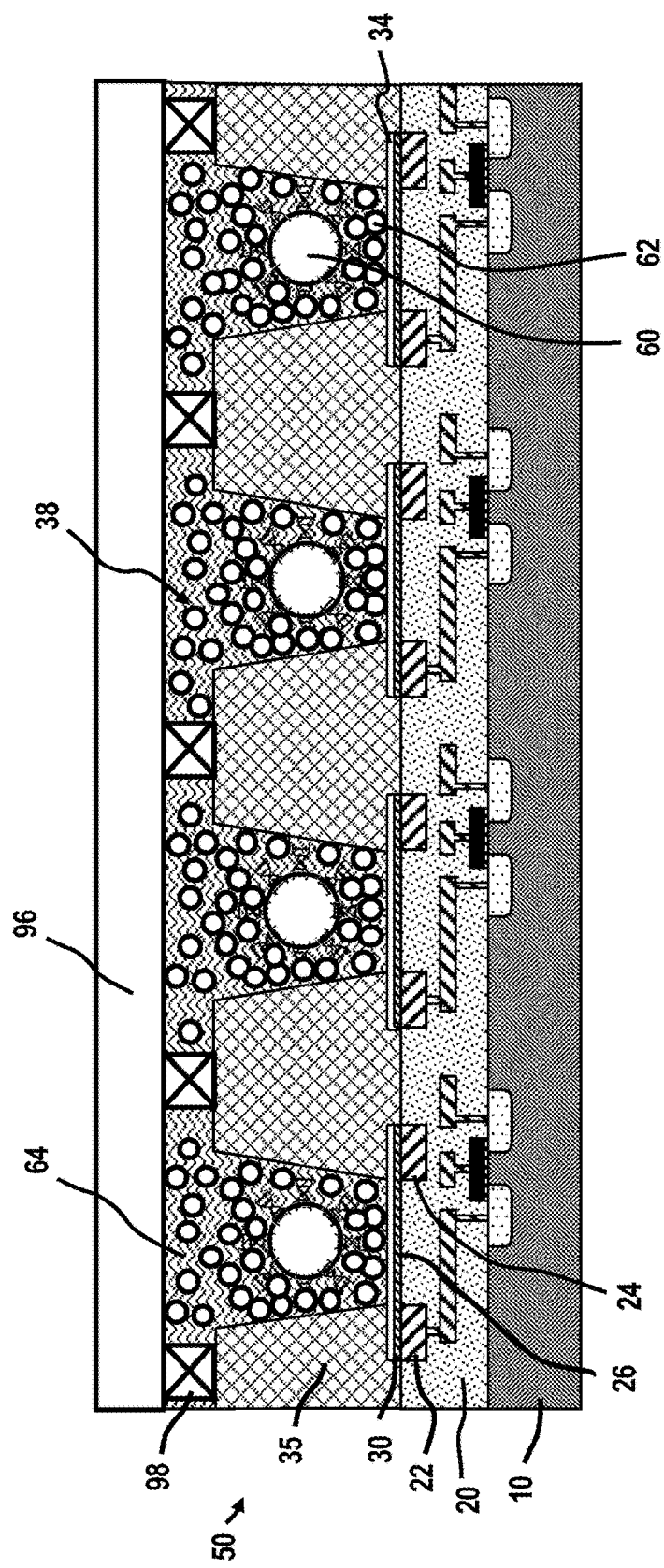

FIG. 38E is a ChemFET sensor IC chip with a flow control member including microvalves.

Figure 39:
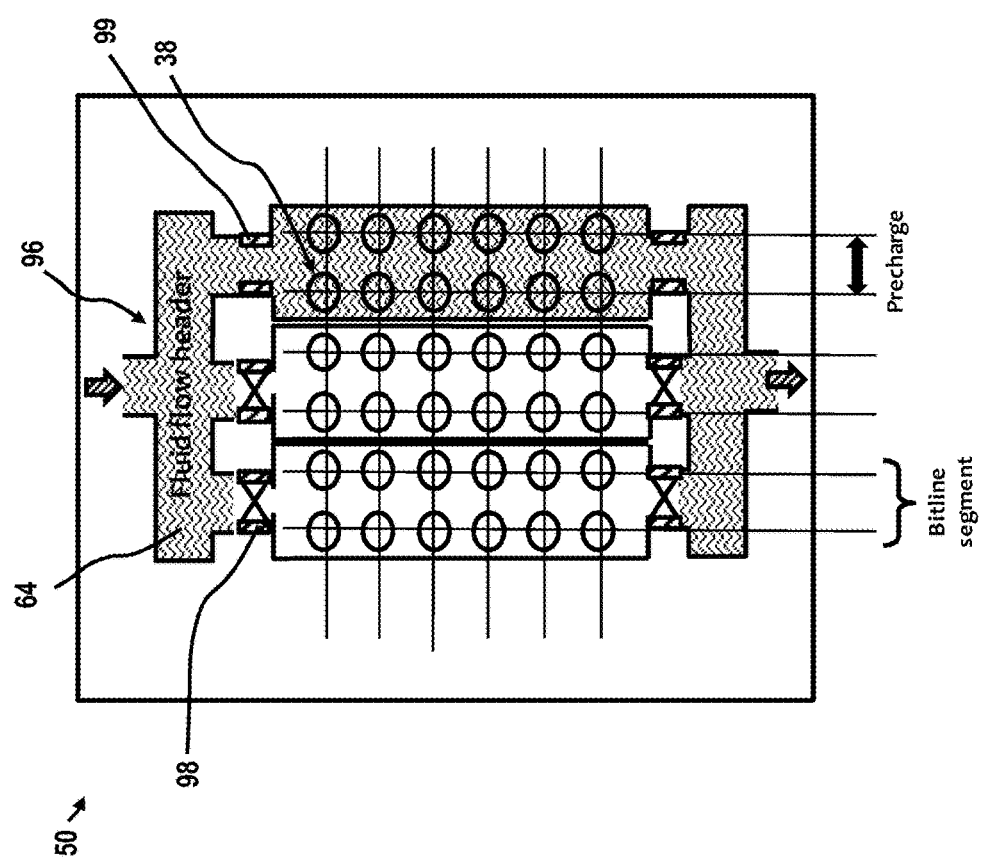

FIG. 39 is a ChemFET sensor IC chip with coordinated bitline segmentation and fluid flow control to reduce read latency and improve read accuracy.

DETAILED DESCRIPTION OF THE INVENTION

Overview

ChemFET and ChemFET Sensor Array Overview

Provided herein are devices, systems, and methods of employing the same for the performance of genomics, bioinformatics, analyte or biologic reaction detection or analysis. The devices, systems, and methods of the disclosure are directed in part to Chemically-sensitive Field Effect Transistor (ChemFET) sensors, integrated circuits, and arrays employing the same for analyte detections and measurements. The present ChemFET sensors, arrays, and integrated circuits may be fabricated using conventional semiconductor processing techniques, e.g. CMOS techniques, based on improved ChemFET sensor and array designs that increase measurement sensitivity and accuracy, and at the same time facilitate significantly small sensor sizes and dense 1D, 2D, or 3D, e.g., GFET, sensor based arrays. Particularly, improved fabrication techniques, as well as improved sensor devices, and their use, employing one dimensional (1D) or two dimensional (2D) nanomaterial channel layers and/or having a three-dimensional (3D) structured layer incorporated therein, provide for rapid data acquisition from small sensors to large sensors, including dense arrays of sensors.

Such arrays may be fabricated, as described herein, and employed to detect the presence of an analyte, changes in analyte concentration, biologic activity and/or the identity of various analyte types in a wide variety of chemical and/or biological processes, including DNA hybridization and/or sequencing reactions. More particularly, presented herein are ChemFET based sensor arrays that have been configured to facilitate DNA hybridization and sequencing techniques, as well as the resultant detection of the same, which take place proximate a sensing zone that has been adapted to include or otherwise be proximate to a 1D or 2D or 3D nanomaterial channel element. Specifically, in various embodiments, ChemFET devices are provided, where the devices include one or more, e.g., a plurality, of sensing zones that have been adapted to have a 1D or 2D nanomaterial channel associated therewith so as to decrease sensor length and/or increase sensor width at the same time as increasing sensor sensitivity. Further, in various instances, a 3D structural layer may be included, such as to extend the vertical dimension of the sensing zone. In such instances, the devices may include one or a number of sensing zones that have been configured to receive a fluid or solution containing one or more reactants, wherein when conditions are such to favor a reaction, the result thereof is detectable by the ChemFET.

Accordingly, presented herein are improved biochemical sensor devices that are configured for detecting changes in or near to a channel region and/or solution that result from the occurrence of a reaction between two reactants or biologic activity proximate a sensing zone of the device, such as within the channel region. In particular instances, the detectable changes may be based on monitoring fluctuations in an ion, e.g., hydrogen ion, concentration (pH), variations in analyte concentration, biologic activity and/or reactions associated with chemical processes relating to DNA synthesis or hybridization, biomolecule detection, analyte detection or cell monitoring, such as within a sensing chamber of a 1D or 2D or 3D based biosensor chip. Specifically, the present disclosure is at least in part directed to a ChemFET for analysis of biological or chemical analytes or reactions or biologic activity that solves many of the current problems associated with nucleic acid sequencing and genetic diagnostics as well as analyte detection. Methods of fabricating such devices as well as their use in the detection of biochemical reactions or analytes are also provided. Other types of ChemFETs contemplated by the present disclosure include enzyme FETs (EnFETs) which employ enzymes to detect analytes, Schottky Barrier FETs, Tunneling FETs and Junctionless FETs, in addition to MOSFETs or ISFETs. It should be appreciated, however, that the present disclosure is not limited to ISFETs and EnFETs, but more generally relates to any FET, such as Schottky Barrier FETs, Tunneling FETs and Junctionless FETs, that is configured for some type of chemical sensitivity. As used herein, chemical sensitivity broadly encompasses sensitivity to any molecule of interest, including without limitation organic, inorganic, naturally occurring, non-naturally occurring, chemical and biological compounds, such as ions, small molecules, polymers such as nucleic acids, proteins, peptides, polysaccharides, or reactions or biologic activity related to those molecules and compounds and the like.

Generally a ChemFET device will include a conductive source and a conductive drain in or on a dielectric material, a channel extending between the source and drain, e.g. comprised of a 1D or 2D nanomaterial, that functions as a sensing layer, an insulating passivation layer with an opening or well on or over the channel and a gate to control the conductance of the channel. In some embodiments the ChemFET may also comprise an analyte or reaction sensitive material layer over or on the nanomaterial channel.

In various instances, the structures may further include or be functionally connected to a ROIC or a processor, such as for processing generated data, such as sensor-derived data. Accordingly, the structures may be configured as, or otherwise include, an integrated circuit, and/or may be an ASIC, a structured ASIC, a processor, or an FPGA or include analog to digital converters, row and column addressing circuitry, amplifying or filtering or other readout circuits. In particular instances, the structures may be configured as a semiconductor IC, such as a Complementary Metal-Oxide Semiconductor (CMOS) IC, which in turn may be configured to include a ChemFET, e.g., a GFET, containing one or more of a conductive source, a conductive drain, a gate, which may be a solution gate, and/or a channel. For instance, the sensor array IC chip may include a CMOS configuration having an integrated circuit that is fabricated on a silicon wafer, which may further be adapted to include a nanomaterial-based ChemFET.

ChemFET Primary Base and Dielectric Layer Structure

For instance, in one aspect of the present disclosure, a chemically-sensitive transistor, such as a ChemFET that is fabricated on a primary base structure, such as a wafer, e.g., a silicon wafer, is provided. The primary base structure may include diffusions or doped areas to define source and drain regions used to create typical semiconductor transistors such as CMOS transistors. These transistors may be useful for creating circuits for interfacing with the chemically sensitive transistors (ChemFETs)—but they are separate from the chemically sensitive transistors (ChemFETs). In various instances, the primary base structure may include one or more additional structures, for instance, in a stacked configuration, such as including at least a dielectric material layer. For example, the primary base structure may include a secondary structure, such as composed of a dielectric material, which may be included on top of, over, or otherwise associated with, the primary base structure, and may form a dielectric layer. Particularly, the secondary dielectric layer may be an inorganic material layer, such as including a silicon oxide, e.g., a silicon dioxide, or a silicon nitride or a silicon carbide or mixtures of these materials, or an organic material, such as a polyimide, BCB, PBO or other like material.

ChemFET Source and Drain

The secondary structure and/or dielectric layer may include a further structure containing one or more of a conductive source and/or a conductive drain, such as separated one from another by a space, and embedded in the secondary structure materials and/or may be planar or non-planar with a top surface of the dielectric. In such an instance, the dielectric layer may include the ChemFET conductive source and drain such as where the source and drain are composed of a conductor, such as metal or polysilicon, such as a damascene copper source and a damascene copper drain. Other metals such as tungsten, aluminum, platinum, titanium or gold could also be used as the conductive source and drain. In other instances, such as for a semiconductor NW, e.g. a Si NW, portions of the NW itself may be doped to form conductive sources or drains and these in turn may be contacted by a metal or polysilicon conductive material.

The conductive source and drain may contact the channel at the bottom of the channel nanomaterial, at the top of the channel nanomaterial or from both the top and the bottom of the channel nanomaterial. In other instances holes or trenches may be formed in the channel nanomaterial and conductive source or drain material may be deposited in those holes or channels so that not only is a surface of the channel nanomaterial contacted but also one or more edges of the nanomaterial, defined by the holes or trenches, are contacted.

In other embodiments the conductive source and drain material, or an intermediary material between the conductive source or drain and the channel nanomaterial is chosen so that the work function of those materials more closely matches the work function of the channel nanomaterial.

In various instances the dielectric layer may further include structures such as interconnects that are used to connect to the semiconductor transistors or to the conductive sources and conductive drains of the ChemFETs or the dielectric layer may include contacts that contact diffusion regions that define sources and drains for the semiconductor, e.g. CMOS, transistors.

ChemFET Channel

In various instances, one or more of the structures having the metal layers therein may include a surface, e.g., a side and/or top surface, which surface(s) may include or incorporate a ChemFET channel, such as where the surface and/or channel may be configured to extend from the conductive source to the conductive drain. The ChemFET channels are physical structures formed of 1D or 2D nanomaterials. The ChemFET channels contrast with the channels of a typical semiconductor transistor which are formed in the semiconductor material between the source and drain diffusion regions only when a sufficient gate voltage is applied greater than the transistor threshold voltage. An exemplary length of the surface and/or channel from the source to the drain of a ChemFET may range from about 0.001 microns to about 10 microns, such as from about 0.01 microns to about 5 microns, for instance, from about 0.05 micron to 3 microns, including about 0.1 or about 0.5 microns to about 1 or about 1.5 or about 2 microns. Note that in some cases it may be desirable to fabricate a ChemFET with substantially longer channel length—even up to several millimeters in length. An exemplary width of the surface and/or channel from side to side may range from about 0.001 microns to about 10 microns, such as from about 0.01 microns to about 5 microns, for instance, from about 0.05 microns to 3 microns, including about 0.1 or 0.5 microns to about 1 or about 1.5 or about 2 microns.

In some instances there may be multiple ChemFET channels formed between one source and one drain. This may particularly be true for channels comprised of 1D nanomaterials such as Si NWs or CNTs. When multiple channels are formed between a source and a drain the channels may be aligned with each other (ordered), e.g. parallel to each other, or they may not be aligned with each other (unordered). Multiple channels may be arranged in either a horizontal plane, a vertical plane, or as an array of channels arranged in 3D space both horizontally and vertically.

ChemFET Channel Transconductance

Particularly, in various instances, it may be useful to maximize channel transconductance, such as by decreasing the channel length and/or increasing channel width and/or dimensionality, so as to increase the sensitivity of the sensors, such as in a sensor array. For instance, to achieve enhanced transistor transconductance, the channel may be configured so as to include a short channel length, e.g., as short a length as possible, while at the same time including a larger channel width, e.g., as large as width as possible, within the sensor array, in a manner adapted for keeping the overall dimensions of the array as compact as possible. For example, the equation for transconductance of a field effect transistor, such as for a transistor presented herein, is: $g_m \propto \mu \, Cov \, W/L \, V_{sd}$; where $g_m$ is the transconductance, $\mu$ is the carrier mobility, $C_{ov}$ is the overall capacitance of the oxide or other layers over the transistor channel, W is the channel width, L is the channel length, and $V_{sd}$ is the voltage from the source to the drain. Since gm directly relates to the sensitivity of the sensor it may be desirable to increase gm through moderating the terms shown in the equation.

In particular increasing the W/L ratio (maximizing W and minimizing L) will increase $g_m$. In particular instances, a useful length of the channel from the source to the drain ranges is less than 1 micron, such as less than 500 nm, such as less than 50 nm, and may be as short as the fabrication process will allow without generating defects or results that render the device unusable. A particularly useful channel length may be 20 nm or less.

Conversely, the width of the channel may be as wide as possible. In such instances, the width of the channel is not governed by the fabrication process as much as by the design requirements of the overall sensor chip. In various instances, hundreds of thousands to many millions of sensors may be positioned on the sensor chip. With this large number of sensors the individual sensor size and pitch (e.g., which may directly affect the channel width) may be kept small, such as reasonably small, so as to prevent the chip from being so large as to be unable to be fabricated (e.g., exceeds the photolithography reticle size) or too expensive (due to the effect of defect density on a large chip size). A practical range of channel width in particular instances may be from 0.1 micron to 2 microns, e.g., for a simple rectangular channel design. In some cases, it may be desirable to increase the channel length to channel width ratio through the use of design techniques—for example, structured and/or an interdigitated 2D or 3D tooth and comb designs can provide for short channel lengths and large channel widths within a relatively compact area. In some instances there may be multiple alternating layers of dielectric material and channel nanomaterial, which can significantly increase the W/L ratio of the channel thereby increasing the transconductance and ultimately the sensitivity of the device.

In other instances the ChemFET channel transconductance may be improved by applying a material or process that can help to repair or improve grain boundaries, wrinkles or other transconductance-limiting artifacts or defects in the channel nanomaterial layer. For example, tin atoms may preferentially deposit at grain boundaries or defect areas on graphene and in so doing they will "stitch" across the grain boundaries or defects allowing charge carriers (holes or electrons) to move more freely and with higher mobility. An improvement in mobility directly improves channel transconductance and ultimately sensor sensitivity.

In other instances an isolation layer may be applied between the channel nanomaterial and the dielectric layer. Often the dielectric layer on a silicon semiconductor chip is a silicon oxide. Silicon oxide is known to trap charges which impedes the mobility of the carriers in the channel and which also contributes to transistor noise. An isolation layer, such as a charge trap screening layer, may be formed between the ChemFET channel and the dielectric layer. In some instances this material may be an organic material such as parylene, HMDS or a Self-Assembling Monolayer (SAM) and in other instances this material may be an inorganic material such as aluminum oxide or preferentially hexagonal boron nitride (hBN).

ChemFET Channel Nanomaterial

In certain instances, the ChemFET channel may include a one-dimensional transistor nanomaterial, a two-dimensional transistor nanomaterial, a three-dimensional transistor nanomaterial, and/or the like. In various instances, a one-dimensional (1D) transistor nanomaterial may be included, which 1D nanomaterial may be composed of, for example, a Carbon NanoTube (CNT) or a semiconductor nanowire, such as a Silicon NanoWire (Si NW). In various instances, a two-dimensional (2D) transistor material may be included, which 2D nanomaterial may be composed of a graphene layer, silicene, molybdenum disulfide, black phosphorous (phosphorene), borophene, tungsten disulfide, boron nitride, tungsten diselenide, stanene, germanane, nickel HITP, and/or metal dichalcogenides or Mxenes such as Ti2C, (Ti0.5, Nb0.5), V2C, Nb2C, Ti3C2, Ti3CN, Nb4C3, or Ta4C3. In particular instances, a three-dimensional (3D) structural material, such as proximate a sensing zone and/or channel layer may be provided. In various embodiments, the channel may be situated on, over, under or sandwiched between dielectric layers. In particular embodiments, the channel may include a graphene layer.

ChemFET Analyte or Reaction-Sensitive Layer

Additionally, in various instances, a reaction or analyte or reaction-sensitive layer such as an ion sensitive layer, e.g., an inorganic or organic material layer, may be disposed on or over the surface and/or channel, such as layered or otherwise deposited on the 1D, 2D, e.g., graphene, or 3D layer, and/or an included dielectric layer. Such an inorganic may be an oxide layer or a nitride layer may be an aluminum oxide, tantalum oxide, titanium oxide, hafnium dioxide, hafnium silicate, zirconium silicate, zirconium dioxide, lanthanum oxide, iron oxide, yttrium oxide or a silicon oxide, such as silicon dioxide. Generally an oxide with high intrinsic buffer capacity is preferred. In some instances it may be advantageous to stack two or more different inorganic reaction-sensitive layer on top of each other to form an overall reaction-sensitive layer. In some embodiments, the oxide layer may have a thickness of about 150 nanometers, such as about 100 nanometers, such as about 50 nanometers, such as about 20 nanometers or less, such as about 15 nanometers, such as 10 or 9 or 7 or 5 nanometers or less. It may be advantageous to minimize the thickness of this oxide layer in order to increase the Cov term in the aforementioned formula for gm thus maximizing gm. Many 1D and 2D nanomaterials are relatively difficult to coat with a reaction-sensitive inorganic material and in these instances the nanomaterial may be pretreated or activated so that the reaction-sensitive layer will adhere or stick to it. Pretreatment or activation may include ozone plasma, PVD metal deposition and oxidation of that metal, a sol gel layer, fluoridation, chlorination, oxidation, hydrolysis or other techniques. After the pretreatment or activation the reaction-sensitive material may be applied by PVD, CVD, ALD or other processes. In some instances an organic material layer may be used as a reaction-sensitive layer such as an ion sensitive layer. An organic reaction-sensitive layer ideally will be one that easily adheres or bonds to the underlying nanomaterial layer. In the case of 2D nanomaterial channels with chemical ring structures, such as graphene, a good choice for an organic reaction-sensitive material is a material with a ring structure and that includes functional groups such as OH or O—the ring structure of the reaction-sensitive material may align with the ring structure of the 2D nanomaterial and allow so-called Pi-Pi bonding of the two materials. Candidate materials are phenols, hydroquinone and others.

Analyte Permeable Layers and Getter Materials

In various instances, the analyte or reaction-sensitive layer, the well or chamber or passivation opening, or adjacent structures may be further modified to be even more selective to the particular analyte or reaction to be detected or sensed. In some embodiments wherein the analyte to be sensed are ions or a concentration of ions an ion-permeable layer that is selective for the desired ions to be sensed may be formed on or over the analyte or reaction-sensitive layer. In this case the ion permeable preferentially lets ions of interest pass through it to interact with the analyte or reaction-sensitive layer while not allowing or at least reducing the number of ions that are allowed to pass through it, which ions are not of interest. Furthermore in other instances a "getter" material that "gets" or sequesters unwanted ions may be placed on the passivation surface, well or chamber sidewalls, lid of the package sensor chip or other surfaces with the purpose of sequestering or "getting" unwanted ions or analytes away from the sensing region so that they do not interfere with the proper sensing of the analyte or reaction of interest.

Passivation Layer

In various instances, a passivation layer may be disposed on the surface and/or channel, such as layered or otherwise deposited on the 1D, 2D, or 3D nanomaterial layer and/or on an associated reaction or analyte or reaction-sensitive layer on the surface and/or channel. Such a passivation layer may have a thickness of about 5 microns or less, such as about 3 microns or about 1 micron or about 0.5 microns, such as about 0.1 microns or less. The passivation layer may be formed of an inorganic material, such as an oxide, nitride, carbide or mixtures thereof or may be formed of an organic material, such as a polymer, e.g. polyimide, PBO or BCB.

ChemFET Well or Passivation Opening

In particular instances, the primary and/or secondary and/or tertiary layers or structures may be fabricated or otherwise configured so as to include a chamber or well structure or opening in and/or on the passivation surface. For instance, a well structure may be positioned on a portion of a surface, e.g., an exterior surface, of the primary and/or secondary structures, such as over or adjacent to a channel region within one or more of the structured layers. For example, in some instances, the well structure may be formed on top of, over or may otherwise include, at least a portion of the 1D, 2D, and/or 3D nanomaterial, and/or may additionally include the reaction or analyte or reaction-sensitive, e.g., oxide, and/or passivation layers. In various instances, the chamber and/or well structure may define an opening, such as an opening that allows access to an interior of the chamber, such as allowing direct or indirect contact or coupling with the 1D nanomaterial, e.g., carbon nanotube or nanowire, 2D nanomaterial, e.g., graphene, or 3D surface and/or channel or direct contact with a reaction or analyte or reaction-sensitive layer that is on or over the nanomaterial channel. In other instances the passivation layer may be relatively thin (e.g. on the order of 1 micron or less) and openings in the passivation layer create exposed surfaces of the 1D or 2D nanomaterial or reaction-sensitive material without creating structures that might be considered wells or chambers. In either such instances, the ChemFET device may be configured so that a solution or fluid is used to transport reactants to the well/chamber or exposed surfaces.

ChemFET Gate

The fluid or solution used to transport reactants to the well/chamber or exposed surfaces may also be used to supply a gate voltage to the ChemFET device (e.g. a probe or electrode, such as a reference electrode, having a controlled voltage communicates with the fluid or solution to imply its voltage on the fluid or solution) as a solution gated sensor device. The reference or solution gate electrode may be implemented as a separate element communicating with the fluid or solution or may be incorporated on the sensor chip or in the sensor chip package. In some instances it is advantages to have a dual gate on the ChemFET, such as a solution gate and a backgate. The backgate would allow a gate voltage to be applied to the ChemFET from an opposite direction from the solution gate, e.g. the solution gate may be on top of or over the channel and the backgate may be under the channel. The backgate may be implemented as a global backgate (voltage applied globally to the primary base substrate) or as a local backgate (voltage applied locally in the channel region, e.g. through use of a conductive electrode or interconnect configured to supply the backgate voltage). The combination of both a backgate and solution gate used in concert, i.e. a dual gate, can lead to improved ChemFET sensitivity—even beyond the Nernst limit of 59 mV/pH. In other instances the ChemFET channel may be exposed or suspended such that the gate can surround a portion of the channel, i.e. in the case of a solution gate the solution would surround a portion of the channel, providing a Gate All-Around (GAA) structure. Dual gate or GAA structures offer the benefit of better channel control and for sensors may also improve the sensitivity and accuracy.

Manufacturing Processes for Gate All Around ChemFET

A typical nanomaterial-based ChemFET has a conductive source, a conductive drain, a nanomaterial channel such as graphene, a well structure and associated chamber, a fluid and a gate voltage applied through the fluid such as applied by a gate or reference electrode in order to form a nanomaterial-based, solution-gated ChemFET. The ChemFET may in some instances comprise an analyte or reaction-sensitive layer, which may further improve the sensitivity of the ChemFET for detection of certain analytes or chemical reactions or biologic activity.

An improvement over the typical ChemFET just described to is provide a second gate, i.e. a backgate for the device such that the backgate and solution gate can both apply voltages to the channel in a dual-gate fashion. Having two gate voltages, on opposite the other around the channel has the advantage of more precisely controlling the ChemFET which in turn leads to better sensor sensitivity.

An even more enhanced embodiment of this concept is to completely surround a portion of the channel with gate material so that the whole channel circumference in some portion of the channel is fully enclosed by the gate material. This gives the highest degree of control over the channel through the gate all around structure.

A gate all around ChemFET is comprised of a conductive source, conductive drain, channel, such as a graphene channel, an optional analyte or reaction-sensitive layer over the channel, a well structure providing a chamber that holds a fluid wherein a gate or reference electrode applies a gate voltage to the fluid. In the gate all around embodiment the dielectric and metal under a relatively large portion of the channel region have been removed, such as by etching. In this fashion the fluid is free to flow over, under and around the exposed portion of the channel—hence forming a gate all around structure.

In one instance the gate all around structure is achieved by providing an etch stop structure configured as a tub-like shape and positioned in the dielectric material under the channel. A wet chemical etch can be used to remove the dielectric layer under the channel and within the etch stop layer-defined tub. In this embodiment the etch is preferably a wet chemical etch and not a dry, e.g. plasma, etch since dry etch processes tend to damage or destroy the graphene. A suitable wet etchant is a hydrofluoric (HF) acid-based etchant, such as a mixture of HF and a buffer such as ammonium fluoride. This etchant has high selectivity to silicon dioxide in comparison to silicon and thus silicon of the sensor IC chip wafer should not be damaged. Furthermore an HF-based etch should not have bad effect on the graphene channel.

In a second instance of the preferred gate all around structure, the graphene is first deposited or formed on a metal interconnect material that may form one of the source or drain conductive electrodes. If the interconnect material is copper, such as formed in trenches in a damascene process and with the upper portions of the electrodes exposed to the surface, i.e. copper is exposed to the surface then the possibility exists for forming the graphene (i.e. growing the graphene) directly on the semiconductor IC wafer rather than on a separate growth wafer and then transferring the graphene to the IC wafer. This may be possible since copper is one of the preferred growth substrates for graphene (graphene does not diffuse into copper during the growth) and if the growth temperature is kept low enough, such as lower than 400 C, so as not to affect the semiconductor transistors, such as CMOS transistors, It may be possible that a plasma-enhanced CVD (PECVD) or other enhanced CVD process will allow growth of good quality graphene directly on the exposed copper surfaces on an IC wafer. Once the graphene is formed or deposited on the copper areas then in a subsequent process step the dielectric underlying the channel area, which at this time includes both graphene and a thin layer of copper, is etched. For a silicon dioxide dielectric a wet HF acid etchant is suitable. The etch may be further controlled or confined by an etch stop layer formed in a tub-like shape under the channel. Finally the thin copper layer under the graphene channel can be etched by a suitable copper etchant, such as ammonium persulfate or ferric chloride., resulting in the central portion of the graphene channel to be free of any dielectric, or metal and available for contact by the fluid to form a gate all around structure.

In another gate all around embodiment there is no etch stop layer provided under the channel sensing region. In this case the wet etching of the silicon dioxide dielectric will be isotropic and will result in a bowl-shaped cavity beneath the channel. Furthermore since the etching is not confined by an etch stop layer, the etched cavity may not be fully uniform in size and shape.

All of the process embodiments just discussed may result in a gate all around structure.

Accordingly, a further aspect of the present disclosure is a biosensor or chemsensor. The biosensor or chemsensor includes a CMOS structure that may include a conductive source, e.g., a damascene copper source, as well as a conductive drain, e.g., a damascene copper drain, a 1D or 2D nanomaterial layered or 3D layered, e.g., a graphene layered, surface or channel extending from the source to the drain, and a well or chamber structure or passivation opening that may be positioned on or over a portion of an exterior surface of the 1D or 2D nanomaterial channel and/or 3D layered well or an analyte or reaction-sensitive layer over the channel. In particular instances, the well structure or passivation opening may be configured so as to define an opening that allows for direct or indirect fluidic contact or coupling with the 1D nanomaterial, e.g., nanotube, nanowire, and/or 2D nanomaterial, e.g., graphene, analyte or reaction-sensitive layer over the channel, or well or chamber or passivation opening surface. In various instances, the well structure is further configured to include a 3D structural element, such as incorporated into one or more of the well bounding members. Further, an oxide and/or passivation layer may be disposed in or on the chamber surfaces. Hence, in certain instances, a ChemFET e.g., a GFET, including one or more nano- or micro-wells may be provided.

Nanomaterial Growth and Transfer

In view of the above, in one aspect, the present disclosure is directed to a method of fabricating a ChemFET, such as a transistor having one or more of a 1D, 2D, or 3D nanomaterial associated therewith, such as in proximity to a sensing zone configured within the ChemFET. Any suitable method may be employed in such a fabrication process, however, in various instances, the method may involve the growing and/or transferring of the one-dimensional (1D) or two-dimensional (2D) nanomaterial for use in the sensor. In such an instance, the method may include the growing of the 1D or 2D nanomaterial layer, such as on a suitable growth platform, which may be a silicon platform or substrate. Particularly, the method may include releasing the 1D and/or 2D nanomaterial layer from the growth platform and/or transferring the nanomaterial layer to the semiconductor structure or substrate.

ChemFET Sensor Array

Accordingly, in some embodiments, the ChemFET sensor chip may include a plurality of wells and may be configured as an array, e.g., a sensor array. Such an array or arrays may be employed such as to detect a presence and/or concentration change of various analyte types in a wide variety of chemical and/or biological processes, including nucleic acid hybridization (e.g., DNA/DNA, DNA/RNA) and/or DNA or RNA sequencing reactions. For instance, the devices herein described and/or systems including the same may be employed in a method for the analysis of biological or chemical materials, such as for whole genome analysis, genome typing analysis, microarray analysis, panels analysis, exome analysis, microbial/microbiome analysis, genotyping analysis, and/or clinical analysis, such as cancer analysis, NIPT analysis, cfDNA, blood/plasma/serum analysis, UCS (upstream conserved sequence) analysis, biomolecule analysis and/or analyte analysis. In a particular embodiment, one or more surfaces within the wells of the ChemFET may be configured as a sensing zone, which sensing zone may include an additional structure, such as a 1D, 2D, e.g., graphene, or 3D nanomaterial layer, and hence, the FET may be a graphene FET (GFET) array. It may be noted that having multiple wells sensing the same analyte or reaction allows statistical improvement of the sensing result.

Such FET sensors as herein described may be employed to facilitate DNA hybridization and/or sequencing techniques, such as based on monitoring changes in ion concentration, e.g., hydrogen ion concentration (pH), changes in other analyte concentrations, and/or binding events associated with chemical processes (e.g., relating to DNA synthesis), such as within a solution gated sensing chamber or well or passivation opening of the GFET based sensor, such as proximate the sensing zone(s). For example, the ChemFET may be configured as or coupled to a CMOS IC to form a biosensor and/or may be adapted to increase the measurement sensitivity and/or accuracy of the sensor and/or associated array(s), such as by including one or more surfaces or wells having a surface layered with a 1D and/or 2D and/or 3D nanomaterial, a dielectric layer, a channel layer used for sensing, an analyte or reaction-sensitive layer, a passivation layer, and the like. In particular instances, the increased sensitivity of the sensors may, in part, be due to the presence of the 1D or 2D or 3D nanomaterial, and/or further enhanced by its relationship to one or more of the analyte or reaction sensitive and/or passivation layers, which in turn allows for smaller sensor configurations, therefore smaller channels and/or gates, and thus a greater density of sensors and/or arrays.

ChemFET Channel Nanomaterial Growth and Transfer

For instance, in a particular embodiment, a chemically-sensitive ChemFET is provided, where the ChemFET sensor, e.g., biosensor, may include a semiconductor substrate, such as a silicon wafer with CMOS circuitry, and at least a first dielectric layer that may itself be configured so as to incorporate one or more of a 1D, 2D, and/or 3D nanomaterial channel structure therein. For example, a 1D nanomaterial structure, such as a CNT or a Si NW grown or formed separately from the biosensor substrate, may be layered within or coated on top of the dielectric layer, such as via spin coating, casting or other deposition method. In another embodiment, a Si NW may be formed from a silicon or other semiconductor layer that is over or on the first dielectric layer. In that case the silicon or other semiconductor layer may be patterned and etched to form a semiconductor NW from the bulk semiconductor layer. The semiconductor NW may have regions that are appropriately doped, such as by implant and diffusion of appropriate materials, to create n or p-type regions or to create junctions.

Additionally, or alternatively, a 2D structure or nanomaterial layer may be applied to the first dielectric layer of the semiconductor structure, such as by the growth, or release, and/or transfer of the 2D nanomaterial thereon. Particularly, in various embodiments, the 2D nanomaterial may be graphene, silicene, molybdenum disulfide, black phosphorous (phosphorene), borophene, tungsten disulfide, boron nitride, tungsten diselenide, stanene, germanane, nickel HITP, and/or metal dichalcogenides or Mxenes such as Ti2C, (Ti0.5, Nb0.5), V2C, Nb2C, Ti3C2, Ti3CN, Nb4C3, or Ta4C3.

More particularly, in certain embodiments, the 2D nanomaterial may be grown and/or transferred onto the substrate and/or dielectric surface of the semiconductor, e.g. CMOS, structure, which structure may therefore be a read-out integrated circuit (ROIC). For instance, there are several growth mechanisms that may be implemented for the growth of such a 2D nanomaterial on a growth substrate, such as including the growth on a metal plate, a metal foil, a thin film metal, or a metal, e.g., silicon, wafer, and the like. Likewise, the 2D nanomaterial may be applied to the growth material by chemical vapor deposition ("CVD") (atmospheric, low or very low pressure), PECVD, ALD, or grown in a hot wall or cold wall reactor.

ChemFET Nanomaterial Transfer

Once grown, the 2D nanomaterial may be transferred to the ROIC structured IC chip, such as by one or more of the following transfer mechanisms including direct transfer from the growth substrate to a ROIC wafer using Van der Waal's forces, fusion bonding, and/or using temporary bonding. Further, there are several release mechanisms that may be implemented for effectuating the release of the 2D nanomaterial from the growth medium and/or substrate pursuant to the transfer of the 2D nanomaterial to the ROIC, which release mechanisms may include aqueous electrolyte electrolysis, e.g., with the growth platform as the cathode, and separation due to hydrogen evolution. Another release mechanism may be by separating a temporary adhesive from the growth platform using a laser, a UV light, a temperature increase, or physical peeling or pulling, and the like.

Additionally, in various embodiments, the ChemFET structure may additionally include a further insulating layer, such as positioned on top of the second insulating layer, which first and/or second insulating layer(s) may be positioned one on top of the other, such as with the 1D or 2D nanomaterial positioned there between. In particular instances, the first and/or second insulating layers may include a well structure, such as a well or chamber having a 3D structural layer, such as within or otherwise associated with a surface of the well or chamber. Further, in various embodiments, the ChemFET structure may include an analyte or reaction-sensitive layer, e.g. an oxide layer, such as a layer that is deposited, e.g., via CVD deposition, or may be otherwise disposed on the surface of the well or chamber so as to increase the measurement sensitivity and/or accuracy of the sensor and/or associated array(s). The oxide layer, when present, may be composed of metal oxide, for example, an aluminum oxide, a tantalum oxide, a hafnium oxide, and the like. Particularly, the oxide layer may have a suitable thickness such as of from about 100 nm to about 75 nm, such as from about 50 nm to about 30 nm, from about 40 nm to about 25 nm, such as from about 20 nm to about 10 nm or 9 nm or less, respectively. Preferably, the passivation layer may have a suitable thickness such as of from about 5 micron to about 3 micron, such as from about 2 micron to about 1 micron, from about 500 nm to about 100 nm or less.

Accordingly, the present ChemFET integrated circuits, sensors, and/or arrays of the description may be fabricated such as using any suitable semiconductor fabrication (fab) processing techniques known in the art. In certain instances, such a semiconductor processing technique may be configured to increase the measurement sensitivity and/or accuracy of the sensor and/or array, and at the same time facilitate significantly small channels having relatively smaller sensor sizes and more dense ChemFET chamber sensor regions. Particularly, in various embodiments, the improved fabrication techniques herein described result in sensor devices containing sensing zones employing a 1D or 2D nanomaterial layer, and/or may include a 3D structural layer. For instance, a 1D or 2D nanomaterial layer may be grown, such as on a growth platform, and once grown may be released from the growth platform, and then be transferred to a semiconductor structure, such as a CMOS substrate, so as to be employed as a ChemFET sensor therein.

ChemFET Fabrication with Electrode Contacts Through the Nanomaterial

Additionally, during or after manufacture one or more surfaces or layers of the ChemFET structure may be treated so as to contain one or more additional analyte or reaction-sensitive layers, such as an oxide layer, which structures and layers, alone or in combination provide for rapid data acquisition, such as from small sensors to large and dense arrays of sensors. In certain embodiments, one or more of such layers may be fabricated along with the manufacture of the array, such as via one or more chemical vapor deposition techniques. Further, in particular embodiments, an ion-selective permeable membrane layer may be included, such as where the membrane may include a polymer, such as a perfluorosulphonic material, a perfluorocarboxylic material, PEEK, PBI, Nafion, and/or PTFE. In some embodiments, the ion-selective permeable membrane may include an inorganic material, such as an oxide or a glass. In more particular embodiments, one or more of the various layers disclosed herein, e.g., the 1D or 2D nanomaterial layer, the analyte or reaction-sensitive layer, passivation, and/or permeable membrane layers, and the like may be fabricated or otherwise applied by a spin-coating, anodization, PVD, CVD, ALD and/or sol-gel method.

Accordingly, in a particular fabrication process, a method of forming an integrated circuit, such as for use in performing a sensing, such as a nucleic acid sequencing and/or detection sensing, is provided. The method(s) may include one or more steps of providing a semi-conducting substrate having a plurality of extended planar surfaces, such as a top and a bottom surface, that are offset from one another by a first thickness, and are surrounded by one or more side members, such as a circumferential side member, if the substrate is circular, elliptical, or round, or a plurality of opposed side members contacting each other at their edges, such as if the substrate is square, and the like. In various instances, the substrate may include one or more transistor elements and/or interconnects that may be positioned within the thickness between the plurality of surfaces.

Additionally, a second step may include depositing a first insulating dielectric layer onto the top of the planar surface of the substrate so that the dielectric layer extends at least partially across the planar surface, such as from one side portion to another side portion, e.g., edge to edge. A plurality of trenches, e.g., opposed trenches, may then be formed in the first insulating dielectric layer, such as where each trench is offset from the other by a distance, which distance may be configured so as to form a channel region.

A third step may include depositing a first layer of conductive material into each of the trenches so as to form an electrode within each trench. For instance, a first electrode in a first trench may be configured so as to serve as a source electrode, and a second electrode in a second trench may be configured to serve as a drain electrode, such as where the source and drain electrodes are offset by the channel region, and may be in contact with the one or more transistor elements.

In certain instances, once the electrodes have been formed a 1D or 2D nanomaterial layer, e.g., graphene, may be positioned over the dielectric layer in a manner to cover the source and drain electrodes as well as the region therebetween. However, in some instances, the first insulating dielectric layer may be conditioned prior to depositing the 1D or 2D nanomaterial layer over it, such as in a manner so that a side and/or top surface of each of the plurality of electrodes is made to extend above the surface of the surrounding insulating dielectric layer, and in some instances, only after this conditioning is the 1D or 2D nanomaterial, e.g., graphene, layer deposited or otherwise formed over the insulating layer, such as onto the side and top surface of each of the plurality of electrodes and across the channel region to thereby form a channel between the electrodes.

In various embodiments, the conditioning may be accomplished by etching, such as wet or dry etching. Likewise, an additional plating and/or polishing, e.g., electroless chemical polishing, and/or other conditioning steps may be included, such as by being inserted between one or more of the other recited process steps. For example, in some embodiments, after the first conductive material is added and/or the 1D or 2D nanomaterial layer is to be added, one or more openings may be made in the 1D or 2D nanomaterial so as to allow the conductive electrode material to push through and rise above the surface of the 1D or 2D nanomaterial layer. Such a step as this may be performed in addition to or substitution for the conditioning step. In such an instance, a second layer of conductive material may then be deposited on at least a portion of the 2D nanomaterial so as to contact each of the plurality of electrodes so that combined conductive material of each of the plurality of electrodes extends further above the surface of the insulating dielectric layer.

Nevertheless, where conditioning takes place, an opening of the 1D or 2D nanomaterial layer may also take place so as to form an opening in the 2D nanomaterial layer, such as proximate each electrode, so as to expose at least the top surface of each electrode. In such an instance, a second layer of conductive material may be deposited over each opening of the 2D nanomaterial layer so that the second layer of conductive material contacts the first conductive material, fills the opening, and further extends above the 2D nanomaterial layer so as to contact at least one of a side and top surface of the 2D nanomaterial layer. In any of these instances, a patterning step may take place, such as employing a mask and photoresist process, so as to pattern the 1D or 2D nanomaterial layer forming the channel.

Additionally, in various embodiments, a second insulating passivation material layer may be deposited over the patterned 2D nanomaterial layer, which second insulating passivation layer may itself be patterned so as to form a chamber having a bottom surface proximate the channel region. In particular instances, this chamber may be configured as a well so as to form a sensing chamber wherein a nucleic acid sequencing reaction, a hybridization reaction, or other detection reaction, may take place.

Consequently, in various instances, the result of these methods is the production of an integrated circuit chip, which as indicated above, may be used in performing a nucleic acid sequencing and/or detection reaction. In such an instance, the integrated circuit chip may include one or more of a semiconducting substrate that includes a plurality of extended planar surfaces offset from one another by a first thickness, which are surrounded by one or more circumferential or edged side members, such as where the substrate may be configures as a CMOS circuit, and therefore may have one or more transistor elements positioned between the plurality of surfaces. Hence, in particular embodiments, the substrate may include an array of CMOS field effect transistors that may be arranged in or on the substrate.

Accordingly, the substrate may form or otherwise include a primary layer that forms a base layer for the integrated circuit. Additionally included may be a secondary layer that is positioned over the primary layer. Such a secondary layer may be formed of a first non-conductive material, so as to be a dielectric and may include a plurality of trenches, such as where each trench is offset by a distance one from the other, where that distance forms a channel region. The trench may be configured so as to include an electrically conductive material so as to form an electrode, and the trench may further be configured in such a manner that a side and top surface of the electrode extends above the top surface of the of the insulating layer. Further, each of the electrodes may be orientated with respect to one another so as to form a channel region there between, and thus, each electrode on either side of the channel region may be either a source electrode or a drain electrode.

Further, a tertiary layer may be included and positioned over the secondary layer, such as where the tertiary layer includes a 1D and/or 2D nanomaterial, which may be formed over one or more of the side and top of the source and drain electrodes. In such an instance, the 2D nanomaterial may be formed within or over the channel region so as to electrically connect the source and the drain electrodes and thereby form the channel. In some embodiments, the structure of the integrated circuit may include a fourth layer, which fourth layer may extend across the surfaces of the second and/or third layers, and may further include a surface structure that overlaps the source and the drain in the secondary layer. For example, the fourth layer surface structure may rise above the second and third layers but may include a chamber that defines a well having sidewalls and a bottom, such as a bottom that corresponds with the channel region and/or extends over at least a portion of the 2D nanomaterial so as to form a sensing chamber for the performance of a sequencing, hybridization, detection, or other reaction.

ChemFET Sensor IC Chip and System

Accordingly, in a further aspect, a system is provided, such as a system configured for running one or more reactions so as to detect a presence and/or concentration change of various analyte types in a wide variety of chemical and/or biological processes, including DNA hybridization and/or sequencing and/or other detection reactions. As such, the system may include an array including one or more, e.g., a plurality of sensors, such as where each of the sensors includes a ChemFET having a conductive source, a conductive drain, and a sensing surface or channel extending from the conductive source to the conductive drain. In particular instances, the array may include one or more wells configured as one or more sensing chambers having the sensing surface or channel positioned therein. In some instances, the surface and/or channel of the chamber may include a one-dimensional (1D) or two-dimensional (2D) transistor nanomaterial, a three-dimensional (3D) structural layer may be included, as well as a dielectric or sensing layer, an ion sensitive permeable membrane, a passivation layer, and/or the like.

The system may further include one or more of a fluidic component, such as for performing the reaction, a circuitry component, such as for running the reaction processes, and/or a computing component, such as for controlling and/or processing the same. For instance, a fluidics component may be included where the fluidic component is configured to control one or more flows of reagents over the array and/or one or more chambers thereof. Particularly, in various embodiments, the system may include a plurality of sensing locations, such as surfaces or wells, which in turn includes a plurality of sensors and/or a plurality of channels, and further includes one or more fluid sources containing a fluid having a plurality of reagents and/or analytes for delivery to the one or more surfaces and/or wells for the performance of one or more reactions therein. In certain instances, a mechanism for generating one or more electric and/or magnetic fields is also included.

The system may additionally include a circuitry component, such as where the circuitry component may include a sample and hold circuit, an address decoder, a bias circuitry, and/or at least one analog-to-digital converter. For instance, the sample and hold circuit may be configured to hold an analog value of a voltage to be applied to or on a selected column and/or row line of an array of a device of the invention, such as during a read interval. Additionally, the address decoder may be configured to create column and/or row select signals for a column and/or row of the array, so as to access a sensor with a given address within the array. The bias circuitry may be coupled to one or more surfaces and/or chambers of the array and include a biasing component such as may be adapted to apply a read and/or bias voltage to selected ChemFETs of the array, e.g., to one or more gate terminals of the transistor. The analog to digital converter may be configured to convert an analog value to a digital value.

Computing Component

A computing component may also be included, such as where the computing component may include one or more processors, such as a signal processor; a base calling module, configured for determining one or more bases of one or more reads of a sequenced nucleic acid; a mapping module, configured for generating one or more seeds from the one or more reads of sequenced data and for performing a mapping function on the one or more seeds and/or reads; an alignment module, configured for performing an alignment function on the one or more mapped reads; a sorting module, configured for performing a sorting function on the one or more mapped and/or aligned reads; and/or a variant calling module, configured for performing a variant call function on the one or more mapped, aligned, and/or sorted reads. Other modules that may be included are alignment modules, variant call modules, and any other module useful in analyzing the results of detection or sequencing reactions. In various embodiments, one or more of these modules may be in a hardwired configuration, for example, configured as an integrated circuit. In particular instances, the base caller of the base calling module may be configured to correct a plurality of signals, such as for phase and signal loss, to normalize to a fiducial, internal nucleotide standard, and/or to a generate a plurality of corrected base calls for each flow in each sensor to produce a plurality of sequencing reads. In various instances, the device and/or system may include at least one reference electrode.

Particularly, the system may be configured for performing a nucleic acid sequencing and/or hybridization reaction. In such an instance, the FET device may include an array of sensors having one or more ChemFETs associated therewith. Such transistors may include a cascode transistor having one or more of a source terminal, a drain terminal, and or one or more gate terminals, such as composed of a damascene copper. In such an instance, the source terminal of the transistor may be directly or indirectly connected to the drain terminal of the ChemFET, such as by, a one or two dimensional nanomaterial channel or other suitably configured surface element that may extend from the source terminal to the drain terminal, such as where the 1D channel nanomaterial may be a carbon nanotube or semiconductor, e.g. silicon, nanowire, and the two-dimensional channel nanomaterial may be composed of graphene, silicene, molybdenum disulfide, black phosphorous (phosphorene), borophene, tungsten disulfide, boron nitride, tungsten diselenide, stanene, germanane, nickel HITP, and/or metal dichalcogenides or Mxenes such as $Ti_2C$, $(Ti0.5,Nb0.5)$, $V_2C$, $Nb_2C$, $Ti_3C_2$, $Ti_3CN$, $Nb_4C_3$, or $Ta_4C_3$.

Read Out Integrated Circuits

The device may further be configured to include a plurality of column and row lines coupled to the sensors in the array of sensors. In such an instance, each column line in the plurality of column lines may be directly or indirectly connected to or otherwise coupled to the drain terminals of the transistors, e.g., cascode transistors, of a corresponding plurality of sensors and/or pixels in the array, and likewise each row line in the plurality of row lines may be directly or indirectly connected to or otherwise coupled with the source terminals of the transistors, e.g., cascode transistors, of a corresponding plurality of sensors in the array. In some instances, the sensors in such an array may be independently addressable.

In some instances, a plurality of source and drain terminals having a plurality of sensing surfaces, e.g., channel members, extended there between may be included, such as where each channel member includes a one or two or even three dimensional material. In such an instance, a plurality of first and/or second conductive lines, and so forth, may be coupled to the first and second source/drain terminals of the ChemFETs in respective columns and rows in the array, and so forth. Additionally, control circuitry may be provided and coupled to the plurality of column and row lines such as for reading a selected sensor connected to a selected column line and/or a selected row line. The circuitry may also include a biasing component having a bias circuitry such as is configured to apply a read voltage, while a sample and hold circuit may be configured to hold an analog value of a voltage on a selected column line of the array during a read interval.

Particularly, the bias circuitry may be configured for applying a read voltage to the selected row line, and/or to apply a bias voltage such as to a gate terminal of a transistor, such as FET and/or cascode transistor of the selected sensor. In a particular embodiment, the bias circuitry may be coupled to one or more chambers of the array and be configured to apply a read bias to selected ChemFETs via the conductive column and/or row lines. Particularly, the bias circuitry may be configured to apply a read voltage to the selected row line, and/or to apply a bias voltage to the gate terminal of the transistor, e.g., cascode transistor, such as during a read interval.

A sense circuitry may also be included and coupled to the array so as to sense a charge coupled to one or more of the gate configurations of a selected ChemFET. In some instances the sense circuitry may sense a voltage level or a current level of a selected ChemFET. The sense circuitry may be configured to read the selected sensor based on a sampled voltage level on the selected row and/or column line. In such an instance, the sense circuitry may include one or more of a pre-charge circuit, such as to pre-charge the selected column line to a pre-charge voltage level prior to the read interval; and a sample circuit such as to sample a voltage level at the drain terminal of the selected transistor, such as during the read interval. A sample circuit may further be included and contain a sample and hold circuit configured to hold an analog value of a voltage on the selected column line during the read interval, and may further include an analog to digital converter to convert the analog value to a digital value.

In particular embodiments, the computer component of the ChemFET sensor IC chip structure may include a processor configured for controlling the performance of one or more reactions involving a biological or chemical material so as to obtain reaction results, and for analyzing those results, for instance, based on detecting and/or measuring changes in a voltage (V) potential, current (I), charge (Q) or capacitance (C) occurring on or near the ChemFET. Particularly, the processor, such as a microprocessor, a microcontroller or a signal processor, may be configured so as to generate one or more current (I) vs. voltage (V) curves, such as where the current I of the I–V curve is the current flowing at the drain of the ChemFET and/or where the gate voltage (Vgs) of the Id–Vgs curve is a gate voltage applied between the gate and source of the ChemFET. In such an instance, the gate voltage Vgs of the Id–Vgs curve may be a top, e.g., solution, and/or a back gate voltage that may be applied to the ChemFET through a top (or front) and/or back of the device, respectively.

In particular instances, a suitably configured device of the disclosure may be adapted as a front and/or back-gated device, which may further be configured as a solution gate. Accordingly, in various embodiments, a device of the invention may be a field-effect transistor that includes a chamber adapted for measuring ion concentrations in a solution; such as where, when the ion concentration (such as $H^+$ or $OH^-$ in a pH scale) within the chamber changes, the current through the transistor, e.g., a channel region thereof, will change accordingly. In such an instance, the solution, when added to the chamber forms, or otherwise serves as, a gate electrode.

Hence, in specific embodiments, the gate voltage $V_{gs}$ of the $I_d$-$V_{gs}$ curve may be a solution gate voltage such as applied to the ChemFET through a solution flowed over a portion, e.g., a chamber, of the device. In some embodiments, a reference $I_d$-$V_{gs}$ curve and/or a chemical sensing $I_d$-$V_{gs}$ curve may be generated in response to the biological activity, analyte material and/or chemical reaction that is to be detected and/or occurs over or near the ChemFET, such as within a chamber or well of the FET structure. In various embodiments, the processor may be configured to determine differences in relationships between a predetermined or generated reference $I_d$-$V_{gs}$ curve and/or chemical sensing $I_d$-$V_{gs}$ curve. In certain instances, the circuitry component may include at least one analog-to-digital converter that is configured for converting analog signals, such as obtained as a result of the performance of the reaction(s) within the sensing well, or array of wells, into digital signals.

Accordingly, in another aspect, a ChemFET device may be provided, wherein the device may include a structure having a conductive source and drain as well as having a surface or channel or other functionally equivalent surface structure extending from the conductive source to the conductive drain, such as where the surface or channel may include a one-, two-, or three-dimensional transistor nanomaterial. The device may also include a processor such as where the processor is configured for generating or otherwise determining, e.g. via a look-up-table, a reference $I_d$-$V_{gs}$ curve and/or generating a chemical sensing $I_d$-$V_{gs}$ curve, in response to the chemical reaction occurring within a chamber of the chemically-sensitive field effect transistor, and may be configured to determine a difference between the reference $I_d$-$V_{gs}$ curve and the chemical sensing $I_d$-$V_{gs}$ curve.

In some instances, the difference between the reference $I_d$-$V_{gs}$ curve measurement and the chemical sensing $I_d$-$V_{gs}$ curve measurement is a shift in a minimum point of the $V_g$ value of the chemical sensing $I_d$-$V_{gs}$ curve relative to a minimum point of the $V_g$ value of the reference $I_d$-$V_{gs}$ curve. In other instances, the difference between the reference $I_d$-$V_{gs}$ curve and the chemical sensing $I_d$-$V_{gs}$ curve is a shift in an Ion value of the chemical sensing $I_d$-$V_{gs}$ curve relative to an Ion value of the reference $I_d$-$V_{gs}$ curve, for instance, where the Ion values are taken from a p-type or n-type section of the $I_d$-$V_{gs}$ curve. For example, the measurements of the slopes (one type of parameter of an $I_d$-$V_{gs}$ curve) may be taken from the steepest and/or flattest sections on the p-type and/or n-type portions of the $I_d$-$V_{gs}$ curves.

In particular instances, the difference between the reference $I_d$-$V_{gs}$ curve and the chemical sensing $I_d$-$V_{gs}$ curve is a shift in an $I_{off}$ value (another representative $I_d$-$V_{gs}$ curve parameter) of the chemical sensing $I_d$-$V_{gs}$ curve relative to an $I_{off}$ value of the reference $I_d$-$V_{gs}$ curve. In one embodiment, the difference between the reference $I_d$-$V_{gs}$ curve and the chemical sensing $I_d$-$V_{gs}$ curve is a change in the slope of the chemical sensing $I_d$-$V_{gs}$ curve relative to a change in the slope of the reference $I_d$-$V_{gs}$ curve. In another embodiment, the difference between the reference $I_d$-$V_{gs}$ curve and the chemical sensing $I_d$-$V_{gs}$ curve is an overall change in shape (another $I_d$-$V_{gs}$ curve parameter) of the chemical sensing $I_d$-$V_{gs}$ curve relative to an overall change in shape of the reference $I_d$-$V_{gs}$ curve. In other embodiments, the difference in overall shape of the $I_d$-$V_{gs}$ curves is determined by first fitting a polynomial or other fitting line to each of the $I_d$-$V_{gs}$ curves and then comparing the coefficients of those fitting lines. In other embodiments, the difference between a reference $I_d$-$V_{gs}$ curve and the chemical sensing $I_d$-$V_{gs}$ curve is based on more than one chemical sensing $I_d$-$V_{gs}$ curve.

Accordingly, in particular embodiments, the FET and/or processor may be configured to respond to a shift in the I-V or $I_d$-$V_{gs}$ curve, such as where the curve is shifted in response to the detection of an analyte, biologic activity and/or the result of a reaction taking place near or on a surface of the FET device. In some instances, the I-V/$I_d$-$V_{gs}$ curve may be produced and/or shifted in response to a chemical reaction occurring proximate to a sensing layer and/or the surface of a 1D or 2D nanomaterial, e.g., graphene, surface of the field effect transistor, such as resulting from the detection of a biological compound or reaction occurring within the well structure of the device. Hence, the FET and/or processor may be configured so as to shift the reference I-V curve or chemical sensing (or "test") $I_d$-$V_{gs}$ curve such as in response to the chemical reaction. In various embodiments, one or more elements and/or methods, as herein described, may be used to shift a reference I-V or $I_d$-$V_{gs}$ curve and/or a chemical sensing $I_d$-$V_{gs}$ curve so that the difference between the reference $I_d$-$V_{gs}$ curve and a chemical sensing $I_d$-$V_{gs}$ curve is more pronounced. For instance, the device may include a structure, such as a membrane, other surface layer, and/or other element configured for enhancing the ability of the processor to determine the difference between various I-V and/or $I_d$-$V_{gs}$ curves.

Hence, in a further aspect, a ChemFET transistor that is fabricated on a primary structure having a stacked configuration including one or more of an inorganic base layer, e.g., a silicon layer; a dielectric and/or an organic or inorganic dielectric layer, such as a silicon dioxide layer; a 1D, 2D, or 3D nanomaterial layer, such as a carbon nanotube, nanowire, or graphene layer; an analyte or reaction-sensitive layer, e.g., oxide layer and a passivation layer; and further having a conductive source and drain embedded in one or more of the layers, with the nanomaterial forming a channel between the source and drain, and a gate structure, e.g., a solution gate region, may be provided. In various embodiments, the sensing region may be configured so as to form a chamber or well and the 1D or 2D nanomaterial and/or oxide layers may be positioned between the conductive source and drain in such a manner as to form a bottom surface of the chamber. The structures may further include or otherwise be associated with an integrated circuit and/or a processor, such as for generating and/or processing generated data, such as sensor derived data.

Ion Permeable Layer and Ion Getter

In particular embodiments, a further structured layer, e.g., a secondary or tertiary structure, may also be provided, such as where the further structured layer may be included and/or present within the well or chamber, such as to enhance the ability of the processor to determine the difference between the current and/or voltages as well as their respective associated curves. Particularly, the additional structure may include an additional layer, e.g., an ion-selective permeable membrane, such as an ion-selective permeable membrane that allows ions of interest to pass through the membrane while blocking other ions, such as to enhance the ability of the processor to determine the difference between the reference I-V or $I_d$-$V_{gs}$ curve and the chemical sensing I-V or $I_d$-$V_{gs}$ curve (or corresponding parameters thereof), and thus enhance the ability of the processor to detect a desired chemical reaction. In various instances, the FET may be configured such that the I–V or $I_d$–$V_{gs}$ curve (s) may be shifted so as to better respond to, detect, and/or otherwise determine a biological compound and/or a chemical reaction, such as a biological compound and/or a chemical reaction occurring on or near the 1D or 2D nanomaterial, e.g., graphene, surface of the ChemFET. In particular instances, the ion-selective permeable membrane may include a 2D transistor nanomaterial, e.g., graphene, which may or may not be electrically connected to the source and/or drain layer and/or channel.

Accordingly, in various instances, the ion-selective permeable membrane may be positioned within the well and/or over a passivation layer, an ion sensitive or sensing layer, a 1D and/or a 2D transistor nanomaterial layer, and/or a dielectric layer that itself may be positioned over and/or otherwise form a part of the chamber or channel. In certain embodiments, the membrane layer or an additional structural layer may be, or otherwise be associated with, an ion getter material. Such an ion getter material may be any suitable material that traps ions that may not be relevant to the biological species, biologic activity and/or chemical reaction to be sensed and/or determined, such as to enhance the ability of the processor to determine the difference between the reference I–V or $I_d$–$V_{gs}$ curve and/or the chemical sensing I–V or $I_d$–$V_{gs}$ curve (or corresponding parameters thereof), e.g., because there are fewer interfering ions, thus enhancing the ability of the processor to detect the desired biological species and/or results of the chemical reactions. Particularly, the ion getter material may be arranged within proximity to the chamber and/or surface thereof so that the action of gettering (or sequestering) the unwanted ions improves the detection capability of the ChemFET. In some instances, one or more of the various layers herein, such as the ion getter material may be placed over one or more of the other layers, such as the dielectric layer, oxide layer, or 1D or 2D or 3D nanomaterial layers, positioned in proximity to one or more of the chambers, channels, or surfaces of the FET device. For instance, a ChemFET of the invention may include a secondary or tertiary structure that includes a 2D nanomaterial transistor channel or surface that may include an ion-sensitive material over the channel or surface. In such an instance, the material may be sensitive to ions that are different from the ions associated with the biological molecule or chemical reaction that is to be detected. Particularly, in some instances, the action of sensing ions that are different from the ions associated with the biologics and/or chemical reactions that are to be detected allows the processor to filter out the signal from the unwanted ions from the signal of the ions of interest thereby decreasing the overall noise in the system.

Charge Trap Screening Material

In particular instances, an additional material, e.g., HMDS, parylene, hexagonal boron nitride (hBN), aluminum oxide or other material, may be included so as to manage the interaction of the channel and/or associated 1D or 2D or 3D nanomaterial transistor layer with the dielectric layer under the channel or nanomaterial. It is known in the art that certain dielectrics, particularly such as silicon dioxide, when adjacent to a channel may trap charges and interfere with the ideal functioning of the channel, such as by creating noise in the FET. Alternate dielectric materials, and especially materials that may be smooth and have lattice parameters similar to the 1D or 2D nanomaterial of the channel, can significantly reduce the charge trapping effect. In particular when the channel nanomaterial is graphene then hBN is a good material choice (both materials have a lattice parameter of about 2.5 angstroms) to attenuate any charge trapping and thus reducing the noise generated in the ChemFET.

Fluidics Component

In a further aspect of the present disclosure, systems having a chemically-sensitive transistor, such as a ChemFET including one or more chambers, e.g., a plurality of chambers having a well structure(s) formed therein is provided. In such an instance, the well(s) may be structured as a sensing location, wherein one or more chemical reactions may take place or one or more analytes may be detected or biologic activity may be sensed. In such an embodiment, the system may include a fluidics component having a fluid source, e.g., a reservoir, containing one or more fluids therein and configured for delivering the fluid from the reservoir to the sensing chamber, such as for the detection of a biologic and/or the performance of one or more chemical and/or biological reactions, such as a nucleic acid sequencing reaction. Hence, the fluidics component, e.g., the fluid source, may be in fluidic communication with the FET device configured for biological and/or chemical analysis.

Use of Magnetic or Electric Fields to Position Microbeads

Accordingly, in certain instances, the fluid may include one or more reactants, such as one or more components necessary for performing a sequencing and/or detection reaction, as herein described. In a particular embodiment, the fluid may include one or more, e.g., a plurality of, microbeads or particles having nucleic acid templates attached thereto, for instance, where the template is complementary to a portion of, and thus hybridizes to, a DNA or RNA molecule to be sequenced or detected, and the fluid containing the microbead is to be delivered to the well such as for carrying out the sequencing reaction. In such embodiments, one or more of, e.g., each, of the plurality of microbeads or particles may be configured so as to have electric charge and/or paramagnetic properties. The device may additionally include an electric and/or magnetic field component, e.g., having an electric and/or magnetic field generator, such as where the electric and/or magnetic field component is configured to generate an electric and/or magnetic field so as to interact with the electric and/or magnetic charge properties of each of the plurality of microbeads or particles to attract them into a sensing location, such as a sensing surface, a channel, a well, a chamber, and/or a sensor of the FET device, such as by using electrophoresis and/or magnetism.

Hence, one or more, e.g., a plurality of microbeads, may be drawn onto or into a sensing location of the plurality of sensing locations, which locations may be formed as wells and/or chambers, e.g., one or more thin wells or deep chambers. The microbeads may include a reagent such as a biological material or a chemical material, e.g., one or more nucleotide sequences. Particularly, a fluid including the reagent, such as containing microbeads containing the reagent, may be introduced into the wells and/or chambers, such as by a fluidics component of the disclosure.

Accordingly, the reagent may be a nucleic acid sequence having negative charge properties and/or the reagent may be coupled to a magnetic micro- or nano-bead, as such, in certain embodiments, an electric and/or magnetic field may be applied individually or collectively to the wells and/or chambers, so as to draw the reagent, e.g., a reagent containing microbead, onto each sensing location, e.g., into each well, chamber, and/or or sensor containing channel. In various instances, the electric and/or magnetic field component generates an electric and/or magnetic field so as to interact with the electric charge properties of the reagent and/or microbeads, thereby drawing it to the sensing location. In certain instances, the microbeads or particles themselves may be charged and/or may have electric and/or paramagnetic properties, and thereby may be drawn to the sensing location using electrophoresis and/or magnetism.

The use of electrophoresis and/or magnetism allows for thinner sensing location structures. In particular instances, therefore, an electric and/or magnetic field generator may be configured for drawing and/or positioning a microbead or particle within the well structure, such as in proximity to a channel or chamber of the device, and in other instances, the electric and/or magnetic field generator may be configured for reversing the electrical and/or magnetic field so as to repulse the microbead or particle from the sensing location, channel, and/or chamber. In various instances, an array of sensing locations may be provided each having a magnet that allows for selective filling of the sensing locations with different numbers and/or types of reactants and/or microbeads, such as at select sensing locations. In such an instance, multiple electric and/or magnetic field generators for selective filling of sensing locations, e.g., wells, may be provided.

Accordingly, one aspect of the present disclosure concerns systems and/or methods for positioning one or more, e.g., a plurality, of reactants and/or microbeads, e.g., containing one or more DNA and/or RNA templates attached thereto, within a sensing or plurality of sensing locations for biological or chemical analysis, such as for nucleic acid sequencing and/or detection. Such a system may include a CMOS FET device having an integrated circuit structure configured for performing a biological or chemical analysis, such as within a plurality of nano- or micro-sensing wells, as described above, having a fluidic component, a circuitry component, and/or a computing component, and the method may include one or more of the following steps.

For instance, the method may include the fluidic component introducing a fluid to be in contact with the device, such as where the fluidics component is configured to control a flow a fluid of reagents over the array, and where the fluid may include one or more microbeads or particles that may have electric charge and/or paramagnetic properties. In such an instance, the device may include an integrated circuit structure, a plurality of sensing locations having one or more chambers and/or wells, a plurality of sensors and/or a plurality of channels, and/or an electric and/or magnetic field component. The electric field and/or magnetic field component may be configured to activate the electronic and/or magnetic field, and the method may also include activating an electric and/or magnetic field so as to interact with the electric and/or paramagnetic properties of each of the microbeads. The method may additionally include drawing the one or more microbeads or particles into a sensing location of the plurality of sensing locations using electrophoresis and/or magnetism. In certain instances, the method may include positioning the one or more microbeads and/or particles within the one or more sensing locations for biological or chemical analysis.

In particular instances, the electric and/or magnetic fields may be generated by the plurality of electric and/or magnetic field generators, e.g., included in the integrated circuit structure, in all or only a subset of the plurality of sensing locations so as to only attract a plurality of microbeads to the subset of sensing locations, such as for selectively filling the plurality of sensing locations with the plurality of microbeads. In such an instance, different types of microbeads may be attracted to different sensing locations, such as by pulsing the voltage and/or magnetic generators and/or keeping the same constant. Particularly, where an electric field generator is provided the voltage applied to the device may be variable or constant and may be less than about 10V, such as about less than 8V, or less than about 6V, including less than about 4V or about 2V or 1V. The voltage may be applied between a location above the fluid and a location on or below the sensing location, such as above the package lid and/or below the metal plate below the package. In certain instances, the location below the sensing location may be a metal or conductive layer such as within the package or package substrate. The methods may also include the step of reversing the electric or magnetic field so as to eject the plurality of bead or particles from the plurality of wells, sensors, and/or channels, either entirely or selectively.

Further, as indicated, each or a subset of the plurality of sensing locations may be utilized in correspondence with generating electric fields to attract a microbead or particle into or proximate the sensing location, thereby allowing for programmability or addressing capability to each or a subset of sensing locations, for instance, 99% or 95% or 90% or 85%, or 80% or less of the plurality of wells are occupied with a microbead and/or particle or other sensing location.

Additionally, in another aspect of the disclosure, a device, system, and/or method for verifying well occupancy for a plurality of wells or chambers for analysis of biological or chemical materials may be provided. For instance, a device of the system may include a plurality of wells or chambers being associated with a plurality of sensors, such as where each well or chamber includes or is otherwise associated with or configured as a chemically sensitive FET. In such instances, the system may include a device for receiving a fluid containing the plurality of microbeads, particles, reactants, and/or other carriers compatible with microfluidic fluid flow in automated chemical/biological analysis devices.

Particularly, the ChemFET IC chip may include a processor, a semiconductor IC structure, e.g. a CMOS structure having an integrated circuit, a plurality of wells and/or chambers, and a plurality of sensors within the IC chip structure. Each of the plurality of wells or chambers may be configured to receive a microbead or particle of the plurality of microbeads and/or particles, and the ChemFET sensor IC chip structure may include a mechanism for drawing and/or ejecting the microbeads or particles into or out of the wells. Hence, the method may include the step of flowing the plurality of microbeads and/or particles over and/or into the plurality of sensing locations and/or wells and/or chambers and/or may include determining, e.g., through electrical and/or magnetic sensing if a sensing location and/or well and/or chamber is occupied or unoccupied and/or if a sensing location contains one or multiple microbeads.

Consequently, the processor may be configured to determine if a location, e.g., a well and/or chamber, is unoccupied and/or if the well and/or chamber contains one or more, e.g., multiple microbeads. In certain instances, the processor may also be configured to eliminate or modify one or more of the measurements, such as based on the number of wells and/or chambers occupied or unoccupied, e.g., the number of wells containing none, one or multiple microbeads. For instance, the processor may be configured to eliminate from the measurement the number of wells and/or chambers unoccupied and the number of wells and/or chambers containing multiple microbeads, or compensate in the measurement for the number of wells and/or chambers unoccupied and the number of wells and/or chambers containing multiple microbeads, and the like. Such compensation can be provided as part of a calibration step of a ChemFET sensor IC chip prior to its use. The results of the calibration step may be recorded and referred to a later time when the ChemFET sensor IC chip is being used for detection or analysis of an analyte, chemical reaction or biologic activity.

Detailed Description of Representative Aspects and Embodiments

Accordingly, provided herein are devices, systems, and methods of employing the same for analysis of biological or chemical materials. Particularly, the devices, systems, and methods of the disclosure are directed in part to 1D, 2D, or 3D nanomaterial channel ChemFET sensors, integrated circuits, and arrays employing the same for analyte, reaction or biologic activity measurements. The present ChemFET sensors, arrays, and integrated circuits may be fabricated using conventional semiconductor, e.g. CMOS, processing techniques based on improved 1D, 2D, or 3D nanomaterial ChemFET sensor and array designs that increase measurement sensitivity and accuracy, and at the same time facilitate significantly smaller sensor sizes and dense sensor array designs and real-time detection.

ChemFET Structure

Generally a ChemFET device will include a conductive source and a conductive drain in or on a dielectric material, a channel extending between the source and drain, e.g. comprised of a 1D or 2D nanomaterial, that functions as a sensing layer, an insulating passivation layer with an opening or well on or over the channel and a gate to control the conductance of the channel. In some embodiments the ChemFET may also comprise an analyte or reaction sensitive material layer over or on the nanomaterial channel.

One aspect of the present disclosure is a ChemFET that is fabricated in a stacked configuration including a primary structure, such as a wafer, e.g., a silicon wafer, as well as one or more additional structures. For instance, a dielectric material layer may also be included and positioned on top of the primary structure, and may be an inorganic material. The first and/or second structures may further be configured to include an additional structure or structure layer that includes one or more of a conductive source and a conductive drain. The conductive source and the conductive drain may be orientated so as to be separated one from another by a space, which space may be spanned by a ChemFET channel made of a 1D or 2D nanomaterial. The source, drain, and channel can be embedded in the primary and/or secondary structures and/or may be planar or non-planar with a top surface of the secondary structure or a further layer or structure associated therewith. In various embodiments, the structures further include a processor, such as for processing generated data, such as sensor-derived data. Accordingly, the structures can be configured as, or otherwise include, an integrated circuit chip, and/or may be a ROIC, an ASIC, a structured ASIC, or an FPGA.

Figure 1A:
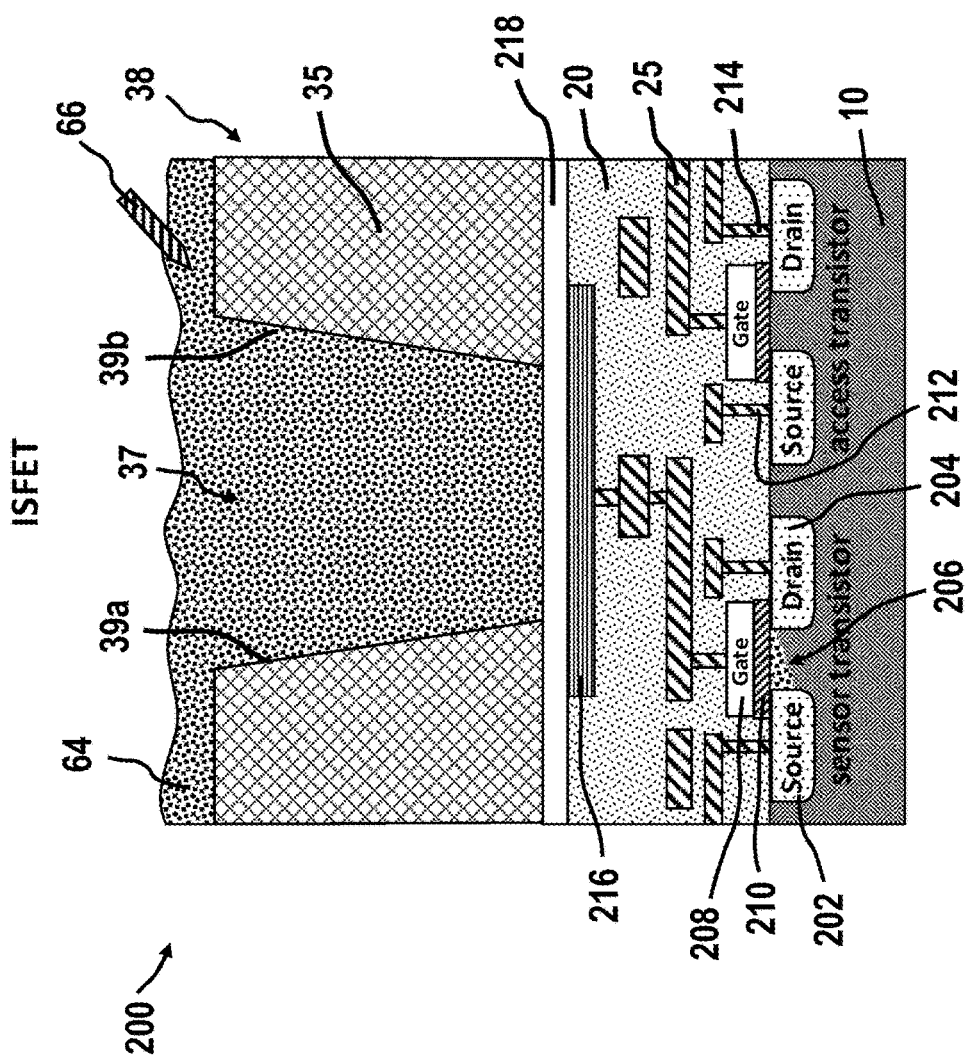
FIG. 1A is a side sectional illustration of an ISFET device fabricated using traditional semiconductor FET transistor technology for the sensor transistor.
Figure 1B:
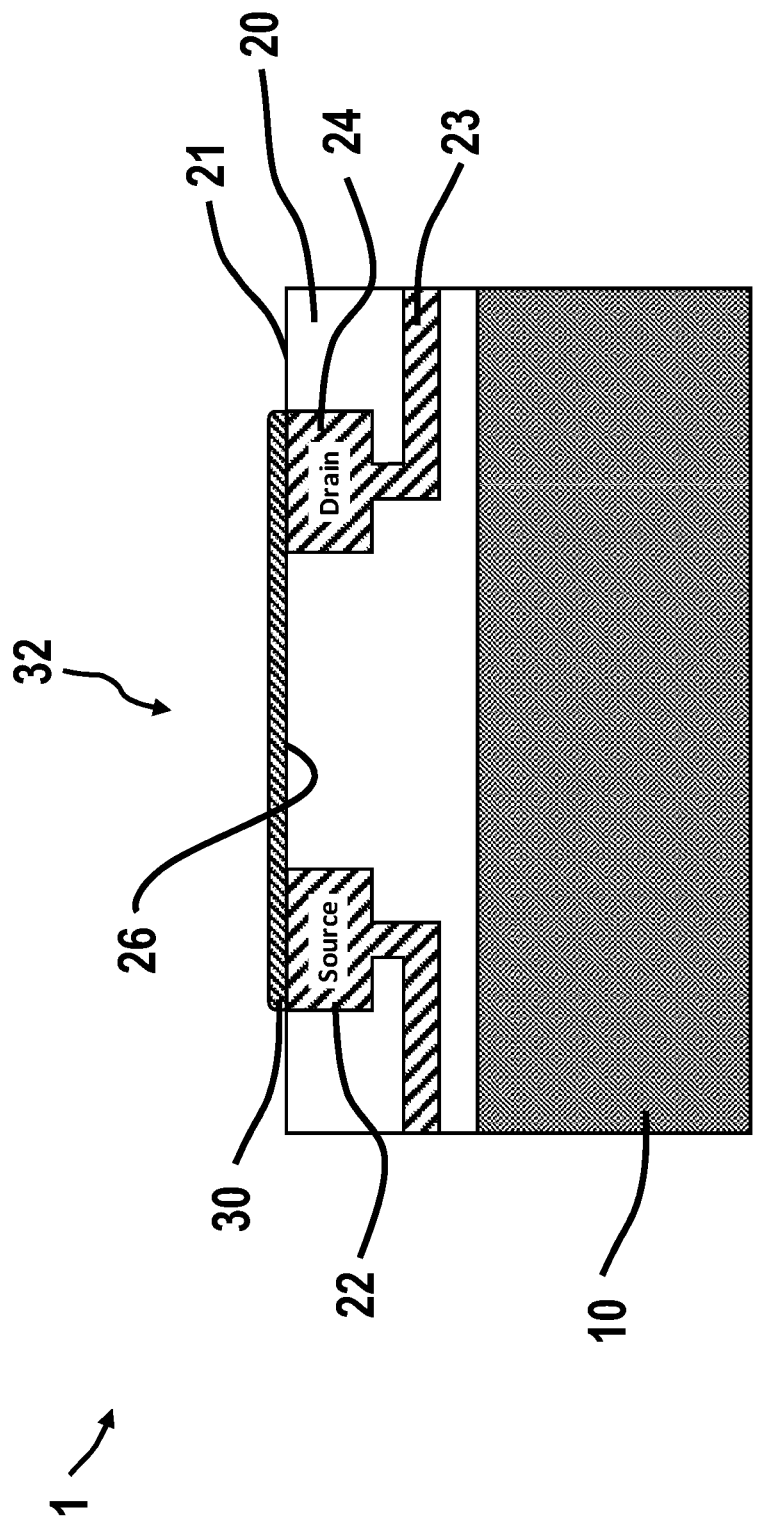
FIG. 1B is a side sectional illustration of a substrate for use in a ChemFET, such as for a system for analysis of biological and/or chemical materials. In this instance, the substrate includes a dielectric layer having a source and a drain, and further includes a sensing zone having a graphene nanomaterial layer associated therewith.
Figure 1C:
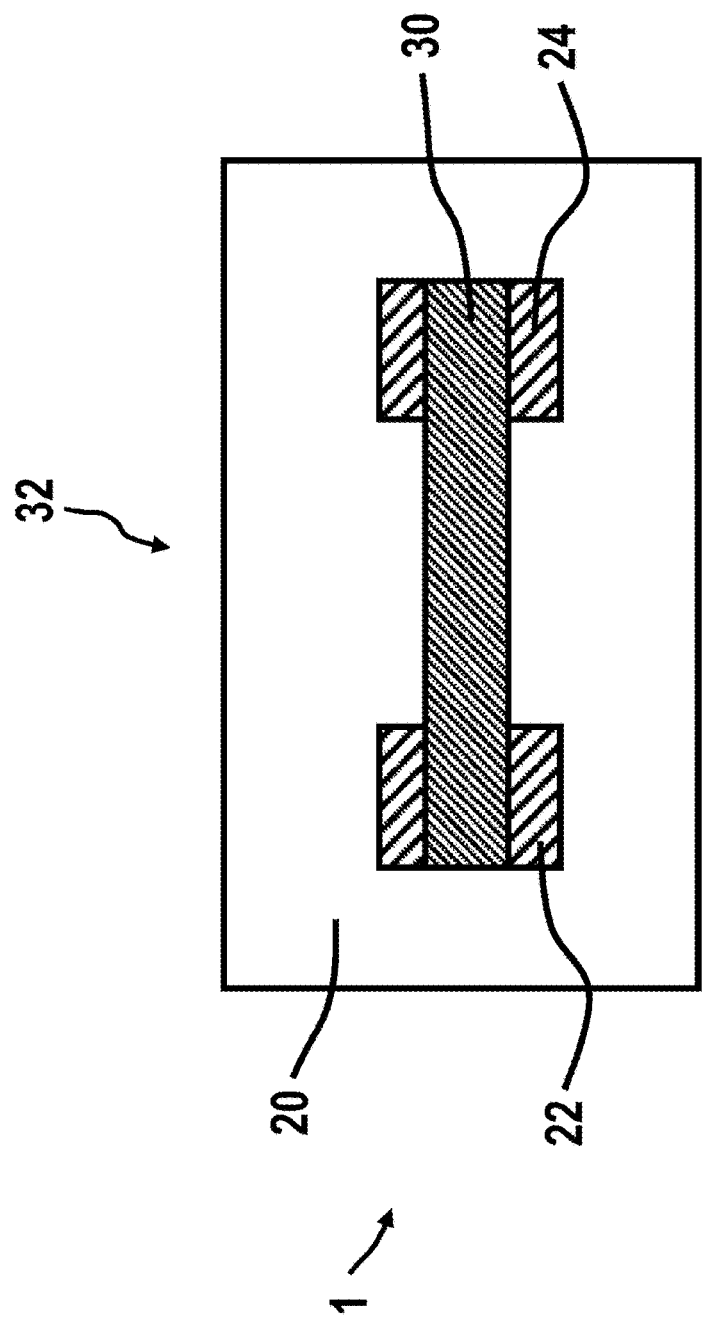
FIG. 1C is a top down illustration of a substrate for use in a ChemFET, such as for a system for analysis of biological and/or chemical materials. In this instance, the substrate includes a dielectric layer having a source and a drain, and further includes a sensing zone having a graphene nanomaterial layer associated therewith.

For instance, as can be seen with respect to FIG. 1B (side sectional view) and FIG. 1C (top down view), a 2D nanomaterial layered substrate (1), such as a graphene layered substrate, for a ChemFET, such as for a system for the analysis of chemical and/or biological materials, is provided. The layered substrate (1) includes a primary base structure (10), such as composed of a semiconductor material such as silicon. In various embodiments, the semiconductor-based primary base structure (10) can be configured to support a semiconductor, e.g. CMOS, construct. The primary base structure (10) can support one or more additional structures such as a dielectric material layer (20). For example, the layered substrate (1) may be in a stacked configuration such as where a secondary structure, e.g., including a dielectric material (20), is deposited or otherwise fabricated on top of the primary base structure (10). The secondary structure includes conductive interconnects (23) located in or on the dielectric material (20).

The primary base structure (10) and/or dielectric layers (20) may further include a channel region (26) having a channel 30 that extends from a conductive source (22) to a conductive drain (24), the conductive channel comprised of a 1D transistor material, e.g. Si NW or CNT or a 2D transistor material, e.g., graphene. For instance, the stacked structured layers are configured to include a channel region (26), which in turn may be adapted as the sensing layer. Particularly, in certain instances, the dielectric layer (20) includes a channel (30) and a conductive source (22) and a conductive drain (24), wherein the source and drain are separated from one another by a space that is spanned by channel region (26), which source and drain may be, in this instance, planar with a top surface (21) of the dielectric layer (20). The source (22) and drain (24) are conductive and may be made of metal, such as aluminum or copper or other conductor such as polysilicon. In various embodiments, the dielectric material is an organic or an inorganic material. In some embodiments, the organic material is a polymer, polyimide, BCB, PBO or other like material. In other embodiments, the inorganic material may be a silicon oxide, e.g., a silicon dioxide, or a silicon nitride or other oxide, carbide or nitride or mixtures thereof.

In particular embodiments, the layered structures are configured as a semiconductor device, such as a CMOS device, further configured with a ChemFET containing one or more of a conductive source (22), a conductive drain (24), and a channel 30. In some embodiments, a processor may be operably associated with the ChemFET. For instance, the ChemFET (1) chip may include a CMOS structure having an integrated circuit that is fabricated on a silicon wafer (10), which further includes a silicon dioxide dielectric layer (20), including a conductive damascene copper source (22) and a conductive damascene copper drain (24), which are embedded in or on at least the dielectric layer (20). In various instances, the structures may include a surface (21), e.g., a top surface, which surface may include the channel region (26), such as where the surface and/or channel region may be configured as a sensing zone (26) that extends from the conductive source (22) to the conductive drain (24). An exemplary length of the sensing surface and/or channel region (26) from the source to the drain may range from about 0.001 microns to about 10 microns, such as from about 0.01 microns to about 5 microns, for instance, from about 0.05 micron to 3 microns, including about 0.1 or about 0.5 microns to about 1 or about 1.5 or about 2 microns. An exemplary width of the surface and/or channel from side to side may range from about 0.001 microns to about 10 microns, such as from about 0.01 microns to about 5 microns, for instance, from about 0.05 microns to 3 microns, including about 0.1 or 0.5 microns to about 1 or about 1.5 or about 2 microns.

In certain embodiments, the surface and/or channel region may form a sensing layer (26) that include a chemically-sensitive 1D or 2D nanomaterial transistor layer (30) forming a channel. Accordingly, in various embodiments, a 1D transistor material may be included, which 1D nanomaterial can be composed of a carbon nanotube or a semiconductor nanowire. In other embodiments, a 2D transistor material is included, which 2D nanomaterial may be a graphene layer, silicene, molybdenum disulfide, black phosphorous (phosphorene), borophene, tungsten disulfide, boron nitride, tungsten diselenide, stanene, germanane, nickel HITP, and/or metal dichalcogenides or Mxenes such as Ti2C, (Ti0.5, Nb0.5), V2C, Nb2C, Ti3C2, Ti3CN, Nb4C3, or Ta4C3

Figure 1D:
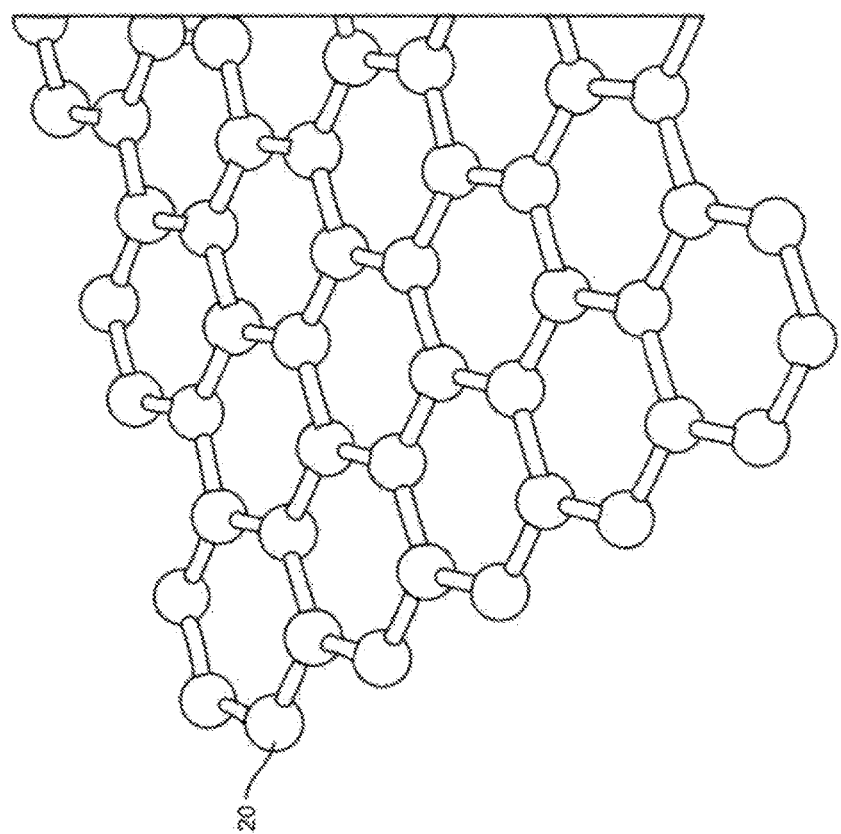
FIG. 1D is an illustration of a graphene nanomaterial, such as for use in the substrate of FIG. 1C.

For instance, in various embodiments, the chemically-sensitive 1D or 2D nanomaterial transistor layer (30) may be a single layer or a 2D nanomaterial such as a graphene. Particularly, as can be seen with respect to FIG. 1D, graphene is a two-dimensional, monolayer of carbon atoms that are arranged as a lattice structure. This lattice structure forms regular hexagons with a carbon atom at each vertex. In such a structure, the bond length between adjacent carbon atoms is about 1.42 Å and the lattice constant is about 2.46 Å. This molecular structure is very unique in that each carbon atom shares one of its four free valence electrons with three of its adjacent and planar carbon atoms such that each of the three planar carbon atoms is orientated at about a 120° with respect to the other three carbon atoms. Such an orientation gives graphene its honeycomb, lattice structure. Additionally, the fourth valence electron forms a pi bond, which may be perpendicular to the three planar sigma-bonded carbon atoms, which is responsible for the unique electronic characteristics of graphene.

Particularly, the single-layer, two-dimensional structure of graphene gives it at least three important characteristics with respect to its use herein: it has a large surface area to volume ratio; it makes the graphene layer a semimetal or ambipolar material; and it promotes rapid charge transport (high carrier mobility) at room temperature. Hence, in various instances, a graphene FET as herein described performs better as a biosensor or chemsensor than a typical MOSFET device not having such a nanomaterial channel layer. For instance, with respect to nucleic acid hybridization detection and/or sequencing, a traditional MOSFET transistor may have fundamental limitations in its sensitivity (due to channel thickness and intervening insulating and interconnect layers), whereas the present FET, e.g., GFET, with its single atom thickness, can be employed to form a solution-gated sensing zone and/or channel, wherein the graphene layer (30) may be in direct contact with or coupled to a chemical sensing zone (26) proximate. Specifically, the channel layer (30) may include a 1D or 2D transistor nanomaterial configured so as to have a much higher carrier mobility than the typical doped silicon commonly used in MOSFET or ISFET devices. This gives the instant 1D and 2D nanomaterial ChemFET-based sensor devices increased sensitivity to and faster detection of chemical reactions, analytes or biologic activity. Further, in various embodiments, the surface and/or channel region (26) may include or comprise an analyte or reaction-sensitive insulating layer (not shown in FIG. 1B or FIG. 1C), such as for further increasing sensor sensitivity and/or functioning.

Figure 1E:
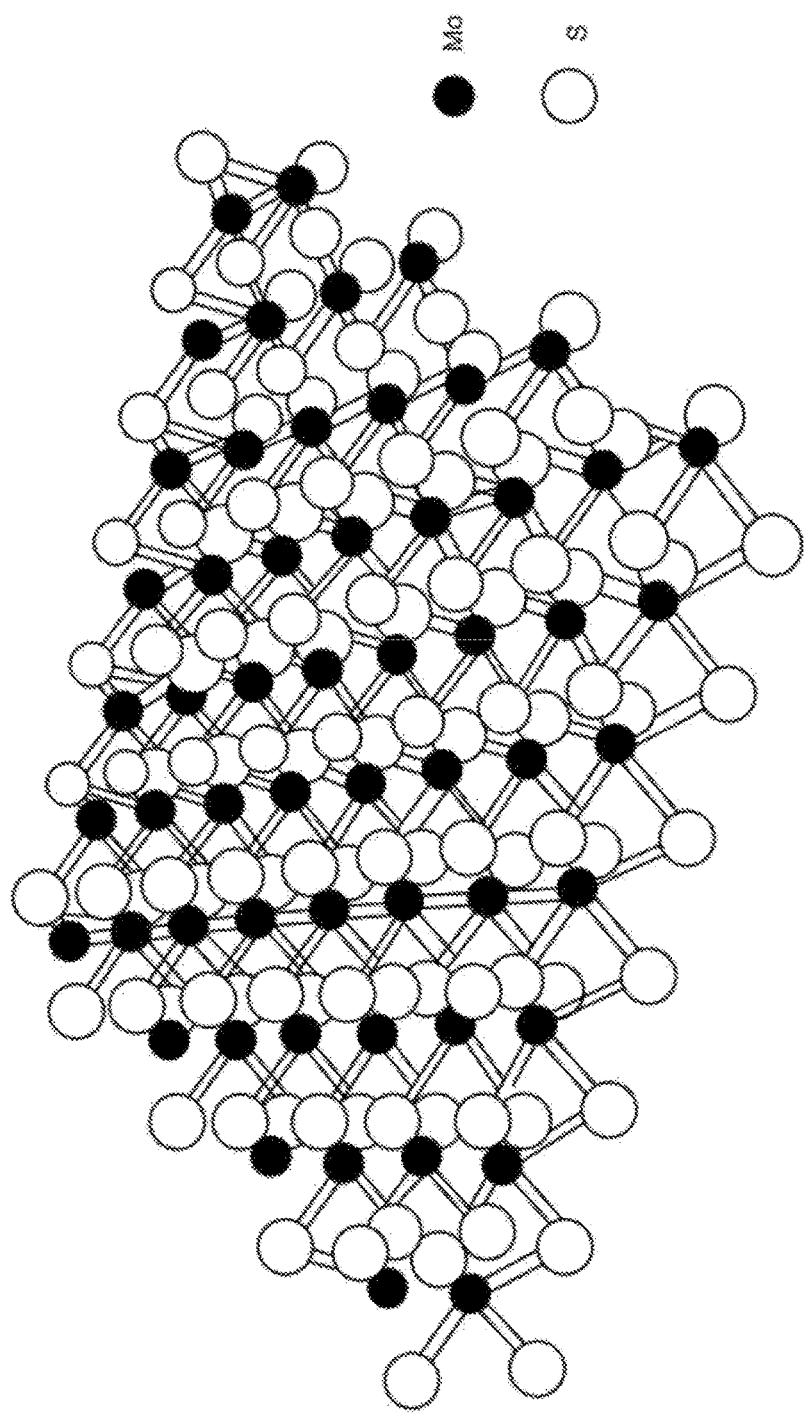
FIG. 1E is an illustration of molybdenum disulfide nanomaterial.
Figure 1F:
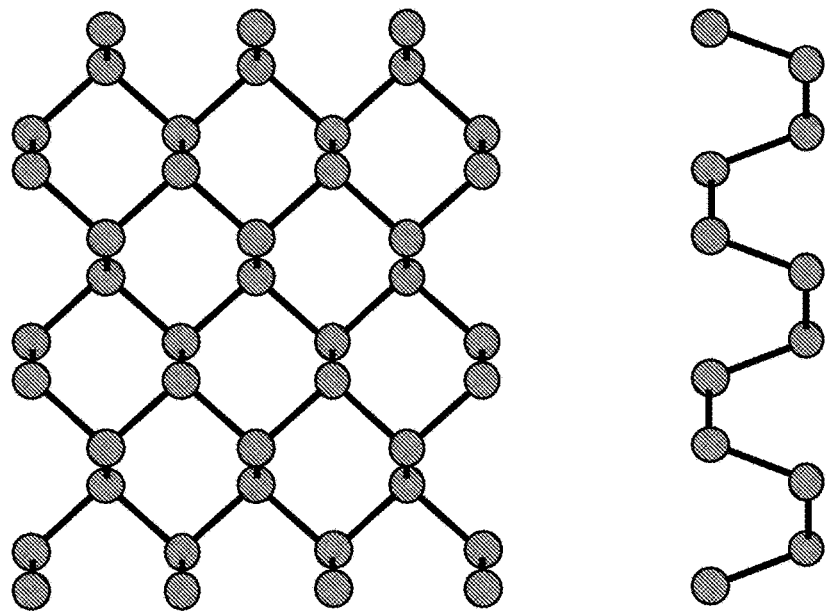
FIG. 1F is an illustration of black phosphorous or phosphorene nanomaterial. The upper illustration is a top down view and the lower illustration is a side view of the nanomaterial.
Figure 1G:
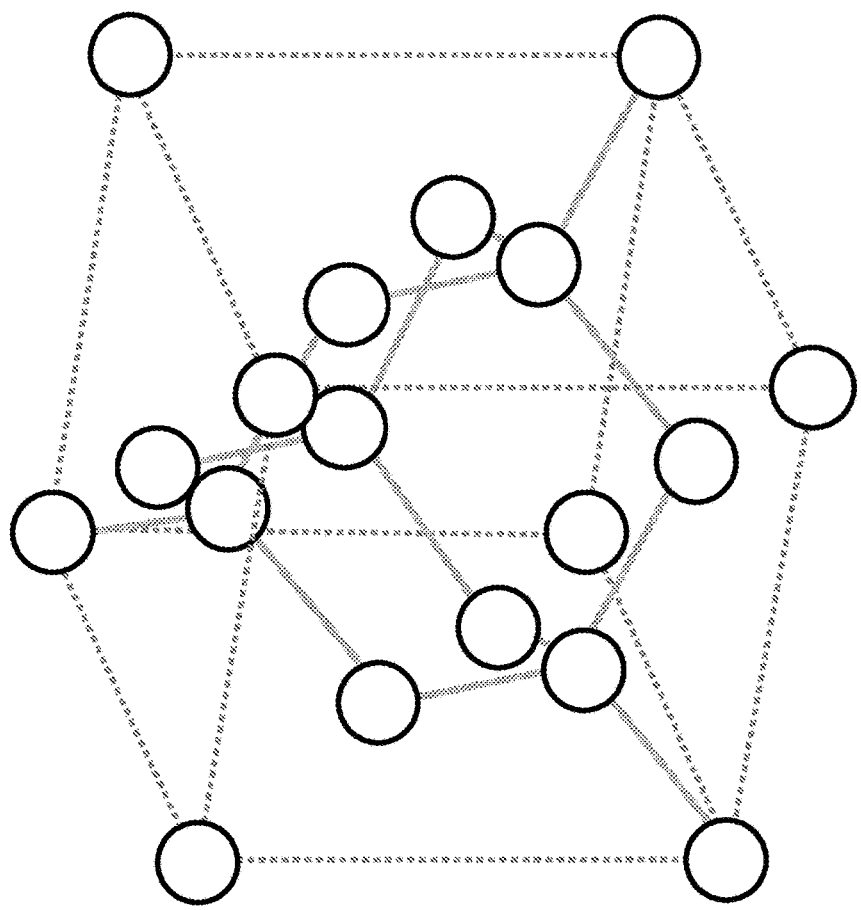
FIG. 1G is an illustration of silicon in its crystalline state.
Figure 1H:
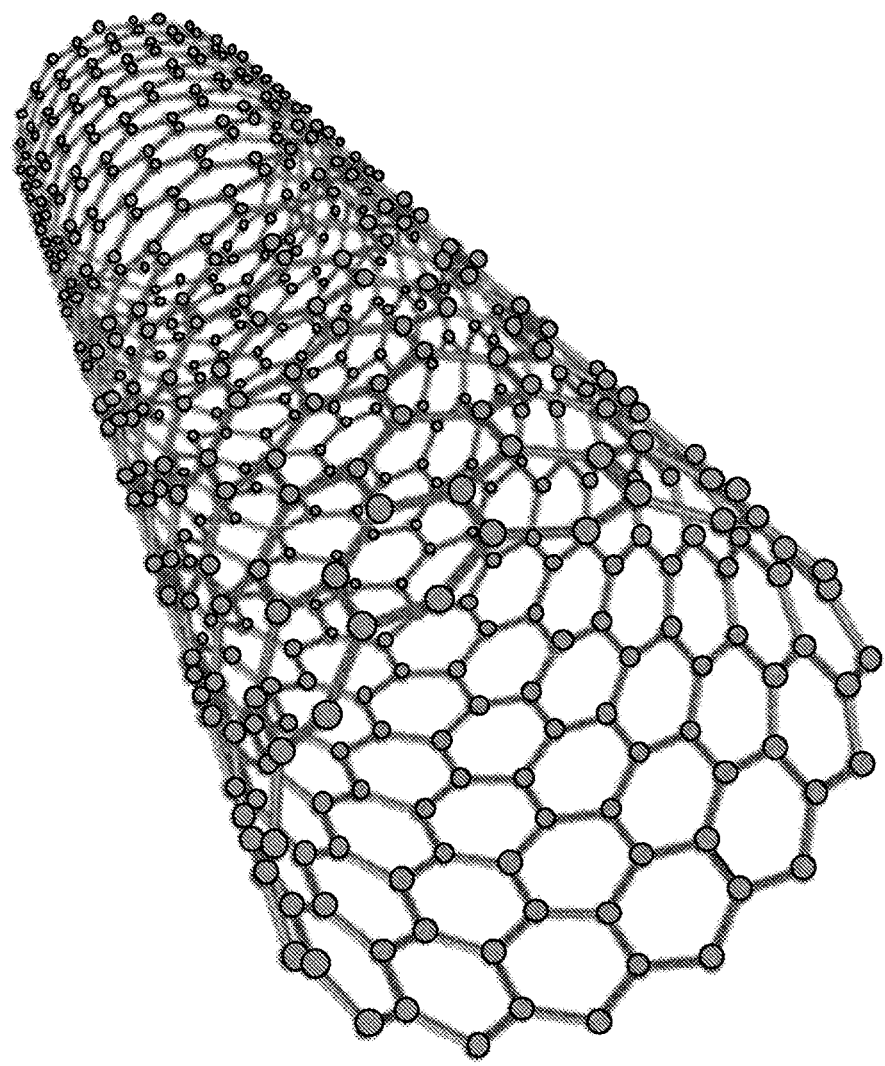
FIG. 1H is an illustration of a carbon nanotube (CNT).
Figure 1I:
FIG. 1I is an illustration of a semiconductor nanowire (NW) structure formed as nanowire.
Figure 1J:
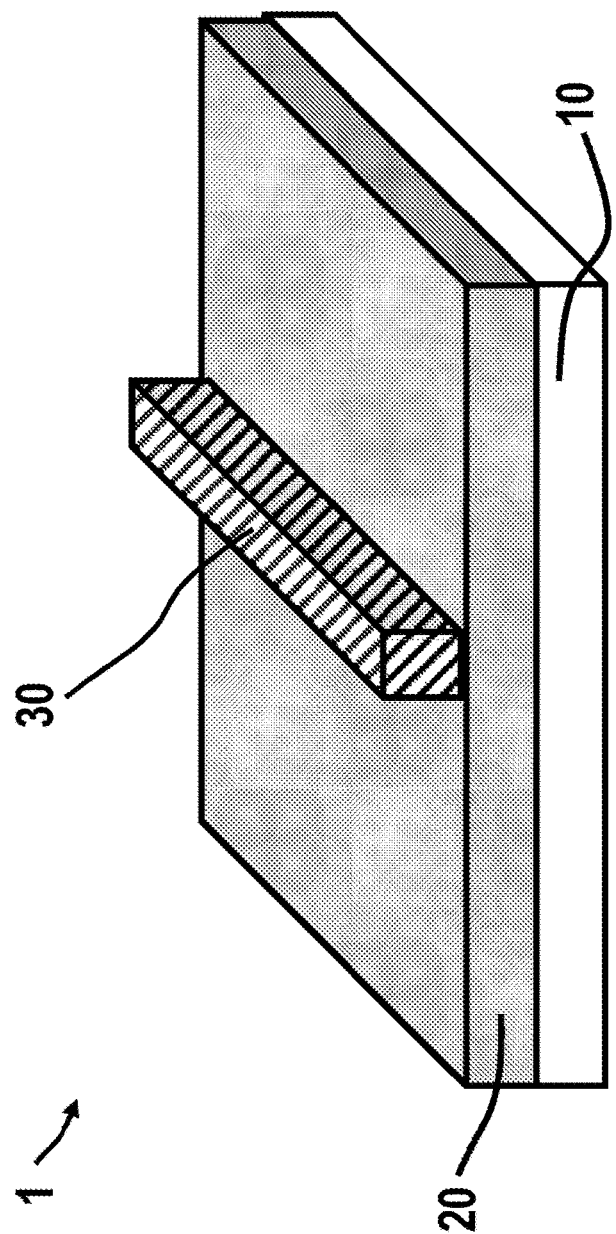
FIG. 1J is an illustration of a semiconductor nanowire (NW) structure formed from a bulk semiconductor layer.

Additionally, FIG. 1E depicts an alternative 2D transistor nanomaterial layer (30) that can be employed so as to increase sensitivity of the sensor so as to better enable the FET (1) to determine the presence and/or identity of one or more reactants and/or products thereof that results from the occurrence of a chemical and/or biological reaction or activity that takes place proximate to the ChemFET (1). As can be seen with respect to FIG. 1E, the 2D nanomaterial layer in this instance is molybdenum disulfide. Further 2D nanomaterials, as presented herein to increase sensitivity of the sensors include a black phosphorous layer (phosphorene), as depicted in FIG. 1F, and crystalline silicon as depicted in FIG. 1G. Alternatively, a 1D nanomaterial, such as a carbon nanotube may be employed for these enhancement purposes, such as presented in FIG. 1H. A semiconductor nanowire structure may also be used, such as depicted in FIG. 1I for a nanowire formed separately as a nanowire or as depicted in FIG. 1J for a nanowire formed by etching or depositing of a semiconductor layer. FIG. 1J depicts a primary base substrate (10), e.g. a semiconductor, a dielectric layer (20), e.g. a Buried Oxide layer (BOX), and a semiconductor nanowire channel (30).

Figure 1K:
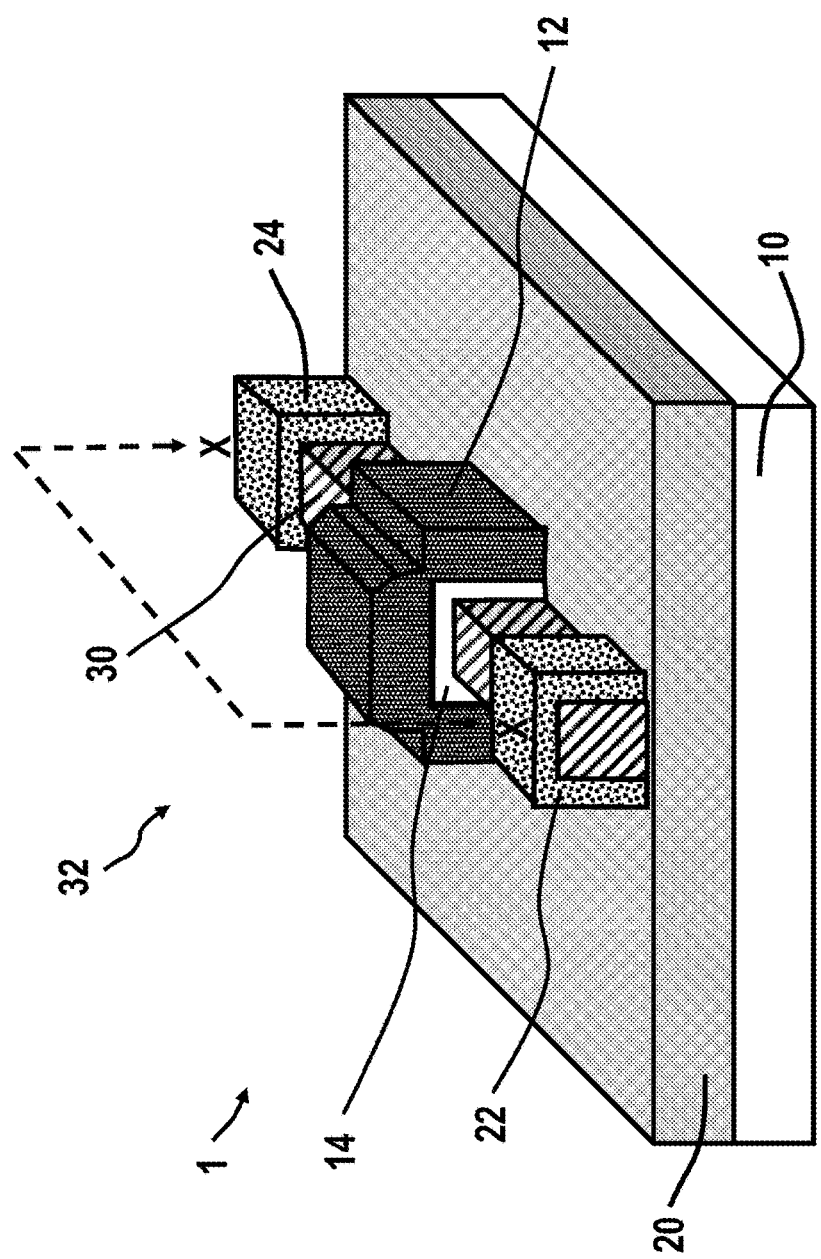
FIG. 1K is an illustration of a transistor comprised of a semiconductor nanowire (NW) and including a gate, gate dielectric and source and drain contacts.

FIG. 1K depicts a layered substrate (1) configured as a ChemFET (32) comprising a primary base substrate (10), a dielectric layer (20), a semiconductor nanowire channel (30) formed by etching or deposition of a semiconductor material, a gate (12) and a gate dielectric (14) to insulate the gate from the channel, a conductive source (22) and a conductive gate (24). The dotted line X-X is a section line that will be referred to in other drawings. Although FIG. 1K, FIG. 1L, FIG. 1M, FIG. 1N and FIG. 1O all show a conductive gate (24), such as a metal gate, over the channel region (26) it is to be understood that the gate could also be a solution gate in any of these embodiments.

Figures 1L, 1M:
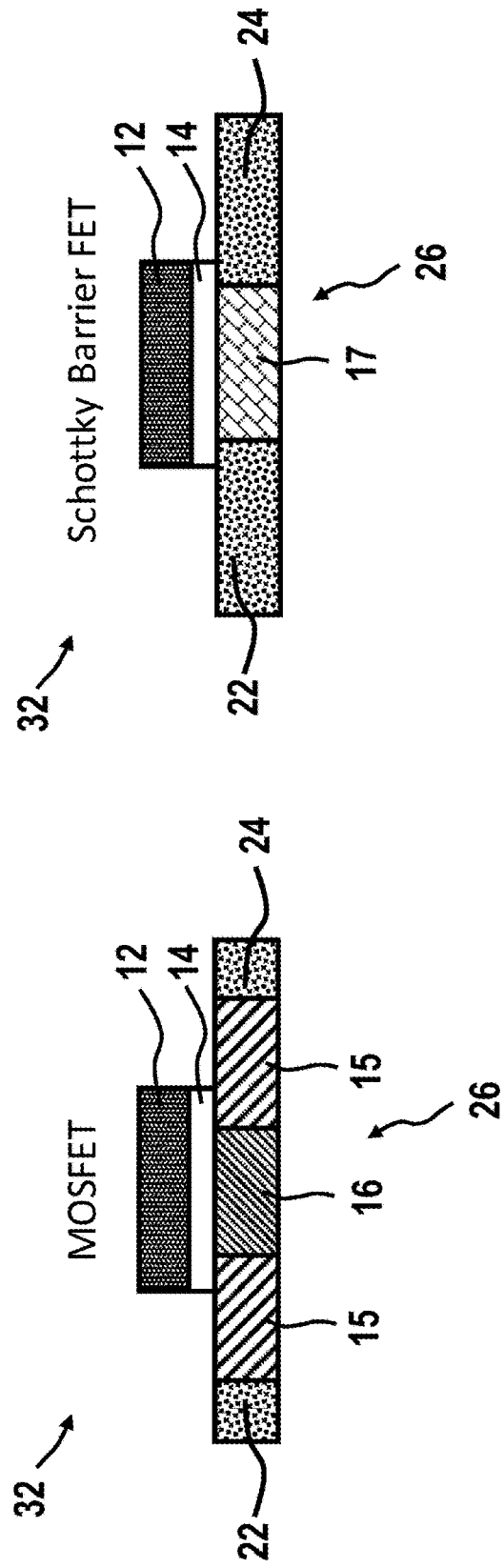
FIG. 1L is a side sectional illustration, along section X-X of FIG. 1K, of a semiconductor nanowire transistor configured as a MOSFET.
FIG. 1M is a side sectional illustration, along section X-X of FIG. 1K, of a semiconductor nanowire transistor configured as a Schottky Barrier FET.

FIG. 1L depicts a side sectional view of one embodiment of the semiconductor NW ChemFET (32) of FIG. 1K (section X-X), wherein the ChemFET (32) is configured as a MOSFET. In this embodiment the semiconductor NW channel is doped so that an n semiconductor region (15), a p semiconductor region (16) and another n semiconductor region (15) form an n-p-n junction in the sensing region (26) of the channel. Source (22) and drain (24) contacts are provided that contact the channel and a gate (12) is formed over the channel region (26) and electrically isolated from the channel by a gate dielectric (14). Because the semiconductor NW width and cross-sectional area are so small it is difficult to dope the semiconductor channel nanomaterial uniformly and precisely, so that the MOSFET ChemFETs (32) may vary one to another.

FIG. 1M depicts a side sectional view of one embodiment of the semiconductor NW ChemFET (32) of FIG. 1K (section X-X), wherein the ChemFET (32) is configured as a Schottky Barrier FET. In this embodiment the semiconductor NW channel is not doped so that an intrinsic semiconductor region (17) is formed in the sensing region (26) of the channel. Conductive source (22) and drain (24) contacts are provided that contact the intrinsic semiconductor channel forming Schottky barrier junctions and a Schottky Barrier FET and a gate (12) is formed over the channel region (26) and electrically isolated from the channel by a gate dielectric (14). Because the semiconductor NW channel is not doped in this embodiment the semiconductor channel nanomaterial is relatively uniform and precise, so that the Schottky Barrier FET ChemFETs (32) may be similar in characteristics one to another.

FIG. 1N depicts a side sectional view of one embodiment of the semiconductor NW ChemFET (32) of FIG. 1K (section X-X), wherein the ChemFET (32) is configured as a Junctionless FET. In this embodiment the semiconductor NW channel is uniformly doped in the sensing region (26) of the channel, in this case depicted as n doped (15). Source (22) and drain (24) contacts are provided that contact the uniformly doped semiconductor channel forming a Junctionless FET and a gate (12) is formed over the channel region (26) and electrically isolated from the channel by a gate dielectric (14). Because the semiconductor NW channel is uniformly doped in this embodiment the semiconductor channel nanomaterial is relatively uniform and precise, so that the Junctionless FET ChemFETs (32) may be similar in characteristics one to another.

FIG. 1O depicts a side sectional view of one embodiment of the semiconductor NW ChemFET (32) of FIG. 1K (section X-X), wherein the ChemFET (32) is configured as a Tunnel FET. In this embodiment the semiconductor NW channel is doped so that an n doped semiconductor region (15), an undoped semiconductor region (17) and a p doped semiconductor region (17) form a tunnel FET in the sensing region (26) of the channel. Source (22) and drain (24) contacts are provided that contact the channel and a gate (12) is formed over the channel region (26) and electrically isolated from the channel by a gate dielectric (14). Because the semiconductor NW width and cross-sectional area are so small it is difficult to dope the semiconductor channel nanomaterial uniformly and precisely, so that the Tunnel Junction ChemFETs (32) may vary one to another. However, due to the way the Tunnel Junction ChemFET works it has a lower subthreshold swing than the other embodiments and therefore may offer lower power requirements for the sensor IC chip.

Figure 1P:
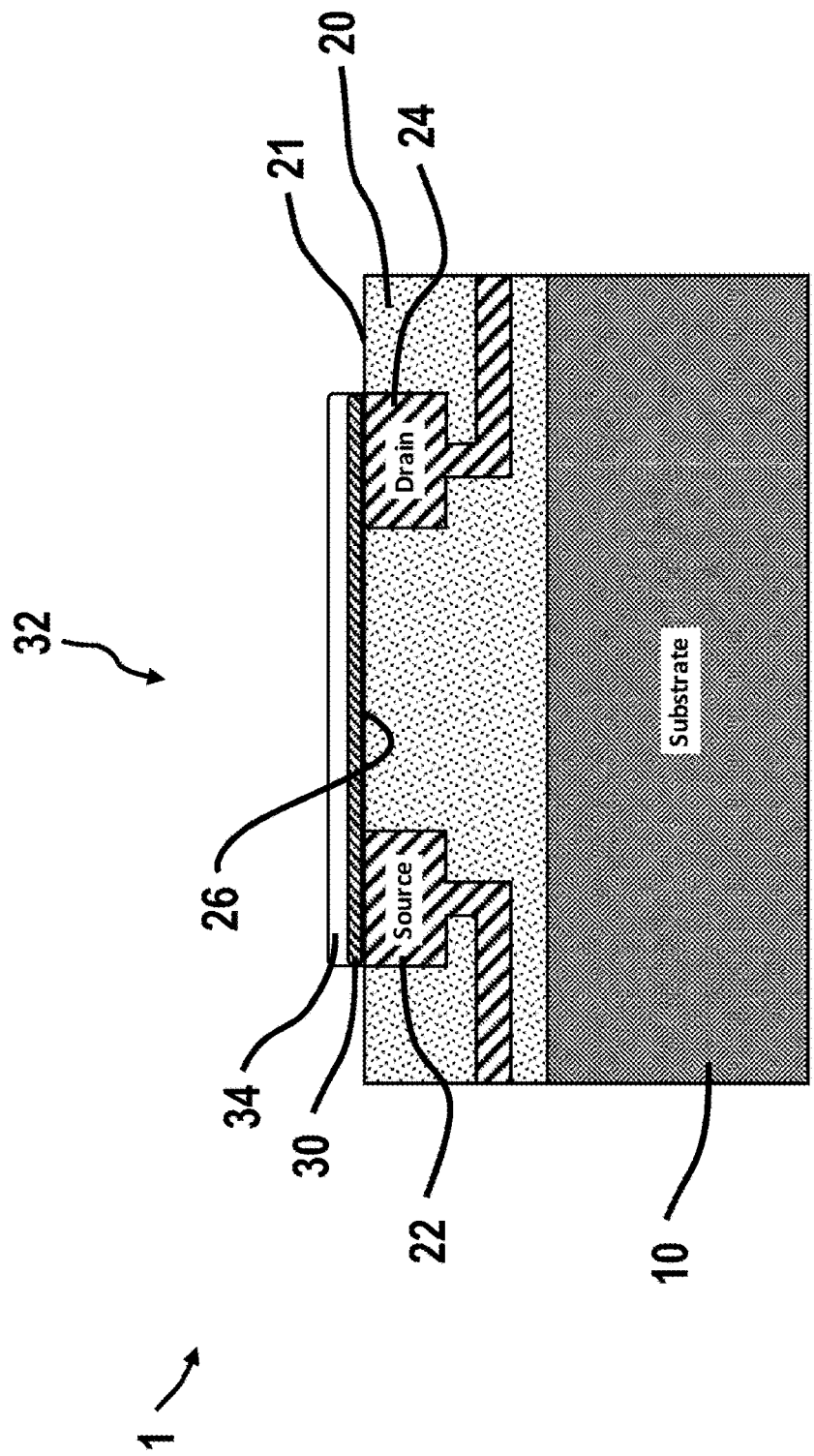
FIG. 1P is a side sectional illustration of a graphene layered substrate of FIG. 1C configured as a ChemFET having an analyte or reaction-sensitive layer associated with the graphene layer, such as for use in a system for analysis of biological and/or chemical materials.

In various embodiments, as can be seen with respect to FIG. 1P, an analyte or reaction-sensitive layer (34), e.g., an oxide layer, can be disposed on the channel 30 and/or surface (21) and/or channel region (26), such as layered or otherwise deposited or formed on the 1D or 2D nanomaterial (e.g., graphene) channel layer (30). Such an oxide layer (34) may be an aluminum oxide, hafnium oxide or a tantalum oxide or any other oxide with high intrinsic buffer capacity. In some embodiments, the oxide layer may have a thickness of about 30 nanometers, such as about 20 nanometers, such as about 15 nanometers, such as 10, 9, 7, or 5 nanometers or less. Particularly, the analyte and reaction-sensitive layer (34), when present, may be composed of an inorganic material such as aluminum oxide, hafnium oxide, tantalum oxide, or other insulating or non-conductive material including organic materials such as polymers, and the like.

In various instances, as depicted in FIG. 1P, a passivation layer (36) may be disposed or otherwise be included on the surface (21) and/or channel region (26) and/or oxide layer (34), such as layered or otherwise deposited on the 1D or 2D nanomaterial (e.g., graphene) channel layer (30) and/or on an associated analyte or reaction-sensitive layer (34) on the surface and/or channel region (26). More particularly, the oxide layer (34) may have a suitable thickness such as of from about 100 nm or about 75 nm to about 10 nm or 9 nm or less, such as about 0.5 microns or about 0.1 microns or about 50 nanometers or less to about 20 nanometers, such as about 15 nanometers, such as about 7 or about 5 nanometers or less, respectively. Such a passivation layer may have a thickness of about 5 microns or less, such as about 3 microns or about 1 micron or about 0.5 microns. The thickness of the passivation layer is chosen in consideration of the fluid flow to the sensor chip and the method of providing the ChemFET with targets or templates used for detection. For example, the target or template may be affixed on a microbead that in turn is located within a well or chamber of the passivation material—in which case the polymer layer tends to the thicker end of the thickness range (e.g. 2 to 5 microns thick). Alternatively if the targets or templates are affixed to the channel (30) or to an analyte or reaction-sensitive layer (36) on or over the channel (30) then the passivation layer (36) can be thinner, such as 1 micron thick or 0.5 micron thick or less, and only an opening is required in the passivation layer and not a well or chamber.

Once the appropriate electrode and channel structures have been formed proximate the dielectric insulating layer, a second insulation layer may then be deposited over the dielectric, electrodes, and channel layers, which secondary insulating layer may also be patterned, such as by etching to form one or more chambers or wells, where the opening of the chamber and/or well corresponds to the formed channel region(s). Hence, in a manner such as this, the substrate may be configured so as to include one or more nano and/or micro chambers that may further be configured to form one or more sensing wells.

Accordingly, as presented with respect to FIG. 2A, a further aspect of the present disclosure is a biosensor (1). The biosensor includes a semiconductor structure (10) that may include a dielectric layer (20) having a metal layer containing a source (22), e.g., a damascene copper source, as well as a metal layer containing a drain (24), e.g., a damascene copper drain, such as embedded within or on an insulating and/or dielectric layer (20), e.g., positioned on top of the structure (10). The insulating layer may be an inorganic material, such as a silicon oxide, silicon carbide, or a silicon nitride, or mixtures thereof or an organic material, such as a polyimide, BCB, BPO or other like material. The biosensor may also include a 1D or 2D nanomaterial layered, e.g. a graphene layered, surface or channel (30) extending horizontally from the source (22) to the drain (24), so as to at least be proximate therewith and thereby form a sensing zone (26).

In this instance, the surface structure or channel (30) completely overlaps the source (22) and drain (24) regions. In other instances the surface structure or channel (30) partially overlaps the source (22) and drain (24) regions. A further layer of passivation material (35) may be positioned over the surface and/or channel (30), which layer of material may further be etched or otherwise configured to include a well or chamber structure (38) having a bottom surface that may be positioned on or proximate a portion of an exterior surface of the 1D or 2D or 3D nanomaterial layer (30), such as to be coincident with the sensing region (26). In such an instance, the well structure (38) may be a layered structure and may include a plurality of surfaces, such as first (39a) and second (39b) wall structures, such as extending from or otherwise being coincident with the surface (21) of the sensing zone (26). For instance, the wall structures (39a, 39b) may partially overlap the surface structure (30). Accordingly, FIG. 2A is an illustration of a ChemFET having a graphene-layered well structure (38), such as for a system for analysis of biological and/or chemical materials, reactions or activity.

In particular instances, the well structure (38) may be configured so as to define an opening or chamber (37) that allows for direct contact with the sensing surface (26), and thereby contact with the 1D nanomaterial, e.g., nanotube, nanowire, and/or 2D nanomaterial, e.g. graphene, layer (30). Hence, in various embodiments, the ChemFET device may be a cavitated ChemFET device, which may be configured so as to include a plurality of wells or other chamber structures. In various instances, the ChemFET device (1) may be configured as a biosensor having a well structure (38) that further includes a passivation layer (35), as shown in FIG. 2B, which passivation layer (35) may be disposed in or on one or more of the chamber surfaces (30, 39). The semiconductor, e.g. CMOS, substrate structure (10) may additionally include the componentry typical of a CMOS semiconductor and/or transistor such as used and/or manufactured as a IC chip.

Hence, in certain instances, as illustrated in FIG. 2B, the ChemFET (1) may be configured as a chemically-sensitive transistor, and may be adapted to include one or more structures, such as nano- or micro-wells (38), that are formed as a sensing chamber, into which a fluid or solution, e.g., a solution containing one or more reactants, may be deposited, such as for the performance of one or more biochemical sensings, such as a nucleic acid hybridization and/or sequencing sensing. In particular instances, the chamber (38) may include a sensing region (26) having a 1D, 2D, or 3D nanomaterial channel (30), and/or one or more analyte or reaction-sensitive layers (34) and/or passivation layers (35) deposited therein or thereon. In such instances, the chamber of the ChemFET device may be configured as a solution gate and therefore the ChemFET may be adapted so as to be an ISFET, such as configured for receiving the reactants necessary for performing an analysis of biological and/or chemical materials, reactions or biologic activity, for instance, a hybridization and/or sequencing reaction.

As can be seen with respect to FIGS. 2A, 2B, 3A and 3B, in various embodiments, a ChemFET (1) having a graphene layered well structure (38) is provided. The ChemFET (1) includes a semiconductor substrate layer (10) and an insulating layer (20) within which is embedded the various ChemFET transistor components including a conductive source (22) and conductive drain (24) which may be adapted to form a channel sensing region (26). In this instance, a graphene layer (30) is positioned over the insulating layer (20) and positioned so as to contact at least a proximate portion of the source (22) and a proximate portion of the drain (24) to form a channel (30). In this instance, the substrate layer (10) is composed of silicon, the insulating layer (20) is composed of silicon dioxide, and the source (22) and drain (24) are composed of a conductive metal, for example, as copper.

The source (22) and the drain (24) are separated from one another and positioned relative to the graphene layer (30) so as to form a sensing region (26). In this embodiment, the sensing region (26) is further bounded by chamber walls (39a, 39b), which together form the well (38) into which a fluid may be delivered, such as for the performance of a bio-chemical reaction, and thus, forming a solution gate configuration by way of a gate voltage applied by a gate or reference electrode (66). Particularly, a passivation layer (35), which may also be composed of silicon dioxide, may be positioned above the first silicon dioxide layer (20), and be configured, e.g., via etching, to form a well (38) so as to form a chamber (37), which chamber (37) may be adapted to receive a solution so as to form the solution gate region. The graphene layer (30) is disposed between the first (20) and second (35) silicon dioxide layers such as to form the bottom surface of the chamber (37). In this instance, the ChemFET sensor is configured to detect a change in ion concentration, e.g., pH, which occurs within the well (38) such as when a solution containing reactants is added to the sensor region (26) within the chamber (37), and the reactants interact with an additional element contained within the chamber, such as a bound nucleic acid template.

Particularly, one or more solutions may be added to the chamber (37), such as in the performance of a bio-chemical reaction. For instance, a first solution including a nano- or microbead (60) may be added to the well (38). The nano- or microbead may be treated so as to be associated with one or more biopolymers, such as a DNA and/or RNA template (65). Once the nano- or microbead (60) containing solution is added to the well (38), in such a manner that the bead (65) is retained therein, one or more additional solutions containing reactants, such as for the performance of a biological and/or chemical reaction, may then be added to the well (38). For example, where the biological and/or chemical reaction is a nucleic acid synthesis reaction (as occurs in NGS methods), the analyte containing solution to be added to the well (38) may include a nucleotide and/or polymerase composition that if the conditions are suitable within the chamber (37) will result in a binding and/or incorporation event occurring between the template molecule (65) and the nucleotide reactant, thus resulting in the reaction taking place. Additionally, where the biological and/or chemical reaction is a hybridization reaction, the bound template molecule (65) may be configured as a probe, and the analyte containing solution to be added to the well (38) may include an additional DNA/RNA molecule of interest, which if the conditions within the chamber (37) are suitable will hybridize to the bound probe, thus resulting in the reaction taking place.

In either instance, the ChemFET (1) may be configured for detecting the occurrence of a chemical reaction, such as by detecting a change in the ionic concentration within the solution within the chamber (37). Particularly, if the conditions are suitable for a reaction to take place, e.g., the appropriate reactants are present, a binding and/or incorporation event will occur in such a manner that an ion, such as an H+ ion, will be released into solution, such as within the chamber (37) and/or proximate the sensing region (26). In such an instance, the ChemFET (1) may be configured to sense the evolution of the ion, appreciate the change in pH, and detect that a reaction has taken place. In such a manner as this, a DNA/RNA molecule may be synthesized and/or a hybridization event determined.

Figure 3A:
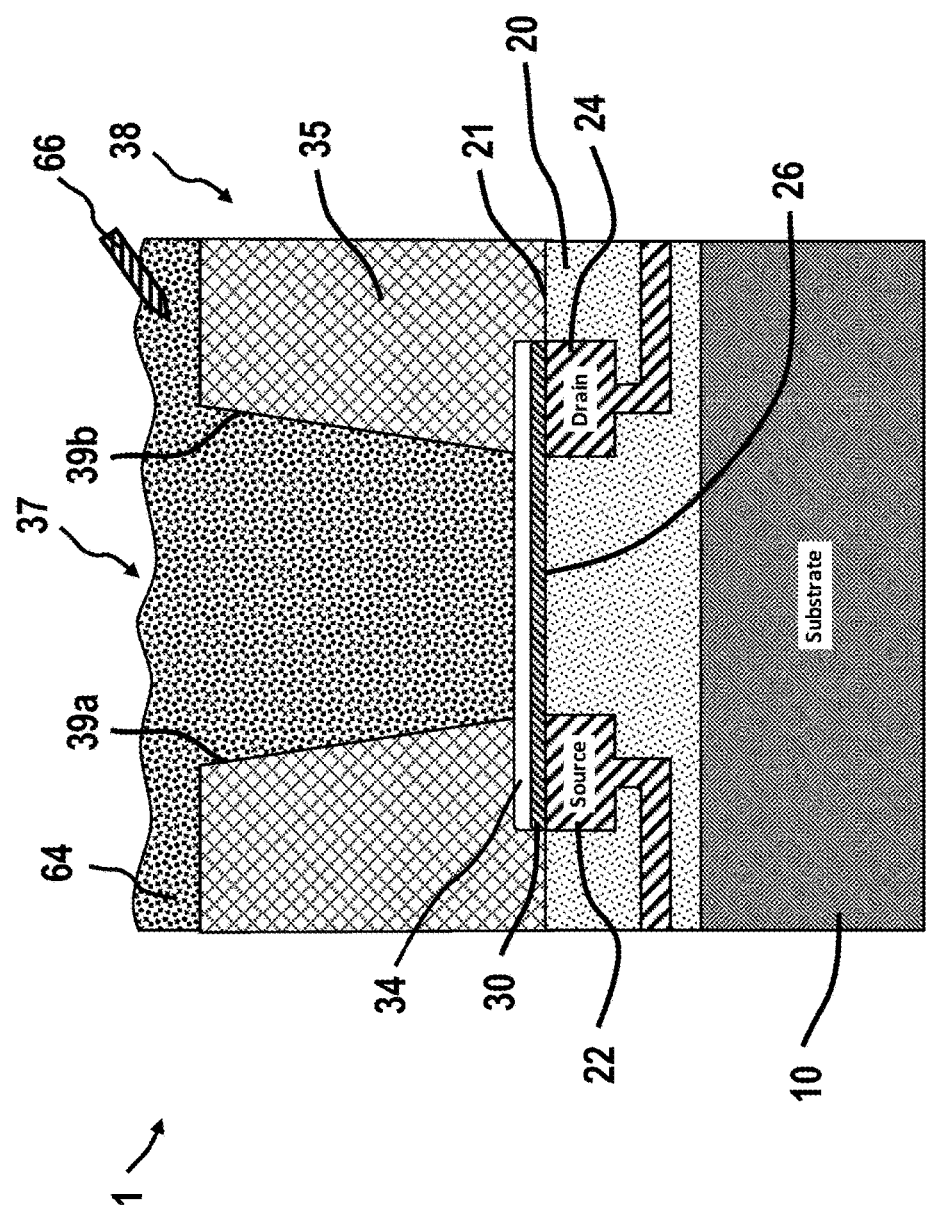
FIG. 3A is a side sectional view of a ChemFET with a solution gate.
Figure 3B:
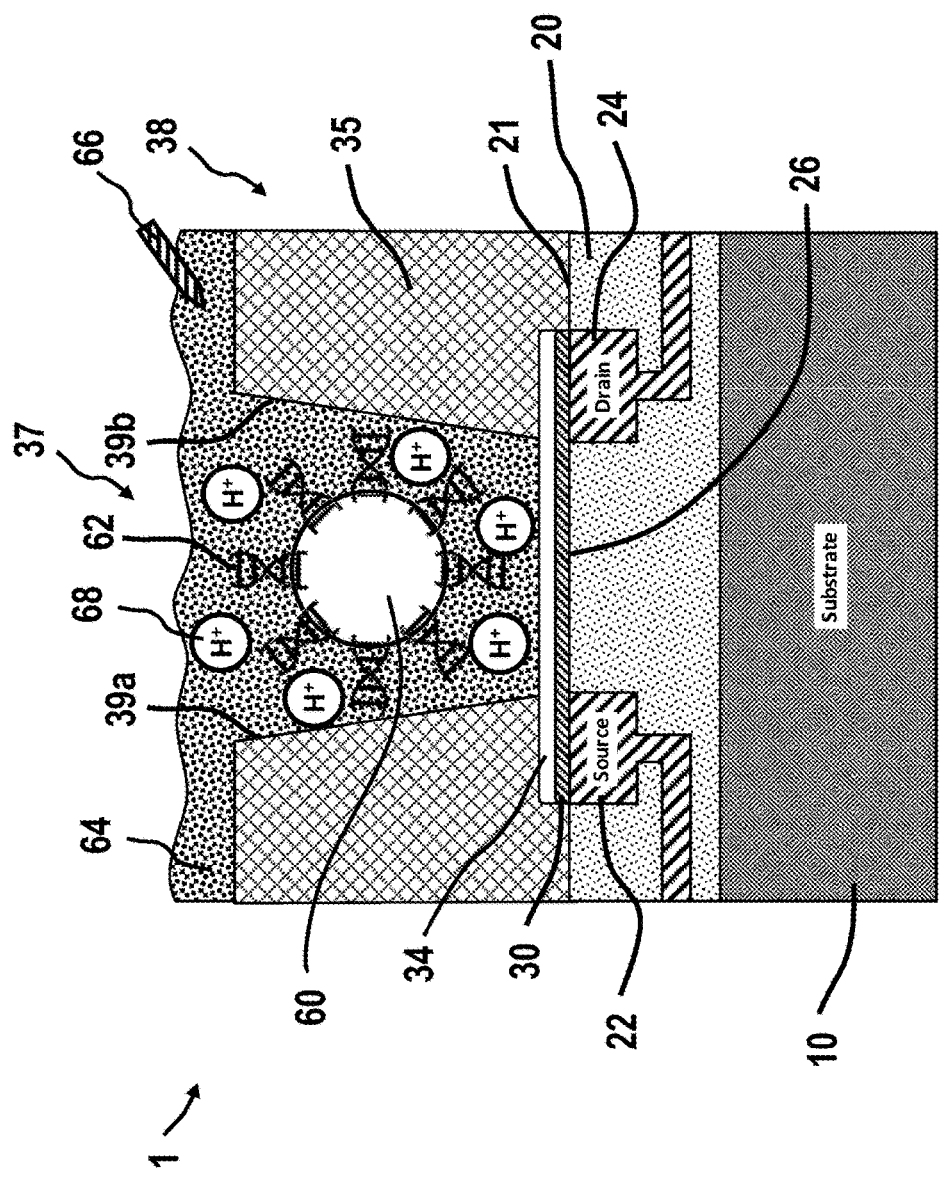
FIG. 3B is an illustration of a ChemFET, having a graphene layered well structure that includes a sensing layer associated with the graphene layer, which further includes a microbead therein with DNA templates for DNA sequencing.

Accordingly, as illustrated with respect to FIG. 3B, a ChemFET (1) is provided wherein the transistor (1) includes a graphene layered well structure (38) containing a nano- or microbead (60) therein, such as where the graphene layer (30) may be coincident with a channel region (26) so as to form a sensing zone therewith. The ChemFET (1) may additionally include a passivation layer (35), in which is defined a well (38), including well sidewalls (39a and 39b). The ChemFET is also configured with a solution gate comprised of a fluid or solution (64) and a reference electrode or solution gate electrode (66). The microbead (60) may be comprised of targets or templates (62) to be analyzed. For example the microbead (60) may be covered with many copies of a single stranded DNA template (62) such that when a complementary nucleotide binds to the DNA template a hydrogen ion (68) is released. In the case where the microbead (60) is covered with many copies of the DNA template (62) then many hydrogen ions (68) may be released when multiple copies of a nucleotide bind to the template DNA strands (68). The ChemFET (1) may sense the buildup of charge due to the release of hydrogen ions thus transducing the chemical reaction of DNA hybridization to an electrical signal output by the ChemFET sensor. Further, in various instances, such as illustrated in FIG. 3A, in addition to a graphene layer (30), the channel region sensing zone (26) within the chamber (37) of the well (38) of the transistor (1) may further include an analyte or reaction-sensitive layer (34), such as an oxide layer, associated with the graphene layer (30). Furthermore, as can be seen with respect to FIG. 3B, in certain embodiments, the ChemFET (1) may include a plurality of nano- or microbeads (60) therein, such as within the chamber (37) of the well (38) of the ChemFET (1), so as to allow a plurality of reactions to take place at the same time involving a plurality of microbeads (60a, 60b) within the well, which increases the surface area for reactions.

Improved Electrode to Channel Contact

As can be seen with respect to FIG. 2B, in particular embodiments, the primary (10) and/or secondary (20) structures can be fabricated to include or otherwise be associated with a tertiary structure (35), such as may be comprised of a non-conducting, insulating layer, such as composed of a silicon dioxide material. In various instances, the tertiary layer can be fabricated or otherwise configured so as to include a chamber or well assembly (38) in and/or on the surface (21), such as proximate the sensing zone (26). For instance, FIG. 2B depicts a ChemFET (1) having a well structure (38), which well structure may be positioned on a portion of a surface, e.g., an exterior surface (e.g., 21) of a primary (10) and/or secondary structure (20). In some instances, the well structure (38) may have a plurality of walls or bounding members (39a) and (39b) set apart from each other by a distance that may (or may not) be equivalent to the space between the source and drain so as to form the vertical boundaries of the chamber (38), with the bottom of the chamber forming the horizontal, bottom boundary.

In particular embodiments, the bottom of the chamber (38) may be configured as a sensing zone so as to form a sensing region within the well (38). Particularly, the boundaries (39a, 39b) may be formed on top of, or may otherwise include at least a portion of the 1D or 2D (e.g., graphene) material (30), and/or may additionally include the sensing, e.g., oxide, and/or passivation layers (36). In various embodiments, the chamber and/or well structure (38) may define an opening (37), such as an opening that allows access, e.g., fluid access, to an interior of the chamber (38), thus allowing direct contact or intimate association with the 1D (e.g., carbon nanotube or nanowire) or 2D (e.g., graphene) structure associated with the surface and/or channel region (26) and/or another material layer associated therewith, e.g., (36).

Certain embodiments of ChemFETs can be fabricated in a manner to increase the contact surface area between the source and drain and the material used to form the channel. For example, a substrate can be provided, e.g. a silicon substrate. An insulating dielectric layer, e.g. an oxide layer, may then be deposited on the substrate, into which a plurality of materials may be deposited so as to form a channel region within the dielectric layer. Thus, the dielectric layer may be processed in a manner of different ways, as set forth herein, so as to produce a channel, such as a channel comprising a 1D or 2D nanomaterial extending between a plurality of electrodes, such as source and drain electrodes. Accordingly, once deposited and suitably positioned above the substrate layer, the dielectric layer may be subjected to further processing so as to form a channel region, the channel region being formed between two opposed electrodes.

For instance, in an exemplary embodiment depicted in FIG. 2B, the ChemFET may be formed using the process steps outlined in FIG. 33. In this case the channel material (30) is deposited or formed over the source (22) and drain (24) electrodes. It is important to insure good physical and electrical contact between the channel material and the source and drain electrodes. One method of insuring good contact is to have the electrode (22, 24) stand proud of the dielectric material (20).

In one instance, illustrated in the side sectional views of FIGS. 5A and 5B, an electrode material (25) is located within trenches within the dielectric layer (20). If the electrode material is copper deposited through a damascene process then it would be typical for a liner (67) to be provided on the trench sidewalls prior to the copper plating. Tantalum or tantalum nitride are two typical liner materials. In a particular process step, as shown in FIG. 5A, the copper electrode material 25 is plated so as to fill the trenches and to overfill the trenches and extend over the surface of the dielectric (20). In a subsequent process step, illustrated in FIG. 5B, Chemical Mechanical Polishing (CMP) is performed to remove the excess overplated copper material and to planarize the top surface. The CMP process can be optimized to reduce the height of the dielectric layer (20) so that it is below the height of the electrodes, essentially resulting in electrode bumps (29) that protrude from the dielectric (20) surface. Protruding bumps are advantageous to insure good physical and electrical contact between the channel material (30) and the electrode material (25).

Figure 5C:
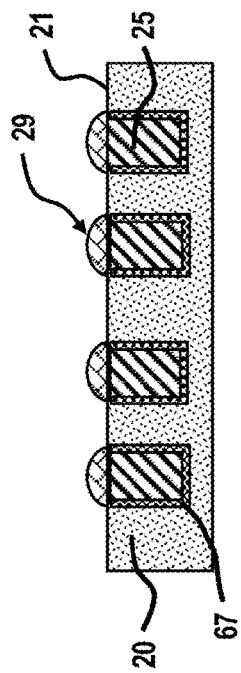
FIG. 5C shows a side sectional view of electrodes in a dielectric layer that have additional material in the form of plated bumps on the contact region of the electrodes.

In another embodiments as seen with respect to FIG. 5C, the processed and/or polished surface of an electrode may be further processed, such as by being subjected to a plating process so as to add additional conductive material to the contact region, e.g., to increase its height above the dielectric layer (20), to increase its surface area and/or to give the contact region of the electrode a desired shape or configuration prior to the deposition of the 1D or 2D nanomaterial layer thereon. Such plating may be performed in a variety of different ways, such as an electrolytic process and/or an electroless plating process, which allows the auto-catalytic plating on top of the deposited electrodes, so as to further build up a configuration, e.g., a bump with a more pronounced offset above the dielectric layer. FIG. 5C shows plated bumps (29) on electrodes (25) that extend above the surface (21) of the oxide layer (20).

In various instances, once formed, the electrodes (22, 24) may then be contacted with a 1D and/or 2D channel forming material in such a manner that a channel (30) forms between the first and second electrodes, that is between the source and drain electrodes. In certain instances, the layering or otherwise depositing of the 1D or 2D nanomaterial over the channel area (26), so as to form the channel (30) between the source (22) and drain (24) electrodes, is performed in such a manner so as to increase the surface area of one or more edges of the channel nanomaterial coming into contact with the electrode material. This is useful because carrier mobility may be increased through the interface of the electrode and the channel member at these one or more edges. Hence, it has been discovered that increasing contact efficiency increases carrier mobility through the channel (30). Accordingly, presented herein are field effect transistors that have optimal channel/electrode interfaces that maximize this contact.

For instance, as described herein above, the 1D or 2D nanomaterial layer positioned between the electrodes can be arranged in such a manner that only a bottom surface of the 1D or 2D nanomaterial contacts the electrode surface, e.g., a bottom side contact. However, in some embodiments, the configuration of the contact area may be configured such that as the 1D or 2D nanomaterial contacts the electrode material it does so in a manner so as to form an edged interface, which edge configuration may be particularly useful in increasing the flow efficiency of carriers through the channel. Further, this contact region may additionally be configured to include one or more of a bottom side contact, an edge side contact, a top-side contact, as well as multiple edge contacts, and interior and exterior side or edge contacts.

Figure 5D:
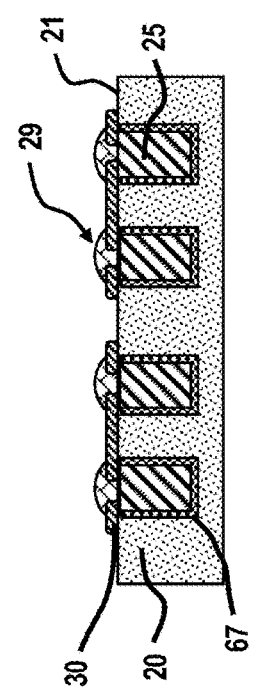
FIG. 5D shows a side sectional view of an electrode in a dielectric layer with a graphene layer on top of the electrode and bump material extending through holes in the graphene layer.
Figure 5E:
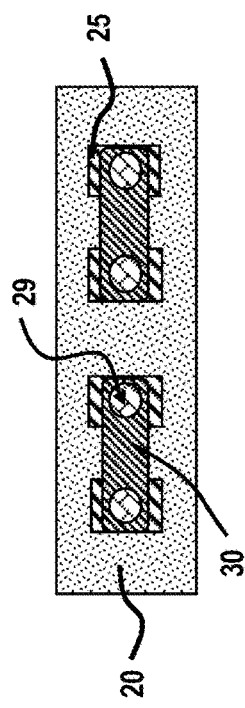
FIG. 5E shows top down view of the electrode and graphene channel structure of FIG. 5D

In various instances, such as those shown with respect to FIGS. 5D and 5E, the graphene and/or electrode layers may be additionally configured to further increase the relevant surface area of the contact. For instance, once the graphene layer (30) has been deposited, one or more openings (31) or holes, vias, or trenches may be made into the channel material layer over source and drain electrode locations, which then may be subjected to another plating process to further build a metal contact surface with the graphene layer (30), thereby increasing contact between the graphene layer (30) and the electrode layer (22). In this respect contact is provided not only at the bottom surface of the channel material, but also on edge surfaces within the holes, and on the top surface of the channel material where the bumps (29) extend horizontally beyond the hole dimension to overlap onto the channel surface.

Accordingly, in various instances, a hole may be made through the graphene layer to the underlying metal layer of the electrode, which hole may then be filled with a secondary metal material, which material may be the same or different metal as the electrode, and thus an enlarged surface area contact is formed, as illustrated by FIGS. 5D and 5E. In some embodiments, the electrode material may come up through the bottom of the holes to cover at least a portion of the top of the transistor material, e.g., graphene, layer; or metal may be plated on top of the graphene layer and travel downwards into the holes thereby contacting the electrode metal layer thereunder.

Accordingly, in various embodiments, once the electrodes have been fashioned and/or the 1D or 2D channel formed in conjunction therewith, e.g., such that the channel nanomaterial extends between the source and drain electrodes, one or more of the contact regions between the channel nanomaterial and that of the electrode material may be further processed. For instance, the contact area of the channel nanomaterial (30) may be patterned, e.g., one or more openings (31a, 31b, 31c) may be made in the channel and other associated material layers, to enlarge an additional surface area, and a second metal portion or cover (29) may be deposited into the openings, thereby creating a further contact interface between the metal electrode material (25) and the channel nanomaterial (30).

The second metal portion may extend vertically above the surface of the 2D nanomaterials, as well as laterally on top of the 2D nanomaterial a distance that is greater than the diameter of each opening. The shape of the openings in the channel material (30) may have any suitable configuration such as round, elliptical, square, rectangular, rhomboidal, and the like, so as to maximize the effective contact area. Hence, in such a configuration, the contact area between the channel nanomaterial and the electrode material may include one or more of a bottom contact area, an outside contact area, an inside contact area, and/or a top contact area. Thus, once the 1D or 2D nanomaterial layer is applied over the electrode layer of the dielectric layer, the 1D or 2D nanomaterial may be patterned, so as to create an opening in the contact region, which opening may then be filled with another metal material layer, such as copper, nickel, platinum, palladium, and the like, which second metal layer may then be patterned as well, if desired.

Particularly, once the electrode area and 1D/2D nanomaterial interface has been formed in the desired configuration, then, if desired, the surface thereof may be patterned. For instance, once the 1D/2D nanomaterial, e.g., graphene, is laid down, a photo-resist and/or mask having the desired configured cutouts may be placed over the channel region and/or graphene, such as where the pattern includes protected regions where patterning, e.g., etching, is not desired. Once suitably protected where desired, then an etching process, e.g., a dry or wet etching process may be employed so as etch the surface of the 1D or 2D nanomaterial and/or channel region into the desired pattern where the 1D or 2D nanomaterial layer is not protected.

Figure 5F:
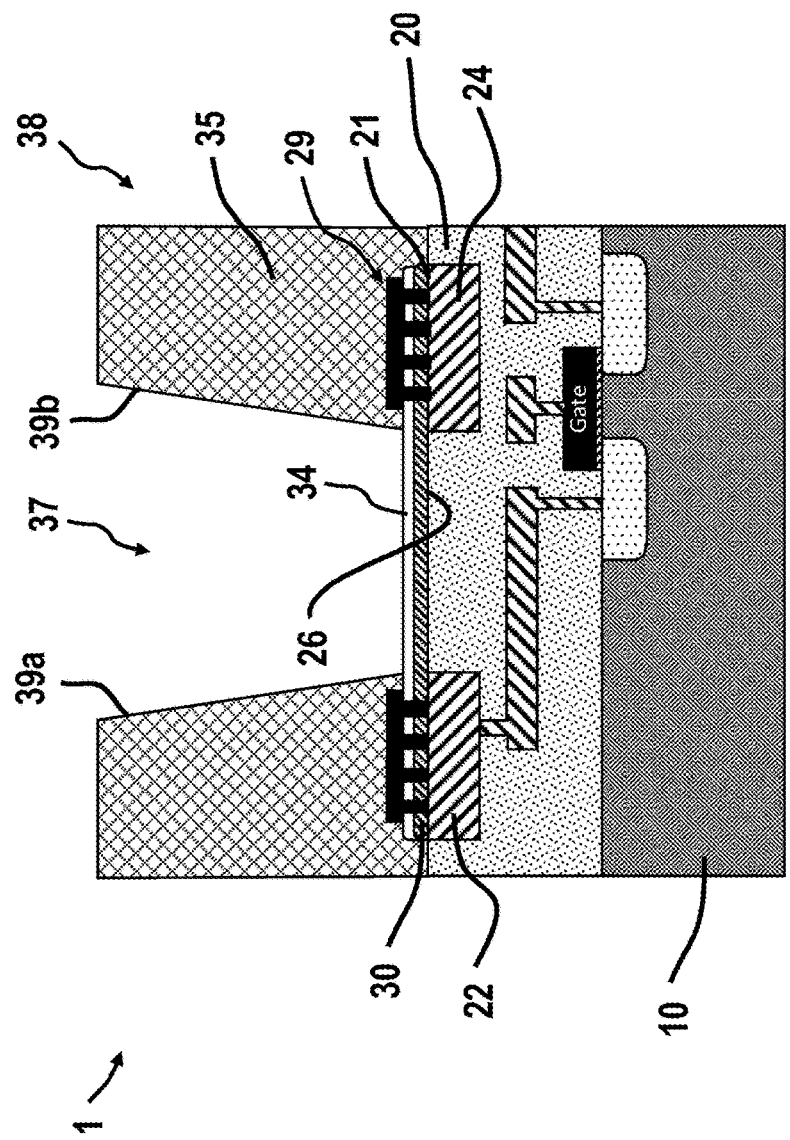
FIG. 5F shows a side sectional view of an embodiment of a top electrode and a bottom electrode sandwiching a graphene layer from above and below, and furthermore portions of the electrode project through holes the graphene layer at several intended locations. The structure provides top, bottom and edge contact between the electrode and the graphene.

In some embodiments, multiple openings or holes may be used to connect 1D, 2D nanomaterial channels (30) to electrodes. FIG. 5F illustrates a ChemFET (1) wherein the practices just described for forming conductive material through holes in the channel (30) to increase contact area with the electrodes (22 and 24) is practiced. In this embodiment the added material that forms the bumps (29) projects through multiple holes in the channel (30)—some holes over the source electrode (22) and some over the drain electrode (24).

In the embodiment shown in FIG. 5F, an ion sensitive layer (34) is positioned over the 2D nanomaterial (30). Multiple holes or openings have been patterned through the 2D nanomaterial (30) and ion sensitive layer (34). Conductive covers or deposits or bumps (20) are positioned proximate respective electrodes (22, 24) and contact respective electrodes (22, 24) through openings in the 2D nanomaterial (30) and ion sensitive layer (34). In some embodiments, the electrodes (22, 24) may be positioned in trenches created in an insulating dielectric layer (20), as described above. The ChemFET nanomaterial transistor connects to a respective drain or source of a semiconductor access transistor positioned in a substrate layer (10), e.g., a silicon semiconductor. A gate allows control of the access transistor.

Biologic and Analyte Detection with a ChemFET

In some embodiments, the ChemFET may include a plurality of wells and a plurality of ChemFETs may be configured as an array, e.g., a sensor array IC chip. It may be noted that having multiple wells sensing the same analyte or reaction allows statistical improvement of the sensing result. Such a ChemFET sensor IC chip is shown in FIGS. 15A and 15B and may be employed such as to detect a presence and/or concentration change of various analyte types in a wide variety of chemical and/or biological processes, including nucleic acid hybridization (e.g., DNA/DNA, DNA/RNA) and/or DNA or RNA sequencing reactions. For instance, the devices herein described and/or systems including the same may be employed in a method for the analysis of biological or chemical materials, such as for whole genome analysis, genome typing analysis, microarray analysis, panels analysis, exome analysis, microbial/microbiome analysis, genotyping analysis, and/or clinical analysis, such as cancer analysis, NIPT analysis, cfDNA, blood/plasma/serum analysis, UCS (upstream conserved sequence) analysis, biomolecule analysis and/or analyte analysis.

In a particular embodiment, one or more surfaces within the wells (38) of the ChemFET (1) may be configured as a sensing zone, which sensing zone may include an additional structure, such as a 1D, 2D, e.g., graphene, or 3D material layer, and hence, the FET may be a graphene FET (GFET). There are several ways in which an analyte or biologic material or reagent may interact with the ChemFET.

In one instance, illustrated in FIG. 3B, a microbead (60) is used to hold reagents, such as single-stranded DNA templates. The microbead (60) with its DNA templates (82)

is introduced into the chamber (37) of the well (38). A fluid (64) may deliver additional reagents to the well (38). The ChemFET (1) senses changes in the electric field due to the presence of the reagents or due to chemical reactions occurring among the reagents. For example incorporation of a nucleotide base onto a template DNA strand will release hydrogen ion. When many (thousands or more) of the templates are on a microbead then thousands or more hydrogen ions will be released during the base incorporation. These charges may be sensed by the ChemFET (1). Use of a microbead with templates may be particularly suited to DNA or RNA sequencing.

Figure 3C:
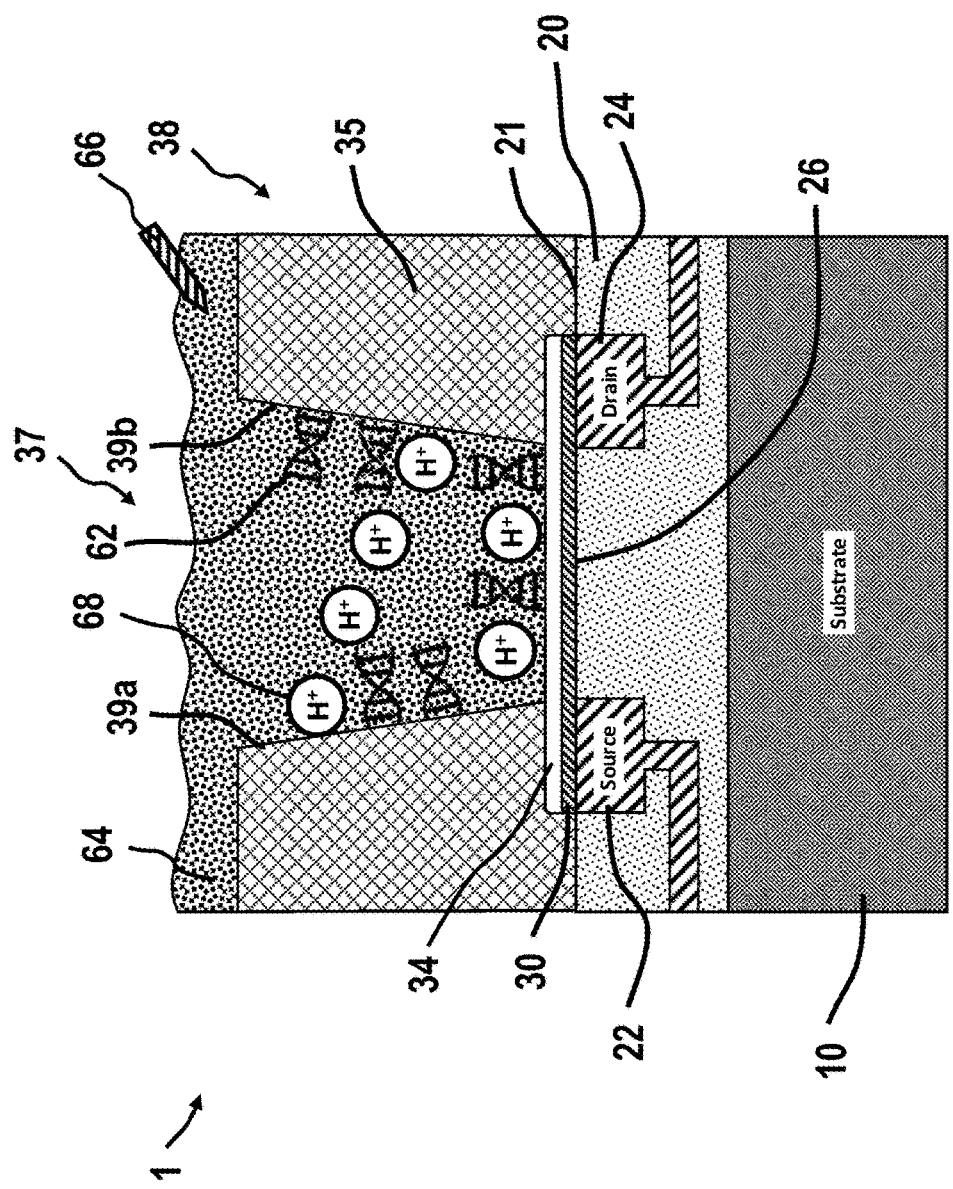
FIG. 3C is an illustration of a ChemFET, having a graphene layered well structure that includes a sensing layer associated with the graphene layer, which further includes DNA templates deposited on the sensing layer for DNA sequencing.

In another instance, illustrated in FIG. 3C, the templates are attached to the sensor surfaces, such as to the bottom of the well (38) or the sidewalls (39) of the well (38). Depending on the configuration of the ChemFET, the attachment may be to an analyte or reaction-sensitive layer (34) over the channel (30) or may be directly to the channel material (30). This configuration can be used for DNA or RNA sequencing among other uses.

Figure 3D:
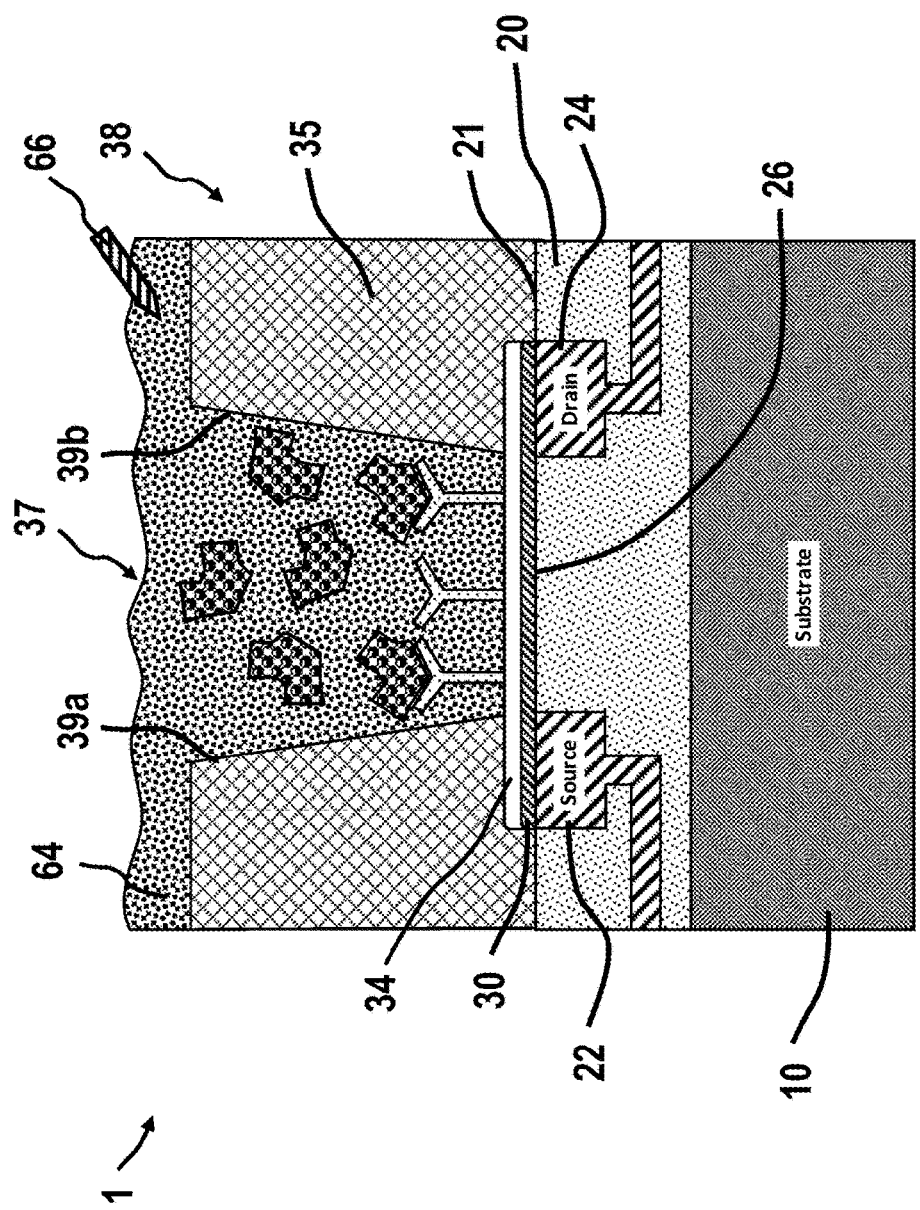
FIG. 3D is an illustration of a ChemFET, having a graphene layered well structure that includes a sensing layer associated with the graphene layer, which further includes antibodies associated with the sensing layer for detection of antigens.

In a further embodiment, shown in FIG. 3D, antibodies may be attached to surfaces of the sensor, such as to an analyte or reaction-sensitive layer (34). In this case the binding of antigens to the antibodies may be sensed by the ChemFET.

Figure 3E:
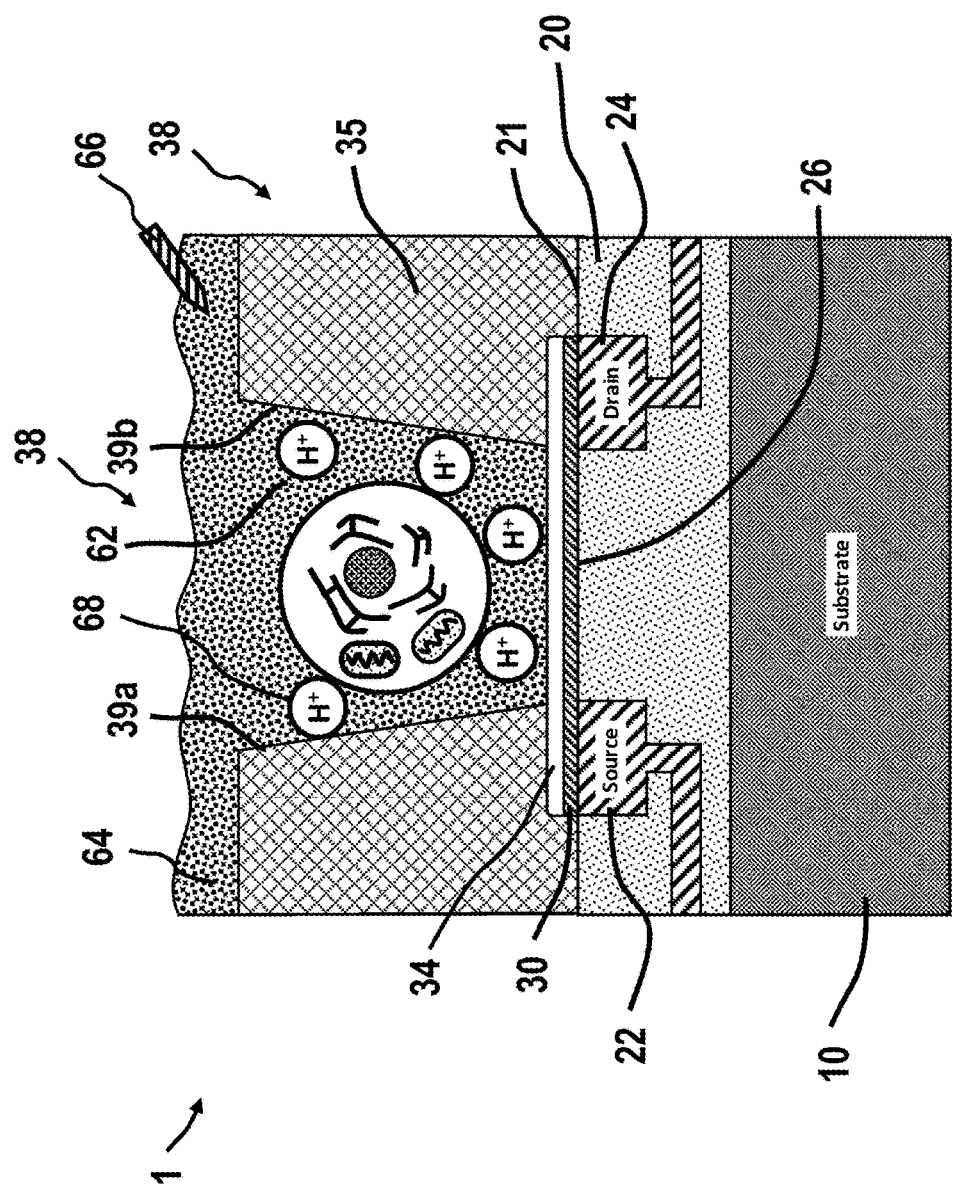
FIG. 3E is an illustration of a ChemFET, having a graphene layered well structure that includes a sensing layer associated with the graphene layer, which further includes a cell to be monitored for cell activity.

In yet another embodiment, shown in FIG. 3E, a cell or other biologic structure or material may be located in the well (38) of the ChemFET (1). Activity of the biologic material or reaction of the biologic material to components within the fluid (64) may be sensed by the ChemFET.

These are but a few examples of methods to interface an analyte or biologic material with the ChemFET.

ChemFET Analyte or Reaction Sensitive Layer

Another aspect of the present invention is the inclusion of an analyte or reaction-sensitive layer, such as an ion sensitive layer, to the channel to improve the sensitivity of the 1D or 2D nanomaterial channel of the ChemFET.

In particular instances, a sensing layer can also be provided, such as a layer associated with the 1D or 2D nanomaterial, e.g., graphene layer or 3D structural layer. For instance, in one embodiment, a thin (0.01 micron) etch stop layer (ESL) may be placed over the channel layer (e.g., graphene), such as in the case where a well etch process affects the channel-forming material. In various embodiments, an oxide layer can be included, such as disposed within the well, chamber and/or channel thereof. Particularly, in various embodiments, a method for depositing the dielectric layer may include Atomic Layer Deposition (ALD). In the case of graphene and other 2D nanomaterials they may have few dangling bonds and therefore it may be difficult to get an initial deposition of a sensing layer to stick or adhere to the nanomaterial. In such cases a preconditioning of the nanomaterial may be required prior to the preferred dielectric deposition process of ALD. Such precondition may include, but is not limited to plasma or ozone treatments, polymer functionalization (especially with thin SAMs), chemical bond functionalization (e.g. replacing some of the carbon atoms in the graphene with Flourine, chlorine or other species), or low temperature and long cycle ALD prior to normal ALD processing.

Another method for creating an analyte or reaction-sensitive layer is to first deposit a metal layer (e.g., by sputtering or evaporation) onto the 1D, 2D, or 3D nanomaterial layer and then oxidizing the metal to form a metal oxide layer. It is further possible to combine material layers using different deposition processes to create an analyte or reaction-sensitive layer. For example, a first layer can be comprised of sputtered metal that is oxidized, followed by a layer comprised of an ALD deposited oxide. It is further possible to combine two or more analyte or reaction-sensitive layers, such as may be comprised of different materials to create an overall analyte or reaction-sensitive layer stack. For example, a first layer of metal, e.g., aluminum oxide, may be formed over the channel nanomaterial and then a second layer of metal, e.g., tantalum oxide, can be formed over the aluminum oxide. In some embodiments, an analyte or reaction-sensitive dielectric layer need not be required nor used.

However, where employed, the oxide or other sensing layer may be configured so as to prevent the nucleic acid template or probe, e.g., present on a microbead, from contacting the 1D or 2D nanomaterial or other sensing layer of the chamber directly. The oxide layer can be composed of an aluminum oxide, tantalum oxide, and/or a hafnium oxide. In various instances, the oxide layer may have a thickness of about 30 nm, such as about 15 nm, such as 9 nanometers or less. In further instances, the ChemFET can read through an oxide layer, if present.

ChemFET with Two Sensing Layers

Figure 3F:
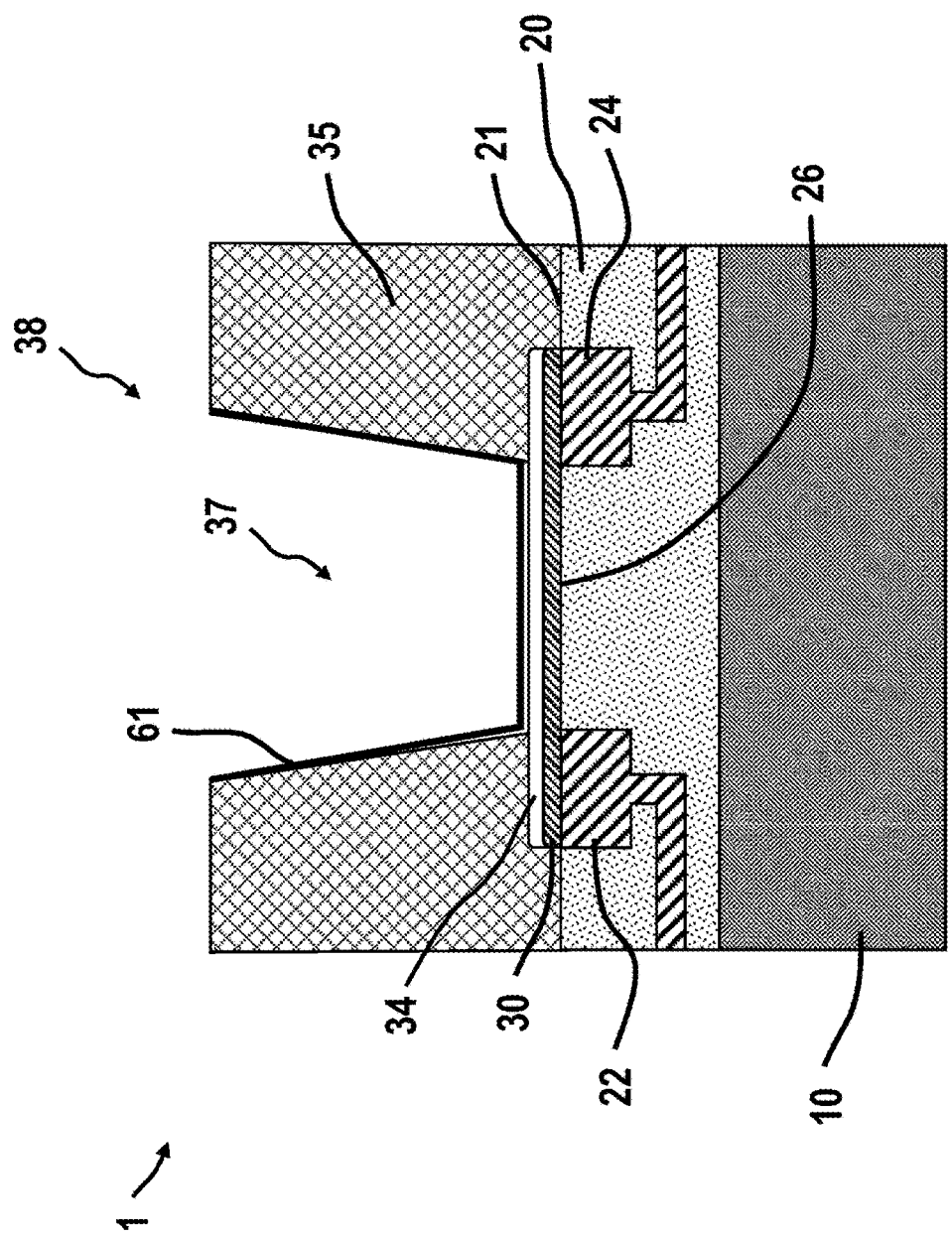
FIG. 3F is an illustration highlighting a second analyte or reaction-sensitive layer coating the walls of a well.

Additionally, as shown in FIG. 3F one or more additional analyte or reaction-sensitive layers (34, 61) can be included in the ChemFET, such as formed on the sidewalls (39) and bottom (21) of the well (38). For instance, FIG. 3F depicts a cut-away view of a substrate (10), wherein the substrate includes a well (38) having a chamber therein, such as a chamber defined by one or more walls. In various instances, one or more of the walls may have a second analyte or reaction-sensitive layer (61) coating the walls (39) of the well (38). Particularly, a substrate (10) may be provided such as where the substrate (10) may be formed of a silicon layer and may include one or more additional layers, such as one or more dielectric layers (20) and a passivation layer (35), which layers may be composed of silicon dioxide. Imbedded within one or more of these layers may be a pair of electrodes, such as a source electrode (22) and a drain electrode (24), which may be in one or more of the configurations set forth in FIG. 5G, or other suitable configuration. As can be seen, one or more of the dielectric layers (20) and/or passivation layer (35) may be configured so as to include a well structure (38), which structure may further be adapted so as to include one or more additional layers (61), such as a plurality of analyte or reaction-sensitive layers (34, 61). For instance, one of the analyte sensitive layers (34) may be positioned on a bottom surface (21) of the well (38), such as layered upon a channel member (30), such as upon a graphene channel layer (30). Additionally, another analyte sensitive layer (61) may be layered upon one or more of the well-bounding members (39a, 39b).

ChemFET Channel Enhancements—Interdigitated Source and Drain

Channel with High W/L Ratio

Accordingly, in one aspect of the present disclosure, the sensor is configured as a ChemFET. Particularly, in certain embodiments, the ChemFET includes a chamber having a channel structure incorporated or associated therein. In particular embodiments, the chamber and/or the channel and/or a structure thereof is optimized in such a manner so as to maximize the ratio of channel width (W) to channel length (L). For instance, the channel may include a 1D or 2D or 3D structure, such as where the channel and/or the channel structure includes a geometry that has been optimized to maximize the ratio of channel width (W) to channel length (L). This can be accomplished, for example, through the use of interdigitated source and drain electrode geometries in a single plane or through the use of 2D and/or 3D electrode structures, such as a 3D interdigitated well structure.

In such embodiments, the transistor includes a channel extending between, or spanning, a conductive source and a conductive drain to form the channel structure. In such embodiments, the opening of the chamber is positioned in relation to the channel so that the opening aligns with the source and drain, and more particularly, with the associated channel. As indicated, in various embodiments, a channel of the ChemFET includes a one-dimensional (1D) transistor nanomaterial (e.g., a carbon nanotube (CNT) or a semiconductor nanowire) or a two-dimensional (2D) transistor nanomaterial, such as composed of graphene, molybdenum disulfide, other metal dichalcogenides, and black phosphorous. In various instances, a three-dimensional (3D) structure may be included.

For example, the transconductance through the channel may be modified in various manners so as to modulate, e.g., increase, the sensitivity of the associated ChemFETs, such as in the sensor array. Particularly, in various instances, it may be useful to configure the chamber and/or well so as to have a short channel length and a wide channel width, such as the shortest channel length and largest channel width possible, given the configuration of the one or more chambers in the one or more sensor arrays. More particularly, an equation for transconductance of the FETs disclosed herein is: $g_m \propto \mu\, C_{ov}\, W/L\, V_{sd}$ where gm is the transconductance, $\mu$ is the carrier mobility, $C_{ov}$ is the overall capacitance of an included oxide or other layers over the transistor, W is the channel width, L is the channel length and $V_{sd}$ is the voltage from the source to the drain. Since gm directly relates to the sensitivity of the sensor it is desirable to increase gm through the terms shown in the equation. In particular, increasing the W/L ratio (maximizing W and minimizing L) will increase $g_m$.

In particular instances, the length of the channel from the source to the drain ranges, and in some instances, may be less than about (1) micron, such as less than about 500 nm, including less than about 50 nm, and in particular instances: as short as the fabrication process will allow without generating defects or results that render the device unusable. In one particular embodiment the channel length is about (20) nm or less. Conversely, the width of the channel may be as wide as feasible and/or possible. In such an instance as this, the width of the channel need not be governed by the fabrication process as much as by the design requirements of the overall sensor chip. For instance, in specific instances, hundreds of thousands to millions of sensors may be included in an exemplary sensor chip.

However, with such a large number of sensors, each individual sensor size and/or pitch, e.g., which may directly affect the channel width, should be kept reasonably small so as to prevent the chip from being so large as to be unable to be fabricated (e.g., such as exceeding the photolithography reticle size) or too expensive (e.g., due to the effect of defect density on a large chip size). Hence, in one implementation, e.g., of a rectangular channel design, a practical range of the channel width is from about 0.1 micron to about 10 microns, such as from about 0.1 to 5 microns. As indicated above, in some instances, it may be desirable to increase the channel length to channel width ratio, such as through the use of various design techniques. In one particular exemplary instance, a structure, such as an interdigitated tooth and comb structure, can be provided such as for short channel lengths and large channel widths, such as within a relatively compact area, such as shown in FIG. 11, which depicts various planar structure designs of interdigitated source and drain electrodes that can be implemented so as to increase the W/L of the channel within a relatively small area.

Figure 5G:
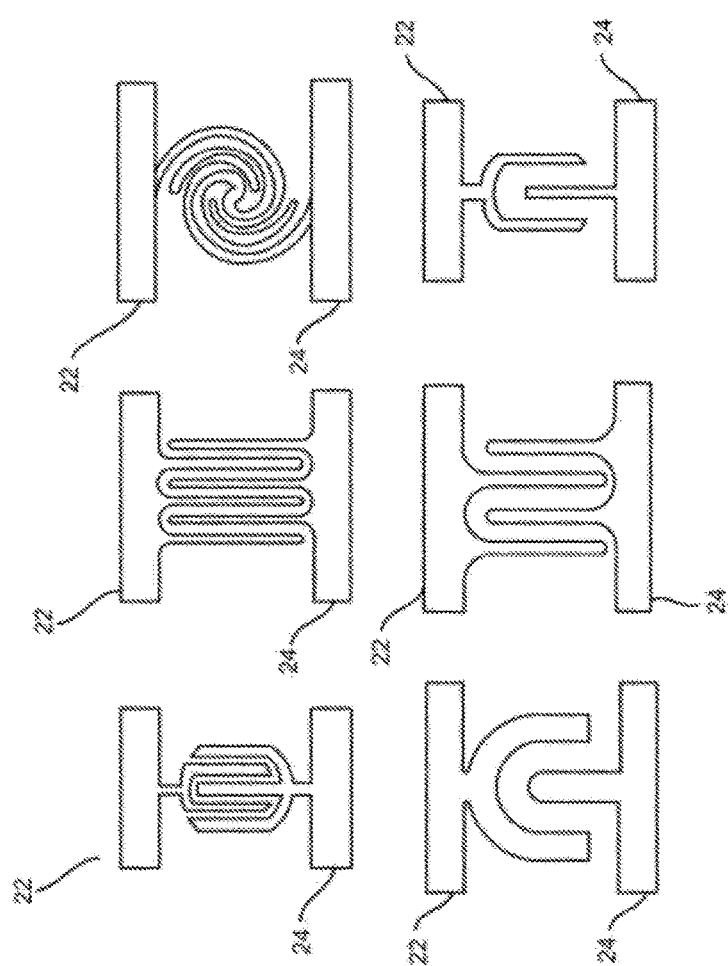
FIG. 5G is an illustration of various planar source and drain electrode designs, including interdigitated designs.
Figure 5H:
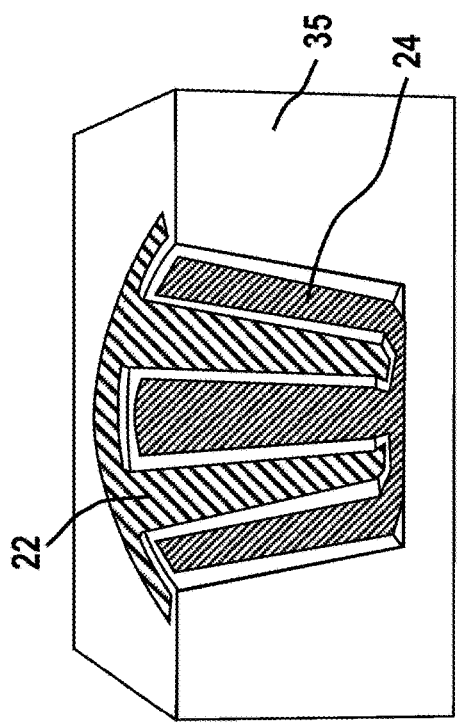
FIG. 5H is an illustration of using the well walls to create 3D interdigitated electrodes.

Further, with respect to FIG. 5H as previously noted, in various instances, it may be desirable to increase the ratio of the channel width W to the channel length L (e.g., W/L). For instance, FIG. 14 depicts a FET device, as herein described, wherein the FET includes a well having one or more walls that may be configured to produce or otherwise include a 3D interdigitated electrodes. Particularly, having a well structure, as set forth in FIGS. 12 and 13, allows the formation of source (22) and drain (24) electrodes not only on the bottom of the well (21), but also may be fabricated on the sides of the well (39), such as in one or more of the configurations set forth in FIG. 5G. Specifically, FIG. 5H depicts a well structure in a cross-section view that has one or more surfaces that have been configured for allowing one or more electrodes to be fabricated therein. In this instance, the source electrodes (22) and drain electrodes (24) are interdigitated and positioned both on the bottom (21) of the well and on the sides 39 of the well. Many geometric patterns can be designed for source (22) and drain (24) electrodes to cover both the sides and bottom of the wells and the pattern shown in FIG. 14) is but one example, while FIG. 5I is another example, such as where the well includes a transistor material or an analyte or reaction-sensitive layer that may be positioned or otherwise coated over the surface of the well bounding member and/or one or more electrodes configured therein.

For example, one possibility for forming the source (22) and drain (24) electrodes in the well (38), such as in a 3D structure as set forth herein, is to use a photopatterning or photolithographic process. In such an instance, a mask with the desired pattern(s) may be used to transfer a pattern onto a photosensitive photoresist material. The pattern in the photoresist material can be used to likewise define a pattern in the conductive electrodes (e.g., by etching, lift-off, plating, and/or other processes known in the art). For instance, it is possible by employing the right optics to expose photoresist into deep trenches and/or wells so as to be able to define conductive traces in those deep trenches or wells. An example of this is shown in FIG. 16, which presents a depiction of an interdigitated well structure that has been fabricated using lithographic methods. Other techniques that can address patterning of photoresist in deep trenches or wells are laser, electron beam, and/or plasma, and the like.

Particularly, in various instances, once the source (22) and drain (24) electrodes are formed on the sides (39) of the well (38) the channel (24) may be formed over the electrodes. The process used to form the transistor channel (24) may be by any suitable process, but may depend on the materials being deposited and the presence of process limits imposed by other devices incorporated into the sensor. For instance, a silicon-based CMOS wafer with conventional transistors (e.g., formed from doped regions in the silicon and polysilicon or metal gates) will typically have a processing temperature limit of 350 to 400 C, above which damage to those transistors may occur. So for a CMOS wafer with added sensors, the deposition of the materials making up those sensors will typically be lower than 400 C, which can be accomplished either by a low temperature in-situ deposition processes, and/or by creating the desired sensor materials separately and transferring them to the appropriate locations on the CMOS wafer.

Figure 5I:
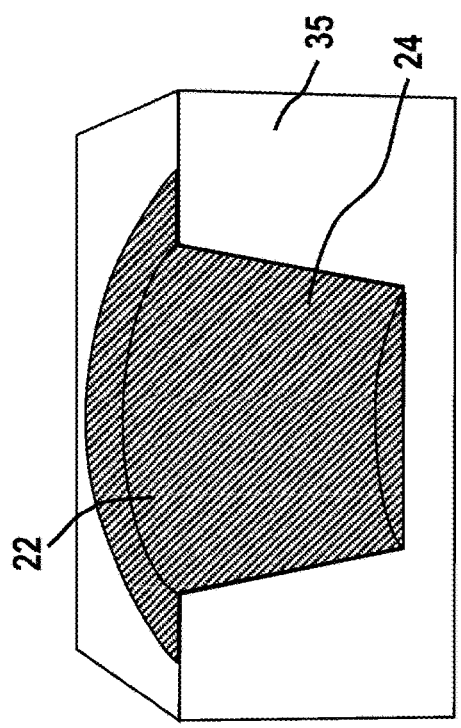
FIG. 5I is an illustration of the well structure of FIG. 5H and including a nanomaterial that covers a sidewall and underlying source and drain electrodes.

In some instances, a 1D or 2D transistor material (30) can be formed separate from the CMOS wafer and then be transferred onto the electrode structures in the wells (38), as shown in FIG. 5I. In another instance, another option may be to deposit a transistor channel nanomaterial on the electrodes (22, 24) and well walls (21, 39). This may be accomplished by low temperature (e.g., below 400 degrees C.) deposition of amorphous silicon or suitable 2D nanomaterial by any suitable means including, but not limited to: CVD, ALD, PVD (e.g., evaporation and/or sputtering), PECVD, and/or the like. Likewise, as depicted in FIG. 5I, one or more of these methods can be used to coat the interior chamber of the well structure with a transistor material, such as an analyte or reaction-sensitive layer.

Figure 5K:
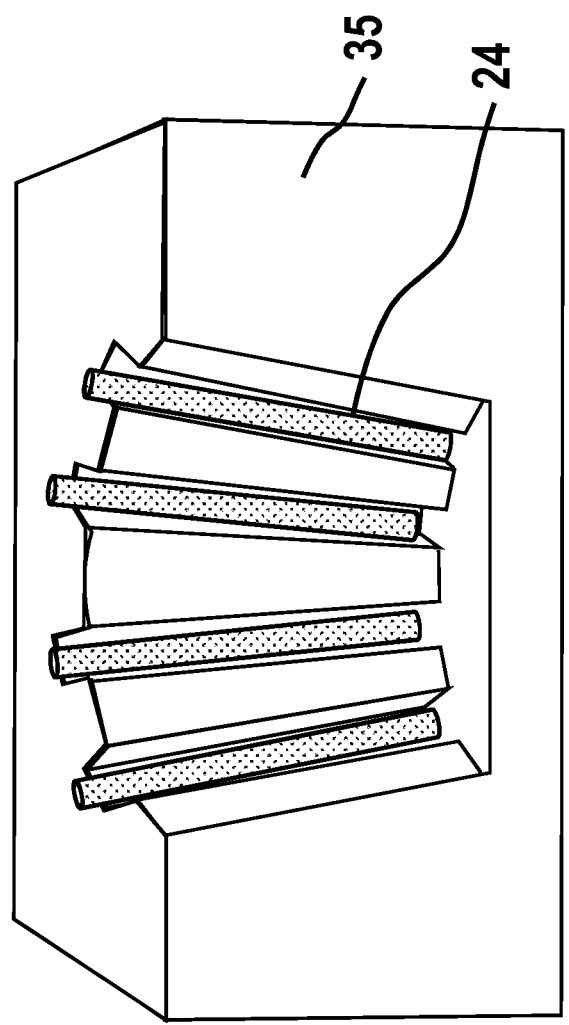
FIG. 5K is an illustration of a well that uses carbon nanotubes to create interdigitated transistors in a vertical direction.

Additionally, FIG. 5K depicts an alternate well structure (1). In this instance grooves or trenches 61 may be formed in the wall boundaries of the well 39. These grooves 61 can help to align and capture the 1D and/or 2D transistor channel nanomaterial—such as carbon nanotubes or silicon wires. Accordingly, FIG. 5K depicts a well that uses carbon nanotubes to create interdigitated transistors, such as in a vertical direction.

Vertically Interdigitated and Stacked 3D Source and Drain

Figure 5L:
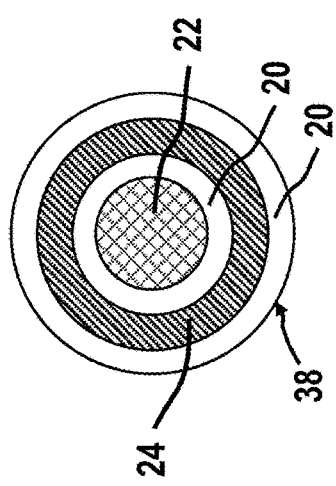
FIG. 5L is an illustration of a top plane view of a source and drain electrodes at the bottom of a well.
Figure 5M:
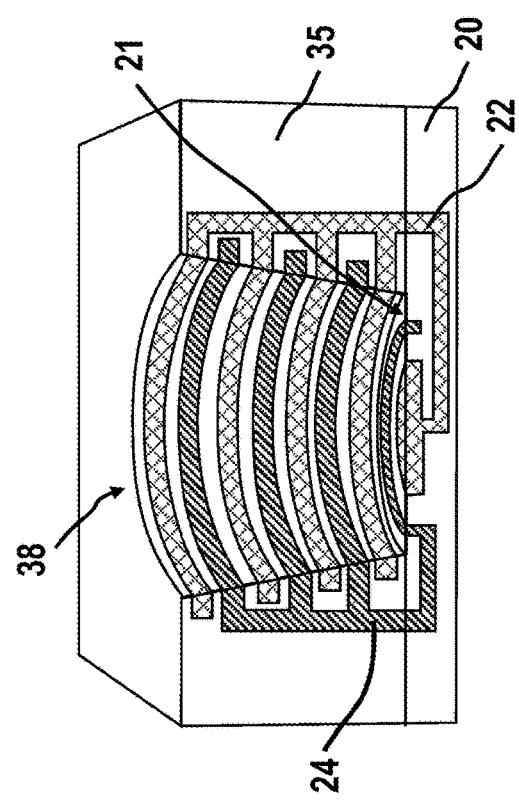
FIG. 5M is an illustration of using alternating vertical metal layers to create an interdigitated type of effect to maximize the of ratio channel width to channel length.

FIG. 5L depicts a top-plane view of a geometric pattern of source (22) and drain (24) electrodes that might be found at the bottom (21) of the well structure (38) shown in cross-section view in FIG. 5M. FIG. 5L shows an alternating pattern of source (22) and drain (24) electrodes at the bottom of the well structure (38), in this case in the form of concentric ring shapes embedded in the dielectric layer (20). In a fashion similar to the previously discussed interdigitated source and drain designs, the channel W/L ratio for concentric source and drain electrode rings can be high—especially if the distance between the rings is small. The channel (30) will later be formed over the source (22) and drain (24) by the deposition of the channel nanomaterial (30) over the source (22) and drain (24).

For instance, FIG. 5M depicts the use of the bottom source (22) and drain (24) electrodes as shown in FIG. 5L as well as the use of alternating vertical metal source (22) and drain (24) electrode layers, which may be positioned, such as within a chamber (37) or the bounding member(s) (39) defining the chamber, so as to create an interdigitated type of effect in the vertical direction and thereby maximize the of ratio channel width W to channel length L, as herein described. Particularly, FIGS. 27 and 28 depict a ChemFET (1) comprised of a dielectric material (20 and/or 35), and having a chamber (38) formed therein, such as by etching. The chamber (38) includes a wall (39) and/or a bottom surface (21) having a plurality of electrodes disposed therein, such as a source electrode (22) and a drain electrode (24), such as where the electrodes have been configured in an interdigitated manner both in a horizontal direction at the bottom (21) of the chamber (37) and in a vertical direction along the height of the chamber (37). It is to be noted that although a particular electrode configuration has been depicted, any suitable configuration can be implemented, such as those depicted in FIG. 5G.

To demonstrate the desirability of forming 3D electrode structures on the well surfaces (39 and/or 21), a comparison of the ratio of channel width to channel length (W/L) can be made of a device that only has electrodes (22) and (24) on the well bottom (21) versus one with electrodes on the well bottom (21) and well walls (39). For instance, with respect to the well structure depicted in FIGS. 5L and 5M, e.g., with a nominal 1 micron well diameter (at the well bottom (21)), the channel length of channels (24) either at the well bottom (21) or on the well walls (39) is 100 nm, for example. For the well bottom (21), the channel (24) width is given by the formula $2\pi R$ (it is the circumferential distance of the channel defined by the gap between the source (22) and drain (24) electrodes). If one assumes the radius of the channel (24) is 150 nm, then the channel width is about 945 nm. This results in a W/L of about 9.45. Further, as depicted in FIGS. 27 and 28, there are multiple electrode layers, such as in a vertically stacked configuration that circumscribes and/or surrounds the well opening (37). In such an instance, the channel length may be about 100 nm. In this instance the channel width is contributed by the circular gap between each electrode layer times the number of such gaps.

Figure 5N:
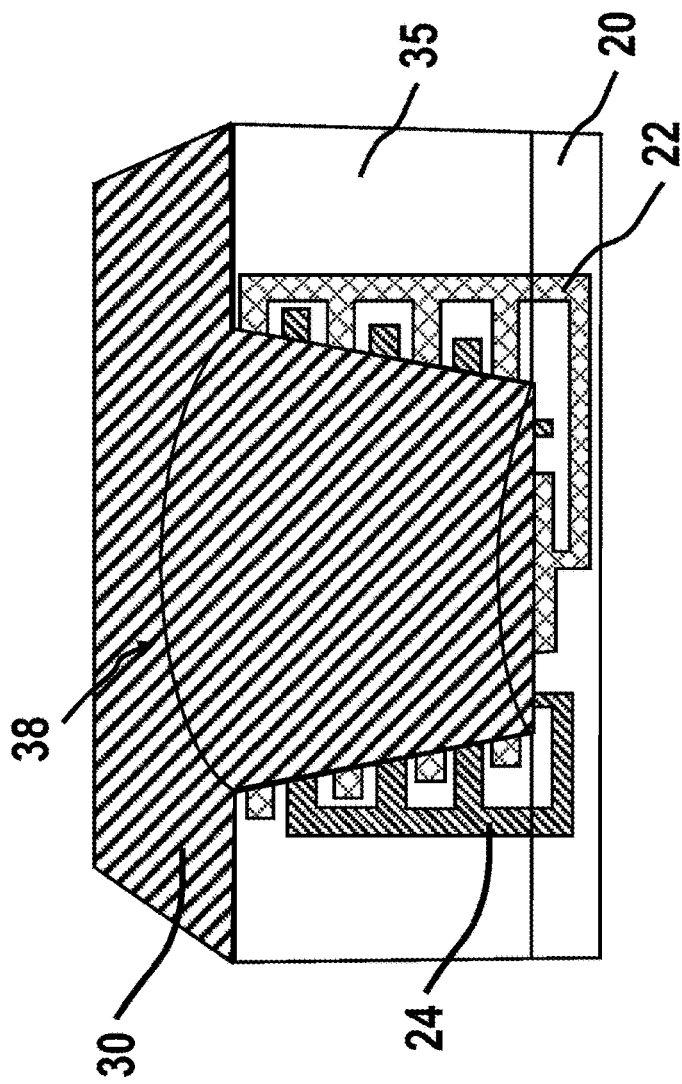
FIG. 5N is an illustration of the structure of FIG. 5M with a transistor material or an analyte or reaction-sensitive layer.

For example, for 6 gaps, where the well diameter is 1000 nm, the channel width due to the sidewall structures is: $W_{vertical} = 2\pi rN = 6.3 \times 500$ nm $\times$ number of levels $= 3150$ nm $\times 6 = 18900$ nm. Further, if the channel width at the well bottom is added, a total channel width is 19845 nm and a W/L of 198. This is more than a (20) times higher W/L than the case with an electrode structure only on the well bottom. As described above, the electrode structures (22), (24) on the well sidewalls (39) and at the well bottom (21) may be covered by a transistor channel nanomaterial (30), such as depicted in FIG. 5N Furthermore, an analyte or reaction-sensitive layer (34) (not shown) may be deposited over the channel nanomaterial (30) on the well boundary walls (39) and bottom (21). Particularly, FIG. 5N depicts a well chamber (38), wherein the chamber (18) may be configured to include a transistor channel nanomaterial (30) and optionally an analyte or reaction-sensitive layer (30) (not shown).

Figure 6A:
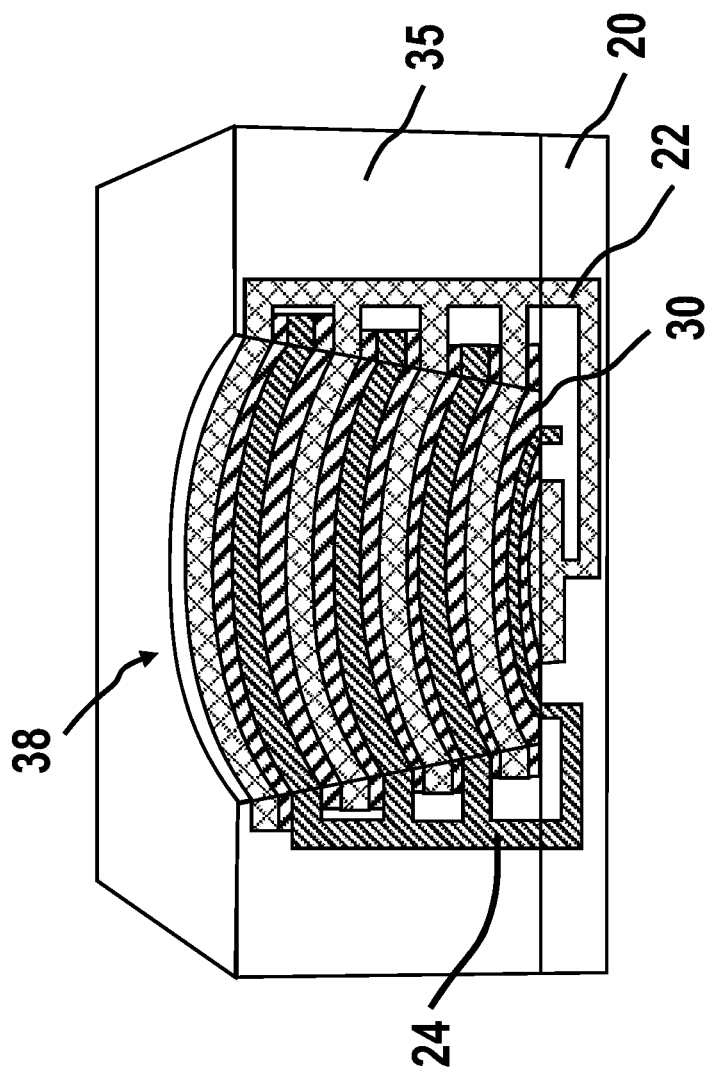
FIGS. 6A-6K illustrate using alternating vertical layers of metal and transistor material to create an interdigitated type of effect to maximize the ratio of channel width to channel length and the process steps used to achieve that structure.

In various instances, the source (22) and drain (24) electrodes can form electrode pairs that are separated one from the other by a distance such as to from an interdigitated source (22) and drain (24) electrode pair. As presented in FIG. 6A, the source (22) and drain (24) electrode pairs may be configured so as to form a channel between the two electrodes, such as in the space between the two electrodes. In such instances, as depicted in FIG. 6A, the channel may be comprised of or otherwise contain a 1D or 2D channel nanomaterial (30), such as a carbon nanotube and/or graphene layer. Hence, an option for forming one or more channels (24) with small lengths and high effective widths is to vertically alternate not only the source (22) and drain (24) electrode layers, but also the transistor channel nanomaterial (30) (e.g., 1D or 2D nanomaterial) layers, as depicted in the well structure (38) cross-section as shown FIG. 6A. In this case, the channel nanomaterial (30), e.g., a series of graphene layers, is interspersed between source (22) and drain (24) electrode layers. Hence, performing the same calculation as before, but in this case using a channel length of 0.345 nm (the thickness of a single layer of graphene is 0.345 nm) results in a W/L ratio of 57,522 which is more than 290 times higher than the previous calculation and demonstrates the effectiveness of using thin channel nanomaterial layers (30) stacked vertically in an alternating fashion with the source (22) and drain (24) electrodes as part of the device structure.

Figure 6B:
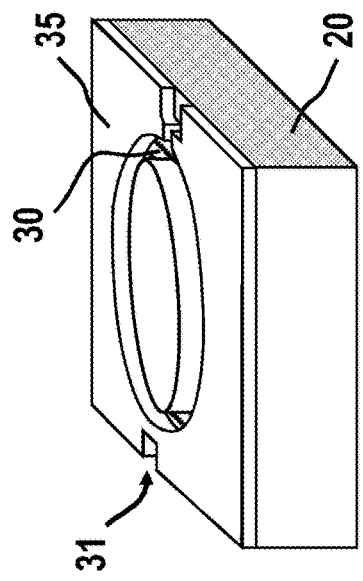

FIGS. 6B-6I depict one implementation of a process flow that may be employed to form the source (22) and drain (24) electrode layers as well as the 1D or 2D channel nanomaterial layer (30). For instance, FIG. 6B depicts the bottom (21) of a substrate or well that may be configured so as to include a conductive source (22) and drain (24) electrodes. These may, for example, be fabricated and/or formed by various fabrication processes as herein described and/or known in the art, such as by using a damascene metal process. The surface of the device may be Chemically Mechanically Polished (CMP'ed), such as after the conductive source (22) and drain (24) electrodes are formed in the well bottom (21). It is to be noted, that FIG. 6B depicts the conductive source electrode (22) and conductive drain electrode (24) at any given level or layer of the device, where electrodes are formed, the electrodes can be formed of the same material during the same process step or different. For example the source (22) and drain (24) electrodes of FIG. 6B could be comprised primarily of copper that is deposited by an electroplating process with both types of electrodes formed in the same process step and in the same material layer.

Figure 6C:
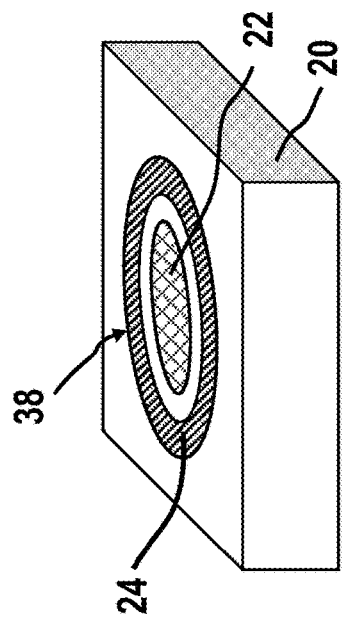

FIG. 6C depicts a layer of a 1D or 2D channel nanomaterial (30) that has been deposited over the electrodes in the well bottom (21). The channel nanomaterial (30) may be patterned so that it just covers all of the underlying conductive electrode pattern or it may be sized smaller or larger than the underlying electrode pattern—as long as it overlaps with a portion of the electrodes.

Figure 6D:
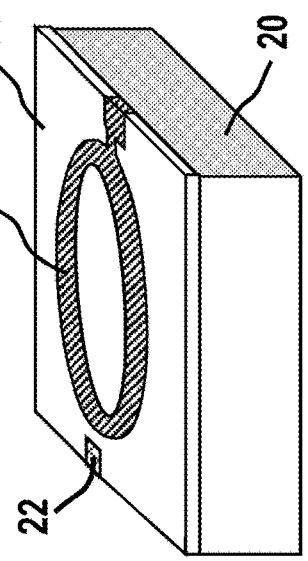

The next step, shown in FIG. 6D, is the deposition of an insulating layer (35) and then the formation of a trench (31) in that layer. At some locations in the trench the underlying channel material (30) is exposed.

Figure 6E:
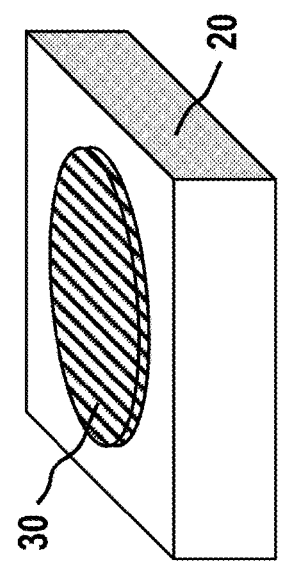

FIG. 6E shows the trench being filled by conductive electrode material to form a source (22) and drain (24) electrode on that layer. During this step vertical electrode connections, e.g., vias, may be formed outside of the electrode patterns. Such vias may be stacked layer by layer as the process progresses allowing the vertical interconnection of source electrodes (22) on different layers, and allowing the vertical interconnection of drain electrodes (24) on different layers.

Figure 6F:
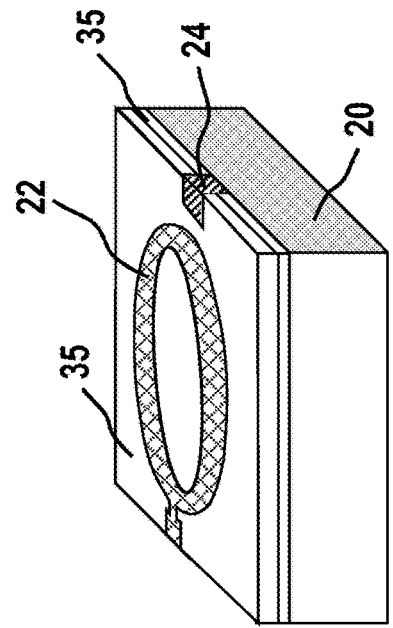
Figure 6H:
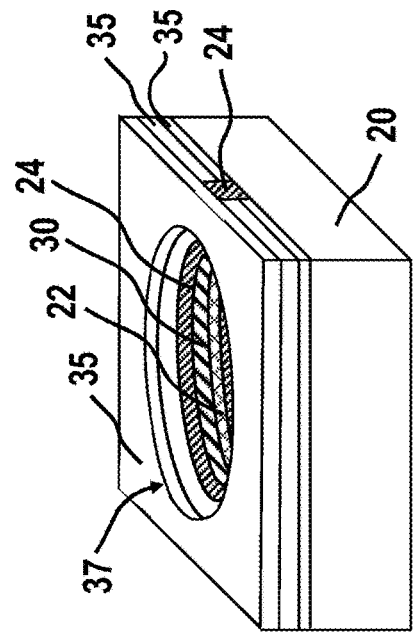
Figure 6G:
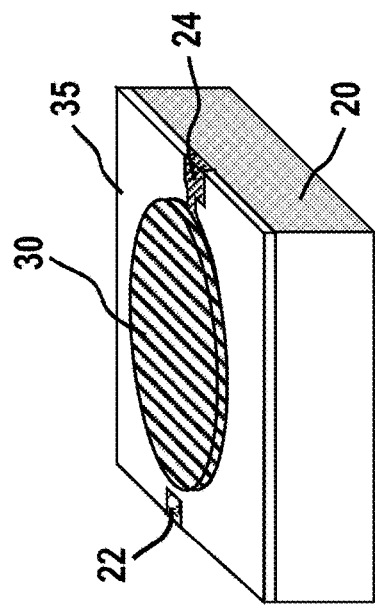

These process steps may be repeated in FIGS. 6F, 6G and 6H to create vertical layers of alternating source electrode (22), transistor channel nanomaterial (30), and drain electrode (24), such as in a vertical interdigitated configuration, as herein described. Duplicating these steps for further repetitions allows higher numbers of alternating source electrode (22), transistor channel nanomaterial (30), and drain electrode (24) layers to be formed.

Figure 6I:
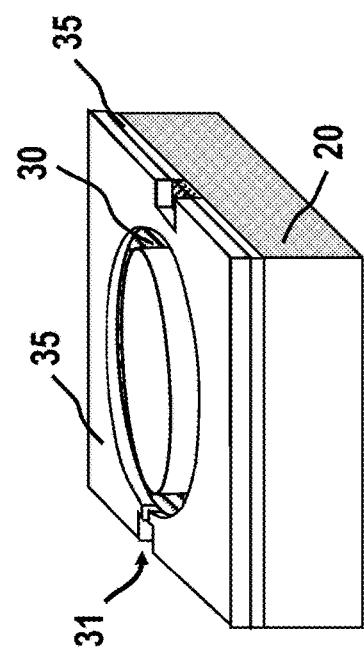

When the selected number of layers have been formed the central portion of the well (38) can be etched (e.g., by plasma, RIE, DRIE or a similar process) as to result in a ChemFET (1) with a well structure (38) and chamber (37) as shown in FIG. 6I. This results in the fully formed layer stack depicted in FIG. 6A, wherein the chamber (37) provides access to the ChemFET transistor for sensing. In this embodiment the ChemFET transistor has multiple channels (31) in parallel due to the vertically stacked and interdigitated source (22), channel (30) and drain (24) structure herein described. Furthermore, since in many applications a fluid will be introduced in the chamber (37) for the purpose of supplying a gate voltage (solution gate) and/or reactants for a chemical reaction to be contained within the chamber (37) it is necessary to cover the exposed source (22) and drain (24) electrodes with an insulating layer so that they are not electrically shorted by the fluid. In one instance an analyte or reaction-sensitive material (24) can be deposited or formed to cover the chamber (37) sidewalls (39) and thus covering the exposed portions of the source (22) and drain (24) electrodes as well as the exposed portions of the channel nanomaterial layers (30). In this embodiment not only does the analyte or reaction-sensitive layer (34) insulate the electrodes (22, 24) from the fluid, but also the layer (34) may improve the sensitivity of the ChemFET (1) due to the the material's sensitivity to certain analytes or reaction products, such as hydrogen ions.

Figure 6K:
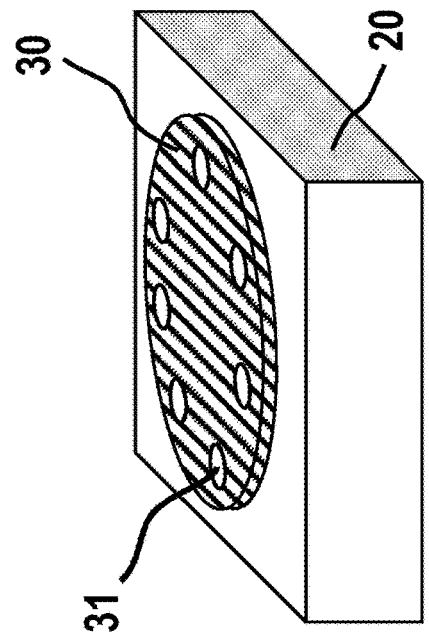
Figure 6J:
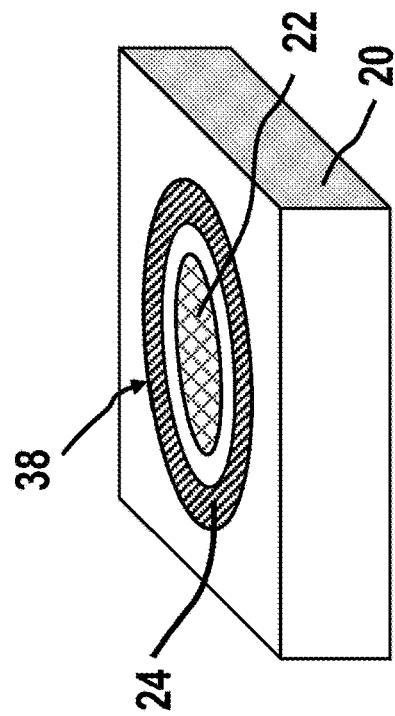

FIGS. 6J and 6K depict a different embodiment for forming alternating layers of electrodes (22, 24) and transistor channel nanomaterial (30). In this case vias, e.g., through-holes, trenches, and/or slots (31) may be formed in the transistor channel nanomaterial (30) as shown in FIG. 6K. In a subsequent step (not shown in the figures) the formation of the electrode material (22 or 24) over or on the patterned channel nanomaterial (30) will also fill these vias. This allows not only a surface area connection from the electrode (22, 24) to the channel nanomaterial (30) but also an edge connection to the channel nanomaterial (30) (e.g., in the via the electrode material (22, 24) may contact the edge of the channel nanomaterial (30)). In some materials, such as graphene, it is known that edge connections from electrodes (22, 24) to the graphene channel nanomaterial (30) may result in lower contact resistance between the two materials and better transistor performance.

Accordingly, in various aspects of the invention, a chemically-sensitive field effect transistor (FET) having a multi-layered structure is provided. For instance, the ChemFET may include a first layer such as a substrate layer. The substrate layer, like all layers described herein, may have an extended body including a proximal portion having a proximal end, a distal portion having a distal end, and a pair of opposed side portions, all of which together define a circumference for the substrate layer. Additionally, a second layer, e.g., a first non-conductive material layer, may be included wherein the first non-conductive material layer may be a dielectric layer and be positioned above the extended body of the substrate layer. In various embodiments, a second non-conductive material layer, which may also be a dielectric layer, may also be included and positioned above the first non-conductive dielectric material layer.

In various embodiments, one or more conductive elements (e.g., composed of an electrically conductive material), such as one or more electrodes, such as a source electrode and a drain electrode for a transistor, may be provided. In various instances, the conductive elements may be separated one from the other and positioned within one or more of the non conductive layers so as to from a channel between the electrodes. In particular embodiments, the source and drain electrodes may have a planar arrangement and may be in an opposed configuration to one another, where one or both of the source and drain electrodes have a geometrical formation or pattern designed to maximize the ratio of the channel width to channel length. For instance, the source and drain electrodes may be configured, e.g., within the insulating layer such that the channel length is less than about 1000 nm, less than about 500 nm, less than about 100 nm, may be less than about 50 nm, or may be less than about (10) nm, less than about 5 or 3 nm or less.

Further, in various embodiments, the ChemFET may include a well structure, provided at least within the first and/or second non-conductive material layers. In such an instance, the well structure may include a chamber, such as a chamber that may be bounded by one or more bounding members. For instance, the bounding member may be configured as a plurality of walls or a circular circumferential surface member. In particular embodiments, the bounding member(s) and/or the surrounding insulating layer(s) may be configured to include the source and drain electrodes. For example, one or more, e.g., both of the source and drain electrodes may be configured so as to be included within a bottom and/or a side surface on the well bounding member. In such an instance, the source and drain electrodes may be configured so as to increase the channel width to length ratio. Particularly, the source and drain electrodes may have a three-dimensional (3D) configuration and may be incorporated on or within the bottom surface member of the chamber and/or be incorporated within one or more side or circumferential surface members of the chamber. In such instances, the source and drain electrodes may be configured so as to increase the channel width to length ratio by a factor of about 10 or 20 or more, e.g., compared to an electrode pattern only at the bottom of the well, such as by a factor of 100 or more, such as a geometric electrode pattern that increases the channel width to length ratio by a factor of 1000 or more.

Particularly, in certain embodiments, the source and drain electrodes may be separated one from the other by one or more spaces, and thus, may be configured to not only have a 3D structure but to also be in an opposed but interdigitated relationship to one another. For instance, one or more of the source and drain electrodes may be formed so as to include an impingement member, and one or more of the source and drain electrodes may be formed so as to include a receiving member, such as where the impingement member is configured for being inserted within the receiving member, and the receiving member is configured for receiving the impingement member, while maintaining a distance between one another, such as to form one or more channels there between.

Hence, in various instances, the source and drain electrodes may have one or more, e.g., a plurality of, prongs or tines so as to give the electrode a fork like configuration, such as can be seen with respect to FIG. 5G, where the tines are capable of being fit one within the other while maintaining a space there between. In such instances, the interdigitated tines of the source and drain electrodes may be disposed within one or both of the first and second nonconductive material layers and be separated from one another by a distance so as to form the channel. In particular embodiments, the bounding member(s) of the chamber may be configured so as to include one or more vias, trenches, or slots that may be formed in the transistor channel nanomaterial, which may then be filled with the electrode material so as to allow the formed electrodes to not only contact the well surface, but to also be in contact with the channel and/or a material layer designed to form or otherwise augment the channel conductivity. Accordingly, in various embodiments, a channel nanomaterial layer may be provided, and the source and/or drain electrodes may be configured so as to contact the channel nanomaterial and/or to also contact an edge of the channel nanomaterial.

Thus, in various embodiments, the chemically sensitive FET may be configured to include a channel, such as a channel that includes or is otherwise composed of a transistor channel nanomaterial, such as is formed over and/or between the electrodes, e.g., the source and drain electrodes. For instance, a 1D, 2D, e.g., a graphene layer, and/or 3D structured layer, may be positioned between the first and second non-conductive material layers. For example, the transistor material channel nanomaterial may be a 1D nanomaterial may be comprised of carbon nanotubes or semiconducting material such as in a nanowire form, such as including Si, Ge or a metal oxide. In other instances, the 2D nanomaterial may be composed of one or more of graphene, molybdenum disulfide ($MoS_2$), $MoSe_2$, phosphorene (black phosphorous), silicene, borophene, tungsten disulfide ($WS_2$), boron nitride, $WSe_2$, stanene (2D tin), graphane, germanane, nickel HITP, Mxenes ($Ti_2C$, ($Ti_{0.5},Nb_{0.5}$), $V_2C$, $Nb_2C$, $Ti_3C_2$, $Ti_3CN$, $Nb_4C_3$, $Ta_4C_3$), and/or transition metal dichalcogenides. The transistor material may be a bulk transistor material such as Si, amorphous Si, Ge, and/or metal oxide. In particular instances, the channel transistor material may be configured so as to extend between a surface portion of the source electrode and a surface portion of the drain electrode. In such an instance, positioning of the transistor channel nanomaterial between the source and drain electrodes is designed to form the channel and thereby control and/or regulate conductivity between the electrodes. Hence, the FET may include a gate structure.

In certain instances, as herein disclosed, the ChemFET may be configured for performing a chemical reaction, such as for the detection of one or more analytes, such as a reactant from a chemical reaction. Accordingly, in various instances, the FET may include an analyte or reaction-sensitive layer. In various embodiments, e.g., to facilitate the performance of a chemical reaction, the ChemFET may include a well structure, within which a chemical reaction may take place. For instance, one or more of the layers of the FET, such as the first and/or second insulating layers may include a chamber, such as a chamber to which the reactants may be added for the performance of the chemical reaction. In such an instance, the channel of the ChemFET may be formed within the chamber and over the channel so as to electrically connect the source and the drain electrodes. Further, one or more solutions, such as containing one or more reactants may be added to the chamber thereby forming a solution gate. In various instances, the gate structure may include the graphene layer.

Further, in various embodiments, the ChemFET and/or the chamber thereof may be configured such that the electrodes, e.g., the source and drain electrodes, are positioned on or in the bounding member of the chamber. For instance, in various instances, the surfaces or walls of the chamber may include one or more trenches, wherein the trench includes one or more of the electrode structures, and/or may include the 1D or 2D nanomaterial, such as the graphene layer. Hence, the electrodes of the source and drain may be included in a bottom or side or circumferential surface of the well or trench. In such an instance, an analyte or reaction-sensitive layer may be formed on the well or trench bottom and/or sidewalls and/or may cover the electrodes and/or channel nanomaterial. In some instances, the 1D channel nanomaterial may be a vertically-oriented 1D channel nanomaterial. Consequently, the chamber may be configured for sensing and/or measuring the analyte such as a reactant that results from the reaction taking place within the chamber.

For example, one or more surfaces of the substrate and/or a well and/or a chamber thereof may be fabricated in such a manner so as incorporate the electrodes therein. Particularly, one or more of the electrodes disclosed herein may be formed by any suitable method, such as by being lithographically photo patterned, which may utilize a light source and/or optics that allow patterning of deep trenches and/or wells. More particularly, in various instances, an electron beam, laser or plasma beam may be utilized to pattern the wells and/or trenches and/or the electrodes. In various instances, the well structure is comprised of alternating vertical layers of source and drain electrodes, such as to define the channel width and the channel length. In particular embodiments, the well structure is comprised of electrodes on a well bottom and/or in conjunction with alternating vertical layers of source and drain electrodes so as to define a channel width and/or channel length. As stated above, the electrodes may have a transistor channel nanomaterial and/or an analyte or reaction-sensitive material over and/or between them, such as in the alternating vertical layer configuration. In various embodiments, the analyte or reaction-sensitive material may be formed by PVD deposition of a metal and oxidization of that metal and/or the analyte or reaction-sensitive material may be formed by ALD deposition of a metal oxide, such where the PVD deposition is a sputter or e-beam deposition, and/or the oxidation is a thermal or plasma oxidation. In particular instances, the analyte or reaction-sensitive material may be comprised of multiple layers, which material may be formed by any process or a combination of processes so as to cover a bottom and/or side of the well, and in certain instances, the analyte or reaction-sensitive material at the bottom of the well may be different from the analyte or reaction-sensitive layer coating the well or trench walls.

Accordingly, in a further aspect of the invention, a method for producing a ChemFET is provided, such as a ChemFET that is configured for performing a chemical reaction and sensing one or more of the products thereof. In such instances, the ChemFET may include a plurality of electrodes, and in various instances may be in an alternating, vertical and/or interdigitated layered configuration. In such an instance, the method may include forming alternating layers of source electrodes, dielectric material and drain electrodes, as well as forming a well or trench within a central portion of the source and drain electrode patterns. The method may include forming a well or trench in one or more of the layers of the ChemFET, such as one or more of the insulating layers, such as in an etching process, such as by wet etching or plasma etching, or the like.

Hence, in various instances, the method for producing a sensor may include forming alternating and/or interdigitated layers of source electrodes, dielectric material, and/or drain electrodes, forming a well or trench within a central portion of the source and drain electrode patterns, and/or forming a transistor channel nanomaterial over or between the source and drain electrodes, such as where an analyte or reaction-sensitive layer may be formed over the transistor channel layer. For instance, a first layer of transistor channel nanomaterial may be formed over a first electrode layer, a dielectric layer may be formed over the first electrode layer, a trench may be patterned in the dielectric layer, a second electrode layer may then be formed within the trench. In various embodiments, the second electrode layer and dielectric layer may be planarized, a second layer of transistor channel nanomaterial may then be formed over the second electrode and second dielectric layer and this process may then be repeated so as to produce the desired number of electrode and channel layers.

Figure 8:
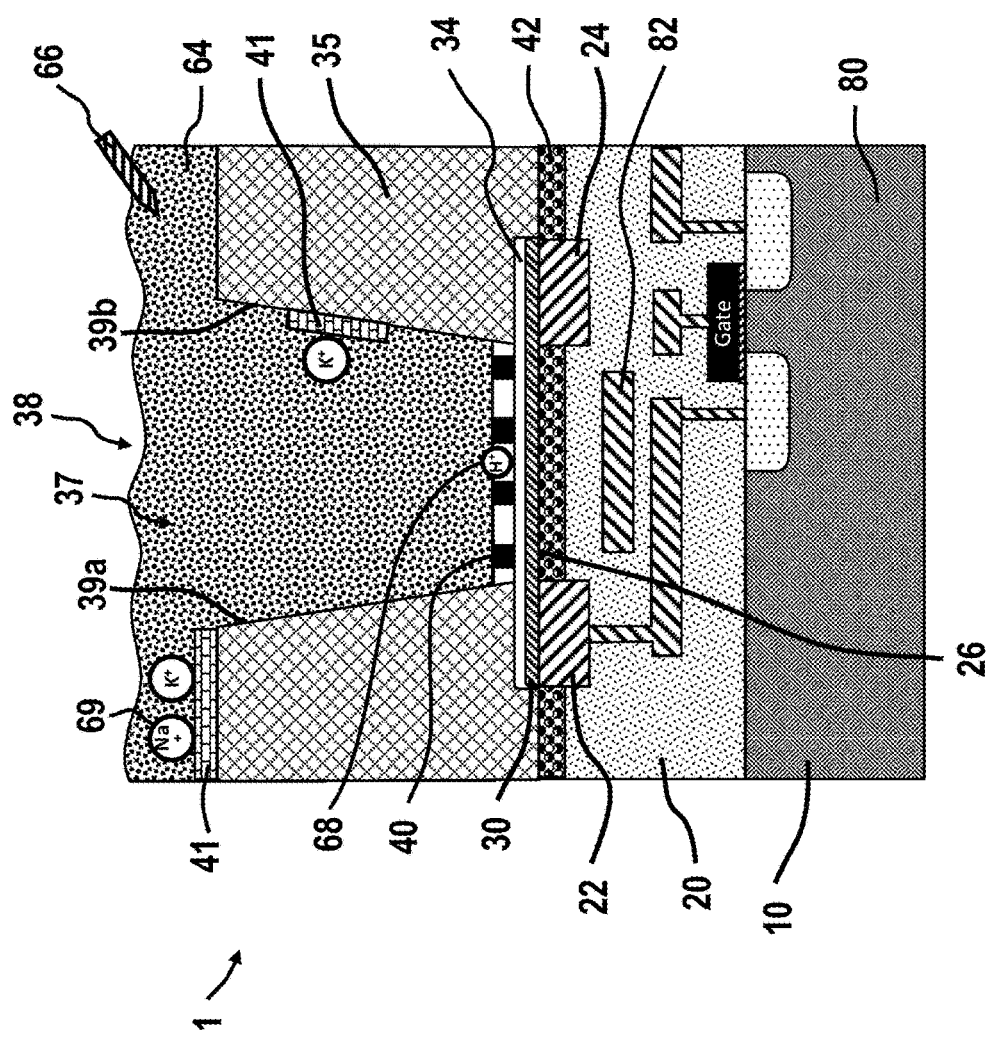
FIG. 8 is a side sectional view of a ChemFET with several improvements combined in one embodiment.

Channel Enhancements—Ion Permeable Layer, Ion Getter and Charge Trap Screening Layer In a further aspect, as seen with respect to FIG. 8, a ChemFET sensor (1) is provided wherein the sensor includes a stacked configuration having a plurality of layers and/or structures therein. For instance, a primary structure (10) includes a semiconductor base layer, e.g., a silicon layer, which is fabricated to contain or may otherwise be configured as CMOS circuits. Accordingly, stacked on top of the base layer (10) may be a secondary structure (20) that may be configured as a dielectric layer and/or another inorganic or organic dielectric layer, such as a silicon dioxide layer. The primary (10) and/or secondary (20) structures may additionally include or otherwise be configured to contain a conductive source (22) and drain (24) embedded in one or more of the structured layers, and between which is formed a channel structure (30). In particular embodiments, an additional structure or passivation layer (35) may be positioned above the primary and secondary layers, which passivation layer (35) may be etched to form one or more well structures (38), which well structure may be coincident with and/or proximate to the channel sensing region (26) which in turn communicates with a solution gate. In various embodiments, the nanomaterial channel (30) region may include or otherwise be formed by the channel (30) as well as the bounding wall members 39a and 39b forming the well structure (38), such as by extending laterally upwards from the surface (21) and/or sensing layer region (26), and having opening (37) positioned therein so as to provide access for the fluid to communicate with the gate electrode.

The well structure (38) may further include one or more additional structures and/or layers, such as a 1D or 2D nanomaterial (30) and/or an oxide (34) and/or passivation (35) layers that may be positioned between the conductive source (22) and drain (24) and/or between wall members (39a, 39b) in such a manner as to form a bottom surface and/or sensing zone (26) of the chamber (37). In various instances, one or more of the structures may further include or otherwise be associated with an integrated circuit and/or a processor, such as for generating and/or processing generated data, such as sensor derived data, e.g. indicative of a sequencing and/or hybridization reaction taking place within the well structure (38). In particular embodiments, a further structured layer (40), e.g., a secondary or tertiary or quartier structure, may also be provided, such as where the further structured layer may be included and/or present on a surface (24) or otherwise within the well or chamber (37), such as to enhance the ability of the sensor and/or the processor to determine the difference between a current and/or voltage applied across the source (22) and/or drain (24) of the transistor, as well as their respective associated charge curves, as described herein.

Figure 4A:
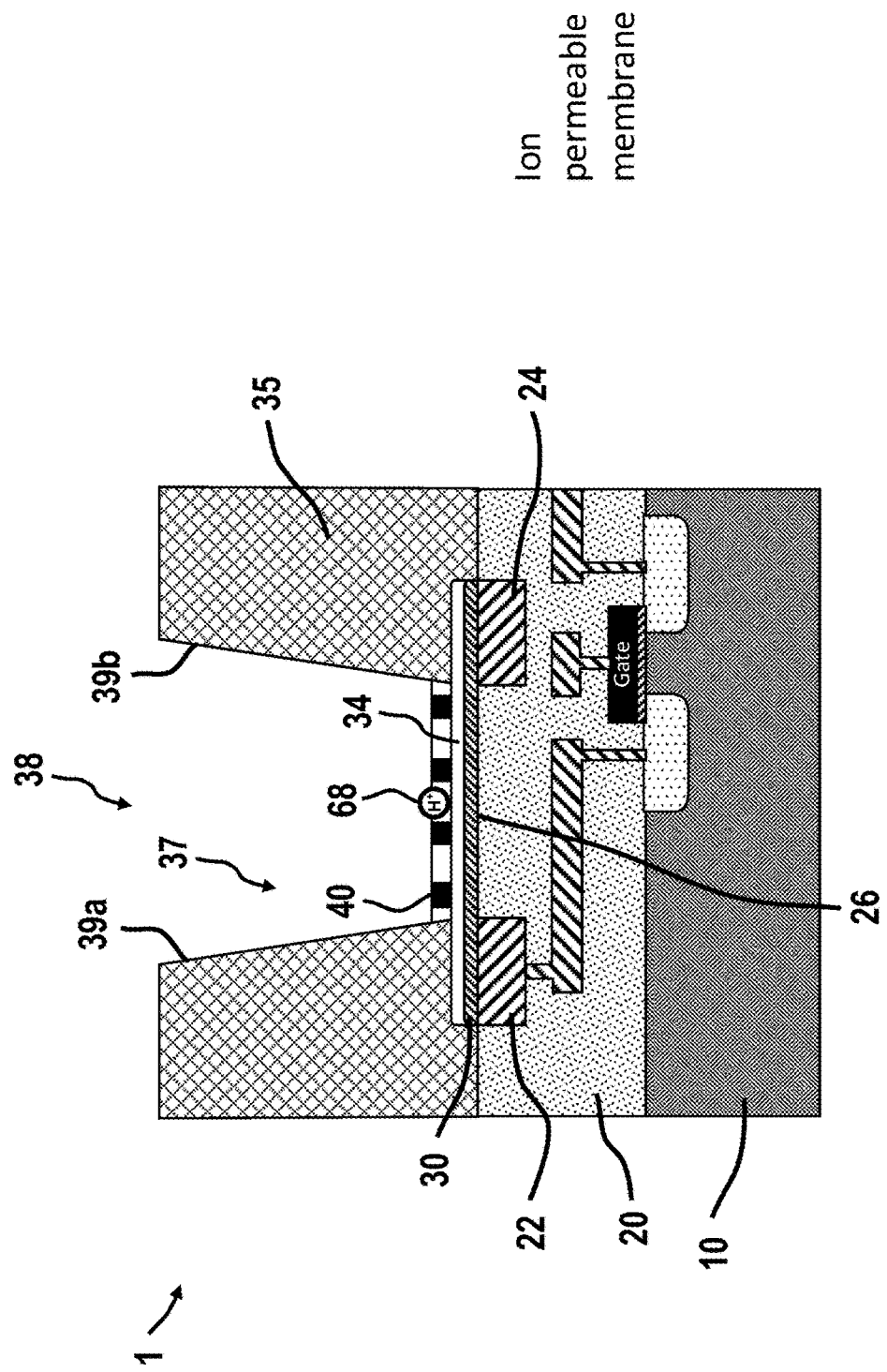
FIG. 4A is an illustration of a ChemFET with a graphene layered well structure and having a permeable membrane associated with the graphene layer.

For instance, in the exemplary embodiment of FIG. 4A, a ChemFET (1) having a graphene layered channel (30), well structure (38) containing a further structured layer (40) configured for enhancing the sensitivity of an associated sensor. In this embodiment, the structured well layer (40) is configured as a permeable membrane that may be associated with the graphene channel (30) and/or analyte or reaction-sensitive (34) layers. Particularly, the ChemFET sensor (1) includes a surface (21), which surface may be within a well chamber (37), and be configured as a sensing region (26). The surface (21) of the sensing region (26) may be coupled to or otherwise include a 1D or 2D nanomaterial such as a graphene layer configured as a channel (30) for detecting the presence of one or more chemical and/or biological events and/or elements resulting thereby. Accordingly, the surface (21) may be configured as a sensing region (26), and the well chamber (37) may be adapted such that a chemical and/or biological reaction may take place therein. The surface (26) and/or graphene structured layer (30) may be coupled with or otherwise include an additional structure, such as an ion permeable membrane (40) or an ion getter material (41) or a charge trap layer screening material (42), all of which are configured to enhance the ability of the graphene-based sensor (1) to detect the presence of a chemical and/or biological reaction. Particularly, the additional structure (40)

may be an ion-selective permeable membrane that is positioned proximate to and/or over a sensing zone (26), which may be configured as a channel (30), and which membrane (40) may be adapted such that it only allows ions of interest to travel through the membrane (40), while excluding those ions that might cause interference with the sensing capabilities of the sensor (1).

Accordingly, as can be seen with respect to FIG. 4A, in various embodiments, the channel sensing region (26) may be configured so as to form a chamber (37) and/or well (38) and the 1D or 2D nanomaterial channel (30) and/or oxide layer (34) may be positioned between the conductive source (22) and drain (24) in such a manner as to form a bottom surface of the chamber (37). In various instances, the structures may further include or otherwise be associated with an integrated circuit and/or a processor, such as for generating and/or processing generated data, such as sensor derived data. And, further, in various embodiments, the chamber (37) may further include a membrane (40) or other element positioned above or between one or more of the 1D or 2D nanomaterials, or 3D structure layer and/or the oxide (34) and passivation layers (35), such as where the membrane structure (40) is configured for enhancing the ability of the processor to determine the difference between various I–V and/or $I_d$–$V_{gs}$ curves. For instance, FIG. 7C depicts a graph of an average sensitivity of a graphene FET ("GFET") calculated as a function of liquid gate potential. The GFET of the present invention approaches the theoretical 59 mVolt per pH maximum for an ISFET type device. This sensitivity of the ChemFET is even more enhanced when an ion permeable membrane (40) is included as part of the device.

In particular embodiments, therefore, as seen with respect to FIGS. 4 and 8, a further structured layer (40), e.g., a secondary or tertiary structure, may also be provided, such as where the further structured layer may be included and/or present within the well or chamber, such as to enhance the ability of the processor to determine the difference between the current and/or voltages as well as their respective associated curves. More particularly, the additional structure may include an ion-selective permeable membrane (40), such as an ion-selective permeable membrane that allows ions of interest (68) to pass through the membrane (40) while blocking other indeterminate ions, such as to enhance the ability of the processor to determine the difference between the reference I–V or $I_d$–$V_{gs}$ curve and the chemical sensing I–V or Id–$V_{gs}$ curve, and thus enhance the ability of the processor to detect a desired chemical reaction. In various instances, the ChemFET (1) may be configured such that the I–V or Id–$V_{gs}$ curve(s) may be shifted so as to better respond to, detect, and/or otherwise determine a biological compound or analyte and/or a chemical reaction and or a biologic activity, such as a biological compound and/or a chemical reaction occurring on or near the 1D or 2D nanomaterial channel, e.g., graphene, surface (30) of the ChemFET (1). In particular instances, the ion-selective permeable membrane (40) may include a 2D nanomaterial material, e.g., graphene, which may or may not be electrically connected to the source and/or drain layer and/or channel (30).

Accordingly, in various instances, the ChemFET (1) may be fabricated on an integrated circuit semiconductor wafer that includes a primary (10) and/or secondary (20) structure as well as a channel structure (30), a processor and/or a tertiary structure (35), such as a passivation structure forming one or more wells (38). For instance, the first and/or secondary structures may include a conductive source (22) and a conductive drain (24), which together with the other components of the ChemFET (1) form a channel sensing region (26). The channel (30) extends from the conductive source (22) to the conductive drain 24, with the channel (30) formed between the two, where a one-dimensional or two-dimensional transistor nanomaterial layer (30) may be positioned above and/or may otherwise be in contact with the source (22) and drain (24). As indicated above, the ChemFET (1) may include a processor, such as where the processor is configured for generating one or more of a reference Id–Vgs curve and a chemical sensing Id–Vgs curve, such as in response to a chemical reaction that is to be detected, for instance, a reaction occurring over or near a sensing zone (26) of the ChemFET (1). In particular embodiments, the processor is configured for determining a difference between the reference Id–Vgs curve and the chemical sensing Id–Vgs curve. Hence, in various embodiments, an additional structure (40) may be included, such as a structure that is configured for enhancing the ability of the processor to determine this and other associated differences.

Particularly, in various embodiments, the additional structure may be an ion-selective permeable membrane (40) that allows one or more ions of interest (68) to pass through the membrane (40) while blocking other ions. More particularly, the additional structure (40) may be configured so as to enhance the ability of the processor to determine the difference between the reference Id–Vgs curve and the chemical sensing Id–Vgs curve (or corresponding parameters thereof), and thus further enhances the ability of the processor to detect a desired chemical reaction. Accordingly, in various instances, the ion-selective permeable membrane (40) may be positioned within the well (38) and/or over a passivation layer (35), an ion sensitive or sensing layer (34), a 1D and/or a 2D transistor material layer (30), and/or a dielectric layer (35) that itself may be positioned over and/or otherwise form a part of the chamber (37) or channel sensing region (26).

In particular instances, the ion-selective permeable structure (40) may include a polymer such as perfluorosulphonic material, a perfluorocarboxylic material, PEEK, PBI, Nafion or PTFE. In other instances, the ion-selective permeable structure may be composed of an inorganic material such as an oxide or a glass. In particular instances, the ion-selective permeable structure (40) may be applied to a surface (e.g. 21) of the ChemFET (1) such as by being deposited thereon, such as by a spincoating, anodization, PVD, CVD, sol gel or other methods. An additional material, e.g., HMDS, may also be included so as to manage the interaction of the chamber (37) and/or channel (30) and/or associated dielectric layer (20) and/or an underlying 2D or 1D nanomaterial transistor layer (30). For instance, a ChemFET (1) of the invention may include an additional structure that includes a 2D nanomaterial transistor channel or surface that may include an ion-sensitive material (34) over the channel or surface. In such an instance, the material may be sensitive to ions that are different from the ions associated with the biological molecule or chemical reaction that is to be detected. Particularly, the ion-selective permeable structure (40) may additionally be composed of an ion sensitive 1D or 2D transistor nanomaterial, such as graphene, that is in addition to the 1D or 2D nanomaterial layer 30, and is not electrically connected to the channel (30).

Figure 4B:
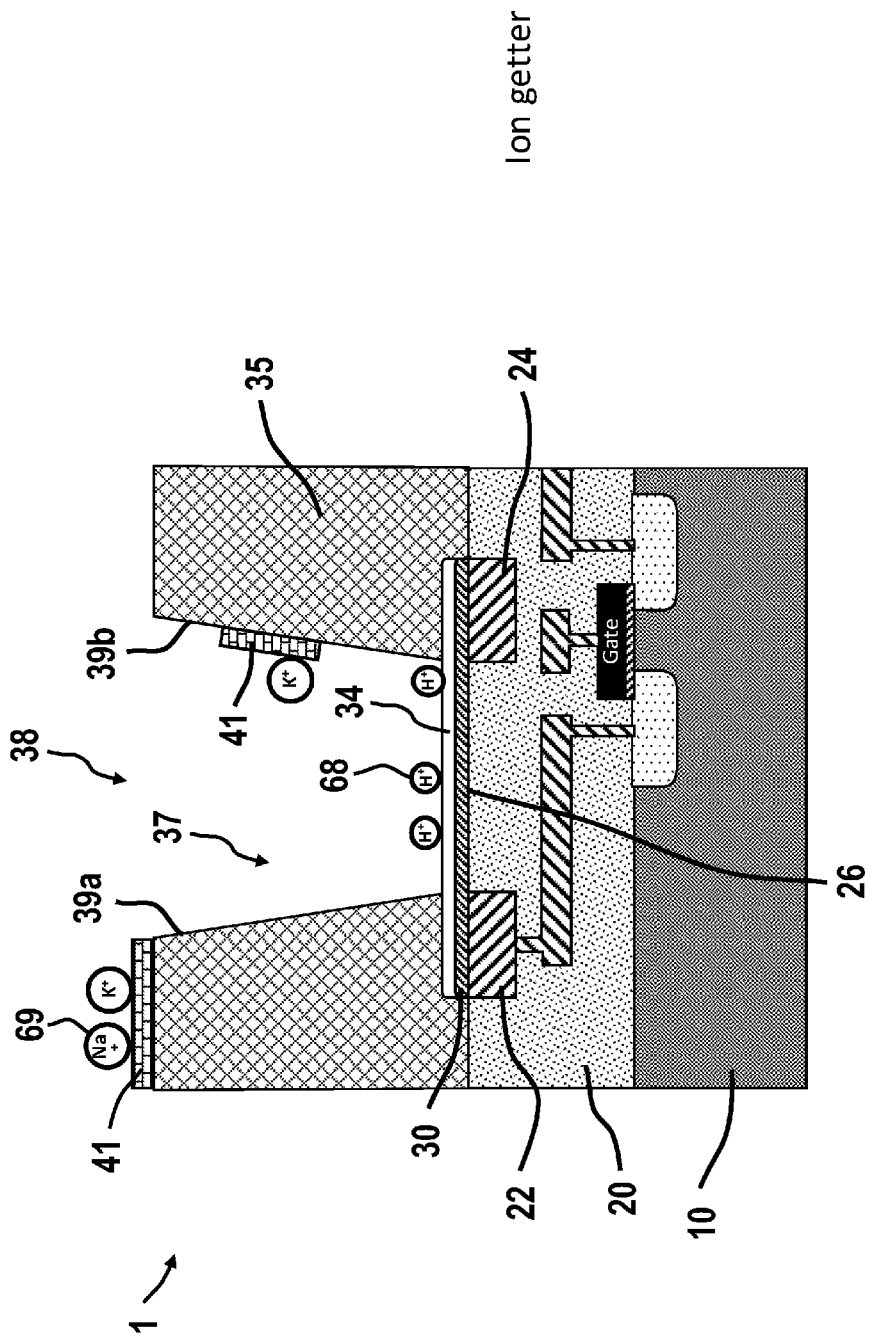
FIG. 4B is an illustration of a ChemFET with a graphene layered well structure and having an ion getter associated with the ChemFET.

In certain embodiments, as depicted in FIG. 4B, the ChemFET may comprise an ion getter material (41), such as an ion getter material (41) that traps or sequesters ions (69) that are not relevant to the biological species and/or chemical reaction to be sensed and/or determined, such as to enhance the ability of the processor to determine the difference between the reference I–V or $I_d$–$V_{gs}$ curve and/or the chemical sensing I–V or $I_d$–$V_{gs}$ curve. This may be useful because reducing the number and/or amount of interfering ions (69), enhances the ability of the processor to detect the desired biological species and/or results of the chemical reactions. Particularly, the ion getter material (41) may be arranged within proximity to the chamber (37) and/or surface (21) thereof so that the action of gettering the unwanted ions improves the detection capability of the ChemFET (1). In some instances, one or more of the various layers herein, such as the ion getter material (41) may be placed over or between one or more of the other layers, such as the dielectric layer (20/35), oxide layer (34), or 2D or 1D nanomaterial layers (30), positioned in proximity to one or more of the chambers, channels, or surfaces of the ChemFET device (1). In yet another alternative the getter material (41) a may be positioned within the chamber (37), such as on a wall (39a and/or 39b) thereof, and/or in a package that is adapted to attract unwanted ions.

Figure 4C:
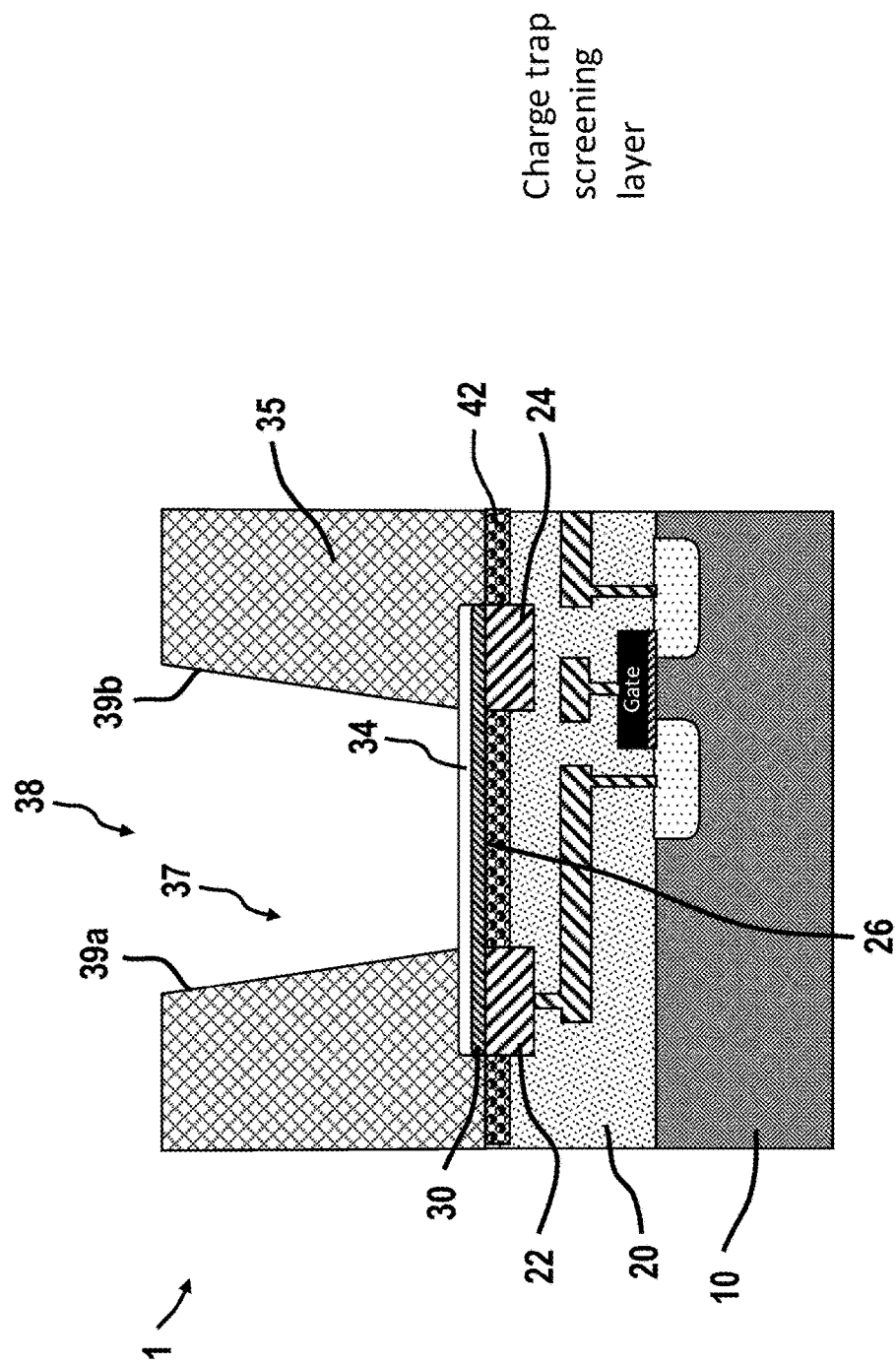
FIG. 4C is an illustration of a ChemFET with a graphene layered well structure and having a charge trap screening layer associated with the channel.

In certain instances, the ion getter structure (41) may be positioned over or near the ion sensitive layer (34) that itself may be positioned over the channel structure or surface (30) or may be position over or near the well structure (38) such as on a top surface of the well or on a sidewall (39) of the well. The ion getter material (41) is configured to trap ions that are not relevant (69) to the chemical reaction to be determined, such as trapping Na+ ions if H+ ions are the ions of interest. Accordingly, in some instances, a suitably configured ion getter material (41) may be useful because the action of sensing ions that are different from the ions associated with the biologics and/or chemical reactions that are to be detected allows the processor to filter out the signal from the unwanted ions from the signal of the ions of interest. The ion getter material (41) may be a metal such as a barium or zirconium alloy, or preferably is a glass such as phosphorous-silicate glass (PSG), argon-silicate glass or arsenic-silicate glass. These getter materials may be especially adept at trapping sodium ions, which may be present due to the buffers used in the fluid. A preferred ion getter material (41) is a 4 to 8% by weight phosphorous-silicate glass (PSG) that is deposited by a CVD process to a thickness of about 10 to 30 nm In particular instances as shown in FIG. 4C, an insulating material (42) may be placed over the dielectric layer (20) and under the 1D or 2D nanomaterial channel layer (30) in order to screen the sensing region (26) from the dielectric layer (20). The dielectric layer (20), typically a silicon oxide, may charge traps within the layer or at the interface between the layer (20) and the channel (30). Furthermore the dielectric layer (20), especially if a silicon oxide, is not atomically smooth and thus affects the carrier mobility through the channel (30). An appropriate screening material (42) can serve to screen the trapped charges from the channel sensing region (26) and if it also has a smooth surface it can enhance carrier mobility through the channel (30). A polymer such as an HMDS material or other siloxane or parylene may be positioned under the graphene channel (30) to act as the charge trap screening layer (42). Alternatively an inorganic material, such as aluminum oxide or preferably hexagonal boron nitride (hBN) may be used as the charge trap screening layer (42).

Accordingly, in various instances, an exemplary ion-selective permeable membrane (40) and/or an additional getter structure (41) may be positioned over or near a channel sensing region (26), where these structures are configured so as to only allow ions of interest (68) to travel to the sensing region (26). In particular instances, the getter material may be positioned within the chamber (37) or elsewhere on the chip or in the package so as to trap or sequester unwanted ions. Another alternative would be to include another ion-selective functional layer(s) over some of the sensors that can detect the presence of unwanted ions (69) so that their interaction with the sensor and thus the determination of the sensor reaction to the desired ion can be filtered out.

In all of these instances, the action of trapping ions that are not relevant to the chemical reaction to be determined enhances the ability of the processor to determine the difference between the reference I–Vg curve and the chemical sensing I–Vg curve, e.g., because there are fewer interfering ions. In such instances, the membrane (40) and/or ion getter material (41) may be arranged within proximity to a sensing zone (26) that is in proximity to a channel (30) so that the action of gettering the unwanted ions improves the detection capability of the ChemFET. Alternatively, the ion getter material (41) may be placed over a dielectric layer that is in proximity to one or more of the sensing zones (26) and/or channels.

In yet another embodiment, a charge trap screening material (42) may be deposited or formed under the channel layer (30), i.e. before depositing or forming the channel (30), such charge trap screening layer (42) effectively screening the channel sensing region (26) from charges trapped in the dielectric layer (20). Furthermore the charge trap screening layer (42) may be smoother than the dielectric layer (20) that having improving the mobility of the charge carriers traveling through the channel (30). The charge trap screening layer (42) may be formed of HMDS or another siloxane, parylene, hexagonal boron nitride (hBN), aluminum oxide or other material, hBN is a preferred material due to its atomic smoothness, close lattice match to graphene (their lattice parameters vary by less than 2%) and lack of dangling bonds that otherwise might trap charges.

ChemFET Reference Electrode

Additionally, as indicated, in certain instances, the ChemFET may include a reference electrode that may be composed of Ru, Pd, Ag, Os, Ir, Pt, Au, Rh, or Ag/AgCl. In certain instances, the reference electrode may be positioned so as to be in electrical communication with the ChemFET, such as through a fluid or solution. In such an instance, the reference electrode may be used to apply a gate voltage to the ChemFET, optionally through the fluid or solution. Hence, the reference electrode may include at least a portion of a metal layer, such as over or on an integrated circuit structure.

Particularly, the reference electrode may be incorporated in a layer of the integrated circuit chip structure that comprises the ChemFET, such as a topmost layer of the integrated circuit structure, or a layer adjacent to one or more ChemFETs on the integrated circuit structure. However, in various instances, the metal layer optionally is part of a separate piece that is attached or affixed to the integrated circuit chip, optionally using a glue, adhesive, polymer, or thermoplastic, or the like. Regardless, the reference electrode is configured so as to be in electrical communication with an interconnect on the integrated circuit structure, such as where the interconnect optionally is (i) integrally connected to the reference electrode through a common metal layer on the integrated circuit, or (ii) connected to the reference electrode through a wirebond, flip-chip, or conductive adhesive connection structure, which connection may optionally be sealed from the fluid or solution while another portion of the reference electrode may be in communication with the fluid or solution.

In certain instances, the reference electrode may be incorporated within a package and/or housing of the integrated circuit structure. For instance, the reference electrode may include at least a portion of a metal layer, e.g., over or on the package substrate or package lid, wherein the metal layer optionally is part of a separate piece that is attached or affixed to the package substrate or package lid, such as using a glue, adhesive, polymer, or thermoplastic, and/or the like. Hence, in particular instances, the reference electrode may be a metal layer deposited by a method that is a PVD, CVD, printing, electroplating, an electroless plating method, and/or the like. In some embodiments, the reference electrode may include two or more reference electrode elements.

As described, an array according to the invention that comprises a plurality of sensors may also further include one or more reference electrodes (66), preferably platinum or Ag/AgCl reference electrodes (66), which are used to apply a gate voltage to the fluid and thus to each of the ChemFETs in the array of ChemFETs on the ChemFET sensor IC chip.

As shown in the following figures, reference electrodes (66) can also be utilized with the ChemFET-based sensors and devices of the invention. There are multiple reference electrode (66) options for use with chemically sensitive sensors. For example, platinum, silver, or other fluid-compatible reference electrodes (66), such as noble metal Ru, Pd, Ag, Os, Ir, Pt, Au, Rh, or Ag/AgCl, can be used. For example, the material for the reference electrodes (66) can be deposited on (or otherwise applied to) the chip surface (e.g., by PVD or CVD). The reference electrodes (66) can then be directly coupled to the conductive lines, e.g. copper lines, forming the other electrodes. Another approach is to plate the reference electrodes (66) on the chip (using an electroless plating process). Yet another approach is to have the reference electrodes (66) as separate pieces adhesively attached to the chip (preferably including over active peripheral circuitry so as to conserve space and not interfere with the wells or other sensing regions of the device) and wirebond interconnected or attached to the package or the chip. Yet another embodiment includes reference electrodes (66) as several pieces as in FIG. 15 so that resistance through the fluid to the reference electrode is more normalized.

Figure 12:
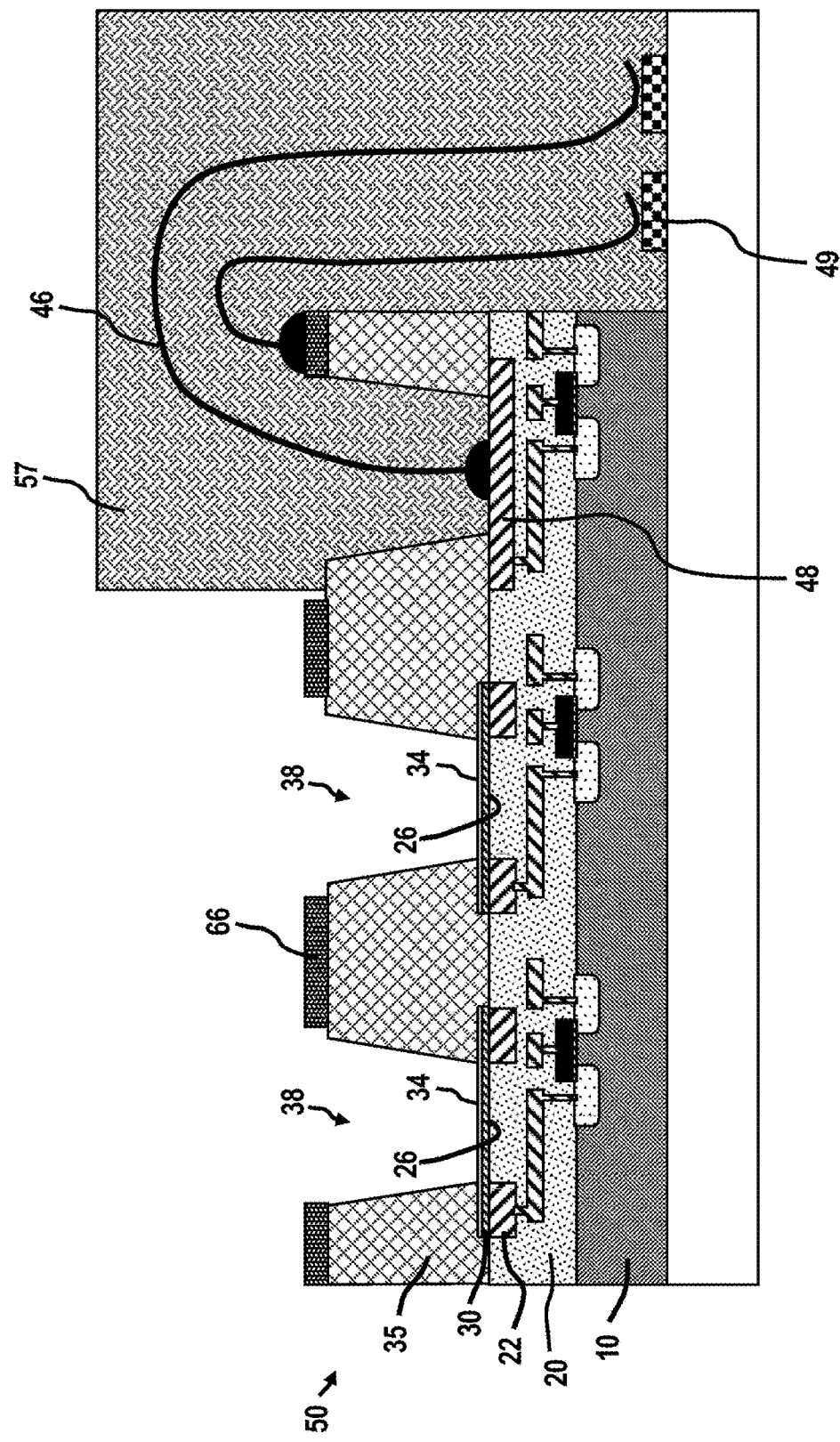
FIG. 12 is an illustration of multiple chemically-sensitive field-effect transistors with a well structures and reference electrodes on top of the wells.

Other embodiments have the reference electrodes (66) incorporated as a metallization layer deposited on top of the wells (e.g., by sputtering, evaporation, or plating). The reference electrode(s) (66) is(are) connected separately from the chip interconnect using wirebonds (46) to the package substrate bond pads (49) as depicted in FIG. 12.

Thus, in some embodiments the chemically-sensitive sensor is based on a ChemFET sensor IC chip (50) according to the invention fabricated on an integrated circuit wafer, which ChemFET sensor IC chip (50) also includes a processor and one or more reference electrodes (66). The processor is configured to determine a chemical reaction based on the electrical characteristics of the ChemFET (1). The reference electrode (66) is preferably selected from the group of Ru, Pd, Ag, Os, Ir, Pt, Au, Rh, and Ag/AgCl The reference electrode (66) is preferably in electrical communication with a ChemFET (1), and is preferably used to apply a gate voltage to the ChemFET (1). The reference electrode can alternatively be used to apply a gate voltage to the ChemFET (1) through a fluid or solution.

The reference electrode (66) is preferably comprised of at least a portion of a metal layer over or on the integrated circuit chip.

In one embodiment, the reference electrode (66) is incorporated in a layer of a ChemFET sensor IC chip (50) that comprises the ChemFET (1). In other embodiments, the metal layer is part of a separate piece that is attached or affixed to the integrated circuit chip.

In some embodiments, the reference electrode(s) (66) is (are) attached or affixed to the integrated circuit chip by a material comprising a glue, adhesive, polymer, or thermoplastic.

In some preferred embodiments, the reference electrode (66) is in electrical communication with an interconnect on the integrated circuit chip. The interconnect is integrally connected to the reference electrode through a common metal layer on the integrated circuit chip, or the interconnect is connected to the reference electrode (66) through a wirebond, flip chip, or conductive adhesive connection. In certain embodiments, the wirebond, flip chip, or conductive adhesive connection to a portion of the reference electrode (66) is sealed from the fluid or solution while another portion of the reference electrode (66) is in communication with the fluid or solution.

In some embodiments, a reference electrode layer (66) is a topmost layer of the integrated circuit.

In some embodiments, a reference electrode layer (66) is adjacent to one or more ChemFETs (1) on the ChemFET sensor IC chip (50).

In other embodiments, the reference electrode (66) is incorporated within the package housing the ChemFET sensor IC chip (50).

In certain embodiments, the reference electrode (66) comprises at least a portion of a metal layer over or on the package substrate or package lid, while in other embodiments, the metal layer is part of a separate piece that is attached or affixed to the package substrate or package lid.

In certain embodiments, the reference electrode (66) is attached or affixed to the package substrate or package lid by a material comprising a glue, adhesive, polymer, or thermoplastic.

In various embodiments, a reference electrode (66) is in electrical communication with an interconnect on the package substrate or package lid.

In some embodiments, the interconnect is integrally connected to the reference electrode (66) through a common metal layer on the package substrate or package lid.

In some embodiments, the interconnect is connected to the reference electrode (66) through a wirebond, flip chip, solder, or conductive adhesive connection.

In certain embodiments, the wirebond, flip chip, solder, or conductive adhesive connection to a portion of the reference electrode (66) is sealed from the fluid or solution while another portion of the reference electrode (66) is in communication with the fluid or solution.

In various embodiments, the reference electrode (66) layer is a topmost layer of the package substrate or a bottommost layer of the package lid. In another embodiment, the reference electrode (66) layer is adjacent to one or more ChemFETs (1) on the ChemFET sensor IC chip (50). The metal layer is deposited by a method comprised of a PVD, CVD, printing, electroplating, or electroless plating method. In some preferred embodiments, the devices include multiple reference electrodes (66).

Accordingly, in one aspect, a ChemFET sensor IC chip (50) may be provided. The ChemFET sensor IC chip (50) may include an integrated circuit structure, such as a CMOS structure, and may also include a conductive source (22) and a conductive drain (24), which source and drain may be separated one from the other so as to form a channel (30)

region. Hence, in various embodiments, a nanomaterial channel (30) may be included where the channel (30) extends at least from the conductive source (22) to the conductive drain (24). In particular implementations, the channel (30) may be composed of a channel nanomaterial such as a one-dimensional transistor nanomaterial or a two-dimensional transistor nanomaterial, such as where the conductance of the channel shifts in response to a chemical reaction occurring over or near, e.g., proximate, the channel (30). In various instances, the length of the channel from an inside or outside edge of the source to the drain may range from 0.05 micron to 3 microns, and may have a width of the conductive channel that ranges from 0.05 micron to 2 microns for a rectangular channel (30). However, in other embodiments where the objective is to increase the channel W/L ratio, the effective channel width may be very large, such as 10 microns, or 100 microns or more. Particularly, in certain embodiments, the channel may include a one-dimensional, e.g., carbon nanotube or semiconductor nanowire transistor material, or a two-dimensional transistor material, such as one or more of graphene, silicene, molybdenum disulfide, black phosphorous (phosphorene), borophene, tungsten disulfide, boron nitride, tungsten diselenide, stanene, germanane, nickel HITP, and/or metal dichalcogenides or Mxenes such as Ti2C, (Ti0.5,Nb0.5), V2C, Nb2C, Ti3C2, Ti3CN, Nb4C3, or Ta4C3. Additionally, in some embodiments, a non-conductive, e.g., an oxide, layer may be disposed over the channel (30) nanomaterial, which layer may be a thin layer, such as having a thickness of 50 nanometers or less.

ChemFET Gate Structure

Figure 7A:
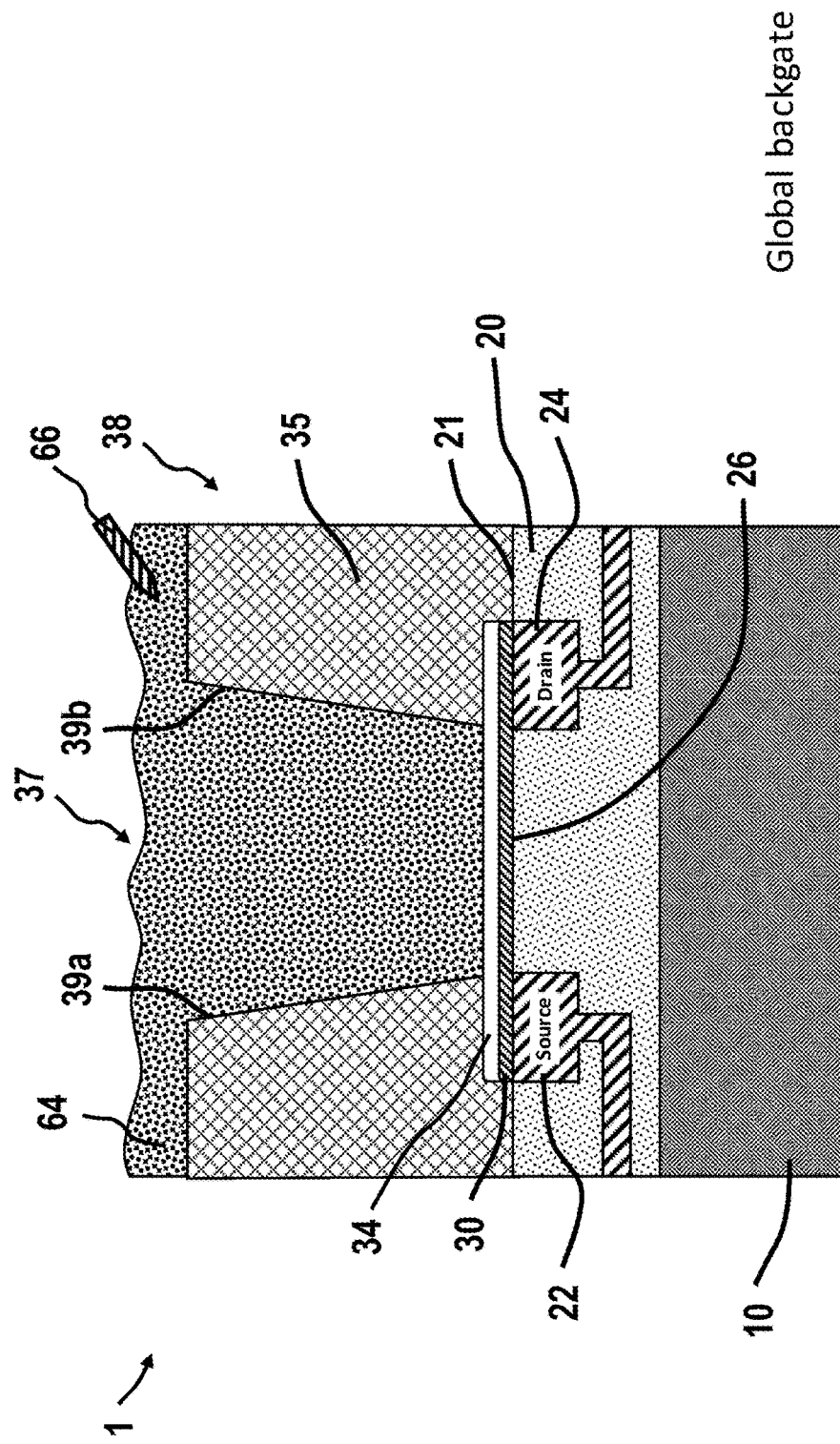
FIG. 7A is a solution gated ChemFET.

FIG. 7A depicts a ChemFET configured with a solution gate. In this instance a nanomaterial channel (30) connects a conductive source (22) and drain (24) and a fluid (64) contained within a chamber (37) of a well structure (38) has a gate voltage applied to it by a gate or reference electrode (66). The gate voltage level affects the conductance through the channel (30). This configuration is referred to as a solution gated ChemFET. The solution gate can be consider a top gate, since the fluid is on top or over of the channel.

The ChemFET of FIG. 7A may have a maximum sensitivity due to the nature of its operation and also the material chosen for the ion sensitive layer (34). FIG. 7C shows a graph of sensitivity versus solution gate voltage for a ChemFET represented in FIG. 7A. There is an upper bound for sensitivity, referred to as the Nernst limit, of 59 mV/pH.

In another embodiment the ChemFET transistor can be fashioned with a bottom or back gate, i.e. a gate oriented underneath the channel. One way to create a backgate is to bias the whole semiconductor substrate 10 with a desired gate voltage. In this case all the ChemFETs (1) on a ChemFET sensor IC chip (50) as shown in FIG. 15B will have the same applied backgate voltage. This scheme is referred to as a global backgate.

Figure 7B:
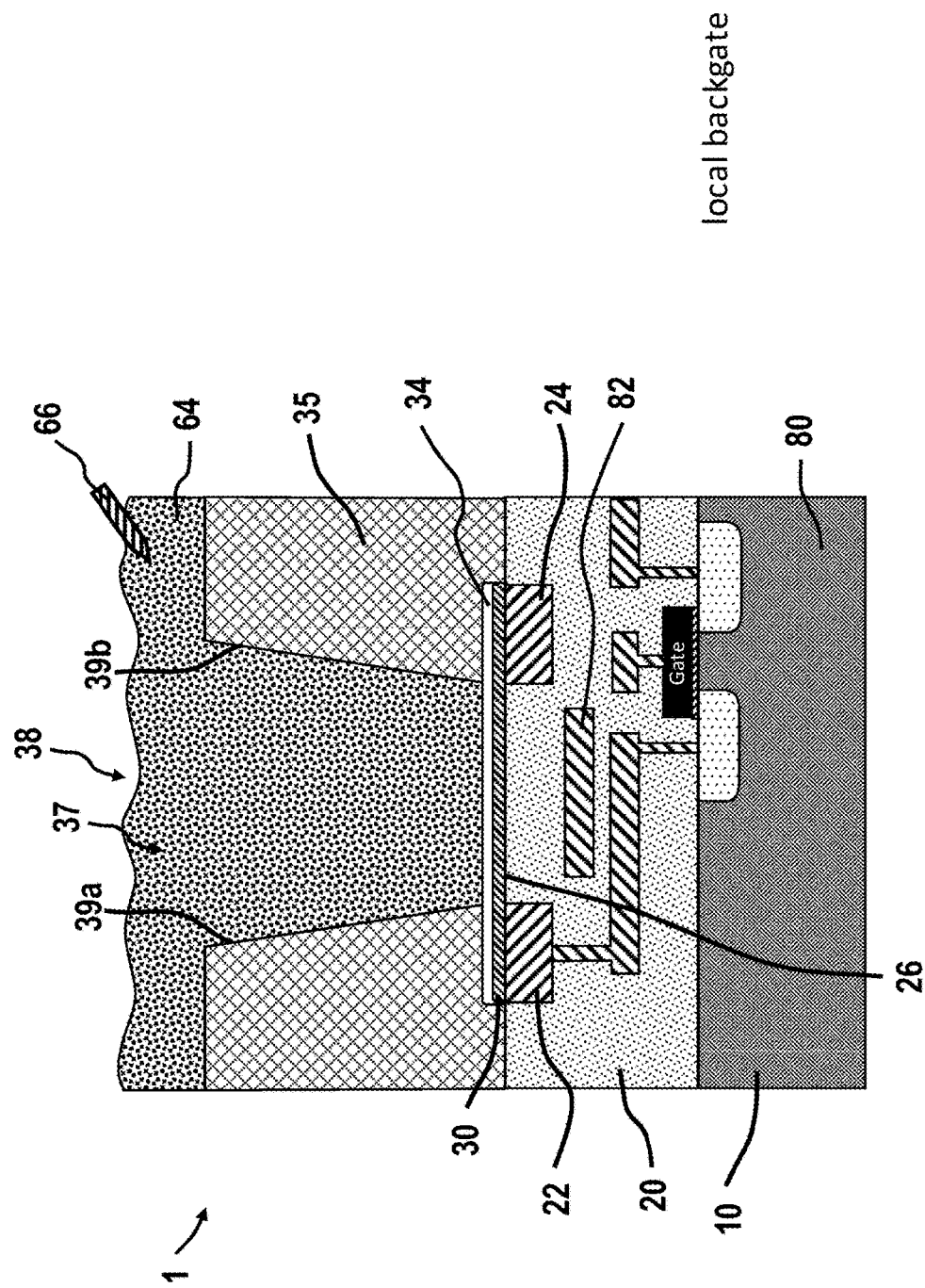
FIG. 7B is an illustration of a ChemFET with multiple enhancements including a local backgate electrode in concert with a solution gate to provide a dual gate ChemFET.
Figure 7C:
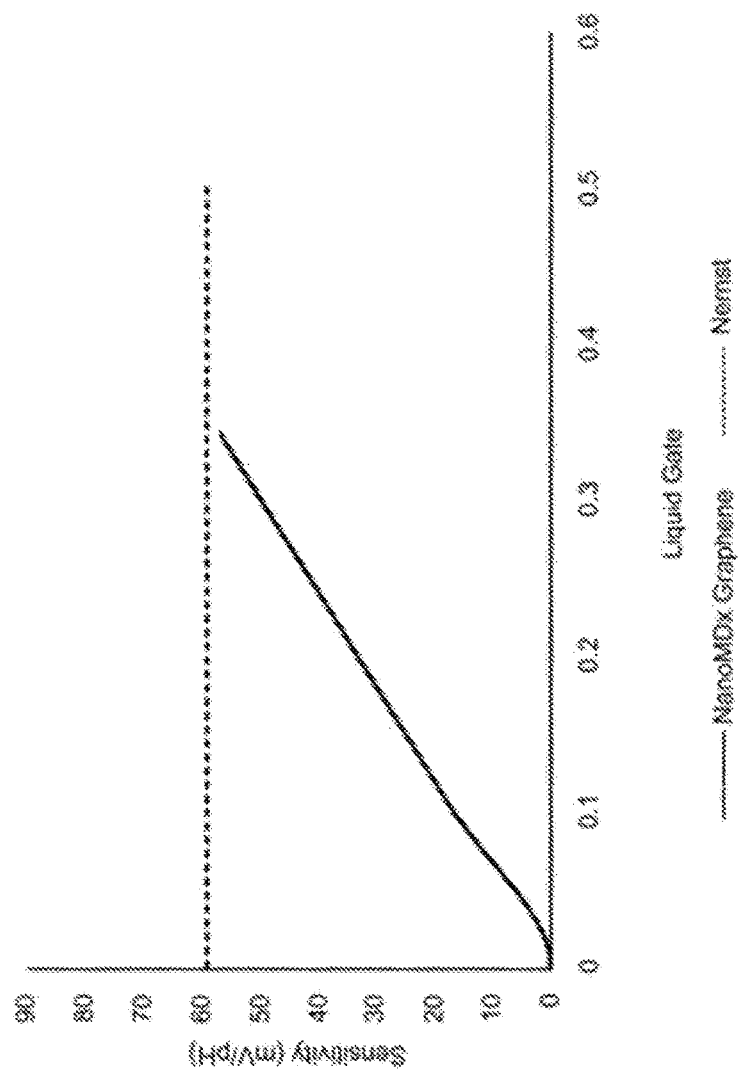
FIG. 7C is a graph of an average sensitivity of a graphene FET ("GFET") calculated as a function of liquid gate potential.

In a further embodiment of the ChemFET transistor an individual backgate (82) for each ChemFET may be provided as shown in FIG. 7B. Since there is a backgate for each ChemFET this is called a local backgate configuration. In this case the backgate (82) is comprised of an interconnect material. The advantage of a local backgate is that its voltage may be tuned or optimized for the particular characteristics of the ChemFET to which it is associated.

It is possible to operate a ChemFET (1) with more than just a single gate, i.e. the ChemFET, such as shown in FIG. 7B, may have both a solution gate (top gate) and a backgate (local backgate (82) or global backgate (not shown)) in operation at the same time. This is referred to as a dual gate and has the benefit of more gate control over the channel (30) or when used as a sensor for providing improved ChemFET sensitivity—even to the point of achieving sensitivity higher than the Nernst limit of 59 mV/pH.

Figure 9C:
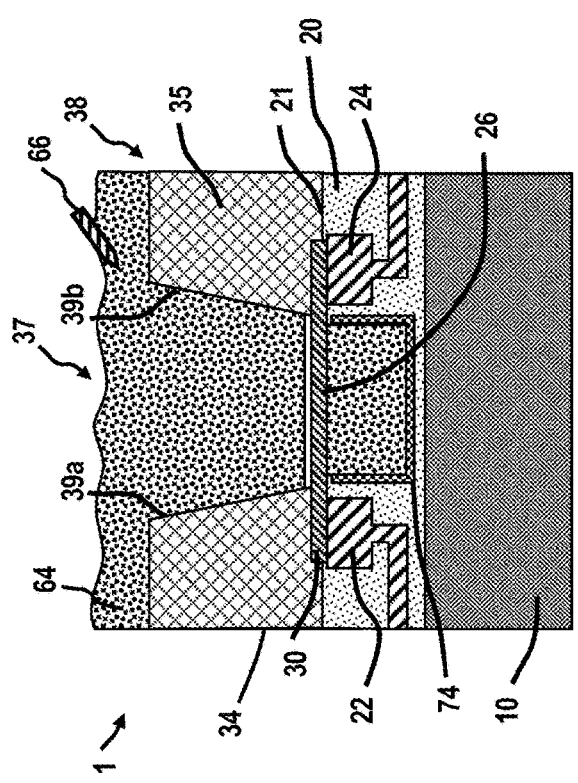
FIG. 9C is an illustration of using the fluid to create a gate all around a suspended graphene channel.

Extending this concept further is a Gate All Around (GAA) configuration where a portion of the channel (30) is fully surrounded by gate material. This may be the best gate configuration for a ChemFET to achieve its maximum sensitivity. FIG. 9C depicts a ChemFET (1) with a gate all around (GAA) configuration. In this case the gate material is the fluid 64 to which is applied a gate voltage through the gate or reference electrode (66). It will be noted that the fluid completely surrounds the central portion of the channel (30).

In one instance the gate all around structure is achieved by providing an etch stop structure (74) configured as a tub-like shape and positioned in the dielectric material (20) under the channel (30) as shown in FIG. 9A. FIG. 9B depicts the ChemFET (1) after the well structure (38) has been formed and after the dielectric (20) under the channel and within the etch stop layer-defined tub has been etched away. In this embodiment the etch is preferably a wet chemical etch and not a dry, e.g. plasma, etch since dry etch processes tend to damage or destroy the graphene. A suitable wet etchant is a hydrofluoric (HF) acid-based etchant, such as a mixture of HF and a buffer such as ammonium fluoride. This etchant has high selectivity to silicon dioxide in comparison to silicon and thus silicon of the sensor IC chip wafer should not be damaged. Furthermore an HF-based etch should not have bad effect on the graphene channel (30).

Figure 10C:
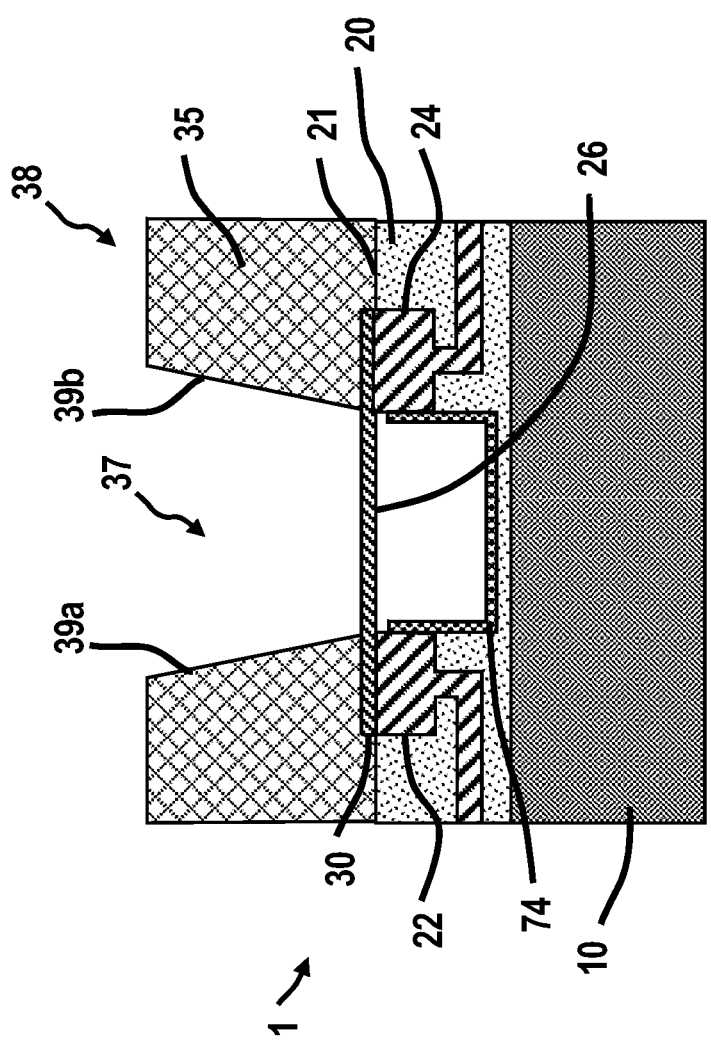
FIG. 10C is an illustration of etching the metal under the graphene to create a gate all around a suspended graphene channel.

In a second instance of the preferred gate all around structure, the graphene is first deposited or formed on a metal interconnect material (25) that may form one of the source (22) or drain (24) conductive electrodes as shown in FIG. 10A. If the interconnect material is copper, such as formed in trenches in a damascene process and with the upper portions of the electrodes exposed to the surface, i.e. copper is exposed to the surface then the possibility exists for forming the graphene (i.e. growing the graphene) directly on the semiconductor IC wafer rather than on a separate growth wafer and then transferring the graphene to the IC wafer. This may be possible since copper is one of the preferred growth substrates for graphene (graphene does not diffuse into copper during the growth) and if the growth temperature is kept low enough, such as lower than 400 C, so as not to affect the semiconductor transistors, such as CMOS transistors, It may be possible that a plasma-enhanced CVD (PECVD) or other enhanced CVD process will allow growth of good quality graphene directly on the exposed copper surfaces on an IC wafer. Once the graphene is formed or deposited on the copper areas, such as shown in FIG. 10A then in a subsequent process step the dielectric underlying the channel area (26), which at this time includes both graphene and a thin layer of copper, is etched. For a silicon dioxide dielectric a wet HF acid etchant is suitable. The etch may be further controlled or confined by an etch stop layer (74) formed in a tub-like shape. As depicted in FIG. 10B. Finally the thin copper layer under the graphene channel (30) can be etched by a suitable copper etchant, such as ammonium persulfate or ferric chloride., resulting in the central portion of the graphene channel to be free of any dielectric, as shown in FIG. 10C, and available for contact by the fluid to form a gate all around structure as shown in FIG. 9C.

Figure 11A:
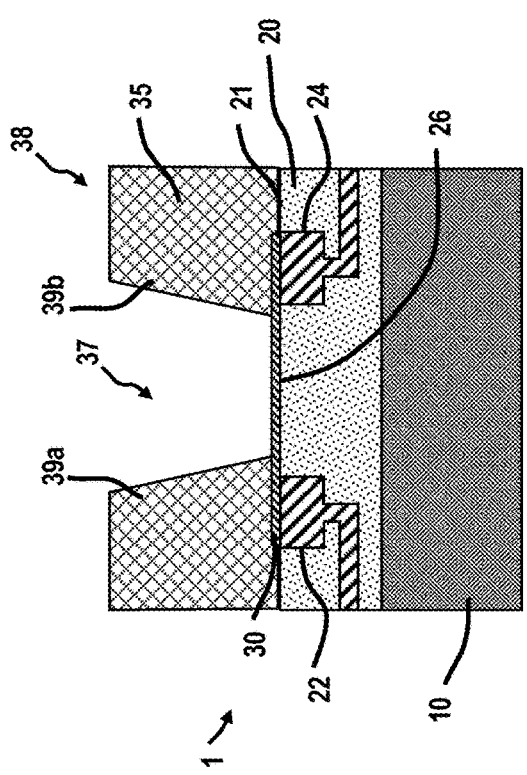
FIG. 11A is an illustration of a CMOS wafer with a graphene layer deposited on exposed metal electrodes and a dielectric surface.
Figure 11B:
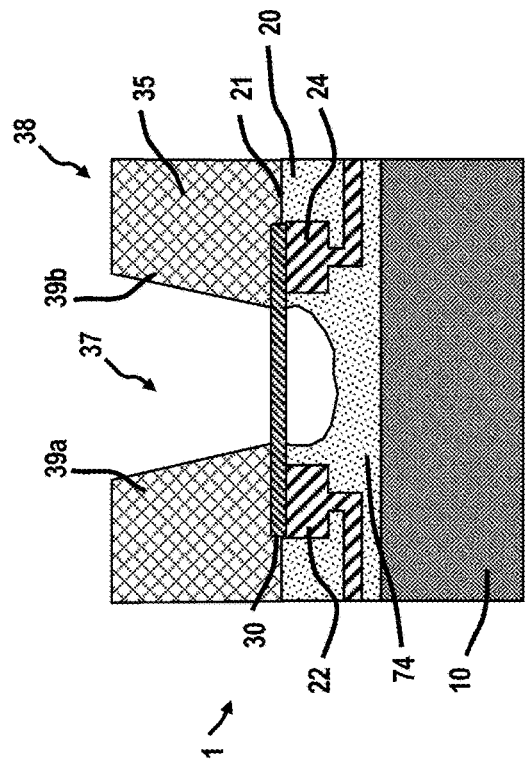
FIG. 11B is an illustration of etching the dielectric under the graphene with an isotropic etch process to create a gate all around a suspended graphene channel.

In another gate all around embodiment, as shown in FIG. 11A, there is no etch stop layer provided under the channel sensing region (26). In this case the wet etching of the silicon dioxide dielectric (20) will be isotropic and will result in a bowl-shaped cavity beneath the channel (30) as shown in FIG. 11B. Furthermore since the etching is not confined by an etch stop layer, the etched cavity may not be fully uniform in size and shape.

ChemFET Electrical Operation and Sensing

As indicated above, in particular embodiments, the FET can be adapted so as to be cavitated so as to include one or more sensing chambers that are positioned so as to align with a channel region of the FET. In such instances, the FET may be in contact with a fluidic source so as to form an ISFET or more specifically a solution-gated ChemFET. Accordingly, the ChemFET may be configured to run one or more chemical and/or biological reactions within its various chambers, such as a DNA hybridization or sequencing reaction, and the like or to detect an analyte or detect biologic activity, such as proximate a solution gated sensing zone. For these purposes, the ChemFET may include or be coupled with a processor configured for detecting the one or more reactions, analytes or biologic activity, e.g., involving a biological or chemical material, so as to obtain reaction, analyte or biologic activity results, and for analyzing those results, for instance, based on detecting and/or measuring changes in a voltage (V) potential, current (I), charge (Q) or capacitance (C) occurring within the channel region on the ChemFET.

Particularly, as can be seen with respect to FIG. 15E, the processor, such as a signal processor 151, may be configured so as to generate one or more current (I) vs. voltage (V) curves, such as where the current Id of the $I_d$–$V_{gs}$ curve is the current flowing through the drain (24) of the chemically-sensitive solution gated ChemFET and/or where the gate voltage ($V_{gs}$) of the $I_d$–$V_{gs}$ curve is the voltage potential applied between the gate and the source of the ChemFET (1). In such an instance, the gate voltage $V_{gs}$ of the Id–Vgs curve may be a top and/or a back gate voltage that may be applied to the ChemFET (1) through a top (or front) and/or back of the device, respectively. In particular embodiments, the gate voltage $V_{gs}$ of the $I_d$–$V_{gs}$ curve may be a solution gate voltage such as applied to the chemically sensitive FET through a solution flowed over a portion, e.g., a chamber (38), of the device (1). In some embodiments, the reference $I_d$–$V_{gs}$ curve and/or a chemical sensing Id–Vgs curve (or a corresponding parameter, e.g., a slope, of such reference and sensing curves) may be generated in response to the analyte, biologic activity and/or chemical reaction that is to be detected and/or occurs over or near the ChemFET, such as within a chamber or well (38) of the ChemFET structure. In various embodiments, the processor (150) may be configured to determine differences in relationships between a generated reference $I_d$–$V_{gs}$ curve and/or chemical sensing $I_d$–$V_{gs}$ curve. In certain instances, a circuitry component (140) may be included where the circuitry component may include at least one analog-to-digital converter (141) that is configured for converting analog signals, such as obtained as a result of the performance of the reaction(s) within the sensing well (38), or array of wells, into digital signals, such as may be sent back to the processor or computing component (150) for further processing.

Accordingly, in another aspect of the invention, a ChemFET(1) may be provided, wherein the device may include a structure having a conductive source (22) and drain (24) as well as having a surface or channel (30) extending from the conductive source to the conductive drain, such as where the surface or channel includes a 1D or 2D transistor nanomaterial (30). The device (1) may also include a computing component (150) having or otherwise being associated with a processor (140) such as where the processor (140) is configured for generating a reference $I_d$–$V_{gs}$ curve and/or generating a chemical sensing $I_d$–$V_{gs}$ curve, in response to the chemical reaction, biologic activity or analyte occurring within a chamber (37) of the ChemFET (1), and may be configured to determine a difference between the reference $I_d$–$V_{gs}$ curve and the chemical sensing $I_d$–$V_{gs}$ curve. Specifically, FIG. 13A depicts a graph illustrating an $I_d$–$V_{gs}$ curve calling out some of the various characteristics that may be used to categorize $I_d$–$V_{gs}$ curves, and FIG. 13B depicts a graph of an $I_d$–$V_{gs}$ curve illustrating the results of a single difference and that of multiple differences.

Figure 13A:
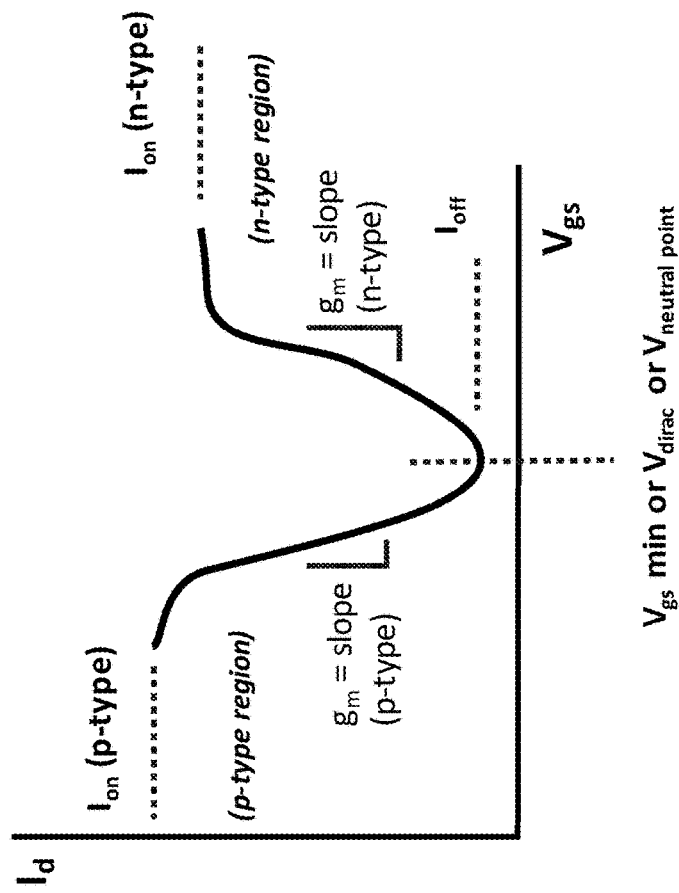
FIG. 13A is a graph of an $I_d$-$V_{gs}$ curve with characteristics that are used to categorize $I_d$-$V_{gs}$ curves.
Figure 13B:
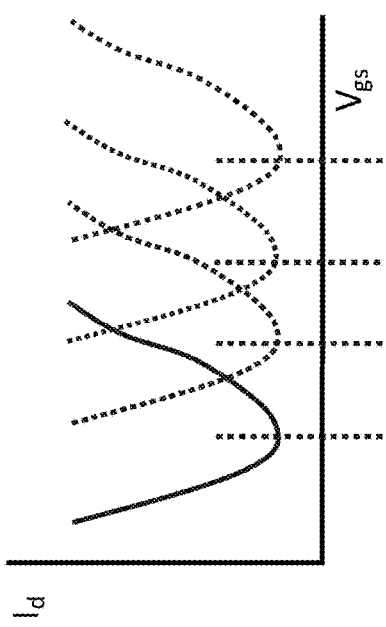
FIG. 13B is a graph of an $I_d$-$V_{gs}$ curve illustrating a single difference or multiple differences.
Figure 13C:
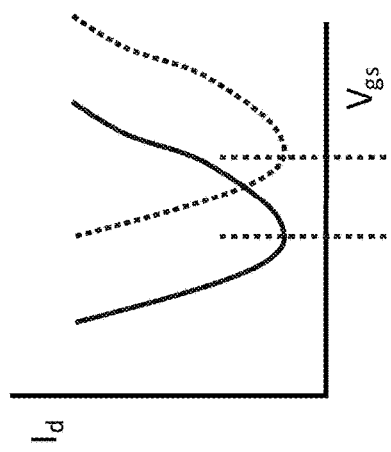
FIG. 13C is a graph of an $I_d$-$V_{gs}$ curve illustrating a shift in the $I_d$-$V_{gs}$ curve.
Figure 13D:
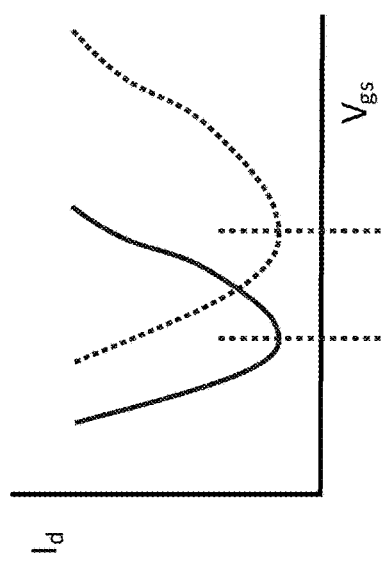
FIG. 13D is a graph of an $I_d$-$V_{gs}$ curve illustrating a change in the shape of the $I_d$-$V_{gs}$ curve.

Particularly, as can be seen with respect to FIG. 13B, the difference between the reference $I_d$–$V_{gs}$ curve measurement and the chemical sensing $I_d$–$V_{gs}$ curve (or corresponding parameters thereof) measurement is a shift in a minimum point of the Vgs value of the chemical sensing $I_d$–$V_{gs}$ curve relative to a minimum point of the $V_{gs}$ value of the reference $I_d$–$V_{gs}$ curve. As can be seen, this shift is from left to right along the $V_{gs}$ axis. Hence, as can be seen with respect to FIG. 13C, in some instances, a change in reaction conditions, biologic activity or analyte that result in a change in the $I_d$–$V_{gs}$ curve may be demarcated by a shift in the $I_d$–$V_{gs}$ curve, or as depicted in FIG. 13D, it may be demarcated by a change in the shape of the $I_d$–$V_{gs}$ curve. More particularly, as exemplified in FIG. 13C, in one embodiment, the difference between the reference $I_d$–$V_{gs}$ curve and the chemical sensing $I_d$–$V_{gs}$ curve may be a change in the slope of the chemical sensing $I_d$–$V_{gs}$ curve relative to a change in the slope of the reference $I_d$–$V_{gs}$ curve. Likewise, as exemplified in FIG. 13D, the difference between the reference $I_d$–$V_{gs}$ curve and the chemical sensing $I_d$–$V_{gs}$ curve may be an overall change in the shape of the chemical sensing $I_d$–$V_{gs}$ curve relative to an overall change in shape of the reference $I_d$–$V_{gs}$ curve.

Figure 13E:
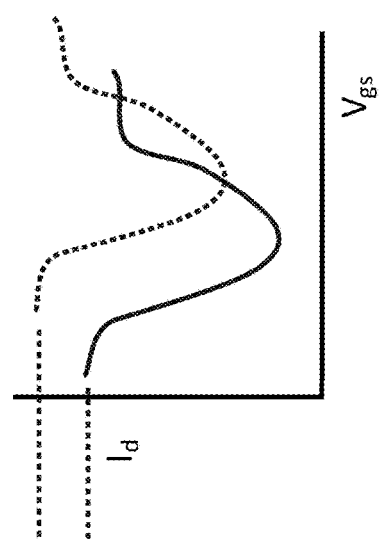
FIG. 13E is a graph of an $I_d$-$V_{gs}$ curve illustrating a change in the level of the I-$V_g$ curve ($I_{on}$ in p-type region).
Figure 13F:
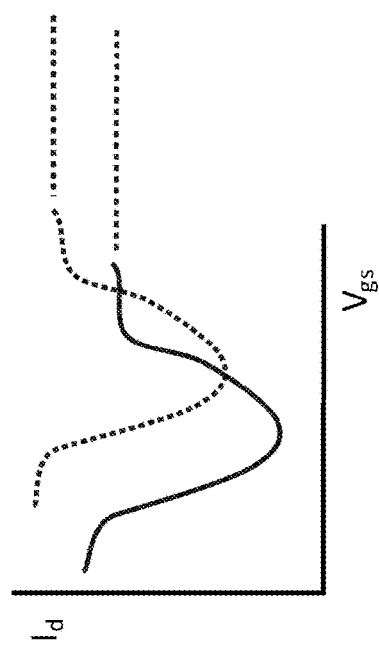
FIG. 13F is a graph of an $I_d$-$V_{gs}$ curve illustrating a change in the level of the $I_d$-$V_{gs}$ curve ($I_{on}$ in n-type region).

In other instances, as can be seen with respect to FIGS. 13E and 13F, the difference between the reference $I_d$–$V_{gs}$ curve and the chemical sensing $I_d$–$V_{gs}$ curve may be a shift in an Ion value of the chemical sensing $I_d$–$V_{gs}$ curve relative to a shift in an Ion value of the reference $I_d$–$V_{gs}$ curve, for instance, where the Ion values are taken from a p-type (FIG. 13E) or n-type (FIG. 13F) section of the $I_d$–$V_{gs}$ curve (see FIG. 13A). For example, the measurements of the slopes may be taken from the steepest and/or flattest sections on the p-type and/or n-type portions of the $I_d$–$V_{gs}$ curves. Specifically, FIGS. 13E and 13F depict graphs of $I_d$–$V_{gs}$ curves illustrating a change in the level of the $I_d$–$V_{gs}$ curve where the $I_{on}$ is in a p-type region (FIG. 13E), and a change in the level of the $I_d$–$V_{gs}$ curve where the $I_{on}$ is in a n-type region (FIG. 13F).

Figure 13G:
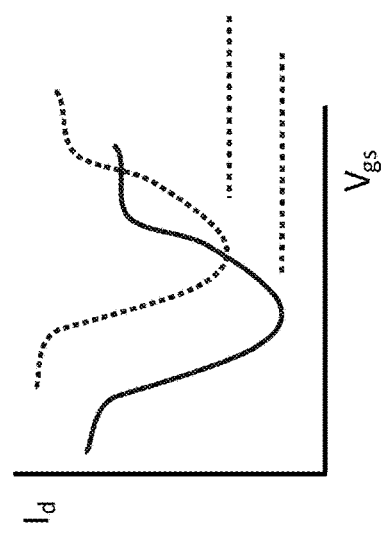
FIG. 13G is a graph of an $I_d$-$V_{gs}$ curve illustrating a change in the level of the $I_d$-$V_{gs}$ curve ($I_{off}$).
Figure 13H:
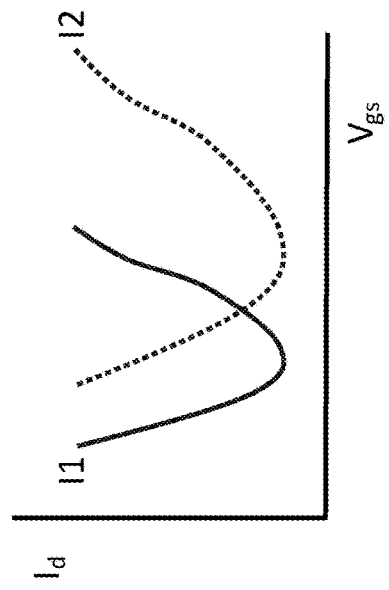
FIG. 13H is a graph of an $I_d$-$V_{gs}$ curve illustrating a fit polynomial or other fitting line to curve and use coefficients as read criterion.
Figure 13I:
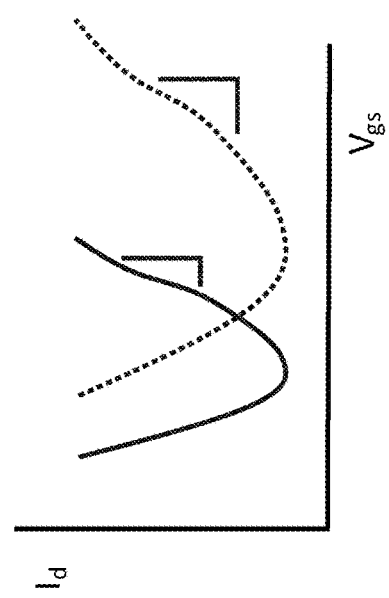
FIG. 13I is a graph of an $I_d$-$V_{gs}$ curve illustrating a slope of the $I_d$-$V_{gs}$ curve on one or both sides and use of a solution gate and back gate in combination to improve a signal and move the curve where desired.

Additionally, in particular instances, the difference between the reference $I_d$–$V_{gs}$ curve and the chemical sensing $I_d$–$V_{gs}$ curve (or corresponding parameters thereof) may be a shift in an $I_{off}$ value of the chemical sensing $I_d$–$V_{gs}$ curve relative to an $I_{off}$ value of the reference $I_d$–$V_{gs}$ curve. Particularly, FIG. 13G depicts a graph of an $I_d$–$V_{gs}$ curve illustrating a change in the level of the $I_d$–$V_{gs}$ curve ($I_{off}$). More particularly, in such embodiments, as depicted in FIG. 13H, the difference in the overall shape of the $I_d$–$V_{gs}$ curves may be determined by first fitting a polynomial or other fitting line to each of the v curves and then comparing the coefficients of those fitting lines. Specifically, FIG. 13H depicts a graph of an $I_d$–$V_{gs}$ curve illustrating a fit polynomial or other fitting line to curve and use coefficients as read criterion. In other embodiments, the difference between a reference $I_d$-$V_{gs}$ curve and the chemical sensing $I_d$-$V_{gs}$ curve is based on more than one chemical sensing $I_d$-$V_{gs}$ curve. Further, FIG. 13I depicts a graph of an $I_d$-$V_{gs}$ curve illustrating a slope of the $I_d$-$V_{gs}$ curve on one or both sides of the curve (it may be noted that the slope of this curve is the transconductance gm, which is proportional to carrier mobility). The use of a solution gate and backgate in combination (a dual gate) can be used to improve signal strength and to change characteristics of I-V curve. Likewise a gate all-around structure will change the characteristics of the ChemFET characterization curves.

It is to be noted, with respect to FIGS. 18A and 18B, when no microbead (60) is present in the well structure (38), an electric signal may be transmitted to the processor (140) or computing component (150). In such an instance, the processor may be configured to eliminate from the measurement the number of wells (38) that are unoccupied, or at least to compensate in the measurement for the number of wells (38) that are unoccupied, such as where the measurement may be a shift in the I-$V_g$ curve and/or $I_d$-$V_{gs}$ curve (or corresponding parameters thereof). Likewise, as shown in FIG. 18C, when two or more microbeads (60a, 60b) are present in the well structure (38), an electric signal may be transmitted to the processor (140) or computing component (150). In such an instance, the processor may be configured to eliminate from the measurement the number of wells (38) containing multiple microbeads 60, or at least compensate in the measurement for the number of wells (38) containing multiple microbeads (60), such as where the measurement may be recognized as a shift in the I-V curves or reference and sensing $I_d$-$V_{gs}$ curves. In some instances, a calibration of the ChemFET sensor array chip may be done prior to its use for detecting a specific analyte, biologic activity or chemical reaction. The calibration procedure may determine wells or sensing locations that have no microbeads or more than one microbead and this information can be stored for later use by a processor (140) or computing component (150) to compensate for wells or sensing locations with no microbeads or multiple microbeads.

Accordingly, as can be seen with respect to FIGS. 13A-13I, in particular embodiments, the FET and/or processor (140) may be configured to respond to a shift in the I-V or Id-Vgs curve, such as where the curve is shifted in response to the detection of a biological compound and/or the result of a reaction taking place in or on a surface (21) of the FET device (1). In some instances, the I-V/$I_d$-$V_{gs}$ curve may be produced and/or shifted in response to a chemical reaction occurring on a sensing layer (34) and/or the surface of a 1D or 2D nanomaterial, e.g., graphene, channel (30) of the field effect transistor (1), such as resulting from the detection of a biological compound or reaction occurring within the well structure (38) of the device. Hence, the FET and/or processor may be configured so as to shift the I-V curve or $I_d$-$V_{gs}$ curve such as in response to the chemical reaction.

It should be noted that FIGS. 13A-13I show I-V curves characteristic of a ChemFET with a graphene nanomaterial channel, i.e. the curves are ambipolar (showing both n-type and p-type characteristics within the same transistor). Other ChemFETs with different 1D or 2D nanomaterial channels will have different characteristic curves, however; the technique of comparing a reference curve to a sensing curve to detect an analyte, biologic activity or chemical reaction proximate a ChemFET is still valid.

For instance, FIG. 14B depicts a graph of an $I_d$-$V_{gs}$ curve for various pH values. Particularly, FIG. 14B illustrates the transfer characteristics of a 20×40 micron graphene-on-SiO$_2$ solution gated ChemFET at a constant drain-source voltage of Vds=50 mV for different pH values. FIG. 14C depicts a graph of current increase versus pH increase. Likewise, FIG. 14D depicts a graph of frequency vs. normalized power spectral density for a silicon ISFET device. FIG. 14E illustrates a graph of frequency vs. normalized power spectral density for a typical graphene ChemFET device of the invention. Additionally, FIG. 14F depicts a graph of frequency vs. normalized power spectral density for a graphene ChemFET of the invention. FIG. 14G depicts a graph of noise vs. bias voltage, and FIG. 14H depicts a graph of Dirac voltage vs. current increase.

Sequencing with the ChemFET

Accordingly, when using the device for sequencing a nucleic acid sample, the target nucleic acid sample (62) may be coupled to, immobilized on, or in proximity with the sensing zone (26) of the ChemFET (1). This template sequence (62) may then be sequenced and/or analyzed by performing one or more of the following steps. For example, a primer, and/or a polymerase, e.g., an RNA and/or DNA polymerase, and/or one or more substrates, e.g., deoxynucleotide triphosphates dATP, dGTP, dCTP, and dTTP, may be added, e.g., sequentially, to the sensing chamber (37), to facilitate a polymerase-mediated elongation reaction. Once the appropriate substrate is incorporated into the growing DNA strand, there will be a concomitant change in the individual electrical characteristic of the associated ChemFET (1), such as a change in voltage, e.g., the source-drain voltage (Vsd), or the drain current $I_d$ measured as a result of the new local gating effect.

Hence, for every elongation reaction with the appropriate, e.g., complementary, substrate there will be a change in the characteristic voltage or current or a change in the transfer characteristic of the ChemFET (for example in the $I_d$-$V_{gs}$ curve). For instance, as described herein, a ChemFET device (1) for nucleic acid sequencing and/or gene detection is disposed in a sample chamber (37) of a flow cell, and a sample solution (64), e.g., containing a polymerase and one or more substrates, may be introduced to the sample solution chamber (37). In various embodiments, a reference electrode (66) may be disposed upstream, downstream, or in fluid contact with the ChemFET device (1) and/or the source and/or drain may themselves serve as electrodes, such as for hybridization detection, and gate voltage may be applied whenever needed.

Particularly, in an exemplary elongation reaction, polynucleotides are synthesized if the added substrate is complementary to the next unpaired base of the template nucleic acid. If the added substrate is not complementary to the next available base, base-pairing does not occur and there is no elongation. Since nucleic acids, such as DNAs and RNAs, have a negative charge in aqueous solutions, hybridization resulting in elongation can be incrementally determined by the change in the charge density in the sensing chamber (37). And because the substrates are added sequentially, it can readily be determined which nucleotide bound to the template to facilitate the elongation reaction. Accordingly, as a result of elongation, the negative charge on the graphene channel surface, sensing layer surface, and/or the sidewall surface of the sensing chamber will be increased. This increase can then be detected, such as a change in the gate source voltage, as described in detail herein. By determining which nucleotide substrate resulted in a signal of change in gate-source voltage, the base sequence identity of the target nucleic acid can be determined and/or analyzed.

More specifically, the ChemFET (1), such as for nucleic acid elongation and/or hybridization detection, may be associated with a salt or analyte solution that is added to the sensing chamber (37), which can then be used to determine if an elongation reaction has taken place. Particularly, once the template is associated with the substrate, the reaction mixture containing a polymerase, e.g., a DNA polymerase, and a first nucleic acid substrate, e.g., dATP, is added to the buffer solution to facilitate an elongation reaction on or in proximity to the graphene channel (30) or the coated sensing layer (34) of the sensing chamber (37) surface. If the dATP is a complement to the next available reaction site in the isolated template, a binding event, i.e., base-pairing, will occur and the antisense strand of the growing sequence will be elongated, which elongation can be detected by the GFET transistor.

For example, if adenine (A) is complementary to the base thymine (T) on the target template adjacent to the 3'-terminus of the nucleic acid template, an elongation reaction occurs, resulting in the polymerase-mediated addition of one adenine base to the growing DNA strand. In such instance, an enzyme, e.g., DNA polymerase, and the substrate may be washed away from the gate portion and sensing chamber, and a buffer solution, e.g., a phosphoric acid buffer solution, e.g., having a pH of about 6, may be introduced on the graphene gate surface to measure changes in the source-drain voltage. If hybridization occurred, there will be a change in the source-drain voltage and it will be detected. However, if the dATP is not a match, there will be no hybridization, and if no hybridization, there will be no elongation and no corresponding signal detected by ChemFET (1) of the well (38) in which the reaction mixture was present. Thereafter, another reaction mixture containing another, different nucleotide substrate, e.g., dCTP, the polymerase enzyme, and other necessary reagents are added to the sensing chamber (37) under conditions suitable for polymerization if base-pairing occurs between the next nucleotide in the template and the added dCTP. If elongation occurs, it will be detected by the GFET. These steps are repeated until the nucleic acid sample has been completely sequenced. In various instances, the temperature within the sensing chamber may be controlled, for instance, it may be set to 74° C., such as by using a temperature sensor and/or a heater integrated in the field-effect device.

If an elongation reaction takes place there will be a resultant change to the Dirac voltage (for a GFET), which will be increased, e.g., by 4 mV, from before the elongation reaction. The shift of the Dirac voltage in the positive direction indicates that a negative charge was generated on the graphene channel surface. It can be understood from this that polymerization of one base to the growing DNA daughter strand caused by the elongation reaction was detectable as a change in Dirac voltage. A second elongation reaction may then take place and be repeated until the entire target nucleic acid has been sequenced.

ChemFET Sensor Array IC Chip and System

In some embodiments, as can be seen with respect to FIGS. 15A and 15B, a ChemFET sensor IC chip (50) may include a plurality of wells (38), having a plurality of openings (37), where each well (38) is associated with one or more sensors, and may thus be configured as an array, e.g., a sensor array. Such an array or arrays may be employed to detect the presence and/or a change in concentration of various analyte types, a chemical reaction or a biologic activity, such as within the wells (38), in a wide variety of chemical and/or biological processes, including DNA hybridization and/or sequencing reactions. For instance, the devices herein described and/or systems including the same may be employed in a method for the analysis of biological or chemical materials, chemical reactions or biologic activity, such as for whole genome analysis, genome typing analysis, microarray analysis, panels analysis, exome analysis, microbial/microbiome analysis, genotyping analysis, and/or clinical analysis, such as cancer analysis, NIPT analysis, cfDNA, blood/plasma/serum analysis, and/or UCS analysis.

In a particular embodiment, as depicted in FIG. 15A or 15B, a multiplicity of the wells (38) of the ChemFET device may include a sensing zone (26) containing a graphene layer (30) so as to form a graphene FET (GFET) array (1). As herein described, the GFET array (1) can be employed to facilitate nucleic acid hybridization and/or sequencing techniques, such as based on monitoring changes in hydrogen ion concentration (pH), changes in other analyte concentrations, and/or binding events associated with chemical processes relating to DNA synthesis and/or hybridization reactions, such as within the gated sensing chamber or well (38) of the GFET based sensor (1). For example, the ChemFET (1) may be configured as an array of ChemFET sensors and/or may be adapted to increase the measurement sensitivity and/or accuracy of the sensor(s) and/or associated array(s), such as by including one or more surfaces (26) or wells (38) having a surface layered with a 1D and/or 2D nanomaterial (30), such as graphene, a dielectric or sensing layer (34), a passivation layer (36), and the like.

For instance, in a particular embodiment, illustrated in FIG. 15A or 15B, a chemically-sensitive graphene field effect transistor (GFET) (1), such as a GFET having a ChemFET structure is provided, where the GFET sensor, e.g., biosensor, may be configured as a ChemFET sensor IC chip, having a plurality of wells (38) configured therein. In such an instance, the IC chip (50) may include a silicon base layer (10) within which the circuit components comprised of semiconductor, e.g. CMOS, transistors may be embedded. A dielectric layer (20), which may be a silicon dioxide layer, may be included, such as where the silicon dioxide layer is embedded with a plurality of conductive sources (22) and conductive drains (24) that are separated from one another so as to form a plurality of channel regions used as sensing regions (26). In particular instances, the channel regions are configured as a plurality of sensing zones (26), wherein each sensing zone may be contained within a well structure (38). In such an instance, the ChemFET IC chip (50) may include a plurality of channel regions (30) that are configured to be solution gated.

Figure 2D:
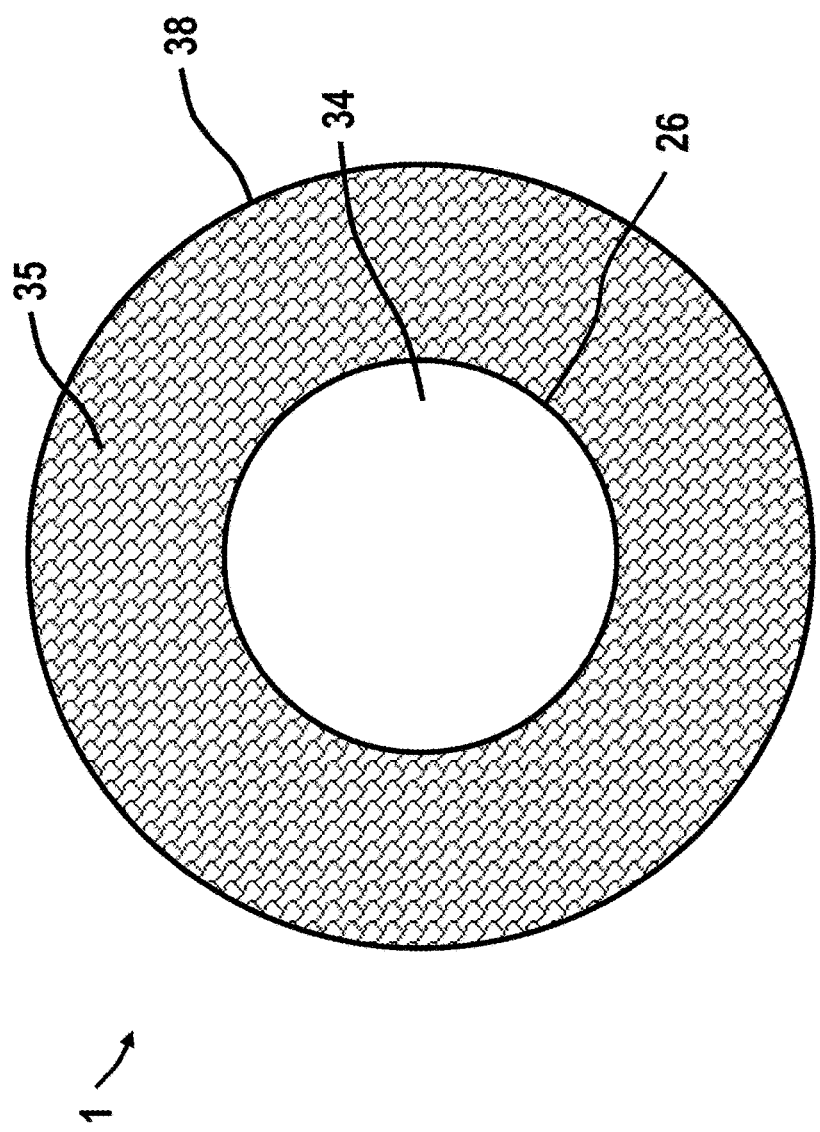
FIG. 2D is a top plan view of a ChemFET with another configuration of a well structure.

Particularly, in various embodiments, each sensor of the plurality of sensors includes a ChemFET, e.g. a GFET. For instance, FIG. 2C depicts a top plane view of a first embodiment of a ChemFET (1) having a sensing region (26) that is surrounded by a well structure (38), wherein the sensing region (26) comprises a nanomaterial channel layer (30), such as a graphene channel layer (30). Visible in the top plane view of FIG. 2C is the passivation layer material (35) which comprises the sidewalls of the well structure (38). FIG. 2D depicts a top plane view of another embodiment of the ChemFET (1) having a sensing region (26) that is surrounded by a well structure (38), wherein an analyte or reaction-sensitive layer (34) is deposited or otherwise positioned over the nanomaterial channel layer (30), e.g. a graphene layer (30). Visible in the top plane view of FIG. 2D is the passivation layer material (35) which comprises the sidewalls of the well structure (38).

FIG. 15A depicts a top plan view of an array of ChemFETs arranged on a ChemFET sensor IC chip (50) for a system for analysis of biological or chemical materials or reactions or biologic activity. In various instances, the ChemFET sensor IC chip (50) may include a plurality of ChemFET sensors (such as arranged in an array), well structures (38) or passivation openings associated with the ChemFET sensors and one or more reference electrodes (66) arranged on the chip surface, such as a platinum or Ag/AgCl reference electrode. FIG. 15B is a side section view that depicts a portion of the wells of the array of FIG. 15A in greater detail.

In various embodiments, one or more of the wells (38) may include a graphene-layered surface (30), which in various instances may further include one or more oxide (34) and/or passivation (35) layers, such as layers that are disposed on the surface(s) of the bounding members of the wells or chambers (37) so as to increase the measurement sensitivity and/or accuracy of the sensors and/or associated array(s). Like above, in such instances, the solution gated chambers (37) of the arrays of the ChemFET device may be configured as an ISFET, and be adapted for receiving the reactants necessary for performing various analyses of biological and/or chemical materials, for instance, one or more hybridization and/or sequencing reactions.

Accordingly, in one aspect, a system is provided, such as a system configured for running one or more reactions on biological and/or chemical materials so as to detect a presence and/or concentration change of various analyte types, a chemical reaction or biologic activity in a wide variety of chemical and/or biological processes. For instance, in some instances, the biological material may be a nucleic acid or other biological molecule, such as a protein, or the like. Hence, in particular instances, the system may be adapted for performing a DNA hybridization and/or sequencing reaction. In other instances, the analysis to be performed is for whole genome analysis, genome typing analysis, microarray analysis, panel analysis, exome analysis, microbial/microbiome analysis, genotyping analysis, and/or clinical analysis, such as cancer analysis, NIPT analysis, cfDNA, blood/plasma/serum analysis, and/or UCS analysis.

As such, the system may include an array (130) including one or more, e.g., a plurality of sensors, such as where each of the sensors includes or is otherwise associated with a ChemFET having a conductive source (22), a conductive drain (24), and a sensing surface or channel (30) extending from the conductive source (22) to the conductive drain (24). In particular instances, the array (130) may include one or more wells (38) configured as one or more sensing chambers (37) having the sensing surface or channel (30) positioned therein. In some instances, the surface and/or channel (30) of the chamber (37) may include a one-dimensional (1D) or two-dimensional (2D) nanomaterial (30), a dielectric or sensing layer (34), a passivation layer (35), and/or the like.

As can be seen with respect to FIG. 15C, the system (100) may include a fluidics component (120) for directing and controlling the flow of various fluids throughout the system (100). The fluidics component (120) may be used for various purposes, such as for use in performing the reaction, e.g., delivering one or more analyte containing solutions to the sensor array (130) for the performance of the reaction thereby, a circuitry component (140), such as for running the reaction and/or detection processes, and/or a computing component (150), such as for controlling and/or processing the same. For instance, a fluidics component (120) may be included where the fluidic component is configured to control one or more flows of analytes and/or reagents over the array (130) and/or one or more chambers thereof. Particularly, in various embodiments, the system (100) includes a plurality of sensing locations, such as sensing regions (26) and/or wells (38), which in turn includes a plurality of sensors and/or a plurality of channels, and further includes one or more fluid sources (120), e.g., containing a fluid having a plurality of reagents and/or analytes therein, and fluid conduits, such as for delivery of the fluids from the source (120) to the one or more sensing regions (26) and/or wells (38) of the sensor array (130) for the performance of one or more reactions thereby. In certain instances, a mechanism for generating one or more electric and/or magnetic fields is also included.

As can be seen with respect to FIG. 15D, the system (100) may additionally include a circuitry component (140), such as where the circuitry component may include an address decoder (144), a sample and/or hold circuit (143), a bias circuitry (142), and/or at least one analog-to-digital converter (141). For instance, the address decoder (144) may be configured to create a column and/or row address for each sensor of the array (130), such as by associating a unique identifier with each sensor, such as based upon its location within a given row and column within the array (130). It may also be configured for inputting or otherwise directing the various operations that rely upon the addressing of operations for a given well of the array. For instance, the address decoder (144) may target select signals to specific wells (38) based on their column and/or row identifiers, so as to access a sensor and/or direct fluid flow to a given location, e.g., address within the array (130). The sample and hold circuit (143) may be configured to hold an analog value of a voltage to be applied to or on a selected well or column and/or row line of an array (130) of a device of the invention, such as during a read interval. Likewise, the bias circuitry (142) may be coupled to one or more surfaces and/or chambers of the array (130) and may include a biasing component such as may be adapted to apply a read and/or bias voltage to selected ChemFETs of the array (130), e.g., such as to a gate terminal of the transistor. The analog to digital converter (141) may be configured to convert an analog value to a digital value (142), for instance, as a result and/or output of the reaction within an identified well (35) or selection of wells, e.g., a line of columns and rows.

Additionally, as can be seen with respect to FIG. 15E, a computing component (150) may also be included, such as where the computing component (150) may include one or more processors, such as a signal processor (151), a base calling module (52), and a mapping, alignment and variant calling module (153) and a processor (154). The signal processor (151) may be configured for determining one or more bases of one or more reads of a sequenced nucleic acid, such as results from a sequencing reaction. The base caller of the base calling module (152) may be configured to correct a plurality of signals, such as for phase and signal loss, to normalize to a key, and/or to a generate a plurality of corrected base calls for each flow in each sensor to produce a plurality of sequencing reads. The a mapping, alignment and variant calling module (153) may be configured for performing one or more analytics functions on the sequenced data, and may include one or more of a mapping module, configured for generating one or more seeds from the one or more reads of sequenced data and for performing a mapping function on the one or more seeds and/or reads; an alignment module, configured for performing an alignment function on the one or more mapped reads; a sorting module, configured for performing a sorting function on the one or more mapped and/or aligned reads; and/or an variant calling module, configured for performing a variant call function on the one or more mapped, aligned, and/or sorted reads. The processor (154) may be a general purpose processor or a processor specialized for tasks other than those performed by the signal processor (151). In various embodiments, the device and/or system may include at least one reference electrode.

The system and its components may be implemented wholly on the ChemFET sensor IC chip (50) with the circuitry to support those components provided by the semiconductor transistors, e.g. CMOS transistors, or the system may be partially implemented on the ChemFET sensor IC chip (50) and partially on a separate system device (not shown). For example the ChemFET sensor IC chip (50) may include the circuitry component (140) that may comprise ROIC circuitry as well as the ChemFET sensor array (130) and the separate system device may include most of the Fluidics component (120) and all of the computing component (150).

Particularly, the system can be configured for performing a nucleic acid hybridization or sequencing reaction. In such embodiments, the device for performing the hybridization or sequencing reaction may be adapted from CMOS circuitry and structures adapted to include one or more sensing chambers (37), e.g., micro or nano-wells (38), so as to form an array (130). The array (130) may be associated with one or more sensors having one or more ChemFETs (1) linked therewith. Such CMOS transistors may include a cascode transistor having one or more of a source terminal, a drain terminal, and or a gate terminal, while the ChemFETs (1) are used to form sensing zones. In such an instance, the source terminal of the cascode transistor may be directly or indirectly connected to the drain terminal of the ChemFET. In some instances, the gate terminal may couple to or may otherwise control or influence the ChemFET channel (30), and such channel may further include a 1D or 2D nanomaterial. The 1D or 2D nanomaterial may extend from the source terminal (22) to the drain terminal (24), such as where the 1D channel nanomaterial may be a carbon nanotube or semiconductor nanowire, and the 2D channel nanomaterial is composed of graphene, silicene, a phosphorene, a molybdenum disulfide, a metal dichalcogenide or other 2D nanomaterial. The device may further be configured to include a plurality of arrays, such as arranged as one or more lines of columns and rows coupled to the sensors in the array of sensors. In such an instance, each column line in the plurality of column lines may be directly or indirectly connected to or otherwise be coupled with the drain terminals of the transistors, e.g., cascode transistors, of a corresponding plurality of sensors or pixels in the array, and likewise each row line in the plurality of row lines may be directly or indirectly connected to or otherwise coupled with the source terminals of the transistors, e.g., cascode transistors, of a corresponding plurality of sensors in the array.

In some instances, a plurality of source and drain terminals having a plurality of channel members and/or associated sensing surfaces, extended there between may be included, such as where each channel member includes a one or two dimensional nanomaterial. In such an instance, a plurality of first and/or second conductive lines may be coupled to the first and second source/drain terminals of the ChemFETs in respective columns and rows in the array. Additionally, control circuitry (140) may be provided and coupled to the plurality of column and row lines such as for reading a selected sensor connected to a selected column line and/or a selected row line. The circuitry may also include a biasing component (142) such as may be configured for applying a read voltage to the selected row line, and/or to apply a bias voltage such as to the gate terminal of a transistor, such as FET and/or cascode transistor of the selected sensor. In a particular embodiment, the bias circuitry (142) may be coupled to one or more chambers of the array (130) and be configured to apply a read bias to selected ChemFETs via the conductive column and/or row lines. Particularly, the bias circuitry (142) may be configured to apply a read voltage to the selected row line, and/or to apply a bias voltage to the gate terminal of the transistor, e.g., cascode transistor, such as during a read interval.

Sense circuitry can be included and coupled to the array so as to sense a charge coupled to one or more of the gate configurations of a selected ChemFET. Sense circuitry can be configured to read the selected sensor based on a sampled voltage level on the selected row and/or column line. In such an instance, the sense circuitry may include one or more of a pre-charge circuit, such as to pre-charge the selected column line to a pre-charge voltage level prior to the read interval; and a sample circuit such as to sample a voltage level at the drain terminal of the selected transistor, e.g., cascode transistor, such as during the read interval. The sample circuit may also be included and contain a sample and hold circuit (143) configured to hold an analog value of a voltage on the selected column line during the read interval, and may further include an analog to digital converter (141) to convert the analog value to a digital value.

Control of Microbead Loading in Wells

In some instances, it may be useful to provide a mechanism for assisting the targeting of the microbead(s) (60) to the sensing zone (26) of the ChemFET (1). Particularly, as can be seen with respect to FIGS. 5A-E, a ChemFET (1) is provided. In this instance, the transistor (1) may be a multi-layered structure including a primary, e.g., a substrate layer 10, a secondary structure layer, e.g., an dielectric layer 20, and may further include an additional passivation layer 35, e.g. a silicon dioxide layer, which layer may be cavitated so as to include a divot (38), such as a divot on a surface (21) of the substrate, and sized to at least partially contain a nano- or microbead (60) therein. In certain instances, the surface of the divot (38) may be centered such that the bead (60) rests within the divot (38) so as to be proximate the sensing zone (26) and/or a channel structure (30) associated therewith. In particular instances, the sensing zone (26) includes a graphene layer (30) positioned at least partially between the primary and tertiary layers, and in such instances, an analyte or reaction-sensitive layer (34) may be positioned above the graphene layer within the sensing zone (26). In this instance, to draw and/or attach the bead(s) (60) to the sensing zone (26), an electromagnetic field may be employed. Hence, as shown in FIG. 19A, a microbead (60) is positioned on the transistor surface 21, within the sensing zone (26), and in proximity to a channel (30).

More particularly, the sensing zone (26) of the ChemFET (1) may be configured to include a channel (30) that is formed to correspond to the region, and create a point of contact or proximity between the surface of the graphene layer (30) and the bead (60). Further, to facilitate this contact or proximity, the ChemFET (1) may include an attracting mechanism (70) that is configured to attract or otherwise draw the bead (60) in to proximity of the sensing zone (26) and/or channel (30). For instance, in particular instances, the nano- or microbead (60) may include a charged and/or metallic element, and the attracting mechanism (70) may be configured so as to generate an electric and/or magnetic field, such as for drawing the microbead (60) to the sensing zone (26). For example, in some embodiments, the electric field generator (70) may be a pulse generator, and in other embodiments, such as illustrated in FIG. 19A, the magnetic field generator (70) may be a magnet.

Particularly, as shown in FIG. 19A, one or more nano- or microbeads (60) of the invention may be configured for facilitating the performance of a bio-chemical reaction such as on a sensing region (26) of the ChemFET (1). For instance, in particular embodiments, each of the one or more microbeads (60) may include a biological material or a chemical material, associated therewith. In such an instance, the microbead (60) may be introduced to the region (26) of the ChemFET (1) of the system, such as for nucleic acid sequencing, in such a manner that it is drawn or otherwise attracted to the region (26), such as by electromagnetism. For instance, the microbead (60) may be configured to include electric charge and/or paramagnetic properties so as to assist it in being drawn into proximity of a sensing location (26) positioned on a surface (21) of the ChemFET (1), such as where the nucleic acid sequencing reaction may take place. Hence, the device may include an electromagnetic field generating component (70) that is configured to apply an electro-magnetic field that is focused within the sensing zone (26) so as to interact with the electric charge and/or paramagnetic properties of the microbead (60) thereby drawing it into proximity of the surface (21) and/or in to the sensing zone (26), such as via electro-magnetism. In this instance, the layers and other components of the ChemFET (1) are configured in such a manner that the sensing zone (26) need not include bounding members, or if included the bounding members may be thin, allowing for a higher density of wells on the array.

Alternatively, in other embodiments, such as presented in FIG. 19B, the ChemFET(1) may include a well structure (38) that is configured for receiving one or more nano- or microbeads (60), such as for nucleic acid sequencing therein. For instance, each of the one or more microbeads includes an analyte and/or reactant, which is configured for participating in a reaction, such as a nucleic acid hybridization and/or sequencing reaction. Accordingly, the ChemFET (1) may include a sensing location (26) that may be configured as a surface within a well (38) of the ChemFET (1), such as where the sensing location (26) is proximate a channel (30) of the ChemFET (1). The nano- or microbead (60) may be configured for use in a system for analysis of biological and/or chemical materials such as on or within a sensing surface (26), such as within a well (38) of the ChemFET (1). In this and other instances, the microbead (60) may be introduced to the surface (21) of the ChemFET (1) of the system in such a manner that it is drawn or otherwise attracted toward the sensing surface (26), e.g., of a well structure (38), where the nucleic acid sequencing reaction may take place, such as by electro-magnetism.

For example, the microbead (60) may be configured to have an electric charge property and the microbead attracting mechanism (60) may be configured to emit an electric field that is opposite in nature to the charge on the microbead and is thereby adapted for draw the microbead (60) into proximity of the sensing surface (26). In such an instance, an electric field component generates an electric field to interact with the electric charge properties of the microbead. Hence, the microbead may be drawn to the sensing location using electrophoresis. In other instances, the microbead (60) may be configured to include paramagnetic properties so as to assist it in being drawn or otherwise attracted toward sensing surface (26), e.g., into the well (38), and into proximity of the sensing zone, where the reaction may take place. The device, therefore, may include a magnetic field generating component (70) that is configured to apply an electro-magnetic field that is focused within the chamber (38) so as to interact with the paramagnetic properties of the microbead (60) thereby drawing it into the chamber (38) and/or proximate the sensing surface (26), such as via magnetism. Particularly, in various embodiments, the microbead or particle attracting mechanism (60) can be configured to emit a magnetic field that is opposite in polarity to the paramagnetic properties of the microbead and is thereby adapted for draw the microbead (60) into proximity of the sensing surface (26). In such an instance, a magnetic field component generates a magnetic field to interact with the polar properties of the microbead. The use of magnetism and/or electrophoresis allows for thinner sensing location structures.

Additionally, as illustrated in FIG. 19B, in some embodiments, the system and its components may be configured such that when the electromagnetic field is generated it interacts with the microbead (60) and/or a component associated therewith so as to pull the microbead toward the sensing zone (26). In other embodiments, as illustrated in FIG. 19C, the system and its components may be configured such that when the electromagnetic field is generated it interacts with the components of the microbead (60) so as to push the microbead away from the sensing zone (26). Accordingly, the electromagnetic fields can be generated and/or reversed so as to attract or repulse the nano-/microbead to or from the sensing location (26), such as to or away from a well (38), and thus utilizing an electronic and/or magnetic field, the nano- or microbead may be positioned within the device, such as within a well thereof.

As illustrated in FIG. 19D a ChemFET (1) is provided, such as for a system for analysis of biological and/or chemical materials, such as by utilizing an electric and/or magnetic field generating mechanism such as for positioning of a nano- or microbead (60) in relation to the sensing surface (26). For instance, in particular instances, a voltage may be applied between a location above the solution of the solution gate (37) and a location on or below the sensing location (26), such as above the package lid (47) and/or below a metal component, e.g., a plate, below the package (not shown). In certain instances, the location below the sensing location (26) may include a metal or other conductive layer such as within the package or package substrate. Hence, in various instances, the field generating mechanism (70) may be employed to generate and/or reverse an electric or magnetic field so as to insert or eject one or more microbeads from one or more wells, sensors, and/or channels associated therewith, either entirely or selectively.

Particularly, as set forth in FIG. 19E, a ChemFET sensor IC chip (50) comprised of ChemFETs (1) for a system for analysis of biological or chemical materials is provided. The ChemFET sensor IC chip (50) includes a multiplicity of wells (38) each forming a sensing location (26) whereon a bio-chemical reaction may take place. Additionally, each sensing location (26) is associated with a field generator (70), e.g., a magnet, which is configured so as allow for the selective filling of the sensing locations (26) with one or more types of nano- or microbeads (60). Accordingly, by utilizing multiple field generators (70), e.g., multiple magnets, for generating a plurality of electro-magnetic fields, the nano- or microbeads (60) may be positioned within the plurality wells (38). Such positioning may be selective such as by selecting which generators will be on, off, or reversed, so as to fill or not fill their respective wells (38), as desired.

In various embodiments, the electromagnetic fields for any given well (38) may be reversed so as to expel a microbead (60) from the well (38) and/or sensing zone (26).

Particularly, in a further aspect of the present invention, a system having an array of ChemFETs including a plurality of chambers (37) having well structures formed therein is provided. In such an instance, the wells (38) may be structured as or may otherwise include sensing locations (26) wherein one or more chemical reactions may take place. In such an embodiment, the system may include one or more fluidics components having one or more fluid sources, e.g., reservoirs, containing one or more fluids therein and configured for delivering the fluid from the reservoir to the sensing chamber (37), such as for the detection of a biologic and/or the performance of one or more chemical and/or biological reactions, such as a nucleic acid sequencing reaction. Accordingly, the fluidics component, e.g., the fluid source, may be in fluidic communication with the FET device configured for biological and/or chemical analysis, and may be configured for controlling a flow of reagents over the array.

Accordingly, in certain instances, the fluid may include one or more reactants, such as one or more analytes necessary for performing a nucleic acid hybridization sequencing reaction, as herein described. In a particular embodiment, the fluid may include one or more, e.g., a plurality of microbeads (60), having a nucleic acid template (65) attached thereto, for instance, where the template is a DNA or RNA molecule to be sequenced, and the fluid containing the microbead (60) is to be delivered to the well (38) such as for carrying out the sequencing reaction. In such an embodiment, one or more of, e.g., each, of the plurality of microbeads may be configured so as to have electric charge and/or paramagnetic properties. The device may additionally include an electric and/or magnetic field component (70), e.g., having an electric and/or magnetic field generator, such as where the electric and/or magnetic field component (70) is configured to generate an electric and/or magnetic field so as to interact with the electric and/or magnetic charge properties of each of the plurality of microbeads (60) to attract the microbeads into a sensing location, such as a sensing surface, a channel, a well, a chamber, and/or a sensor of the FET device, such as by using electrophoresis and/or magnetism.

Hence, one or more, e.g., a plurality of microbeads (60), may be drawn onto or into a sensing location (26) of the plurality of sensing locations (26), which locations may be formed as wells (38), e.g., one or more thin wells. The use of magnetism or electrophoresis allows for thinner sensing location structures. In particular instances, an electric and/or magnetic field generator (70) may be configured for drawing and/or positioning the microbeads within the well structure (38), such as in proximity to a channel (30) or chamber (37) of the device, and in other instances, the electric and/or magnetic field generator (70) may be configured for reversing the electrical and/or magnetic field so as to repulse the microbead(s) (60) from the sensing location (26), channel (30), and/or chamber (37). In various instances, an array of sensing locations (26) may be provided each having a magnet (70) that allows for selective filling of the sensing locations with different numbers and/or types of microbeads (60), such as at select sensing locations (26). In such an instance, multiple electric and/or magnetic field generators for selective filling of sensing locations, e.g., wells.

Accordingly, one aspect of the present invention is a system and/or a method for positioning one or more, e.g., a plurality, of microbeads (60) within a sensing or plurality of sensing locations (26) for biological or chemical analysis, such as for nucleic acid sequencing. The system may include a ChemFET sensor IC chip (50) having an integrated circuit structure configured for performing a biological or chemical analysis, such as within a plurality of nano- or micro-sensing wells (38), as described above, having a fluidic component (120), a circuitry component (140), and/or a computing component (150) and the method may include one or more of the following steps. For instance, the method may include the fluidic component (120) introducing a fluid to be in contact with the ChemFET sensor IC chip (50), such as where the fluidics component is configured to control a flow a fluid of reagents over the ChemFET sensor IC chip (50), and the fluid may include one or more microbeads (60) that may have electric charge and/or paramagnetic properties. In such an instance, the ChemFET sensor IC chip (50), may include an integrated circuit structure, a plurality of sensing locations (26) having one or more wells (38), a plurality of ChemFET sensors (1) and/or a plurality of channels (30), and/or an electric and/or magnetic field component (70). The electric field and/or magnetic field component (70) may be configured to activate the electronic and/or magnetic field, and the method may also include activating an electric and/or magnetic field so as to interact with the electric and/or paramagnetic properties of each of the microbeads (60). The method may additionally include drawing the one or more microbeads (60) into proximity with a sensing zone (26) of the plurality of sensing locations (37) using electrophoresis and/or magnetism. In certain instances, the method may include positioning the one or more microbeads (60) within the one or more sensing locations (37) for biological or chemical analysis.

In particular instances, the electric and/or magnetic fields may be generated by the plurality of electric and/or magnetic field generators (70), e.g., included in the integrated circuit structure of the ChemFET sensor IC chip (50), in all or only a subset of the plurality of sensing locations (37) so as to only attract a plurality of microbeads (60) to the subset of sensing locations, such as for selectively filling the plurality of sensing locations (37) with the plurality of microbeads (60). In such an instance, different types of microbeads (60) may be attracted to different sensing locations, such as by pulsing the voltage and/or magnetic generators and/or keeping the same constant. Particularly, where an electric field generator (70) is provided the voltage applied to the ChemFET sensor IC chip (50), may be variable or constant and may be less than about 10V, such as about less than 8V, or less than about 6V, including less than about 4V or about 2V or 1V. The voltage may be applied between a location above the fluid (47) and a location on or below the sensing zone (26), such as above the package lid and/or below the metal plate below the package. In certain instances, the location below the sensing location may be a metal or conductive layer such as within the package or package substrate. The method may also include the step of reversing the electric or magnetic field so as to eject the plurality of beads from the plurality of wells, sensors, and/or channels, either entirely or selectively.

Further, as indicated, each or a subset of the plurality of sensing locations (26) may be utilized to generate electric fields to attract a microbead (60) thereby allowing for programmability to each or a subset of sensing locations (26), for instance, 99% or 95% or 90% or 85%, or 80% or less of the plurality of wells (38) are occupied with a microbead (60). Hence, the electric and/or magnetic field may be generated in only a subset of the plurality of wells (38), sensor regions (26) or channels (30) to only attract a plurality of microbeads (60) to the subset. Likewise, a plurality of electric and/or magnetic field generators (70) for selective filling the plurality of wells (38), sensor locations (26) or channels (30) with the plurality of microbeads (60), and/or ejecting the plurality of microbeads (60) from the plurality of wells (38), sensor locations (26) or channels (30). In such an instance, the electric and/or magnetic field generator (70) may be an electric source, a permanent magnet and/or an electromagnet. As indicated, the plurality of magnetic field generators (70) is configured to reverse the magnetic field to eject the plurality of microbeads (60) from the plurality of sensing locations (37) or a subset thereof.

Additionally, in one aspect of the present invention, a device, system, and/or method for verifying well occupancy for a plurality of wells (38) for analysis of biological or chemical materials may be provided. The system may include a device for receiving a fluid containing the plurality of microbeads (60). Particularly, the ChemFET sensor IC chip (50) may include a processor, a CMOS structure having an integrated circuit, a plurality of wells (38), and a plurality of ChemFET sensors (1). Each of plurality of wells (38) may be configured to receive a microbead (60) of the plurality of microbeads, and the ChemFET sensor IC chip (50), may include a mechanism (70) for drawing and/or ejecting the microbeads (60) into or out of the wells (38). Hence, the method may include the step of flowing the plurality of microbeads (60) over and/or into the plurality of sensing locations (26/37) and/or wells (38) and/or may include determining, e.g., through electrical and/or magnetic sensing if a sensing location (26/37) and/or well (38) is occupied or unoccupied by a microbead (60) and/or if a location (26/37) contains one or multiple microbeads (60).

Consequently, the processor (154) may be configured to determine if a well (38) is unoccupied and/or if the well (38) contains one or more, e.g., multiple microbeads (60). In certain instances, the processor (154) may also be configured to eliminate or modify one or more of the measurements, such as based on the number of wells (38) occupied or unoccupied, e.g., the number of wells (38) containing none, one or multiple microbeads (60). For instance, the processor (154) may be configured to eliminate from the measurement the number of wells unoccupied and the number of wells containing multiple microbeads (60), or compensate in the measurement for the number of wells (38) unoccupied and the number of wells (38) containing multiple microbeads (60), and the like. In such instances, the measurement may be a shift in an I–V or Id–Vgs curve (or a parameter thereof), as explained below. In particular instances, the processor (154) may be configured to eliminate from the measurement the number of wells (38) unoccupied and the number of wells (38) containing one or multiple microbeads (60) and/or to compensate in the measurement for the number of wells (38) unoccupied and the number of wells (38) containing one or multiple microbeads (60). Accordingly, in some embodiments, the measurement may be a shift in an I–V or $I_d$–$V_{gs}$ curve, such as one or more of: generating a plurality of I–V or $I_d$–$V_{gs}$ curves so as to determine a shift in response to a chemical reaction occurring on or near the ChemFET; generating a ChemFET I–V or $I_d$–$V_{gs}$ curve in response to a chemical reaction occurring on or near the ChemFET so as to detect a change in the slope of the I–V curve; and/or to sense shifts in a capacitance as a function of a gate voltage.

Graphene Growth

For instance, in particular embodiments, improved fabrication techniques for producing a CMOS sensor device containing sensing zones employing a 1D or 2D nanomaterial layer are provided. Specifically, in certain instances, a 1D or 2D nanomaterial layer may be grown, such as on a growth platform, and once grown may be released from the growth platform, and then be transferred to a semiconductor structure, such a CMOS substrate, so as to be employed as a sensor device as herein described. In particular embodiments, the 1D nanomaterial may be a carbon nanotube or a semiconductor nanowire, e.g., grown on a substrate, and in other embodiments, the 2D nanomaterial may be graphene, silicene, molybdenum disulfide, black phosphorous (phophorene), borophene, tungsten disulfide, boron nitride, tungsten diselenide, stanene, germanane, nickel HITP, and/or metal dichalcogenides or Mxenes such as Ti2C, (Ti0.5, Nb0.5), V2C, Nb2C, Ti3C2, Ti3CN, Nb4C3, or Ta4C3.

There are several growth mechanisms that may be implemented for the growth of the 1D or 2D nanomaterial on a substrate. In certain instances, the growth substrate may be a metal plate, a metal foil, or other thin film metal, such as a metal positioned on or over a wafer, such as a silicon wafer. The 1D or 2D nanomaterial may be deposited on the growth substrate, such as for growing, by any suitable mechanism, such as by chemical vapor deposition ("CVD") (atmospheric, low or very low pressure), PECVD, ALD, submergence within a hot wall or cold wall reactor, and the like.

Graphene Transfer

There are several transfer mechanisms for transferring the growing or grown 1D or 2D structure to a substrate, such as a substrate containing an integrated circuit, such as by direct transfer from the growth substrate to the wafer, e.g., a ROIC (Read-out Integrated Circuit)/CMOS wafer, such as by using Van der Waal's forces, fusion bonding, or other suitable form of temporary bonding. Additionally, there are several release mechanisms for effectuating the release of the 1D or 2D nanomaterial from the growth substrate and the attachment to the ROIC wafer, including aqueous electrolyte electrolysis, where the growth platform acts as the cathode and separation is produced due to hydrogen evolution. Another release mechanism may include separation caused by use of a temporary adhesive from the growth platform, and/or by use of a laser, a UV light, a temperature increase, or physical peeling or pulling.

Particularly, a direct transfer method is set forth as FIG. 22. For instance, in an exemplary sequence of steps, a growth substrate is provided. A graphene layer may then be deposited on to the growth substrate, such as by a chemical vapor deposition (CVD) process. Likewise a ROIC/CMOS wafer may be provided, such as in opposed relationship to the graphene containing substrate. Further, a release and transfer step may take place, such as where the graphene is released from the growth substrate and transferred onto the CMOS wafer. The graphene layer may then be patterned and one or more interconnects and/or wells may be deposited and/or patterned. The composition may then be tested, such as with respect to sensor operation of the underlying integrated circuit. The chip may then be assembled into a package, and a package level test may occur, and once passed the chip set may be shipped.

More particularly, an effective method for producing such a transfer, e.g., involving a Van Der Waals Bond transfer mechanism, is illustrated in FIGS. 22A-22F. In FIG. 22A, the 2D nanomaterial, e.g., graphene, is grown on a growth platform such as composed of a thin metal layer, e.g., silver, ruthenium, copper, or platinum layer, that is positioned on a growth wafer. In FIG. 22B, the orientation of the growth platform is flipped with respect to its fabrication process. In FIG. 22C, a silicon ROIC/CMOS wafer containing a suitably configured oxide layer, e.g., silicon dioxide, is prepared, and the flipped growth platform and the silicon wafer are aligned for bonding. In FIG. 22D, the 2D nanomaterial on the growth platform is bonded to the oxide layer, e.g., silicon dioxide layer, on the ROIC wafer using Van der Waals forces. FIG. 22E shows the use of water electrolysis to create hydrogen bubbles to separate the 2D nanomaterial from the metallized growth platform, which acts as a cathode in such a water electrolysis reaction. In FIG. 22F, the growth substrate is removed, leaving the 2D nanomaterial on the ROIC/CMOS wafer.

FIGS. 26A-26F also depicts the same steps of direct bond transfer via Van der Waals forces as in FIGS. 22A-22F, with the distinction that FIGS. 26A-26F show the growth platform is patterned to create one or more channels or divots that allow for better water access and more efficient bubble transfer. Such openings may later be converted into one or more well or chamber boundaries as herein described.

FIGS. 27 and 28 illustrate an alternative method for the above described bubble elution and/or release mechanism as illustrated with respect to FIGS. 26 and 22, For instance, FIG. 27 depicts a modified Langmuir-Blodgett trough. As shown in FIG. 28A, a structure composed of a PMMA substrate, a 2D nanomaterial, e.g., graphene, copper, and a base layer is subjected to a controlled immersion within the trough and subjected to a bubble release protocol. As shown in FIG. 28B, the 2D nanomaterial and the PMMA substrate are fully released from the copper structure. As shown in FIG. 28C, the solution is drained in such a manner that the 2D nanomaterial is aligned with and becomes bonded to a target wafer, e.g., a silicon CMOS wafer, so as to transfer the 2D nanomaterial layer onto the target wafer.

FIG. 21 shows a flow chart of a general method of forming a semiconductor wafer with transistors having 2D nanomaterial layers. A key process step is the transfer of the 2D nanomaterial, such as graphene, from a growth substrate to the target substrate, such as a ROIC wafer. Discussed elsewhere are a variety of different transfer techniques that generally use some release method to release the graphene from its growth substrate and a temporary bonding method, such as adhesive bonding of the graphene to a carrier and then Van der Waals bonding of the graphene to the target wafer with a subsequent second release step, such as by thermal, laser or UV energy to release the adhesive and carrier wafer from the graphene. These transfer processes that require temporary bonding and direct or indirect contact to the graphene layer are not optimal as they open many opportunities for defects in the graphene. A preferred approach uses direct transfer fusion bonding of oxide, such as silicon dioxide layers, as illustrated in FIGS. 23A-23F.

FIGS. 23A-23F visually show the steps of direct bond transfer via fusion bonding. In the direct transfer fusion bonding process, the 2D nanomaterial (530), e.g., graphene, is encapsulated with SiO2 (520) while it is still on the growth wafer and then the growth wafer may be fusion bonded to a properly prepared CMOS ROIC wafer. Platinum, ruthenium, silver, copper or another suitable metal may be used for growing the 2D nanomaterial (530) on the growth substrate. A release or separation mechanism (e.g., bubble process) is used to separate the 2D nanomaterial (530) from the platinum or other metal (528). The growth wafer may be a silicon, sapphire (Al2O3), or other suitable substrate capable of sustaining high temperatures with low thermal expansion.

In FIG. 23A, the 2D nanomaterial (530), preferably graphene, is grown on a growth platform comprised of a platinum layer (528) on a growth wafer (510).

In FIG. 23B, a cover material of silicon oxide is deposited on the 2D nanomaterial and then the oxide is polished or CMP'ed to provide a very flat and smooth surface on the silicon oxide.

In FIG. 23C, the growth platform is flipped.

In FIG. 23D, a ROIC wafer is prepared by polishing or CMP'ing a topmost silicon oxide layer to provide a very flat and smooth surface on the silicon oxide. The ROIC wafer and the growth platform are aligned for bonding.

In FIG. 23E, the silicon oxide cover material (520) is bonded to the ROIC wafer topmost silicon oxide layer (520) through a fusion bonding process.

In FIG. 23F, the growth substrate is separated from the ROIC wafer, leaving the 2D nanomaterial (530), preferably graphene, on the ROIC wafer, i.e. the process effectively transfers the 2D nanomaterial from the growth substrate to the ROIC wafer via fusion bonding. In the direct transfer fusion bonding process, the 2D nanomaterial, preferably graphene, is encapsulated with SiO2 effectively protecting it from handling and process damage, and then the growth wafer is fusion-bonded to a CMOS ROIC wafer.

Platinum, copper, or another suitable metal is used for growing the 2D nanomaterial (530). A release or separation process (e.g., a bubble process) is used to separate the 2D nanomaterial (530) from the platinum or other metal (528). The growth wafer is preferably silicon, sapphire (Al2O3), or another suitable substrate capable of sustaining high temperatures with low thermal expansion. Alternatively, a wafer format is replaced with a panel or sheet. Various encapsulating materials are utilized such as $SiO_2$, Si, Si3N4.

FIGS. 24A-24H show a variation the the fusion bonding process, in this case using the process to first coat the graphene with an analyte or reaction-sensitive layer, such as an ion sensitive oxide layer, and then bonding this ion sensitive oxide layer to a carrier wafer. Releasing the graphene from the growth substrate and fusion bonding are similar to the previously described process, but the resultant final structure is different since the ion sensitive oxide layer is integral to the final layer stack—thus both the graphene layer and the ion sensitive oxide layer are transferred by fusion bonding using this process.

In FIG. 24A, the 2D nanomaterial (530), preferably graphene, is grown on a growth platform comprised of a platinum layer (528) on a growth wafer (510).

In FIG. 24B, an ion sensitive oxide material is deposited on the 2D nanomaterial.

In FIG. 24C the ion sensitive oxide is releasably joined to a carrier wafer.

In FIG. 24D the growth substrate has been removed (e.g. by a bubble release process or other means) exposing the graphene.

In FIG. 24E, a cover material of silicon oxide is deposited on the 2D nanomaterial and then the oxide is polished or CMP'ed to provide a very flat and smooth surface on the silicon oxide.

In FIG. 24F, the carrier platform is flipped and aligned with a previously prepared ROIC wafer (e.g. CMP and/or polished SiO2 surface).

In FIG. 24G, the silicon oxide cover material (520) is bonded to the ROIC wafer topmost silicon oxide layer (520) through a fusion bonding process.

In FIG. 24H, the carrier is separated from the ROIC wafer, leaving the 2D nanomaterial (530), preferably graphene, covered with the ion sensitive layer (on the ROIC wafer, i.e.

the process effectively transfers the 2D nanomaterial from the growth substrate to the ROIC wafer via fusion bonding. In the direct transfer fusion bonding process, the 2D nanomaterial, preferably graphene, is encapsulated with SiO2 effectively protecting it from handling and process damage, and then the growth wafer is fusion-bonded to a CMOS ROIC wafer.

FIG. 25 shows a wafer undergoing a bubble release process whereby generated gas bubbles are intended to gently force the graphene layer from its growth substrate. In practice this may be difficult to do since it is problematic to contact the thin film used on the growth substrate (it is both thin and covered by graphene). To be make electrically contacting the growth wafer easier a TSV 43 can bring an electrical path from the thin film on the growth side of the wafer trough the wafer to a conductive layer on the backside of the wafer. It is easy to access the backside of the wafer for electrical contact Nanomaterial Layer Transfer by Fusion Bonding In view of the above, in various embodiments, FIG. 21 provides a flow chart of a general method of forming a semiconductor wafer with transistors with a 2D nanomaterial layer in accordance with the methods set forth above. FIGS. 24A-24F illustrate the various steps. For instance, an exemplary direct transfer mechanism including direct transfer fusion bonding is provided and shown in FIGS. 25A-25F. FIGS. 25A-25F visually show the steps of direct bond transfer via fusion bonding. In FIG. 25A, the 1D or 2D nanomaterial, such as graphene, is grown or deposited on a growth platform comprised of a platinum layer on a growth wafer. In FIG. 25B, a cover material of silicon oxide is deposited on the 1D or 2D nanomaterial and then the oxide is polished or CMP'ed to provide a very flat and smooth surface on the silicon oxide. In FIG. 25C, the growth platform is flipped. In FIG. 25D, a ROIC wafer is prepared by polishing or CMP'ing a topmost silicon oxide layer to provide a very flat and smooth surface on the silicon oxide. The ROIC wafer and the growth platform are aligned for bonding. In FIG. 25E, the silicon oxide cover material is bonded to the ROIC wafer topmost silicon oxide layer through a fusion bonding process. In FIG. 25F, the growth substrate is separated from the ROIC wafer, leaving the 1D or 2D nanomaterial on the ROIC wafer, i.e. the process effectively transfers the 1D or 2D nanomaterial from the growth substrate to the ROIC wafer via fusion bonding.

In the direct transfer fusion bonding process, the 1D or 2D nanomaterial, e.g., graphene, may be encapsulated with SiO2 and then the growth wafer may be fusion bonded to a CMOS ROIC wafer. Platinum, gold, silver, copper or another suitable metal may be used for growing the 2D nanomaterial or in the case of 1D nanomaterial it is deposited on the growth substrate. A release or separation mechanism (e.g., bubble process) is used to separate the 1D or 2D nanomaterial from the platinum or other metal. The growth wafer may be a silicon, sapphire (Al2O3), or other suitable substrate capable of sustaining high temperatures and thermal expansion. Alternatively, a wafer format may be replaced with a panel or sheet. Various encapsulating materials may be utilized such as SiO2, Si, Si3N4. The same process may also be utilized with other materials that can be bonded such as polymers. Alternative methods for growing and transferring 2D nanomaterials are disclosed in Hoffman et al., U.S. Provisional Patent Application No. 62/175,351, filed on Jun. 14, 2015, for System And Method For Growing And Transferring Graphene For Use As A FET, which is hereby incorporated by reference in its entirety.

FIGS. 29A-29G depict a process for temporary bonding that employs an adhesive material (such as an acrylate) so as to effectuate temporary bonding. In FIG. 29A, a glass carrier including an LTHC and an adhesive is prepared. In FIG. 29B, the growth platform containing the 2D nanomaterial, e.g., grown in accordance with the above, is bonded to the glass carrier such as by being exposed to UV light at room temp. Optionally, a thin Si growth wafer background may be provided, such as where the Si growth wafer is approximately 100 um or less, such as 75 um or less, such as 50 um or 40 um or even 30 um or less, and positioned on top of the glass layer. In FIG. 29C, the 2D nanomaterial is released from the growth platform. In FIG. 29D, the 2D nanomaterial is bonded to a target wafer, and in FIG. 29E, the bond structure is exposed to a laser to release the glass. In FIG. 29F, a tape or other adhesive material-containing strip may be applied to provide an adhesive material layer. In FIG. 29G, this adhesive material layer may be peeled off and the remaining structure may be cleaned.

The glass carrier used may be transparent to UV light, which allows both for curing of the adhesive material and to effectuate release, e.g., by an infrared laser, in the glass release step. As indicated, LTHC is a useful release layer. Particularly, the adhesive material may be filled with Carbon black to absorb IR 1064 laser energy, may be heated to a high temperature, and thereby decomposed. In certain instances, LTHC may be spun on in a thin layer. In particular embodiments, the adhesive material may be an acrylate, such as PMMA. More particularly, the adhesive material may be spun on so as to form an approximately 50 um thick layer. Such adhesive materials are typically available in several different, e.g., four, different tacks, and where desired, other materials may be added to further reduce tackiness. An adhesive material 5032 4% may be employed such as a low tack material.

For bonding, the surface to be bonded may be brought in close proximity to the adhesive material layer (<1 mm) in a vacuum. A top wafer may be dropped onto the adhesive material layer on the glass carrier via gravity. UV or other high intensity light or heat may be applied until fully cured. The adhesive material may be such that it is resistant to solvents, and can be exposed up to 220 C. The 2D nanomaterial may then be released, such as from a metal backing layer, e.g., composed of copper, silver, gold, or platinum, such as through a bubble bath mechanism or a mechanical peel process, as herein described. This process allows for continuous probing of the material layers to insure the presence and/or uniformity of the 2D nanomaterial. After the carrier with the 2D nanomaterial is placed on the target wafer, it may be adhesion baked, such as at 150 C for a short period of time, e.g., two minutes. The mechanism for the release from the glass may be to raster the structure with a UV laser for another short period of time, e.g., two minutes. The tape may be applied by a manual vacuum chuck to hold the wafer, and then a roller tape may be applied, e.g., manually. Alternatively dicing tape may be used. After peeling off the tape and the adhesive layer, anneal cleaning is performed at 400 C.

FIGS. 30 and 31 illustrate an adhesive temporary bond material process using a TZNR adhesive, e.g., from TOK (Tokyo Ohka Kogyo Co., Ltd.). As shown in FIG. 30, the process involves adhesive spin coating of a growth substrate with a 1D or 2D layer, e.g., a graphene layer, so as to deposit the graphene layer onto the growth substrate. The composition may then be subjected to a curing step, such as by pre-baking, and aligned with a support wafer, where bonding may occur. For instance, thermal bonding may be effectuated by applying heat under a vacuum, such as at a low bonding pressure (0.012 MPa). FIG. 31 illustrates the low stress debonding by dissolving the adhesive, such as in addition to solvent injection, pick up, and detachment such as by a handler. The 1D or 2D containing substrate may then be cleaned so as to remove the residue so that no residue is left on the device wafer.

FIGS. 32A-32E illustrate the adhesive temporary bond process with a nickel ("Ni") deposition layer. As shown in FIG. 32A, a metal such as Ni may be deposited on the 2D nanomaterial layer (in black). As shown in FIG. 32B, a tape lamination may be applied to the Ni layer. As shown in FIG. 32C, the tape layer may be peeled away from the growth platform and the tape layer, Ni layer, and 2D nanomaterial layer may be transferred to a target wafer. Alternatively, the structure may be baked to improve the 2D nanomaterial adhesion. As shown in FIG. 32D, the tape may be peeled from the Ni layer (possibly with a release mechanism). As shown in FIG. 32E, a wet etch process may be used to remove the Ni layer.

ChemFET Manufacturing Process

In another aspect of the disclosure, various methods are provided. For instance, as described herein and above, a method for manufacturing a ChemFET may be provided. The method may include depositing a channel nanomaterial, e.g., comprised of a one-dimensional (1D) or two-dimensional (2D) transistor nanomaterial, on an exposed metal layer portion of an integrated circuit structure, such as where the integrated circuit structure includes a semiconductor substrate and/or a dielectric layer. In such an instance, the metal layer may be configured so as to form a source and drain electrode, where the source and drain electrodes are separated from one another so as to form a channel region.

Accordingly, in certain instances, the metal layer(s) may be imbedded within the dielectric layer and exposed so as to stand off therefrom. For instance, a patterned material may be used to expose a portion of the channel area and a plurality of adjacent areas. Particularly, this may be performed such as by etching the dielectric material starting with the adjacent areas thereby exposing a trench under the channel, and/or exposing the metal in the channel area. Additionally, the method may include etching the metal from underneath the channel to create a ChemFET. In certain instances, a channel nanomaterial may be provided such as before, after, or during the etching process so as to form a channel between the exposed source and drain electrodes.

Additionally, a method for manufacturing a well formation for a 1D or 2D nanomaterial FET may include depositing an organic passivation layer over a conductive channel of a 1D or 2D nanomaterial FET of a semiconductor device structure, patterning the organic passivation layer to create well formation locations over the channel, and removing the passivation layer over the channel to expose the channel within the well formation.

Further, in various embodiments, the method for manufacturing a well formation for a 1D or 2D nanomaterial FET may include depositing a passivation layer over a conductive channel of a 1D or 2D transistor material FET of a semiconductor device structure, as described herein. Additionally, the method may include a first etching step for etching through the majority of the passivation layer with a first etching method so as to create a majority of a well formation, such as over the channel. A second etching step may take place for the etching of the remaining passivation layer over the channel to expose the channel within the well formation. In some instances, the depositing of the passivation layer may be over a functional layer that is itself positioned over the conductive channel of 1D or 2D nanomaterial.

Where one or multiple etching steps are provided, the first etching method may be a plasma method or laser method, wherein the plasma method optionally is an RIE, HDP, ICP or ECR method. The first etching method may be performed through a mask material that is patterned to shield parts of the passivation dielectric layer from the first etching method while having openings that expose other parts of the passivation dielectric layer to the first etching method, wherein the mask material optionally is a photoresist or a hard mask material. Additionally, a second etching method may be provided such as where the second etching step is a wet or gaseous etching method, optionally an electrochemical or chemical etching method, wherein the chemical etching method optionally comprises an acid, an aqueous acid solution, or a buffered acid solution, and wherein the second etching method optionally etches the protective layer without substantially etching or affecting the channel nanomaterial. In particular embodiments, the first and/or second etching method(s) is(are) predominantly an anisotropic etching method. In such instances, the first etching method may be performed so as to etch through a controlled depth in the protective material layer wherein the control is provided by a time of etching in conjunction with the rate of etching or the control is provided by an end point detection.

When producing a well structure, the well may have any suitable shape or size of configuration. For instance, in one embodiment, the shape of the well formation when viewed from the top is a round or polygon shape. In such an instance, the largest width of the well formation when viewed from the top may be about 0.1 um to about 10 um. Further, when forming a well, in various instances, an array of two or more well formations may be formed. Hence, the ratio of the pitch of two well formations to the largest width of the well formations when viewed from the top may be greater than 1 and less than 10. Accordingly, when an array of well formations are formed, the variation of the largest widths of the well formations when viewed from the top in an array may be designed to have well formations with the same largest widths, which widths may be less than about 10%. In various instances, the well formation configuration may be chosen with respect to consideration of fluid dynamics of a fluid flowing over or into the well formation, wherein consideration of fluid dynamics includes transport of reagents or particles over or into the well formation.

In various instances, the method may include preparing a growth substrate of a 1D or 2D nanomaterial. In such an instance, the method may include depositing a metal catalyst layer on a substrate, optionally a wafer or a plate and annealing the metal catalyst. The 2D nanomaterial may be a transistor material selected from the group including graphene, molybdenum disulfide (MoS2), phosphorene (black phosphorous), silicene, borophene, tungsten disulfide (WS2), boron nitride, WSe2, stanene (2D tin), graphane, germanane, nickel HITP, Mxenes (Ti2C, (Ti0.5,Nb0.5), V2C, Nb2C, Ti3C2, Ti3CN, Nb4C3, Ta4C3), and a metal dichalcogenides. Further, the metal may be Cu, Ni, or Pt, or the like. Further still, a photoresist may be included, such as where the patterned material is a photoresist, which may be patterned using a photolithographic process. Likewise, the semiconductor substrate may be a Si material, a SiGe material, or a III-V material. Therefore, in accordance with these methods, the semiconductor device structure may be configured as or otherwise based on CMOS, BiCMOS, Bipolar, or other fabrication technology; and the integrated circuit may be configured as or based on FET, BJT, HBT, or other transistor technology.

Accordingly, the methods may include one or more of the following etching steps, which may be executed in any logical order: etching the dielectric, where the etching includes: a plasma etching process, wherein the plasma etching process optionally comprises an RIE, ICP, HDP, or ECR process; etching the dielectric, where the etching includes (i) a wet or gaseous etching method, wherein the wet or gaseous etching method optionally is an electrochemical or chemical etching method, wherein the chemical etching method optionally comprises an acid, an aqueous acid solution, or a buffered acid solution; or (ii) an isotropic etching method; and wherein the etching optionally etches the dielectric without substantially etching or affecting the channel nanomaterial; etching the metal, where the etching includes a plasma etching process, optionally (i) an RIE, ICP, HDP, or ECR process; (ii) a wet or gaseous etching method, optionally an electrochemical or chemical etching method, wherein the chemical etching method optionally comprises an acid, an aqueous acid solution, or a buffered acid solution; and (iii) wherein the etching comprises predominantly an isotropic etching method; etching the metal, where the etching is predominantly an isotropic etching method; and etching the metal, where the etching etches the metal without substantially etching or affecting the channel nanomaterial.

As indicated, the dielectric layer may include a first thin layer of material forming an etch stop layer under the channel to limit the extent of the dielectric etching, wherein the first thin layer of material optionally includes a silicon oxide, a silicon nitride, or a silicon carbide or a non-stoichiometric material, and wherein the first thin layer of material optionally is about 0.1 nm to 100 nm thick. Additionally, one or more functional layers may be deposited over the graphene channel prior to etching the dielectric, wherein etching the dielectric may optionally include (i) a plasma etching process, which plasma etching process optionally is an RIE, ICP, HDP, or ECR process; (ii) a wet or gaseous etching method, wherein the wet or gaseous etching method is an electrochemical or chemical etching method, wherein the chemical etching method optionally comprises an acid, an aqueous acid solution, or a buffered acid solution; and (iii) wherein etching the dielectric optionally etches the dielectric without substantially etching or affecting the channel nanomaterial and without substantially etching or affecting the functional material. The one or more functional layers may be deposited over the graphene channel subsequent to etching the dielectric.

Where a passivation layer is employed, the passivation layer may be comprised of an inorganic material, optionally an oxide, a nitride, a carbide, an oxy-nitride, a carbon-doped oxide or a fluorine-doped oxide material. Additionally, the passivation layer may be comprised of an organic material, optionally a polymer, polyimide, BCB, PBO or other like material. Further, the passivation layer may include multiple layers of material. Hence, the passivation layer may be comprised of both inorganic and organic materials. In certain instances, the passivation layer may be deposited by a CVD, PECVD, PVD, ALD, or spin-on dielectric process. In various instances, the passivation layer may include a first thin layer of material forming an etch stop layer over the channel and a second thicker layer of passivation material over the etch stop layer, wherein optionally (i) the first etching method has high selectivity for etching the second thicker layer of passivation material as compared to the first thin layer of material, (ii) the first thin layer of ESL material is about 0.1 nm to about 100 nm thick and the second thicker layer of material is about 0.1 um to about 10 um thick, (iii) the first thin layer of material is comprised of a silicon nitride or a silicon carbide, (iv) the first layer of thin material may be comprised of a non-stoichiometric material, and (v) the first etching method etches through the second thicker layer of passivation material and stops on the first thin layer of ESL material.

Simple Manufacturing Process Flow with Bottom Contacts

FIGS. 33A-33I provide exemplary diagrams of a semiconductor substrate at different stages of treatment to create ChemFET for biosensing (e.g., nucleic acid hybridization and/or sequencing) as described herein. This method and resulting structure is characterized by the fact that the electrodes contact the nanomaterial, e.g. graphene from underneath the graphene layer (430) (i.e. the graphene is deposited on top of the source and drain electrodes (422 and 424). At FIG. 33A, an insulated dielectric layer 420 is formed on a semiconductor substrate (410), e.g., silicon or other semiconductor. Transistors and interconnects on semiconductor substrate (410) may be present in some embodiments, but are not depicted in FIGS. 33A-33I. A conductive material layer (428) may then be formed over insulated dielectric layer (420, see FIG. 33B). In some embodiments, the conductive material layer may be deposited in trenches formed in a dielectric layer (420).

The conductive material layer (428) may then be patterned to form a source electrode (422) and a drain electrode (424) (FIG. 33C). A 1D or 2D nanomaterial layer (430) may then be applied over the electrodes (422, 424) and insulated dielectric layer (420, FIG. 33D). An analyte or ion sensitive layer (434) may then be applied over the 1D or 2D nanomaterial layer (430, see FIG. 33E). The ion sensitive layer (434) and 2D nanomaterial layer (430) may then be patterned (see FIG. 33F for a side sectional view and see FIG. 33G for a top down view) using techniques described herein. In certain embodiments, holes or openings may be created in ion sensitive layer (434) and 2D nanomaterial layer (430), as described above, and a second conductive layer may be placed on top of the openings or holes to electrically contact the electrodes (422, 424). A passivation layer (435) may then be added on top of electrodes (422, 424) as well as the ion sensitive layer (434) and 2D nanomaterial layer (430, see FIG. 33H) and then patterned to form a chamber (437, see FIG. 33I)

CMOS Integration with Top Down Graphene Contacts

FIGS. 34A-34J are side sectional views that illustrate a preferred CMOS integration method for building the interconnects, dielectric and well structures, as well as the pads for bonding the chip to a package, 1D or 2D nanomaterial transfer to the chip and 1D or 2D material patterning. For instance, FIG. 34A illustrates a graphene material layer (430) deposited or formed on a ROIC semiconductor wafer, such as a CMOS wafer, that includes a semiconductor substrate (410), a dielectric layer over the substrate (420) and one or metal layers in or on the dielectric layer that form interconnects, including a conductive source (422) and drain (424). FIG. 34B illustrates patterning the graphene layer (430) to form a channel, which extends horizontally from the source to the drain. FIG. 34C illustrates an etch stop layer (ESL) (474) deposited over the graphene layer (430). FIG. 34D illustrates a deposited, patterned, and etched thick insulator layer (435) over the ESL (474), with the etched features stopping on the ESL layer (474). FIG. 34E illustrates an etched ESL (474), either dry or wet etched, and further etching of the underlying dielectric layer (420), such as by a plasma etch such as a RIE, stopping on the a metal interconnect layer, i.e. the source (422) and drain (424). FIG. 34F illustrates the filling of the etched trenches, such as by a damascene copper process comprising depositing a barrier, depositing a liner, copper electroplating and Chemical Mechanical Polishing (CMP). There may be an optional addition of a work function matching material prior to the damascene trench fill process. FIG. 34G illustrates a deposit of a barrier/adhesion layer, deposit of a bondable pad material and an interconnect material, such as aluminum, patterning and etching of the aluminum interconnect and the pad layer. FIG. 34H illustrates a deposit of SiO2 (435) (e.g. CVD), CMP, and a pad open etch to expose the bond pad (448). FIG. 34I illustrates a DRIE of the passivation insulator (435) down to the etch stop layer (474), forming a majority of a well structure (438). FIG. 34J illustrates a wet etch of the thin etch stop layer (474) to expose the channel (430) within the chamber (437) of the well structure (438). In a case where there is an analyte or reaction-sensitive layer (not shown) over the channel material there may be a possibility to use a dry etch process to remove the remaining thin etch stop layer (474), in which case the dry etching would stop on the analyte or reaction-sensitive layer. Thus, as illustrated in FIGS. 34A-L a ChemFET is formed which includes metal contacts to the channel (430) from above the channel rather than from below the channel as in FIGS. 33A-I.

Improved fabrication techniques employing 1D, 2D (e.g., graphene), or 3D nanomaterials as a channel layer or sensing layer or structure provide for rapid data acquisition from small sensors to large and dense arrays of sensors. Such arrays may be employed to detect the presence and/or concentration changes of various analyte types in a wide variety of chemical and/or biological processes, including DNA or RNA hybridization, and/or nucleotide and/or protein sequencing and/or detection reactions. Accordingly, in particularly examples, chemically-sensitive graphene field effect transistor (GFET) arrays (as well as arrays made from other chemically-sensitive 1D or 2D nanomaterials) facilitate genetic and/or protein sequencing and/or detection techniques based on monitoring changes in various reactants within a zone associated with the array, such as changes in ion concentration, e.g., changes in hydrogen (pH) or other ion concentration, or changes in other analyte concentrations, and/or binding events associated with chemical or biological processes such as nucleic acid synthesis (as used in NGS and other nucleic acid sequencing approaches), or biologic activity such as within a reaction well or chamber of the GFET based sensor, e.g. a gated sensing location. Particularly, the present disclosure concerns chemically-sensitive 1D or 2D nanomaterial layered FETs for analysis of biological and/or chemical analytes or reactions or biologic activity. Such ChemFETs solve many of the current problems associated with nucleic acid detection, sequencing, genetic, and/or molecular diagnostics.

Accordingly, provided herein are systems for analysis of biological and/or chemical materials or analytes, chemical reactions or biologic activity. In various embodiments, the system includes a ChemFET, such as having a substrate that includes one or more wells or chamber and/or chamber arrangements therein, such as where the well, chamber and/or channel thereof may be associated with one or more sensors. In particular instances, a solution-gated ChemFET with an associated well or chamber structure is provided, such as where the well and/or chamber structure is configured such that a biological and/or chemical reaction can take place within the well or chamber, such as proximate a ChemFET channel structure therein that is comprised of a chemically sensitive 1D or 2D transistor nanomaterial. In various instances, the well or chamber is positioned on a portion of the substrate so as to align with an exterior surface of the channel of each sensor, wherein the channel is a conductive channel that extends from the conductive source to the conductive drain of the ChemFET. The well and/or chamber structure typically defines an opening that allows for direct fluid contact with the channel or an associated member thereof. The well or chamber structure may be made of an insulator passivation material, such as an inorganic material such as silicon oxide or silicon nitride. Alternatively, the insulator material for the well or chamber structure can be an organic material such as a polyimide, BCB, PBO or other like materials.

In various instances, the length of the interior surface, e.g., the channel, of the ChemFET, such as from the source to the drain, ranges from about 0.05 micron to about 3 microns, and a width of the surface and/or channel may range from about 0.5 micron to about 2 microns. In particular instances, the well or chamber structure can be configured to include or otherwise be associated with a nucleic acid template or probe, such as a nucleic acid that may be directly or indirectly immobilized (covalently or non-covalently) on a surface of the well or chamber. For instance, in certain instances, the nucleic acid template (in the context of sequencing reactions) or probe (in the context of hybridization reactions) can be bound to or otherwise immobilized on an interior surface of the well or chamber, such as on the substrate itself, or a layer associated therewith, e.g., a layer composed of a 1D or 2D transistor nanomaterial or a material coating or covering the 1D or 2D transistor nanomaterial, such as a sensing layer and/or passivation layer. In other embodiments, the nucleic acid template or probe can be bound to a secondary substrate, such as a microbead or other particle positioned within the well or chamber so as to be proximate with the chemically-sensitive 1D, e.g. CNT or semiconductor NW, or 2D transistor nanomaterial, e.g., graphene. Additional alternative 2D nanomaterials for the channel may include silicene, molybdenum disulfide, black phosphorous (phosphorene), borophene, tungsten disulfide, boron nitride, tungsten diselenide, stanene, germanane, nickel HITP, and/or metal dichalcogenides or Mxenes such as Ti2C, (Ti0.5,Nb0.5), V2C, Arrangement of Microbeads and Sensing Modality Accordingly, FIG. 20A is an illustration of electrowetting for biomolecule attachment, as described herein. FIG. 20B is an illustration of electrophoresis for biomolecule attachment. FIG. 20C is an illustration of microfluidics for biomolecule attachment. And FIG. 20D is an illustration of an optical readout of DNA sequencing using nanomaterials.

More particularly, in such a configuration as represented in the figures, the drain current of the ChemFET (1) can be modulated by the electrical charge carried by the nucleotide molecules involved in the hybridization and/or sequencing reactions. For example, in one particular configuration of the FET, after hybridization or an elongation step, the charge in the sensing zone increases resulting in a change in the output current that may be measured. This measurement, e.g., for this configuration of the FET, may be made in accordance with the following equation:

$$V_{THF} = V_{TH0} - \frac{Q\text{com} + Q0}{CC + CF}$$

Such as where CC represents the current at the control capacitor, and CF represents the current at the parasitic capacitor. VTHF represents the effective threshold voltage of the ChemFET (1), and VTH0 represents the native threshold voltage. Q0 represents the electric charge initially trapped in the floating gate, and QDNA represents the total charge of hybridization complex.

For instance, a nucleic acid from a sample to be sequenced or representative of a probe to be targeted may be immobilized on the bottom surface (21) or the sidewall (39) of the sample solution well chamber (37). A DNA polymerase (e.g., an isothermal DNA polymerase, e.g., a Bst or Bst-like DNA polymerase), a nucleotide substrate, and other necessary reagents may then be introduced to the sample solution chamber to induce an elongation reaction. As a result, DNAs may be synthesized using the immobilized nucleic acid as the template for DNA synthesis. In such an instance, as the source-drain current vs. gate voltage characteristic changes by the electrostatic interaction with the charged particles (electrons, ions, etc.) in the well, the base sequence of a template nucleic acid having a large base length can be sequenced and/or analyzed. In other embodiments, a nucleic acid probe may be immobilized on the surface of the sensing zone, as described above, and used in a hybridization reaction so as to detect, for example, genetic variation, the presence of a genetic disease, polymorphism, or pathogen.

In various instances, in order to conduct parallel analysis of a plurality of nucleic acid templates, the number of the ChemFETs may be equal to or higher than the number and/or types of DNAs to be sequenced and/or analyzed. In certain instances, each nucleic acid template or probe may be an oligonucleotide or a fragment of DNA or RNA that may be constituted from about 100 to about 1000 bases, such as from 200 to about 800 bases, for instance, from about 300 or about 500 bases to about 600 or 700 bases or more or somewhere in between. However, in various instances, a fragment of nucleic acid having 100 bases or fewer may also be used.

Additionally, as indicated above, the present ChemFET device (1) may also be used in various different DNA/RNA hybridization reactions, such as for the purpose of determining a genetic variation and/or for detecting the presence of a genetic marker for a disease or pathogen. In such an instance, a nucleic acid probe may be coupled to or immobilized on a bottom or side graphene-coated surface of the sensing chamber, per above. As indicated, the probe may be of any suitable length but in various instances from about 5 or 10 to about 1000 bases, such as from 20 or about 50 to about 700 or about 800 bases, for instance, from about 100 or about 200 bases to about 300 bases including about 400 or about 500 bases to about 600 or 700 bases or more or somewhere in between.

For instance, in one exemplary embodiment, a nucleic acid probe or template containing about 20 to 50-100 bases coding for a gene sequence of interest that has been previously amplified or otherwise synthesized (e.g., by solid state synthesis methods), may be immobilized in or proximate to the channel region (30), a channel insulating film, and/or a side surface of the sensing chamber (37) of the ChemFET (1). For example, once isolated and amplified, the base of the probe may be modified so as to be attached to the graphene coated surface, and/or may be coupled to a secondary substrate, such as a polymer or plastic microbead (60) that has been chemically treated so as to be coupled therewith. Once immobilized, the sensing chamber (37) containing the probes, either on a secondary substrate or directly coupled with a chamber surface, may be reacted with a sample solution containing a number genes including a target gene of interest to be measured such that when a nucleic acid probe having a complementary base sequence to the target gene is immobilized on the channel (30), channel insulating film (34), or the sidewall surface (39) of the sample solution well structure (38), or on a secondary substrate immobilized within the sensing chamber of the ChemFET device (1) for gene detection, the target gene hybridizes with the nucleic acid probe under appropriate reaction conditions and the target gene and the nucleic acid probe form a double strand, the result of which hybridization reaction may be detected.

ChemFET and ChemFET Sensor Array IC Chip Review

As depicted in FIG. 15F, a ChemFET sensor array IC chip (50) may be arranged as a two dimensional ChemFET sensor array on an IC chip (50) that in this instance is based on a column and row design, although other designs are also possible. As can be seen with respect to FIG. 15F, the system further includes a row and column decoder (144), as well as circuitry for performing the requisite sensing, detecting, and processing so as to measure the sensory data. Hence, also included is sensing, measurement, and other associated readout data.

Accordingly, as can be seen with respect to FIGS. 14A, 15A and 15B, in various instances, a one or two-dimensional ChemFET array, as described herein, may be fabricated on a ChemFET sensor IC chip (50) in accordance with the methods herein disclosed. In various instances, the sensor array chip may include a number of ChemFET sensors (1) that may be arranged in columns and/or rows. A typical number of sensors may include ChemFET sensor elements (1), described herein as "sensors," that may be arranged in a 16 sensor by 16 sensor column/row array configuration. As depicted, the array includes two columns, but typically may include sixteen columns, arranged side by side, where each column includes 16 rows. Particularly, each column of the array includes up to 16 sensors. Each column may be configured so as to include a current source Is that may be shared by all sensors of the column. However, in various other embodiments, each sensor may have its own current source, or the array itself may have a single current source. Additionally, each ChemFET sensor (1) may include a ChemFET (1), as described above, having an electrically coupled source and/or drain and/or body, and may further include one or more switches, such as a plurality of switches S1 and S2 that may be configured so as to be responsive to one of the up to sixteen row select signals (RSEL, and it's complements). More particularly, a row select signal and its complement may be generated simultaneously to "enable" or select a given sensor of the selected column, and such signal pairs may be generated in some sequence to successively enable different sensors of the column, e.g., together or one at a time, such as sequentially.

A row decoder (144) may also be provided as part of the system. In such an instance, the row decoder may be configured so as to provide up to sixteen pairs of complementary row select signals, wherein each pair of row select signals may be adapted so as to simultaneously or sequentially enable one sensor in each column so as to provide a set of column output signals from the array, e.g., based on the respective source voltages VSa through VSb, etc. of the enabled row of ChemFETs. The row decoder (144) may be implemented as a conventional four-to-sixteen decoder (e.g., a four-bit binary input ROW1-ROW4 to select one of (24)

outputs). The set of column output signals VSa through VSb for an enabled row of the array is applied to switching logic, which may be configured to include up to sixteen transmission gates Sa through Sb (e.g., one transmission gate for each output signal).

As above, each transmission gate of the switching logic may be implemented using an n-channel or p-channel MOSFET, such as where various analog and/or digital transistors and circuits may be included, such as proximate the ChemFET sensor array. The transmission gate may be positioned in a bottom or top gate configuration, or both to ensure a sufficient dynamic range for each of the output signals VSa through VSb. The column decoder (144), like the row decoder (144), may be implemented as a conventional four-to-sixteen bit decoder and may be controlled via the four-bit binary input COL1-COL4 to enable one of the transmission gates Sa through Sb of the switching logic at any given time, so as to provide a single output signal VS from the switching logic. This output signal VS may be applied to a 10-bit analog to digital converter (ADC) (141) to provide a digital representation D1-D10 of the output signal VS corresponding to a given sensor of the array.

As noted earlier, individual ChemFETs and arrays of ChemFETs such as those discussed above may be employed as sensing devices in a variety of applications involving chemistry and biology. In particular, such ChemFETs may be employed as pH sensors in various processes involving nucleic acids such as DNA. In general, the development of rapid and sensitive nucleic acid hybridization and sequencing methods, as herein described, e.g., utilizing automated DNA sequencers, may significantly advance the understanding of biology.

It should be noted, that with respect to the various arrays disclosed herein according to various embodiments of the present invention may be fabricated according to conventional CMOS fabrication techniques, as described above, as well as modified CMOS fabrication techniques (e.g., to facilitate realization of various functional aspects of the ChemFET sensor array IC chip (50) discussed herein, such as additional deposition of graphene and/or other passivation materials, process steps to mitigate trapped charge, etc.) and other semiconductor fabrication techniques beyond those conventionally employed in typical CMOS fabrication (e.g., BiCMOS). Additionally, various lithography techniques may be employed as part of an array fabrication process. For example, in one exemplary implementation, a lithography technique may be employed in which appropriately designed blocks are "stitched" together by overlapping the edges of a step and repeat lithography exposures on a wafer substrate by approximately 0.2 micrometers. In a single exposure, the maximum die size typically is approximately (21) millimeters by (21) millimeters. By selectively exposing different blocks (sides, top & bottoms, core, etc.) very large chips can be defined on a wafer (up to a maximum, in the extreme, of one chip per wafer, commonly referred to as "wafer scale integration").

In one embodiment, the array includes 512 columns with corresponding column bias/readout circuitry (one for each column), wherein each column includes geometrically square sensors, each having a size of approximately 9 micrometers by 9 micrometers (e.g., the array may be up to 512 columns by 512 rows). In various instances, the entire array (including sensors together with associated row and column select circuitry and column bias/readout circuitry) may be fabricated on a semiconductor die as an application specific integrated circuit (ASIC), structured ASIC, or as a field gated programmable array such as having dimensions of approximately 7 millimeters by 7 millimeters.

Various power supply and bias voltages useful for array operation are provided to the array via electrical connections (e.g., pins, metal pads) and labeled for simplicity in block as "supply and bias connections." The array may also include a row select shift register, one or more, e.g., two sets of column select shift registers, and one or more, e.g., two, output drivers, which output drivers are configured to provide two parallel output signals from the array, Vouta and Voutb, representing sensor measurements. The various power supply and bias voltages, control signals for the row and column shift registers, and control signals for the column bias/readout circuitry may be provided by an array controller, which controller may also read the output signals Vouta and Voutb (and other optional status/diagnostic signals) from the array. Configuring the array such that multiple regions (e.g., multiple columns) of the array may be read at the same time via multiple parallel array outputs (e.g., Vouta and Voutb) facilitates increased data acquisition rates.

Accordingly, in various embodiments, a ChemFET sensor IC chip (50) in for performing a sequencing reaction is provided, such as where the sequencing reaction involves the sequencing of strands of nucleic acids, as described herein. In various embodiments, the ChemFET sensor IC chip (50) may include a substrate and an array of graphene ChemFETs (1) arranged on the substrate. In such an embodiment, one or more of, e.g., each, of the graphene field effect transistors may include a primary layer forming a base layer (10), and a secondary, e.g., intermediary, layer positioned over or otherwise associated with the primary layer, the secondary layer (20) being formed of a first nonconductive material and including a source (22) and a drain (24) formed in the first nonconductive material (20), the source (22) and drain (24) being separated one from the other by a channel (30), and being formed of an electrically conductive material. In certain instances, a tertiary layer (35) may be positioned over the secondary layer, such as where the tertiary layer includes a solution gate formed over the channel (30) to electrically connect the source and the drain. In such an instance, the channel (30) may be formed of a graphene layer. The tertiary layer (35) may additionally include a surface structure that overlaps the source and the drain in the secondary layer (20), the surface structure further defining a well (38) having side walls (39) and a bottom (21) that extends over at least a portion of the graphene layer of the channel so as to form a sensing chamber (37) for the performance of the sequencing reaction. In particular embodiments, a nano- or microbead (60) provided in one or more wells (38) of the array of graphene field effect transistors, such as where one or more, e.g., each, microbead (60) may be configured with one or more reactants to interact with portions of the strands of nucleic acids such that the associated chemically sensitive FET detects a change in ion concentration of the reactants by a change in current flow from the source to the drain via an activation of the graphene layer.

It should be noted that, in various embodiments of the ChemFET sensor IC chip (50), one or more of the columns, e.g., the first and last columns, as well as the first and/or last ChemFET sensors (1) of each of the columns may be configured as "reference" or "dummy" ChemFET sensors (1). For instance, the dummy sensors of an array, e.g., the topmost metal layer of each dummy sensor may be tied to the same metal layer of other dummy sensors and may be made accessible as a terminal of the chip, which in turn may be coupled to a reference voltage VREF. Such reference voltage VREF may be applied to the bias/readout circuitry of respective columns of the array. In some exemplary implementations, preliminary test/evaluation data may be acquired from the array based on applying the reference voltage VREF and selecting and reading out dummy sensors, and/or reading out columns based on the direct application of VREF to respective column buffers (e.g., via the CAL signal), to facilitate offset determination (e.g., sensor-to-sensor and column-to-column variances) and array calibration. The calibration data can be stored for each sensor location either just prior to a sequencing session, or at the end of the device manufacturing process. The calibration data can be stored on-chip, such as in non-volatile memory.

Additionally, in a further aspect of the present invention, a ChemFET (1) having a chamber (37) and/or channel (30) including a 1D or 2D nanomaterial and/or 3D material may be provided, such as where the 1D or 2D nanomaterial and/or 3D material is present within and/or proximate the chamber (37) and/or channel (30) and configured in such a manner so that the chamber (37) and/or channel (30) geometry may be optimized so as to maximize the ratio of channel width (W) to channel length (L). In various instances, this can be done through the use of interdigitated source and drain electrode geometries, such as in a single plane or, in other embodiments, such optimization may be achieved through the use of one or more 3D electrode structures, such as configured to at least partially or fully circumscribe the chamber (37) or well (38). For instance, as can be seen with respect to FIG. 5G, various source (22) and/or drain (24) electrodes may be configured as planar structures that are adapted so as to interact with one another in such a manner to more accurately detect the presence of a chemical reaction, e.g., the presence of a biomolecule, that occurs proximate the source (22) and drain (24) electrodes.

In various instances, the source (22) and drain electrodes (24), as set forth in FIG. 5G may be formed in such a manner so as to have an interdigitated configuration, such as where one or more of the electrodes, or a portion thereof, are adapted so as to be fit one within the other, such as where one electrode portion is configured as an impingement member, and the other is configured as a receiving member. In particular embodiments, the source (22) and drain (24) electrodes are configured so as to include pronged, fork-like appendages that are capable of being fitted one within the cavity of the other, such as between adjacent prong members. For example, as seen with respect to FIG. 5G, the source and drain electrodes may form electrode pairs, such as where one or more of the source (22) and drain (24) electrodes may have a planar and/or extended and/or interdigitated design, such as where one, e.g., the first, of the electrode pair forms one or more cavities and the other, e.g., the second, of the electrode pair forms an impingement member for insertion within the one or more of the cavities of the first electrode. Particularly, in various implementations, one or more of the electrode pairs may have a linear configuration, while the second of the pair may have a linear, curved, or curvilinear configuration. In particular embodiments, both the source (22) and drain (24) electrodes may both be curvilinear or curved.

More particularly, as can be seen with respect to FIG. 12, a FET sensor (1) having a well structure (38) is provided. Particularly, FIG. 12 depicts a cross-section of a well opening stopping on an analyte or reaction-sensitive layer (34). For instance, FIG. 12 provides a substrate, such as silicon and/or silicon dioxide substrate (10/20), where the substrate is configured so as to include a chamber, such as a chamber having a formed well (38) that may be positioned over an analyte or reaction-sensitive layer (34) that may be positioned on top of that substrate (10) and/or an associated oxide layer (20). For instance, in accordance with the methods disclosed herein, such a well (38) may be formed by any suitable method such as by a dry etching process, such as by a plasma or RIE process. In particular instances, the etching process may be selective to the well material so that the well etch can be stopped on the analyte or reaction-sensitive layer (34) without significant damage or etching of the analyte or reaction-sensitive layer (34).

Accordingly, in one aspect of the present invention a method for forming a semiconductor wafer is provided, wherein the wafer is configured as transistor on which a 1D or 2D nanomaterial layer may be positioned. The method may include providing a wafer, such as a wafer configured as or to otherwise include an integrated circuit, so as to form a semiconductor wafer. The wafer may include a substrate, such as a silicon substrate. An insulating layer may be applied to the substrate, such as via CVD of a silicon dioxide layer. A 1D or 2D nanomaterial may then be applied, hence, the method may include patterning the 1D or 2D nanomaterial layer so as to define 1D or 2D nanomaterial channels or chambers or wells, where such channels may be aligned with interconnect lines on the semiconductor wafer.

In various instances, the method may also include depositing a first dielectric layer over the channels, chambers, or wells. The method may also include opening holes or trenches in the first dielectric layer wherein some of the holes may be aligned to the channels, chambers, or wells, and some of which may be aligned to the interconnect lines. The method may also include depositing conductive material on the 1D or 2D nanomaterial layer, such as in the holes or trenches so as to create vias that contact the interconnect lines and/or the channels, chambers or wells. Additionally, the method may include depositing and patterning a set of second interconnect lines over the dielectric layer and contacting the vias. In some embodiments, the method may include depositing a second dielectric layer over the first dielectric layer and the second interconnect lines. Particularly, the method may also include patterning and opening holes or trenches in the second dielectric layer to expose portions of the second interconnect lines to be used as pads. The method may also include patterning and opening holes or trenches in the second and first dielectric layers to expose portions of the channels.

Hence, in particular embodiments, a method for forming a semiconductor wafer with transistors on which a 1D or 2D nanomaterial layer may be deposited is provided. The method may include providing a semiconductor wafer having a substrate and/or insulating layer upon which a 1D and or 2D nanomaterial layer is deposited. The method may then include patterning the 1D or 2D nanomaterial layer to define 1D or 2D nanomaterial channels, chambers, or wells, where the channels, chambers, or wells may be aligned with interconnect lines on the semiconductor wafer. The method may also include depositing an etch stop layer over or within the channels, chambers, or wells. The method may also include depositing a first dielectric layer over the etch stop layer, opening holes or trenches in the first dielectric layer, such as where some of the holes or trenches are aligned to the channels, wells, and/or chambers, and some of which are aligned to the interconnect lines.

The method may also include depositing conductive material in the holes or trenches to create vias that contact the interconnect lines and the channels. In such an instance, the method may include depositing and patterning a set of second interconnect lines over the dielectric layer and contacting the vias. The method also includes depositing a second dielectric layer over the first dielectric layer and the second interconnect lines. The method may include patterning and opening holes or trenches in the second dielectric layer to expose portions of the second interconnect lines to be used as pads. The method may additionally include patterning and opening holes or trenches in the second and first dielectric layers to expose the etch stop layer over the channels.

The method also includes opening holes or trenches in the etch stop layer to expose portions of the channels, chambers, or wells.

Particularly, another aspect of the present invention is a method for forming a semiconductor wafer with transistors on which is a 2D nanomaterial layer. The method may include patterning the 2D nanomaterial layer to define 2D nanomaterial channels, chambers, or wells, said channels, chambers, or wells being aligned with interconnect lines on the semiconductor wafer. The method also includes depositing an etch stop layer over the channels and/or depositing a first dielectric layer over the etch stop layer. Holes or trenches may be opened in the first dielectric layer and aligned to the channels, chambers, or wells and/or aligned to the interconnect lines. Conductive material may be deposited in the holes or trenches so as to create vias that may be configured to contact the interconnect lines and the channels, chambers, and/or wells. A set of second interconnect lines may be deposited and patterned over the dielectric layer so as to contact the vias. A second dielectric layer may also be deposited over the first dielectric layer and/or the second interconnect lines, and holes or trenches may be patterned to provide openings in the second dielectric layer so as to expose portions of the second interconnect lines, which may be used as pads. In such an instance, the method may also include patterning and opening holes or trenches in the second and first dielectric layers using an anisotropic etching process to expose the etch stop layer over the channels, wells, or chambers. The method may also include opening holes or trenches in the etch stop layer to expose portions of the channels, chambers, or wells.

In certain instances, a method for forming a semiconductor wafer having one or more transistors on which a 1D or 2D nanomaterial layer may be deposited, as herein described. The method may include patterning the 1D or 2D nanomaterial layer to define 2D nanomaterial channels, said channels being aligned with interconnect lines on the semiconductor wafer. The method may also include depositing an etch stop layer over the channels. The method includes depositing a first dielectric layer over the etch stop layer and/or opening holes or trenches in the first dielectric layer, where some of which may be aligned to the channels and some of which may be aligned to the interconnect lines. In various instances, the method also includes depositing conductive material in the holes or trenches to create vias that contact the interconnect lines and the channels. In such an instance, the method may include depositing and patterning a set of second interconnect lines over the dielectric layer and contacting the vias. In certain instances, a second dielectric layer may be deposited over the first dielectric layer and the second interconnect lines. In such an instance, the method may include patterning and opening holes or trenches in the second dielectric layer to expose portions of the second interconnect lines that may be used as pads. The method may include patterning and opening holes or trenches in the second and first dielectric layers, such as by using an anisotropic etching process to expose the etch stop layer over the channels.

Accordingly, in particular instances, the semiconductor structure may include a plurality of 1D or 2D nanomaterial channels, chambers, or wells composed of a 1D or 2D nanomaterial, an etch stop layer, a plurality interconnect lines on a semiconductor wafer, a first dielectric layer comprising a plurality of holes or trenches, a conductive material, a second plurality of interconnect lines, and a second dielectric layer having a plurality of holes or trenches. And in some embodiments, the semiconductor structure comprises a plurality of 1D or 2D nanomaterial channels, chambers, or wells composed of a 1D or 2D nanomaterial, a plurality interconnect lines on a semiconductor wafer, a first dielectric layer comprising a plurality of holes or trenches, a conductive material, a second plurality of interconnect lines, and a second dielectric layer having a plurality of holes or trenches.

Further, in various instances, the ChemFET (1) may optionally include one or more of an ion-selective permeable membrane (40), a charge trap screening layer (42), such as hexagonal boron nitride (hBN) or HMDS, an ion getter (41) such as phosphorous-silicate glass (PSG) and/or a reference electrode (66). For instance, an ion-selective membrane (40) may be included, such as where the membrane preferentially allows ions of interest (68) to pass through the membrane (40), so as to interact with the channel (30), as compared to ions not of interest (69). Likewise, a charge trap screening material (42), e.g., an HMDS or hBN, may be included and configured to manage the interaction of the channel (30) with an underlying oxide layer (20). In similar fashion, an ion getter (41), such as PSG, may be deposited on or near the channel (30), such as on the chamber (37) sidewalls (39) in order to trap or sequester ions that would interfere with the detection and analysis of ions of interest interacting with the ChemFET (1). And, in various embodiments, the ChemFET (1) may be configured to include a gate, such as a solution gate, and may include a reference electrode (66) applying a gate voltage to the solution. In some embodiments, a back gate region may also be included. Such a back gate can be implemented either as a global back gate (80), i.e. the same backgate voltage is applied to the semiconductor substrate (10) of the ChemFET (1), or as a local backgate (82), wherein there are a plurality of backgate electrodes (82), e.g. one backgate electrode (82) is individually associated with each ChemFET (1) channel (30), the backgate electrode (82) formed in an interconnect layer of the ChemFET (1) and used to apply a local backgate voltage to the channel (30) to which it is associated. Furthermore by applying both a solution gate and a backgate in concert, i.e. as a dual gate, the sensitivity of the ChemFET can be extended past the Nernst limit of 59 mV/pH.

In particular instances, the conductive source and the conductive drain of the ChemFET may include a metal material, such as a copper material, e.g., a damascene copper, an aluminum material, a platinum material, a gold material, and the like. For instance, the conductive source and the conductive drain may be embedded in a dielectric and/or an insulator material, such as an oxide layer, which oxide layer may be positioned over a substrate layer. In particular embodiments, the source and drain may be configured so as to be planar with a top surface of the insulator, and in other embodiments, as described herein above, may be configured so as to extend above the insulator material layer in which they are embedded.

Analyte or Reaction-Sensitive Layer

In certain instances, a further insulating layer, e.g., an oxide layer, may be included and positioned above the first dielectric layer and/or the channel nanomaterial layer. Particularly, the channel nanomaterial may be at least partially covered in a layer that is comprised of an analyte or reaction-sensitive material, such as an ion sensitive oxide material, e.g., a material having a high intrinsic buffer capacity, which may have a thickness of 50 nanometers or less. In one embodiment, the second oxide layer may itself include two or more oxide layers, wherein the oxide layers may be comprised of an aluminum oxide, a silicon dioxide, a hafnium dioxide, hafnium silicate, zirconium silicate, zirconium dioxide, lanthanum oxide, titanium oxide, tantalum oxide, iron oxide, or yttrium oxide.

Passivation and Well Structure

As described herein, in various embodiments, the ChemFET may include a well structure or chamber that is positioned on a portion of an exterior surface of the passivation, e.g., oxide, layer and may be positioned over the channel region and/or channel nanomaterial. For instance, the well structure may be configured so as to define an opening allowing for direct contact with the channel and/or analyte or reaction-sensitive layers, and in some instances the well structure may itself be composed of an insulator material. For example, the passivation material of the well structure may be composed of an inorganic or organic material, such as where the inorganic material may be a silicon oxide, a silicon nitride, a silicon oxynitride, a silicon carbide or other metal oxide, carbide or nitride, and the organic material may be a polymer, polyimide, BCB, PBO or other like material. The ChemFET, e.g., a well or chamber thereof, may be configured for chemical or biological material detection, chemical reaction detection or biologic activity detection, such as where the biological material may be one or more of a nucleic acid, such as DNA or RNA, a protein, a carbohydrate, a lipid, a cell, a virus particle, an antibody, and the like.

In another aspect, a biosensor may be provided. In such an instance, the biosensor may include at least one ChemFET that includes a well structure, as described above, where the well structure is positioned over a portion of an exterior surface of an insulation layer, e.g., a dielectric or oxide layer, of the ChemFET(s). In certain instances, the well structure defines an opening that is configured for receiving and/or retaining reactants thereby allowing for various interactions of compounds produced in a chemical reaction within the well to occur. Accordingly, in various instances, the well may be configured as a solution well and/or may include an electrode, such as a reference electrode, and/or may otherwise be configured as a solution gate. In particular instances, the well structure may be bounded by the first dielectric or oxide layer, or may be bounded by the channel nanomaterial layer, and/or a secondary oxide layer.

Detecting an Analyte or Reaction through a Shift in an I–V Curve

In particular embodiments, the biosensor may include a processor, such as proximate the substrate, which processor may be in electrical communication with the ChemFET(s). In such an instance, the processor may be configured to perform one or more of: (i) generating a reference Id–Vgs curve, such as corresponding to the conductance of the ChemFET channel(s), e.g., in the absence of a chemical reaction occurring in the well and/or in proximity to the channel; and/or (ii) generating a chemical sensing $I_d$–$V_{gs}$ curve in response to a chemical reaction occurring in the well and/or in proximity to the channel; and/or (iii) determining a difference, if any, between the reference $I_d$–$V_{gs}$ curve and the chemical sensing $I_d$–$V_{gs}$ curve. Particularly for ambipolar channel nanomaterials such as graphene, the difference between the reference Id–Vgs curve and the chemical sensing $I_d$–$V_{gs}$ curve may be a shift in a Vgs value of a minimum point of the chemical sensing $I_d$–$V_{gs}$ curve relative to a $V_{gs}$ value of a minimum point of the reference $I_d$–$V_{gs}$ curve.

Specifically, in one instance, the difference between the reference $I_d$–$V_{gs}$ curve and the chemical sensing $I_d$–$V_{gs}$ curve may be in a shift in an $I_d$ value of a minimum point of the chemical sensing $I_d$–$V_{gs}$ curve relative to an Id value of a minimum point of the reference $I_d$–$V_{gs}$ curve. Additionally, the difference between the reference $I_d$–$V_{gs}$ curve and the chemical sensing Id–Vgs curve may be a shift in a final $I_d$ value of the chemical sensing $I_d$–$V_{gs}$ curve relative to a final $I_d$ value of the reference $I_d$–$V_{gs}$ curve. Further, the difference between the reference $I_d$–$V_{gs}$ curve and the chemical sensing $I_d$–$V_{gs}$ curve may be a shift in a parameter of the reference $I_d$–$V_{gs}$ curve with a corresponding parameter of the chemical sensing $I_d$–$V_{gs}$ curve, such as where the parameter is a slope, optionally a steepest slope, of the reference Id–Vgs g and chemical sensing $I_d$–$V_{gs}$ curves.

In some instances the accuracy or sensitivity of the ChemFET detection or analysis maybe be improved by combining one or more of the previously described techniques.

As indicated, in various instances, an ion-selective permeable membrane may be provided, such as where the ion-selective permeable membrane may be positioned within a chamber of a well and/or positioned above or otherwise proximate to the channel. In certain instances, the ion-selective permeable membrane may include a polymer, such as composed of a perfluorosulphonic material, a perfluorocarboxylic material, PEEK, PBI, Nafion, and PTFE material. Alternatively, the ion-selective permeable membrane may include an inorganic material, such as an oxide or a glass. In some instances, an additional 2D transistor material may be included, such as graphene that need not be electrically connected to the channel nanomaterial.

Further, in certain embodiments, the ion-selective permeable membrane may be applied by a spin-coating, anodization, PVD, sol gel method, and the like. Furthermore, in certain instances, the ChemFET may include an ion getter material, such as where the ion getter material preferentially sequesters ion species that are not relevant to a particular chemical reaction to be detected, and optionally reducing noise in signals from the ChemFET, such as where the ion getter material may placed over a dielectric layer forming the well or chamber and/or in proximity to the chamber opening and/or channel.

The invention will be better understood by reference to the following Examples, which are intended to merely illustrate certain preferred embodiments for practicing some aspects of the invention. The scope of the invention is not to be considered limited thereto.

EXAMPLES

Example 1

Manufacture of a 2D ChemFET

In some embodiments manufacturing a well for a 2D nanomaterial FET involves an organic passivation layer or an inorganic passivation layer.

For a well with an inorganic passivation layer, PECVD oxide, LPCVD Oxide, or LPCVD Nitride are preferred, at least for the nitride, as the film has a lower stress and less tendency to crack. Most of the well depth is created by a photoresist pattern process and a plasma etch or RIE. The final amount of well depth can be created by a wet etch process, since in many cases the channel nanomaterial, such as graphene, may be easily damaged or destroyed by a plasma or RIE etch process but is insensitive to a wet etch process. An alternative is to deposit a thin SiN layer, then a thick $SiO_2$ layer. The $SiO_2$ is patterned and etched with a highly selective etch, in a preferred embodiment, SiN acts as an ESL. Then a final wet etch process is performed on the SiN from the bottom of the well. Yet another option is to use a low temperature TEOS oxide, which is a denser, less porous oxide for the passivation layer. It prevents uptake of contaminants or reaction materials in the oxide that may affect results.

There are various methods for forming the oxide or other passivation layer (35) and forming a well structure (38) over the graphene layer. One such process for forming the well of controlled depth is to use a timed plasma etch or an endpoint detection to stop at or near the graphene layer or at or near the analyte or reaction-sensitive layer (34) if it is present, then finish with a wet etch process to remove the last of the passivation material over the channel area. An alternative method is to first deposit a thin SiN layer or other ESL (74) prior to passivation deposition. FIG. 37A depicts the ChemFET before the deposition of the ESL and includes an analyte or reaction-sensitive layer (34) over the graphene channel material (30) and FIG. 37B depicts the ChemFET after the deposition of the ESL (74). FIG. 37C shows the ChemFET after the deposition of a thick SiO2 passivation layer (35), and the subsequent patterning and etching of the SiO2 layer using a plasma anisotropic etch—with the etching highly selective for the passivation layer (35) versus the ESL (74) resulting in the etch process stopping on the ESL (74). In the embodiment depicted here, SiN acts as an ESL (74). Then, the final step involves wet etching the SiN layer or ESL (74) from the bottom of the well with an etchant that is highly selective to the ESL used and not damaging to either the graphene layer (30) or the analyte or reaction-sensitive layer (34), if there is one present, as shown in FIG. 37D.

For organic wells, one possible material is a photoimageable organic material. In such embodiments, since organics tend to stick to 1D or 2D nanomaterials, such as graphene, and are difficult to remove (and reduce the nanomaterial carrier mobility or dope the nanomaterial, such as graphene) it is preferred to first put on a thin inorganic layer, e.g., by Physical Vapor Deposition (PVD) or Chemical Vapor Deposition (CVD) or Atomic Layer Deposition (ALD) of an oxide or nitride or carbide. An easier and lower cost option is to spin on a thin layer of Spin On Glass (SOG), after which the organic material (e.g. polyimide or BCB) to form the organic layer is spun on, followed by imaging, developing, and curing. The protective oxide or nitride or carbide is then wet etched (use of dry etching may destroy or degrade the graphene component) after the organic layer has been patterned.

In an alternate embodiment with inorganic passivation layers, shown in FIGS. 35A to 35C, silicon oxide (20) is etched, preferably with a plasma or RIE dry etch process, to form a well below a top copper layer and the starting surface of the passivation (21). The well is positioned between a source (22) and drain (24) electrode prior to graphene transfer as shown in FIG. 35A. Next, the graphene layer (30) is placed on the wafer and conforms somewhat to the well profile (37) (see FIG. 35B). Thereafter, the graphene layer is patterned to the desired size and configuration for the channel (30) and may be coated with an analyte or reaction sensitive sensing layer (34).

As shown in FIGS. 36A-D, nanoimprinting of polymer material such as SU8 epoxide photoresist passivation (35) (or another suitable polymer material) may be used for ChemFET well formation. As shown in FIG. 36A, the mold (72) is aligned with the passivation polymer (35) and ChemFET channels (30). In FIG. 36B the mold (72) is imprinted into the passivation polymer (35). In FIG. 36C the mold (72) is removed, exposing the wells (38) formed by the imprinting process. In FIG. 36D any residual resist (35) or residual polymer (35) at the bottom of the well (38) is removed.

Preferred methods for manufacturing a well formation for a 2D nanomaterial FET includes depositing a passivation layer (35) on a channel (30) of a 2D nanomaterial FET of a ChemFET structure. Such methods also preferably include etching through the majority of the passivation layer (35) with a first etching method to create a majority of a well (38) disposed over the channel (30). These methods can also include a second etching of the remaining passivation layer (35) over the channel (30) to expose the channel (30) or an analyte or reaction-sensitive layer (34) within the well (38).

The 2D nanomaterial is selected from any suitable material, including graphene, silicene, molybdenum disulfide, black phosphorous (phosphorene), borophene, tungsten disulfide, boron nitride, tungsten diselenide, stanene, germanane, nickel HITP, and/or metal dichalcogenides or Mxenes such as Ti2C, (Ti0.5,Nb0.5), V2C, Nb2C, Ti3C2, Ti3CN, Nb4C3, or Ta4C3.

The semiconductor device structure is preferably based on FET, BJT, HBT, or any other transistor technology.

The semiconductor device structure is preferably based on CMOS, BiCMOS, bipolar, or other semiconductor fabrication technology.

In preferred embodiments, the passivation layer (35) is comprised of an inorganic material, such as an oxide, a nitride, a carbide, an oxy-nitride, a carbon-doped oxide or a fluorine-doped oxide material. In other embodiments, the passivation layer is composed of an organic material, such as a polymer, such as polyimide, BCB or PBO. In yet other embodiments, the passivation layer is composed of both inorganic and organic materials.

The passivation layer is preferably deposited by a CVD, PECVD, PVD, or ALD process.

The first etching method is preferably a plasma or laser etching method. A preferred plasma etching method is an RIE, HDP, ICP, or ECR method. The first etching method is performed through a mask material that is patterned to shield parts of the passivation dielectric layer from the first etching method while having openings that expose other parts of the passivation dielectric layer to the first etching method, such openings generally aligned with ChemFET sensor locations. A preferred mask material is a photoresist or a hard mask material. Alternatively, the first etching method is predominantly an anisotropic etching method, and the second etching method is predominantly an isotropic etching method.

Preferably, the second etching method is a wet or gaseous etching method, such as an electrochemical or chemical etching method. An example of a chemical etching method is an acid, an aqueous acid solution or a buffered acid solution. Preferably, the second etching method etches the passivation layer without substantially etching or affecting the channel nanomaterial.

In one exemplary preferred embodiment, the passivation layer is comprised of a first thin layer of material forming an etch stop layer (ESL) over the channel and a second thicker layer of passivation material over the ESL. The first etching method has high selectivity for etching the second thicker layer of passivation material as compared to the first thin layer of ESL material. The first thin layer of ESL material is preferably 0.1 nm to 100 nm thick and the second thicker layer of passivation material is preferably 0.1 um to 10 um thick. The first thin layer of ESL material is preferably comprised of a silicon nitride or a silicon carbide. The first layer of thin ESL material may be comprised of a non-stoichiometric material. The first etching method etches through the second thicker layer of passivation material and stops on the first thin layer of ESL material.

Preferably, the first etching method etches through a controlled depth in the passivation material layer wherein the control is provided by a time of etching in conjunction with the rate of etching. Alternatively, control can be provided by an end point detection.

Preferably, the shape of the well formation when viewed from the top is a round or polygon shape.

Preferably, the largest width of the well formation when viewed from the top is 0.1 um to 10 um.

Preferably, an array of two or more well formations are formed. The ratio of the pitch of two well formations to the largest width of the well formations when viewed from the top is greater than 1 and less than 10. The variation of the largest widths of the well formations when viewed from the top in an array designed to have well formations with the same largest widths is less than 10%.

Alternatively, the shape of the well formation is chosen with respect to consideration of fluid dynamics of a fluid flowing over or into the well formation. The consideration of fluid dynamics includes transport of reagents or particles or microbeads over or into the well formation.

Other embodiments concern methods for manufacturing a well formation for a 1D or 2D nanomaterial FET with an organic passivation layer. These methods typically include depositing an organic passivation layer on a channel of a 1D or 2D nanomaterial FET of a semiconductor device structure. Such methods also include patterning the organic passivation layer to create well formation locations over the channels. The methods also include removing the passivation layer over each channel to expose the channel within the well formation.

The patterning of an organic passivation layer is preferably by a printing method. The passivation layer is comprised of a photosensitive material and the patterning is by a photolithographic method. The removing is preferably by a developing method.

The organic layer is preferably a polymer such as polyimide, BCB, photoresist, PBO or parylene.

In such embodiments, the removing is preferably by an etching or a developing method such as a wet or gaseous etching or developing method. An example of wet or gaseous etching or developing method is an electrochemical or chemical etching or developing method. The chemical etching or developing method comprises a base material, a photoresist developer, KOH, TMAH, NaOH or other material suitable for etching or developing the target passivation material.

In one example, the removing method is predominantly an isotropic etching or developing method. In another example, the removing method is predominantly an anisotropic etching or developing method. The removing method etches or develops the passivation layer without substantially etching or affecting the channel nanomaterial.

The passivation layer is comprised of a first thin layer of material forming an etch or developing stop layer over the channel and a second thicker layer of material over the etch stop layer. The first etching or developing method has high selectivity for etching or developing the second thicker layer of material as compared to the first thin layer of material.

Example 2

Manufacture of a GAA ChemFET

A preferred representative method for manufacturing a FET for chemical and biological analysis is shown in FIGS. 10A-10C. The method includes depositing a graphene channel on an exposed metal layer of an integrated circuit structure (see FIG. 10A). The integrated circuit structure comprises a semiconductor substrate, a dielectric layer, and the metal layer. The method also includes utilizing a patterned material to expose a portion of a channel area and a plurality of adjacent areas. The method also includes etching the dielectric material starting with the adjacent areas thereby exposing a trench under the channel and exposing the metal in the channel area. The method also includes etching the metal from underneath the graphene channel to create a ChemFET.

This method uses a full CMOS wafer with top copper electrodes exposed by CMP. In this case there is also copper in the channel area (26). A graphene layer (30) is deposited (e.g., via PECVD or another suitable method) on all of the exposed copper areas. Then a pattern photoresist process is performed to pattern the channel areas. A further pholithographic process is used to protect most of the wafer surface but to pattern and expose some areas near the central portions of the channel and extending somewhat farther than the channel width, i.e. exposing the silicon oxide (20) surface (21) nearby the channel (30) or to the side of the channel. Then SiO2 is etched from the sides of the channel to expose a trench under the channel and expose the copper in the central channel area (26). Then, the copper is wet-etched from underneath the graphene channel.

Advantages of this method include: no graphene release and layer transfer. The metal can be any suitable material (or combinations of material) for graphene growth, for example, Ni, Cu, Ru or Pt. The graphene layer can be deposited by CVD, PECVD, or any suitable process. Since semiconductor transistors have already been formed in the IC wafer the graphene deposition process must be limited to about 400 C or less so as not to damage the semiconductor, e.g. CMOS, transistors. The dielectric material can be an oxide, nitride, carbide, or low K dielectric. The dielectric layer can be etched by a dry or wet, preferably predominantly anisotropic, etching process, although the selectivity of the etching process is targeted for the dielectric or metal constituents as compared to the graphene (or any functional layer placed over the graphene).

The patterned material is preferably a photoresist. The photoresist is preferably patterned using a photolithographic process.

The semiconductor substrate is preferably a Si, SiGe, or a III-V material.

The integrated circuit is preferably formed using a CMOS, BiCMOS, Bipolar, or other fabrication technology.

The semiconductor integrated circuit is preferably based on FET, BJT, HBT, or other transistor technology.

Etching the dielectric preferably comprises a wet etching process, since dry etching, e.g. plasma, processes are known to damage graphene.

Etching the dielectric preferably comprises a wet or gaseous etching method. The wet or gaseous etching method is preferably an electrochemical or chemical etching method. The chemical etching method preferably comprises an acid, an aqueous acid solution or a buffered acid solution.

Etching the dielectric preferably comprises predominantly an isotropic etching method. Etching the dielectric alternatively etches the dielectric without substantially etching or affecting the channel nanomaterial.

Etching the metal preferably comprises a wet or gaseous etching method, wherein the wet or gaseous etching method is an electrochemical or chemical etching method, and wherein the chemical etching method comprises an acid, an aqueous acid solution or a buffered acid solution.

Etching the metal alternatively comprises predominantly an isotropic etching method.

Etching the metal alternatively etches the metal without substantially etching or affecting the channel nanomaterial.

The dielectric layer is preferably composed of a first thin layer of material forming an ESL under the channel to limit the extent of the dielectric etching. The dielectric etching has high selectivity for etching the dielectric material as compared to the ESL. The first thin layer of material is preferably 0.1 nm to 100 nm thick. The first thin layer of material is preferably composed of a silicon nitride, or a silicon carbide. The first layer of thin material is alternatively composed of a non-stoichiometric material.

Alternatively the ESL may be configured in a tub-like configuration to more fully restrict the etching of the dielectric material.

One or more functional layers are preferably deposited over the graphene channel prior to etching the dielectric. Alternatively, one or more functional layers are deposited over the graphene channel subsequent to etching the dielectric. Etching the dielectric comprises a wet or gaseous etching method, wherein the wet or gaseous etching method is an electrochemical or chemical etching method, and wherein the chemical etching method comprises an acid, an aqueous acid solution or a buffered acid solution. Etching the dielectric preferably comprises predominantly an isotropic etching method. Etching the dielectric etches the dielectric without substantially etching or affecting the channel nanomaterial and without substantially etching or affecting the functional material. Etching the metal comprises a wet or gaseous etching method, wherein the wet or gaseous etching method is an electrochemical or chemical etching method, and wherein the chemical etching method comprises an acid, an aqueous acid solution or a buffered acid solution.

Alternatively, etching the metal comprises predominantly an isotropic etching method. Alternatively, etching the metal etches the metal without substantially etching or affecting the channel nanomaterial and without substantially etching or affecting the functional material.

Example 3

Nanomaterial Layer Transfer by Fusion Bonding

FIG. 21 shows a flow chart of a general method of forming a semiconductor wafer with transistors having 2D nanomaterial layers. A key process step is the transfer of the 2D nanomaterial, such as graphene, from a growth substrate to the target substrate, such as a ROIC wafer. Discussed elsewhere are a variety of different transfer techniques that generally use some release method to release the graphene from its growth substrate and a temporary bonding method, such as adhesive bonding of the graphene to a carrier and then Van der Waals bonding of the graphene to the target wafer with a subsequent second release step, such as by thermal, laser or UV energy to release the adhesive and carrier wafer from the graphene. These transfer processes that require temporary bonding and direct or indirect contact to the graphene layer are not optimal as they open many opportunities for defects in the graphene. A preferred approach uses direct transfer fusion bonding of oxide, such as silicon dioxide layers, as illustrated in FIGS. 23A-23F.

FIGS. 23A-23F visually show the steps of direct bond transfer via fusion bonding. In the direct transfer fusion bonding process, the 2D nanomaterial (530), e.g., graphene, is encapsulated with SiO2 (520) while it is still on the growth wafer and then the growth wafer may be fusion bonded to a properly prepared CMOS ROIC wafer. Platinum, ruthenium, silver, copper or another suitable metal may be used for growing the 2D nanomaterial (530) on the growth substrate. A release or separation mechanism (e.g., bubble process) is used to separate the 2D nanomaterial (530) from the platinum or other metal (528). The growth wafer may be a silicon, sapphire (Al2O3), or other suitable substrate capable of sustaining high temperatures with low thermal expansion.

In FIG. 23A, the 2D nanomaterial (530), preferably graphene, is grown on a growth platform comprised of a platinum layer (528) on a growth wafer (510).

In FIG. 23B, a cover material of silicon oxide is deposited on the 2D nanomaterial and then the oxide is polished or CMP'ed to provide a very flat and smooth surface on the silicon oxide.

In FIG. 23C, the growth platform is flipped.

In FIG. 23D, a ROIC wafer is prepared by polishing or CMP'ing a topmost silicon oxide layer to provide a very flat and smooth surface on the silicon oxide. The ROIC wafer and the growth platform are aligned for bonding.

In FIG. 23E, the silicon oxide cover material (520) is bonded to the ROIC wafer topmost silicon oxide layer (520) through a fusion bonding process.

In FIG. 23F, the growth substrate is separated from the ROIC wafer, leaving the 2D nanomaterial (530), preferably graphene, on the ROIC wafer, i.e. the process effectively transfers the 2D nanomaterial from the growth substrate to the ROIC wafer via fusion bonding. In the direct transfer fusion bonding process, the 2D nanomaterial, preferably graphene, is encapsulated with SiO2 effectively protecting it from handling and process damage, and then the growth wafer is fusion-bonded to a CMOS ROIC wafer.

Platinum, copper, or another suitable metal is used for growing the 2D nanomaterial (530). A release or separation process (e.g., a bubble process) is used to separate the 2D nanomaterial (530) from the platinum or other metal (528). The growth wafer is preferably silicon, sapphire (Al2O3), or another suitable substrate capable of sustaining high temperatures with low thermal expansion. Alternatively, a wafer format is replaced with a panel or sheet. Various encapsulating materials are utilized such as SiO2, Si, Si3N4.

FIGS. 24A-24H show a variation the the fusion bonding process, in this case using the process to first coat the graphene with an analyte or reaction-sensitive layer, such as an ion sensitive oxide layer, and then bonding this ion sensitive oxide layer to a carrier wafer. Releasing the graphene from the growth substrate and fusion bonding are similar to the previously described process, but the resultant final structure is different since the ion sensitive oxide layer is integral to the final layer stack—thus both the graphene layer and the ion sensitive oxide layer are transferred by fusion bonding using this process.

In FIG. 24A, the 2D nanomaterial (530), preferably graphene, is grown on a growth platform comprised of a platinum layer (528) on a growth wafer (510).

In FIG. 24B, an ion sensitive oxide material is deposited on the 2D nanomaterial.

In FIG. 24C the ion sensitive oxide is releasably joined to a carrier wafer.

In FIG. 24D the growth substrate has been removed (e.g. by a bubble release process or other means) exposing the graphene.

In FIG. 24E, a cover material of silicon oxide is deposited on the 2D nanomaterial and then the oxide is polished or CMP'ed to provide a very flat and smooth surface on the silicon oxide.

In FIG. 24F, the carrier platform is flipped and aligned with a previously prepared ROIC wafer (e.g. CMP and/or polished SiO2 surface).

In FIG. 24G, the silicon oxide cover material (520) is bonded to the ROIC wafer topmost silicon oxide layer (520) through a fusion bonding process.

In FIG. 24H, the carrier is separated from the ROIC wafer, leaving the 2D nanomaterial (530), preferably graphene, covered with the ion sensitive layer (on the ROIC wafer, i.e. the process effectively transfers the 2D nanomaterial from the growth substrate to the ROIC wafer via fusion bonding. In the direct transfer fusion bonding process, the 2D nanomaterial, preferably graphene, is encapsulated with SiO2 effectively protecting it from handling and process damage, and then the growth wafer is fusion-bonded to a CMOS ROIC wafer.

FIG. 25 shows a wafer undergoing a bubble release process whereby generated gas bubbles are intended to gently force the graphene layer from its growth substrate. In practice this may be difficult to do since it is problematic to contact the thin film used on the growth substrate (it is both thin and covered by graphene). To ba make electrically contacting the growth wafer easier a TSV 43 can bring an electrical path from the thin film on the growth side of the wafer trough the wafer to a conductive layer on the backside of the wafer. It is easy to access the backside of the wafer for electrical contact Example 4

Improved Signal, Reduced Noise ChemFET

A preferred embodiment of the invention is shown in FIG. 8. The invention provides several enhancements to a graphene-based ChemFET sensor. In an enhancement embodiment, the ChemFET is fabricated on an integrated circuit wafer and comprises a first structure, a channel (30) and a second structure. A processor (not shown) is either included in the ChemFET sensor IC chip, e.g. fabricated from CMOS transistors, or is coupled to the ChemFET IC chip. The first structure comprises a conductive source (22) and a conductive drain (24). The channel (30) extends from the conductive source to the conductive drain, with the channel comprised of a one-dimensional nanomaterial or a two-dimensional nanomaterial. The processor is configured to generate a reference $I_d$–$V_{gs}$ curve and a chemical sensing $I_d$–$V_{gs}$ curve in response to a chemical reaction, and analyte or biologic activity that is to be detected occurring over or near the ChemFET. The processor is also configured to determine a difference between the reference and chemical sensing Id–Vgs curve (or a parameter, e.g., slope, associated with such curves). The second structure enhances the ability of the processor to determine the difference. The second structure may be an ion-selective permeable layer or an ion getter or a charge trap screening layer or a local backgate, each of which will be described herein.

One enhancement embodiment is an ion-selective permeable membrane (40) over the channel (30) and analyte or reaction sensitive layer (34), if present, that only allows ions of interest, such as hydrogen ions (68), to travel through the membrane. One preferred ion-permeable material is an inorganic material such as an oxide. An alternative material is a separate layer of graphene that is note electrically connected to the FET. Another alternative material is a polymer such as Nafion, PEEK, a perfluorosulphonic or a perfluorocarboxylic material.

Another alternative enhancement is a charge trap screening layer (42) under the graphene channel (30) that screens the graphene channel (30) from charges trapped in the dielectric layer (20), which is typically a silicon dioxide layer. The charge trap screening layer (42) may be formed of a polymer, such as HMDS, other siloxane or parylene. The charge trap screening layer (42) may also be formed of an inorganic material, such as aluminum oxide or most preferably hexagonal boron nitride (hBN). hBN has a lattice parameter very similar to graphene's lattice parameter (about 2.5 angstroms) and is also very smooth, both of which factors attenuate any charge trapping between the graphene channel (30) and the charge trap screening layer (42) and lead to higher carrier mobility in the channel (30). The thickness of the charge trap screening layer (42) may be 100 nm, or 75 nm, or 50 nm or less.

Yet another alternative enhancement is a getter material (41) elsewhere on the ChemFET sensor IC chip (1) or in the package to attract and sequester unwanted ions so that their interaction with the sensor can be reduced or eliminated and thus the determination of the sensor reaction to the desired ion is improved.

The second structure is preferably comprised of an ion-selective permeable membrane (40). The ion-selective permeable membrane allows ions of interest, e.g., H+ ions, to pass through the membrane while blocking the passage of other ion species. The action of passing only ions of interest through the membrane enhances the ability of the processor to determine the difference between the reference and chemical sensing Id–Vgs curves (or a parameter, e.g., slope, associated with such curves) and thus enhances the ability of the processor to detect the desired chemical reaction, analyte or biologic activity (which is responsible for liberating the ion species of interest for subsequent detection).

The ion-selective permeable membrane (40) is preferably comprised of a polymer such as perfluorosulphonic material, a perfluorocarboxylic material, PEEK, PBI, Nafion or PTFE, although the membrane type will vary depending upon the chemical reaction and ion species desired to be detected.

Alternatively, the ion-selective permeable membrane (40) is composed of an inorganic material such as an oxide or a glass.

The ion-selective permeable membrane is preferably applied by a spin-coating, anodization, PVD, or sol gel method, which method may vary depending upon the chemical composition of the membrane to be applied.

Alternatively, the ion-selective permeable membrane (40) can be composed of a 2D nanomaterial, such as graphene, that is not electrically connected to the channel (30).

In one embodiment, an ion-selective permeable membrane (40) can be positioned over an ion sensitive layer (34) that is over the channel (30).

In an alternative embodiment, the second structure is composed of an ion getter material (41), wherein the ion getter material (41) traps or sequesters ions (69) that are not relevant to the chemical reaction to be determined and thus reduces unwanted signal or noise effects of the ChemFET. The action of trapping ions (69) that are not relevant to the chemical reaction to be determined enhances the ability of the processor to determine the difference between the reference $I_d$-$V_{gs}$ and chemical sensing $I_d$-$V_{gs}$ curves (or a parameter, e.g., slope, associated with such curves) because there are fewer interfering ions (69) and thus enhances the ability of the processor to detect the desired chemical reaction. Preferably, the ion getter material (41) is arranged proximate to the channel (30), such as on the sidewall (39a or 39b) of the well (38), so that the action of "getting" the unwanted ions improves the detection capability of the ChemFET of the invention. Alternatively, the ion getter material (41) can be placed over a dielectric layer in proximity to one or more of the channels. The ion getter material (41) may be a metal such as a barium or zirconium alloy, or preferably is a glass such as phosphorous-silicate glass (PSG), argon-silicate glass or arsenic-silicate glass. These getter materials may be especially adept at trapping sodium ions, which may be present due to the buffers used in the fluid. A preferred ion getter material (41) is a 4 to 8% by weight phosphorous-silicate glass (PSG) that is deposited by a CVD process to a thickness of about 10 to 30 nm.

In another embodiment, the second structure is comprised of a material to manage the interaction of the 2D transistor channel (30) with an underlying oxide dielectric layer (20)—i.e. the second structure is a charge trap screening layer (42). In such an embodiment, the material may be comprised of a polymer such as HMDS, a siloxane or parylene or comprised of an inorganic material such as aluminum oxide or preferably hexagonal boron nitride (hBN). If an hBN layer is used its thickness may be 100 nm, or 50 nm or less.

In another embodiment, the second structure is comprised of a 2D transistor channel (30) with an ion-sensitive material (34) over the channel (30), wherein the material (34) is sensitive to ionic species that are different from the ions associated with the chemical reaction to be detected, and wherein the action of sensing ions that are different from the ions associated with the chemical reaction to be detected assists in filtering unwanted noise from signals sent from the biosensor.

A further enhancement embodiment is a backgate for the ChemFET (1). In this embodiment a dual gate configuration is preferred wherein the solution gate applies a gate voltage from the top or upper side of the channel (i.e. through a gate or reference electrode (66) in communication with the fluid (64) that fills the chamber (37), which fluid (64) is in contact with or proximate to the channel (30) and a backgate that applies a gate voltage from the bottom or backside of the channel. Dual-gate ChemFETs (1) have higher sensitivity than just solution-gated or just backgated ChemFETs (1), even in some cases exceeding the Nernst limit of 59 mV/pH. In one backgate embodiment the backgate is a global backgate, meaning that one backgate voltage is applied globally to all the ChemFETs (1) on the ChemFET sensor IC chip (50), such as applying a voltage to the conductive base structure (10). In a preferred embodiment there is a local backgate (82) associated with the channel (30) of each ChemFET (1). A local backgate (82) may have a voltage that is tailored for the ChemFET to which it is applied, so for example multiple ChemFETs may have multiple different local backgate (82) voltages applied to them depending on the characteristics and circumstances of each individual ChemFET (1). The local backgate (82) will typically be implemented in a portion of an interconnect layer and is comprised of interconnect material 25, such as polysilicon, aluminum or copper or other metal. The local backgate will be of approximately similar area and shape to the outline of the channel to which it applies.

Example 5

Analysis of $I_d$-$V_{gs}$ Curves

As described above, the ChemFETs of the invention will find various applications, including as biosensors. In such biosensing applications, a ChemFET-based biosensor senses a desired reaction that can be detected, for example, by using a processor to detect an alteration, e.g., a shift, in an I–V curve, for example, an $I_d$-$V_{gs}$ curve that examines the relationship between the drain current $I_d$ and the voltage between the gate and the source Vgs, or a parameter of an $I_d$-$V_{gs}$ curve, e.g., the curve's slope, corresponding to the ChemFET. In such applications, a processor functionally associated with the ChemFET preferably compares a reference I–V curve for the well (or other capture region or structure) and an I–V curve generated in connection with a chemical reaction in the well (or other capture region or structure associated with the ChemFET). If the processor detects a difference between the reference and reaction-associated curves that exceeds a predetermined threshold, a positive result can be indicated. Examples of such curves are presented in FIGS. 13B-13I, while FIG. 13A illustrates various components and parameters of an $I_d$-$V_{gs}$ curve In an alternative embodiment, the difference between the reference $I_d$-$V_{gs}$ curve and the chemical sensing $I_d$-$V_{gs}$ curve is a shift in an Ion value of the chemical sensing $I_d$-$V_{gs}$ curve relative to an Ion value of the reference $I_d$-$V_{gs}$ curve. The $I_{on}$ shift can be evaluated in the n-type or p-type region of the curve if the curve is generated by an ambipolar nanomaterial such as graphene. See FIGS. 13E, 13F.

In an alternative embodiment, the difference between the reference $I_d$-$V_{gs}$ curve and the chemical sensing $I_d$-$V_{gs}$ curve is a shift in an Ion value of the chemical sensing $I_d$-$V_{gs}$ curve relative to an Ioff value of the reference $I_d$-$V_{gs}$ curve. See FIG. 13G.

In an alternative embodiment, the difference between the reference $I_d$-$V_{gs}$ curve and the chemical sensing $I_d$-$V_{gs}$ curve is an overall change in shape of the chemical sensing $I_d$-$V_{gs}$ curve relative to an overall change in shape of the reference $I_d$-$V_{gs}$ curve. See FIG. 13D.

In an alternative embodiment, the difference between the reference $I_d$-$V_{gs}$ curve and the chemical sensing $I_d$-$V_{gs}$ curve is a change in the slope of the chemical sensing $I_d$-$V_{gs}$ curve relative to a change in the slope of the reference $I_d$-$V_{gs}$ curve. The change in slope can be evaluated in the n-type or p-type region of the curve if the curve is generated by an ambipolar nanomaterial such as graphene. See FIG. 13I.

The $I_{on}$ values may be taken from the p-type section or the n-type section of an $I_d$-$V_{gs}$ curve. In a preferred embodiment, the slopes of the reference and test curves are measured on the steepest sections on the n-type portions of the $I_d$-$V_{gs}$ curves, whereas in another preferred embodiment, the slopes of the curves can measured on the steepest sections on the p-type portions of the $I_d$-$V_{gs}$ curves. In yet another embodiment, the slopes are measured on the steepest sections on both the p-type and n-type portions of the reference and test $I_d$-$V_{gs}$ gs curves. See FIG. 13I.

In some embodiments, the difference between a reference $I_d$-$V_{gs}$ gs curve and a chemical sensing $I_d$-$V_{gs}$ curve is an overall change in shape of the chemical sensing (or test) $I_d$-$V_{gs}$ curve relative to an overall change in shape of the reference $I_d$-$V_{gs}$ curve. The difference in overall shape of the $I_d$-$V_{gs}$ curves can be determined, for example, by first fitting a polynomial or other fitting line to each of the $I_d$-$V_{gs}$ gs curves and then comparing the coefficients of those fitting lines. See FIG. 13H.

In some embodiments, the gate voltage, $V_{gs}$, of the $I_d$-$V_{gs}$ curve is a gate voltage applied to the chemically-sensitive field effect transistor of the invention.

In other embodiments, the gate voltage $V_{gs}$ of the $I_d$-$V_{gs}$ curve is a back gate voltage applied to a ChemFET through the back of the device.

In some another embodiments, the gate voltage of the $I_d$-$V_{gs}$ curve is a top gate voltage applied to the ChemFET through the top of the device.

In yet other embodiments, the gate voltage of the $I_d$-$V_{gs}$ curve is a solution gate voltage applied to the ChemFET through a solution over the device.

In some instances the accuracy or sensitivity of the ChemFET detection or analysis maybe be improved by combining one or more of the previously described techniques.

Although the curves shown in FIGS. 13A-13I are representative of an ambipolar ChemFET channel nanomaterial, such as graphene, similar shifts in I–V curves can be evaluated for other 1D or 2D ChemFET channel nanomaterials.

Example 6

Preparing FETs

Alternative methods for growing and transferring 2D nanomaterials are described, for example, in Hoffman et al., U.S. Provisional Patent Application No. 62/175,351, filed on Jun. 14, 2015, for System And Method For Growing And Transferring Graphene For Use As A FET, which is hereby incorporated by reference in its entirety.

FIGS. 34A-34M illustrate a preferred CMOS integration method for building interconnects, dielectric, and well structures, as well as the pads for bonding the transferred 2D nanomaterial to the chip.

FIG. 34A illustrates a graphene on a ROIC wafer step of a CMOS integration method. FIG. 34B illustrates a patterning a graphene layer to form channels step of a CMOS integration method. FIG. 34C illustrates a depositing an etch stop layer over a graphene layer step of a CMOS integration method. FIG. 34D illustrates a deposit, pattern and etch of a thick insulator layer step of a CMOS integration method. FIG. 34E illustrates a wet etch ESL, pattern and DRIE oxide over interconnects step of a CMOS integration method. Not shown is an optional addition of work function matching material prior to a via fill step of a CMOS integration method. FIG. 34F illustrates a deposit a barrier, liner, copper plate, CMP step of a CMOS integration method. FIG. 34G illustrates a deposit a barrier/adhesion layer, deposit aluminum, pattern, etch aluminum interconnect and pad layer step of a CMOS integration method. FIG. 34H illustrates a deposit of passivation material such as silicon oxide or silicon nitride (e.g. by CVD or PECVD) and pad open etch step of a CMOS integration method. FIG. 34I illustrates a DRIE well insulator down to an etch stop layer step of a CMOS integration method. FIG. 34J illustrates a wet etch (with a liquid or gaseous etchant) of a thin etch stop layer step of a CMOS integration method.

The substrate may be composed of at least one of Si, Si/SiO$_2$, SiO$_2$, sapphire/Al$_2$O$_3$, and a metal plate. An adhesion layer, as needed, is composed of at least one of Ti, Cr, Ta, W, WN, and TaN. The adhesion layer has a thickness of 5 to 200 angstroms and preferably approximately 100 angstroms. The metal layer is formed by at least one of PVD (sputtering, ebeam evaporation, thermal evaporation), CVD, electrochemical plating, and ALD.

Optional surface polishing, e.g., mechanical polishing, electropolishing, or CMP, after metal deposition is performed. Also, an optional plasma treatment (best done just before growth) with plasma with H2 and N2 or ammonia at approximately 0.1 Torr, 300-400 C can be performed.

An analyte or reaction-sensitive layer (not shown) could be deposited over the channel and prior to deposition of the ESL. In other embodiments such an analyte or reaction-sensitive layer could act as the ESL, in which case there would be no wet etch of this layer as was described with respect to FIG. 34J.

Example 7

Sensor Stacked with Other IC Chips

FIG. 15B depicts a ChemFET sensor IC chip (50). Such an IC chip comprises one or more ChemFET sensors, as previously described, and Read-Out Integrated Circuits (ROIC), access transistors or other circuitry formed in the lower semiconductor portion of the IC chip using normal semiconductor transistors, such as CMOS transistors. Although some amount of ROIC, signal processing, processor or other circuitry may be included in the ChemFET sensor IC chip (50) it may be the case that not all the circuitry needed for sensor signal detection and processing and data storage is able to be included on the ChemFET sensor IC chip (50) due to practical limitations with the size of the chip and the number of semiconductor transistors that may be integrated on the chip due to wafer fabrication limits. In such a case the ChemFET sensor IC chip would normally communicate either with other IC chips (such as a processor or memory chip) or with a computing system in order to perform the detection and analysis functions required, wherein typically these other IC chips would be located on a printed circuit board embedded in a system. In one embodiment of the instant invention, other IC chips can be bonded directly to the ChemFET sensor IC chip and by doing so improved electrical performance (faster operation and lower power) may be achieved since the interconnect length between the chips can be drastically reduced. Furthermore the overall size of the solution (ChemFET sensor IC chip, processor chip(s), memory chip(s) or others) may be significantly reduced, as well as reducing the size of any system that includes those chips.

FIG. 16 depicts a stacked arrangement of IC chips, including a ChemFET sensor IC chip (50), a processor IC chip (52), a memory controller IC chip (54) and a memory IC chip (56). Physical and electrical communication between the IC chips is provided by Through Silicon Vias (TSVs) (43) and connections members (44), such as solder joints.

Example 8

Sensor IC Chip Stacked to Create Flow Channels

FIGS. 57A-C depict various methods of physically stacking ChemFET sensor IC chips (50) to create fluid flow channels between the ChemFET sensor IC chips (50) to create fluid flow channels between the ChemFET sensor IC chips (50). Stacking of the ChemFET sensor IC chips (50) can have multiple benefits, one of which being that without increasing the area taken up by the sensor chip and with minimal increases in the vertical distance (due to the chip stacking) the number of sensors can be increased significantly (2 times for 2 stacked chips, 3 times for 3 stacked chips, etc). This is of benefit because larger numbers of sensors can lead to overall improved detection accuracy since there are more detection signals to combine and a statistically more accurate detection can be made. Furthermore sensor chip stacking allows larger ChemFET sensors to be used, which have lower noise and therefor better detection sensitivity, while still fitting in a small volume.

The stacked ChemFET sensor IC chips (50) can be of the same design (e.g. identical copies of each other) or they may be of different designs, for example optimized to detect different analytes, chemical reactions, or biologic activity. A stacked combination of different ChemFET sensor IC chips (50) can made detection of a target much more efficient since one fluid flow or sample exposure to the stacked chips can allow simultaneous sensing or detection of different analytes, chemical reactions or biologic activity that may be associated with the fluid or sample. Furthermore, if different ChemFET sensor IC chips are used in the chip stack they may not only be of different design, but they may have ChemFET sensors based on different nanomaterials, e.g. one chip may have GFET sensors and another chip may have Si NW sensors. In this fashion the chips may be further optimized for different purposes yet used simultaneously for detection or sensing when included in the same chip stack.

FIG. 17A depicts a stack of two ChemFET sensor IC chips oriented face to face. Physical connection members (45) hold the chips in proper orientation and may also be used to define flow channels between the ChemFET sensor IC chips (50).

FIG. 17B depicts a stack of two ChemFET sensor IC chips oriented face to face. The chips are held in proper orientation by an external means (not shown) and thus the fluid flow between the chips is not restricted by physical connection members.

FIG. 17C depicts a stack of two ChemFET sensor IC chips, each oriented in the same direction, e.g. face up. Physical connection members (45) hold the chips in proper orientation and may also be used to define flow channels between the ChemFET sensor IC chips (50). A lid (47), such as a package lid, defines the fluid flow area for the topmost ChemFET sensor IC chip (50).

FIG. 16 depicts a stacked arrangement of IC chips, including a ChemFET sensor IC chip (50), a processor IC chip (52), a memory controller IC chip (54) and a memory IC chip (56). Physical and electrical communication between the IC chips is provided by Through Silicon Vias (TSVs) (43) and connections members (44), such as solder joints.

Example 9

Gate All Around Structures

A typical nanomaterial-based ChemFET (1), such as depicted in FIG. 3A has a conductive source (22), a conductive drain (24), a nanomaterial channel (30) such as graphene, a well structure (38) and associated chamber (37), a fluid (64) and a gate voltage applied through the fluid (64) such a applied by a gate or reference electrode (66) in order to form a nanomaterial-based, solution-gated ChemFET (1). The ChemFET (1) may in some instances comprise an analyte or reaction-sensitive layer (34), which may further improve the sensitivity of the ChemFET (1) for detection of certain analytes or chemical reactions or biologic activity.

An improvement over the typical ChemFET (1) just described to is provide a second gate, i.e. a backgate for the device such that the backgate and solution gate can both apply voltages to the channel in a dual-gate fashion. Having two gate voltages, on opposite the other around the channel (30) has the advantage of more precisely controlling the ChemFET which in turn leads to better sensor sensitivity.

An even more enhanced embodiment of this concept is to completely surround a portion of the channel with gate material so that the whole channel circumference in some portion of the channel is fully enclosed by the gate material. This gives the highest degree of control over the channel through the gate all around structure.

Figure 9D:
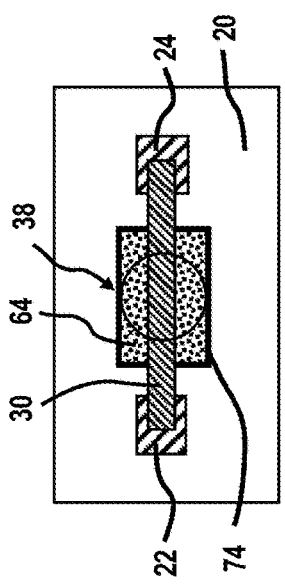
FIG. 9D shows a top view of the gate all around ChemFET shown in FIG. 9C.

FIGS. 9C and 9D depict a side sectional view and a top down view, respectively, of a gate all around ChemFET (1) comprised of a conductive source (22), conductive drain (24), channel (30) such as a graphene channel, an optional analyte or reaction-sensitive layer (34) over the channel (30), a well structure (38) providing a chamber (37) that holds a fluid (64) wherein a gate or reference electrode (66) applies a gate voltage to the fluid. In the gate all around embodiment the dielectric and metal under a relatively large portion of the channel region have been removed, such as by etching. In this fashion the fluid (64) is free to flow over, under and around the exposed portion of the channel—hence forming a gate all around structure.

In one instance the gate all around structure is achieved by providing an etch stop structure (74) configured as a tub-like shape and positioned in the dielectric material (20) under the channel (30) as shown in FIG. 9A. FIG. 9B depicts the ChemFET (1) after the well structure (38) has been formed and after the dielectric (20) under the channel and within the etch stop layer-defined tub has been etched away. In this embodiment the etch is preferably a wet chemical etch and not a dry, e.g. plasma, etch since dry etch processes tend to damage or destroy the graphene. A suitable wet etchant is a hydrofluoric (HF) acid-based etchant, such as a mixture of HF and a buffer such as ammonium fluoride. This etchant has high selectivity to silicon dioxide in comparison to silicon and thus silicon of the sensor IC chip wafer should not be damaged. Furthermore an HF-based etch should not have bad effect on the graphene channel (30).

In a second instance of the preferred gate all around structure, the graphene is first deposited or formed on a metal interconnect material (25) that may form one of the source (22) or drain (24) conductive electrodes as shown in FIG. 10A. If the interconnect material is copper, such as formed in trenches in a damascene process and with the upper portions of the electrodes exposed to the surface, i.e. copper is exposed to the surface then the possibility exists for forming the graphene (i.e. growing the graphene) directly on the semiconductor IC wafer rather than on a separate growth wafer and then transferring the graphene to the IC wafer. This may be possible since copper is one of the preferred growth substrates for graphene (graphene does not diffuse into copper during the growth) and if the growth temperature is kept low enough, such as lower than 400 C, so as not to affect the semiconductor transistors, such as CMOS transistors, It may be possible that a plasma-enhanced CVD (PECVD) or other enhanced CVD process will allow growth of good quality graphene directly on the exposed copper surfaces on an IC wafer. Once the graphene is formed or deposited on the copper areas, such as shown in FIG. 10A then in a subsequent process step the dielectric underlying the channel area (26), which at this time includes both graphene and a thin layer of copper, is etched. For a silicon dioxide dielectric a wet HF acid etchant is suitable. The etch may be further controlled or confined by an etch stop layer (74) formed in a tub-like shape. As depicted in FIG. 10B. Finally the thin copper layer under the graphene channel (30) can be etched by a suitable copper etchant, such as ammonium persulfate or ferric chloride., resulting in the central portion of the graphene channel to be free of any dielectric, as shown in FIG. 10C, and available for contact by the fluid to form a gate all around structure as shown in FIG. 9C.

In another gate all around embodiment, as shown in FIG. 11A, there is no etch stop layer provided under the channel sensing region (26). In this case the wet etching of the silicon dioxide dielectric (20) will be isotropic and will result in a bowl-shaped cavity beneath the channel (30) as shown in FIG. 11B. Furthermore since the etching is not confined by an etch stop layer, the etched cavity may not be fully uniform in size and shape.

All of the process embodiments just discussed result in the preferred gate all around structure shown in FIG. 9C.

Example 10

Sealing of Chambers for Improved Sensing

FIG. 38A depicts a ChemFET sensor IC chip (50). During operation it is often the case that an analyte to be detected, a biologic to be monitored or a reaction to be detected will generate ions. For example a base nucleotide incorporation onto a template DNA strand will release a hydrogen ion. The ChemFET can be used to sense these ions. However, as shown in FIG. 38A the ions (62) are not confined and may travel through the fluid (64). This can cause problems if more ions appear in one well (38) than another well, resulting in a larger signal in one well versus the other and possible leading to a false interpretation of the ChemFET signal. In an ideal case the ions generated in a well would remain within that well.

In one embodiment, FIG. 38B depicts a ChemFET sensor IC chip (50) which comprises a movable seal (90) shown in an upper or unsealed position. The seal may be raised up during times when fluid (64) needs to flow over the IC (50), such as when new reagents must be brought to the ChemFETs. However, as soon as the flow is done the movable seal may be placed in a downward or sealed position as shown in FIG. 38C. In this case the reagents and resulting reaction products, such as ions, are confined to their wells (38). This minimizes the chance for false signal generation and interpretation. Furthermore the ions are more concentrated to the wells since none are flowing outside the well areas so the overall density of ions per well is increased from the normal situation of FIG. 38A. This higher ion concentration will result in higher signal strength and higher sensor sensitivity.

In another embodiment, FIG. 38D depicts a ChemFET sensor IC chip (50) which comprises barrier generators (92) at the top surfaces of each well structure (38). These barrier generators (92) are used to create electromagnetic barrier fields (94) around the periphery of each well. For example a positively charged electromagnetic barrier filed (94) could repel positively charged hydrogen ions (62) and thus confine them to their individual chambers (38). This confinement, similar to the discussion above, results in higher ion concentration, improved signal strength, and better sensor sensitivity.

The generation of the barrier field may need to be provided such that the field does not interfere with the ChemFET operation. For example the barrier fields may be pulsed on and off. Pulsed on when the ions are to be confined and pulsed off when a read of a sensor is to be taken and the read should not be disturbed by the barrier field. Alternatively the barrier fields may be operated in such a fashion, such as operated as high frequency AC fields, that any extraneous signals generated by these barrier fields (94) during the ChemFET reading operation are easily determined by signal processing techniques and are eliminated from the readout.

In another embodiment, FIG. 38E shows a ChemFET sensor IC chip (50) which comprises a flow control member (96) which includes microvalves (98). In this embodiment the flow control member (96) and associated flow control microvalves (98) are fixably attached to the top of the ChemFET sensor IC chip (50). Flow channels that bring reagents or analytes to each well (38) are controlled by the microvalves which can allow flow to the chambers when the microvalve is open or prevent flow to or from the wells when the microvalve is closed. The flow control member (96) and associated microvalves (98) may be manufactured by MEMS (MicroElectroMechanical Systems) techniques. This may be necessary because the size of the wells on the ChemFET sensor IC chip (50) are small and the microvalves likewise need to be small. As with the other embodiments, when the wells are closed off by the microvalves (98) the ions are concentrated in the wells resulting in higher sensor sensitivity.

Example 11

Read Latency Reduction and Accuracy Improvement

In a ChemFET sensor IC chip (50) a fluid is used to introduce analytes or flow reagents over the chip and into the wells (38) of each ChemFET. Ideally the reading of sensors would be timed so that reading occurs as a new fluid wavefront with new analyte or reagents flows over those sensors, i.e. you want to read the sensors as the reactions are ongoing in their well (38).

The ChemFET sensors in the ChemFET sensor IC chip (50) are arranged in an array similar to an array of memory cells or an array of image sensor pixels. Likewise wordlines and bitlines may be used on the ChemFET sensor IC chip (50) to access and read any individual ChemFET sensor (1). During a read operation, especially for large chips with many cells, there can be a delay or latency in the time needed to charge up the bitlines before a read can occur of the desired sensor. Read latency can be reduced by making the accessed bitlines (columns) shorter by segmenting them (shorter lines can react faster to applied voltage changes) and by precharging them (so that the bitline is already at the read/bias voltage prior to a read).

Furthermore the concepts of bitline segmentation and precharging can be combined with the desire to read sensors only when the fluid wavefront has recently passed that sensor location. These concepts can be combined with microfluidics control to segment the read areas on the ChemFET sensor IC chip (50) for higher accuracy and reduced latency.

One can use a microfluidics structure and control the flow analyte or reagent fluid flow segment by segment over the area of the ChemFET sensor IC chip (50). In concert with the fluid flow control, one can precharge the bitlines for those segments to be read next, which are also the segments that will see fluid flow next, to reduce read latency. Other tasks (address decoding, output driving) can be performed simultaneously with the bitline precharging, either within the same segment or in other segments to reduce latency. Also in segments that are not being read the bitlines can be turned off, or more accurately their precharge circuits can be turned off, thereby reducing power.

FIG. 39 illustrates a ChemFET sensor IC chip (50) that includes a flow control member (96) and associated microvalves (98 and 99). The ChemFET sensor IC chip (50) includes multiple ChemFET sensors and related wells (38) arranged in an array over the area of the chip (50). As previously described access to segments of sensors (e.g. columns) for a read operation is done by toggling bitlines associated with those columns. Likewise toggling a wordline (row) in combination with a bitline allows a specific individual sensor to be read (each sensor is at a unique row and column location). The bitlines can be segmented so that only the bitlines in that segment need to be precharged and toggled for sensors in that segment to be read. It is preferable to coordinate the reads of the sensor segments with the fluid (64) flow to those sensor segments. FIG. 39 shows a fluid control member (96) that is allowing fluid (64) flow only to the rightmost segment because the microvalves controlling fluid flow to that segment are open (99). Conversely the microvalves (98) controlling fluid flow to the leftmost and middle segments are closed and therefore no fluid (64) is flowing to those segments).

Coordination of reading segments of sensors on the ChemFET sensor IC chip (50) by controlling fluid flow to be timed with read operations in certain segments will result in improved read accuracy since the reads will occur when fresh analyte or reagents have reached the sensors in that segment. Such segmentation and coordination is provided by fluid control members with microvalves and by bitline segmentation.

A useful detailed description is set forth in van Rooyen et al., U.S. Patent Publication Number 20140371110 for Bioinformatics Systems, Apparatuses, and Methods Executed On An Integrated Circuit Processing Platform, which is "hereby incorporated by reference in its entirety.

A useful detailed description is set forth in van Rooyen et al., U.S. Patent Publication Number 20140309944 for Bioinformatics Systems, Apparatuses, and Methods Executed On An Integrated Circuit Processing Platform, which is hereby incorporated by reference in its entirety.

A useful detailed description is set forth in van Rooyen et al., U.S. Patent Publication Number 20140236490 for Bioinformatics Systems, Apparatuses, and Methods Executed On An Integrated Circuit Processing Platform, which is hereby incorporated by reference in its entirety.

A useful detailed description is set forth in van Rooyen et al., U.S. Patent Publication Number 20140200166 for Bioinformatics Systems, Apparatuses, and Methods Executed On An Integrated Circuit Processing Platform, which is hereby incorporated by reference in its entirety.

A useful detailed description is set forth in McMillen et al., U.S. Provisional Patent Application No. 62/127,232, filed on Mar. 2, 2015, for Bioinformatics Systems, Apparatuses, And Methods Executed On An Integrated Circuit Processing Platform, which is hereby incorporated by reference in its entirety.

A useful detailed description is set forth in van Rooyen et al., U.S. Provisional Patent Application No. 62/119,059, filed on Feb. 20, 2015, for Bioinformatics Systems, Apparatuses, And Methods Executed On An Integrated Circuit Processing Platform, which is hereby incorporated by reference in its entirety.

A useful detailed description is set forth in van Rooyen et al., U.S. Provisional Patent Application No. 61/988,128, filed on May 2, 2014, for Bioinformatics Systems, Apparatuses, And Methods Executed On An Integrated Circuit Processing Platform,which is hereby incorporated by reference in its entirety.

A useful detailed description of a GFET is set forth in van Rooyen, U.S. Provisional Patent Application No. 62/094,016, filed on Dec. 18, 2014, for Graphene FET Devices, Systems, And Methods Of Using The Same For Sequencing Nucleic Acids,which is hereby incorporated by reference in its entirety.

A useful detailed description of a GFET is set forth in Hoffman et al., U.S. Provisional Patent Application No. 62/130,594, filed on Mar. 9, 2015, for Chemically Sensitive Field Effect Transistor, which is hereby incorporated by reference in its entirety.

A useful detailed description of a GFET is set forth in Hoffman et al., U.S. Provisional Patent Application No. 62/130,598, filed on Mar. 9, 2015, for Method And System For Analysis Of Biological And Chemical Materials, which is hereby incorporated by reference in its entirety.

A useful method for growing and transferring graphene is disclosed in Hoffman et al., U.S. Provisional Patent Application No. 62/175,351, filed on Jun. 14, 2015, for a System And Method For Growing And Transferring Graphene For Use As A FET, which is hereby incorporated by reference in its entirety.

As A FET,which is hereby incorporated by reference in its entirety.

A use for 2D nanomaterials is disclosed in Hoffman et al., U.S. Provisional Patent Application No. 62/175,384, filed on Jun. 14, 2015, for a CMOS Integration Of A Two-Dimensional Material,which is hereby incorporated by reference in its entirety.

The following U.S. Patent Applications discuss the processing component of the a system for analysis of biological and chemical materials: U.S. patent application Ser. No. 14/279,063, titled, Bioinformatics Systems, Apparatuses, and Methods Executed on an Integrated Circuit Processing Platform, filed May 15, 2014; U.S. patent application Ser. No. 14/180,248, titled Bioinformatics Systems, Apparatuses, and Methods Executed on an Integrated Circuit Processing Platform, filed Feb. 13, 2014; U.S. patent application Ser. No. 14/179,513, titled Bioinformatics Systems, Apparatuses, and Methods Executed on a an Integrated Circuit Processing Platform, filed Feb. 12, 2014; U.S. patent application Ser. No. 14/158,758, titled Bioinformatics Systems, Apparatuses, and Methods Executed on an Integrated Circuit Processing Platform, filed Jan. 17, 2014; U.S. patent application Ser. No. 14/279,063; U.S. Provisional Application No. 61/826,381, titled System and Method for Computation Genomic Pipeline, filed May 22, 2013; U.S. Provisional Application No. 61/943,870, titled Dynamic Genome Reference Generation For Improved NGS Accuracy And Reproducibility, filed Feb. 24, 2014; all of which are hereby incorporated by reference in their entireties herein.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

All of the devices and methods described and claimed herein can be made and executed without undue experimentation in light of the present description. While the devices and methods of this invention have been described in terms of preferred embodiments, it will be apparent to those of skill in the art that variations may be applied to the compositions and methods. All such similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

I claim:

1. A chemically-sensitive field effect transistor having a multi-layered structure, comprising:
    a substrate layer having an extended body;
    a first and second insulating layer positioned above the extended body of the substrate layer, the second insulating layer being positioned above the first insulating layer;
    a source electrode and a drain electrode each having one or more surfaces, the one or more surfaces defining a boundary between an interior portion and an exterior portion of each electrode, at least a portion of the one or more surfaces of the source and drain electrodes being disposed at least partially within the first insulating layer, the source electrode being separated from the drain electrode by a distance;
    a graphene layer positioned between the first and second insulating layers and contacting at least the exterior portion of the one or more surfaces of each of the source and drain electrodes, the graphene layer extending a length a first exterior portion of the source electrode to a first portion of the drain electrode thereby forming a channel between the source and drain electrodes; and
    one or more surface structures forming a gate that overlaps at least a portion of the source and the drain electrodes, the one or more surface structures being at least partially positioned in the second insulating layer.

2. The chemically-sensitive field effect transistor according to claim 1, wherein the multi-layered structure is configured so as to shift an I–V curve or an I–Vg curve in response to a chemical reaction occurring within the well of the chemically-sensitive field effect transistor.

3. The chemically-sensitive field effect transistor according to claim 2, wherein the substrate layer comprises silicon, and the first insulating layer comprises silicon di-oxide.

4. The chemically-sensitive field effect transistor according to claim 3, wherein the first and second insulating layers comprise a single layer.

5. The chemically-sensitive field effect transistor according to claim 2, wherein a length of the channel from the source to the drain ranges from 0.05 micron to 3 microns, and a width of the channel ranges from 0.05 micron to 2 microns.

6. The chemically-sensitive field effect transistor according to claim 2, wherein one or more of the first and second insulating layers comprise an analyte-sensitive dielectric layer.

7. The chemically-sensitive field effect transistor according to claim 6, wherein the analyte-sensitive dielectric layer comprises an oxide layer.

8. The chemically-sensitive field effect transistor according to claim 7, wherein the analyte-sensitive dielectric layer is comprised of one of an aluminum oxide, a silicon dioxide, a hafnium dioxide, a zirconium dioxide, a lanthanum oxide, a tantalum oxide, a titanium oxide, an iron oxide, and a yttrium oxide.

9. The chemically-sensitive field effect transistor according to claim 8, wherein the second insulating layer is composed of a polyimide, BCB, silicon oxide, a silicon nitride, a silicon oxynitride or a silicon carbide.

10. The chemically-sensitive field effect transistor according to claim 6, further comprising a well structure, the well structure being positioned in one or more of the first and second insulating layers and having side walls and a bottom defining a reaction chamber, the bottom being positioned proximate at least a portion of the graphene layer of the channel, the reaction chamber being configured for the performance of a biological reaction.

11. The chemically-sensitive field effect transistor according to claim 10, wherein the biological reaction involves a biological material, wherein the biological material comprises one or more of a nucleotide, a nucleic acid, a protein, or other biological molecule.

12. A chemically-sensitive field effect transistor having a multi-layered structure, comprising:
    a substrate layer having an extended body;
    a first drain electrode and a first source electrode each having a top surface and a bottom surface, the top surface separated from the bottom surface by opposing outer and inner side portions, each pair of opposed side portions and each of the bottom surfaces of the first drain and first source electrodes being at least partially disposed within the substrate layer, the first drain electrode being separated from the first source electrode by a first distance;
    a first insulating layer positioned above the extended body of the substrate layer;

a first structure positioned at least partially in the first insulating layer and extending at least the first length so as to form a gate between the first drain and first source electrodes, the gate contacting at least a portion of each of the first drain and first source electrodes;

a second source electrode and a second drain electrode each having a top surface and a bottom surface, the top surface separated from the bottom surface by opposing outer and inner side portions, each of the opposed side portions and each of the bottom surfaces of the second source and second drain electrodes being disposed at least partially within the first insulating layer, the second source electrode being separated from the second drain electrode by a second distance;

a second insulating layer positioned above the first insulating layer;

a graphene layer positioned between the first and second insulating layers and extending a length from at least the inner side portion of the second source electrode to the inner side portion of the second drain electrode thereby forming a channel between the source and drain electrodes, the graphene layer contacting the top surface of the second source and second drain electrodes and not extending beyond either outer side portion of the source and drain electrodes; and one or more second structures forming a second gate that overlaps at least a portion of the second source and the second drain electrodes.

13. The chemically-sensitive field effect transistor according to claim 12, wherein the multi-layered structure is configured so as to shift an I–V curve or an I–Vg curve in response to a chemical reaction occurring within the chamber of the chemically-sensitive field effect transistor.

14. The chemically-sensitive field effect transistor according to claim 13, further comprising a well structure, the well structure being positioned in one or more of the first and second insulating layers and having side walls and a bottom defining a reaction chamber, the bottom being positioned proximate at least a portion of the graphene layer of the channel, the reaction chamber being configured for the performance of a biological reaction.

15. The chemically-sensitive field effect transistor according to claim 14, wherein the biological reaction involves a biological material, wherein the biological material comprises one or more of a nucleotide, a nucleic acid, a protein, or other biological molecule.

16. The chemically-sensitive field effect transistor according to claim 15, wherein one or more of the first and second insulating layers comprise an analyte-sensitive dielectric layer.

17. A chemically-sensitive field effect transistor having a multi-layered structure, comprising:
a substrate layer having an extended body;
a first insulating layer positioned above the extended body of the substrate layer; and
a first and a second pair of source and drain electrodes being at least partially positioned in the first insulating layer, each source and drain electrode of each pair being separated from one another by a distance, the first pair of source and drain electrodes being coupled together by a first gate structure, and the second pair of source and drain electrodes being coupled together by a channel, the channel being formed of a graphene layer, the graphene layer contacting a surface of each of the second pair of source and drain electrodes.

18. The chemically-sensitive field effect transistor according to claim 17, wherein the multi-layered structure is configured so as to shift an I–V curve or an I–Vg curve in response to a chemical reaction occurring within the well of the chemically-sensitive field effect transistor.

19. The chemically-sensitive field effect transistor according to claim 18, further comprising a well structure, the well structure being positioned in one or more of the first and second insulating layers and having side walls and a bottom defining a reaction chamber, the bottom being positioned proximate at least a portion of the graphene layer of the channel, the reaction chamber being configured for the performance of a biological reaction.

20. The chemically-sensitive field effect transistor according to claim 19, wherein the biological reaction involves a biological material, wherein the biological material comprises one or more of a nucleotide, a nucleic acid, a protein, or other biological molecule.

* * * * *

UNITED STATES PATENT AND TRADEMARK OFFICE
CERTIFICATE OF CORRECTION

PATENT NO. : 10,429,381 B2  
APPLICATION NO. : 16/014838  
DATED : October 1, 2019  
INVENTOR(S) : Paul Hoffman Page 1 of 1

It is certified that error appears in the above-identified patent and that said Letters Patent is hereby corrected as shown below:

On the Title Page

"(72) Inventors: Paul Hoffman, San Diego, CA (US);"  
Should read:  
"(72) Inventors; Paul Hoffman, San Diego, CA (US); Brett R. Goldsmith, San Diego, CA (US);"

Signed and Sealed this  
Fourth Day of August, 2020

Andrei Iancu  
*Director of the United States Patent and Trademark Office*